US010517756B2

(12) United States Patent
Andino et al.

(10) Patent No.: US 10,517,756 B2
(45) Date of Patent: *Dec. 31, 2019

(54) APPARATUS AND METHODS FOR OCULAR INJECTION

(71) Applicant: CLEARSIDE BIOMEDICAL, INC., Alpharetta, GA (US)

(72) Inventors: Rafael Victor Andino, Grayson, GA (US); Vladimir Zarnitsyn, Atlanta, GA (US); Jesse Yoo, Snellville, GA (US); Christopher John Brooks, Glen Cove, NY (US); Trent John Kahute, Atlanta, GA (US); Justin William Arsenault, Atlanta, GA (US); David Jackson Trettin, Atlanta, GA (US); Andrew Kent Bauer, Atlanta, GA (US); Stephanie Elaine Lewis, Atlanta, GA (US)

(73) Assignee: CLEARSIDE BIOMEDICAL, INC, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/381,213

(22) Filed: Apr. 11, 2019

(65) Prior Publication Data
US 2019/0231592 A1 Aug. 1, 2019

Related U.S. Application Data

(63) Continuation of application No. 15/946,838, filed on Apr. 6, 2018, which is a continuation of application (Continued)

(51) Int. Cl.
*A61F 9/00* (2006.01)
*A61M 5/46* (2006.01)
(Continued)

(52) U.S. Cl.
CPC ............. *A61F 9/0017* (2013.01); *A61J 1/201* (2015.05); *A61J 1/2055* (2015.05); *A61J 1/2096* (2013.01);
(Continued)

(58) Field of Classification Search
CPC ............ A61M 5/34; A61M 5/46; A61M 5/20; A61M 5/2033; A61M 5/2053;
(Continued)

(56) References Cited

U.S. PATENT DOCUMENTS

| 2,187,259 A | 1/1940 | Barnhart |
| 2,841,145 A | 7/1958 | Epps |

(Continued)

FOREIGN PATENT DOCUMENTS

| CA | 2639322 | 3/2009 |
| CN | 1229679 A | 9/1999 |

(Continued)

OTHER PUBLICATIONS

Office Action for U.S. Appl. No. 11/743,535, dated Aug. 19, 2010, 7 pages.
(Continued)

*Primary Examiner* — Nathan R Price
*Assistant Examiner* — Anh Bui
(74) *Attorney, Agent, or Firm* — Cooley LLP

(57) ABSTRACT

An apparatus includes a housing coupled to a medicament container, which is coupled to a needle. An injection assembly is disposed within the housing and includes an energy storage member and an actuation rod. A distal end portion of the actuation rod is disposed within the medicament container. The energy storage member can produce a force on a proximal end portion of the actuation rod sufficient to move the distal end portion of the actuation rod within the medicament container. This can convey at least a portion of a
(Continued)

substance from the medicament container via the needle when a distal tip of the needle is disposed within a first region of a target location. The force is insufficient to move the distal end portion of the actuation rod within the medicament container when the distal tip of the needle is disposed within a second region of the target location.

28 Claims, 95 Drawing Sheets

Related U.S. Application Data

No. 15/714,441, filed on Sep. 25, 2017, now Pat. No. 9,937,075, which is a continuation of application No. 15/472,551, filed on Mar. 29, 2017, now Pat. No. 9,770,361, which is a continuation of application No. 15/399,239, filed on Jan. 5, 2017, now Pat. No. 9,636,253, which is a continuation of application No. 14/268,687, filed on May 2, 2014, now Pat. No. 9,539,139.

(60) Provisional application No. 61/953,147, filed on Mar. 14, 2014, provisional application No. 61/944,214, filed on Feb. 25, 2014, provisional application No. 61/827,371, filed on May 24, 2013, provisional application No. 61/819,052, filed on May 3, 2013, provisional application No. 61/819,048, filed on May 3, 2013.

(51) Int. Cl.
```
A61M 37/00      (2006.01)
A61M 5/20       (2006.01)
A61M 5/48       (2006.01)
A61J 1/20       (2006.01)
A61M 5/31       (2006.01)
A61M 5/34       (2006.01)
A61M 5/32       (2006.01)
A61M 5/315      (2006.01)
```

(52) U.S. Cl.
CPC ........ *A61M 5/2033* (2013.01); *A61M 5/2053* (2013.01); *A61M 5/31* (2013.01); *A61M 5/3293* (2013.01); *A61M 5/34* (2013.01); *A61M 5/344* (2013.01); *A61M 5/346* (2013.01); *A61M 5/347* (2013.01); *A61M 5/348* (2013.01); *A61M 5/349* (2013.01); *A61M 5/46* (2013.01); *A61M 5/482* (2013.01); *A61M 37/0015* (2013.01); *A61F 2250/0007* (2013.01); *A61F 2250/0069* (2013.01); *A61M 2005/31508* (2013.01); *A61M 2037/0023* (2013.01); *A61M 2037/0061* (2013.01); *A61M 2210/0612* (2013.01)

(58) Field of Classification Search
CPC .......... A61M 5/482; A61M 2037/0023; A61M 2037/0061; A61M 37/0015; A61M 2210/0612; A61F 9/00736; A61F 9/0026; A61F 9/0017
See application file for complete search history.

(56) References Cited

U.S. PATENT DOCUMENTS

| | | |
|---|---|---|
| 2,939,459 A | 6/1960 | Lazarte et al. |
| 3,376,999 A | 4/1968 | De Hart et al. |
| 3,788,320 A | 1/1974 | Dye |
| 3,838,690 A | 10/1974 | Friedman |
| 3,962,430 A | 6/1976 | O'Neill |
| 4,377,897 A | 3/1983 | Eichenbaum et al. |
| 4,383,530 A | 5/1983 | Bruno |
| 4,417,887 A | 11/1983 | Koshi |
| 4,432,964 A | 2/1984 | Shell et al. |
| 4,525,346 A | 6/1985 | Stark |
| 4,601,708 A | 7/1986 | Jordan |
| 4,615,331 A | 10/1986 | Kramann |
| 4,689,040 A | 8/1987 | Thompson |
| 4,708,147 A | 11/1987 | Haaga |
| 4,717,383 A | 1/1988 | Phillips et al. |
| 4,755,169 A | 7/1988 | Sarnoff et al. |
| 4,826,490 A | 5/1989 | Byrne et al. |
| 4,826,871 A | 5/1989 | Gressel et al. |
| 4,889,529 A | 12/1989 | Haindl |
| 4,941,874 A | 7/1990 | Sandow et al. |
| 4,966,773 A | 10/1990 | Gressel et al. |
| 5,024,662 A | 6/1991 | Menes et al. |
| 5,066,276 A | 11/1991 | Wang |
| 5,098,389 A | 3/1992 | Cappucci |
| 5,137,447 A | 8/1992 | Hunter |
| 5,181,909 A | 1/1993 | McFarlane |
| 5,206,267 A | 4/1993 | Shulman |
| 5,273,530 A | 12/1993 | del Cerro et al. |
| 5,279,564 A | 1/1994 | Taylor |
| 5,300,084 A | 4/1994 | Johnson |
| 5,312,361 A | 5/1994 | Zadini et al. |
| 5,320,609 A | 6/1994 | Haber et al. |
| 5,354,286 A | 10/1994 | Mesa et al. |
| 5,358,489 A | 10/1994 | Wyrick |
| 5,364,373 A | 11/1994 | Waskonig et al. |
| 5,364,374 A | 11/1994 | Morrison et al. |
| 5,397,313 A | 3/1995 | Gross |
| 5,399,159 A | 3/1995 | Chin et al. |
| 5,409,457 A | 4/1995 | del Cerro et al. |
| 5,547,467 A | 8/1996 | Pliquett et al. |
| 5,575,780 A | 11/1996 | Saito |
| 5,632,740 A | 5/1997 | Koch et al. |
| D383,049 S | 9/1997 | Concari et al. |
| 5,667,491 A | 9/1997 | Pliquett et al. |
| 5,681,825 A | 10/1997 | Lindqvist et al. |
| 5,766,198 A | 6/1998 | Li |
| 5,779,668 A | 7/1998 | Grabenkort |
| 5,788,679 A | 8/1998 | Gravlee, Jr. |
| 5,792,099 A | 8/1998 | DeCamp et al. |
| 5,817,075 A | 10/1998 | Giungo |
| 5,911,223 A | 6/1999 | Weaver et al. |
| 5,952,378 A | 9/1999 | Stjernschantz et al. |
| 5,968,022 A | 10/1999 | Saito |
| 6,083,199 A | 7/2000 | Thorley et al. |
| 6,159,218 A | 12/2000 | Aramant et al. |
| 6,280,470 B1 | 8/2001 | Peyman |
| 6,299,603 B1 | 10/2001 | Hecker et al. |
| 6,309,347 B1 | 10/2001 | Takahashi et al. |
| 6,309,374 B1 | 10/2001 | Hecker et al. |
| 6,319,225 B1 | 11/2001 | Sugita et al. |
| 6,319,240 B1 | 11/2001 | Beck |
| 6,334,856 B1 | 1/2002 | Allen et al. |
| 6,378,526 B1 | 4/2002 | Bowman et al. |
| 6,387,078 B1 | 5/2002 | Gillespie, III |
| 6,397,849 B1 | 6/2002 | Bowman et al. |
| 6,432,090 B1 | 8/2002 | Brunel |
| 6,494,865 B1 | 12/2002 | Alchas |
| 6,503,231 B1 | 1/2003 | Prausnitz et al. |
| 6,524,581 B1 | 2/2003 | Adamis |
| 6,530,904 B1 | 3/2003 | Edwards et al. |
| 6,540,725 B1 | 4/2003 | Ponzi |
| 6,551,299 B2 | 4/2003 | Miyoshi et al. |
| 6,569,123 B2 | 5/2003 | Alchas et al. |
| 6,611,707 B1 | 8/2003 | Prausnitz et al. |
| 6,743,211 B1 | 6/2004 | Prausnitz et al. |
| 6,773,916 B1 | 8/2004 | Thiel et al. |
| D499,153 S | 11/2004 | Kuo |
| 6,883,222 B2 | 4/2005 | Landau |
| 6,918,889 B1 | 7/2005 | Brunel |
| 6,929,623 B2 | 8/2005 | Stone |
| 6,936,053 B1 | 8/2005 | Weiss |
| 6,979,316 B1 | 12/2005 | Rubin et al. |
| 7,025,774 B2 | 4/2006 | Freeman et al. |
| 7,150,735 B2 | 12/2006 | Hickle |

(56) References Cited

U.S. PATENT DOCUMENTS

| | | |
|---|---|---|
| 7,207,965 B2 | 4/2007 | Simon |
| 7,207,980 B2 | 4/2007 | Christian et al. |
| 7,211,062 B2 | 5/2007 | Kwon |
| 7,214,212 B2 | 5/2007 | Pommereau et al. |
| 7,226,439 B2 | 6/2007 | Prausnitz et al. |
| 7,316,676 B2 | 1/2008 | Peyman et al. |
| 7,425,207 B2 | 9/2008 | Miller et al. |
| 7,435,237 B2 | 10/2008 | Tan |
| 7,468,057 B2 | 12/2008 | Ponzi |
| D590,690 S | 4/2009 | Bertini |
| D598,543 S | 8/2009 | Vogel et al. |
| 7,569,035 B1 | 8/2009 | Wilmot et al. |
| 7,615,041 B2 | 11/2009 | Sullivan et al. |
| 7,648,482 B2 | 1/2010 | Edwards et al. |
| 7,678,077 B2 | 3/2010 | Harris et al. |
| 7,678,078 B1 | 3/2010 | Peyman et al. |
| 7,722,581 B2 | 5/2010 | Peyman |
| 7,914,803 B2 | 3/2011 | Chowhan et al. |
| 7,918,814 B2 | 4/2011 | Prausnitz et al. |
| 7,918,874 B2 | 4/2011 | Siegal |
| 7,947,660 B2 | 5/2011 | Clark et al. |
| 7,967,772 B2 | 6/2011 | McKenzie et al. |
| 8,003,124 B2 | 8/2011 | Varner et al. |
| 8,114,110 B2 | 2/2012 | Bednarek et al. |
| 8,137,312 B2 | 3/2012 | Sundar et al. |
| 8,172,830 B2 | 5/2012 | Christian et al. |
| 8,173,617 B2 | 5/2012 | Clark et al. |
| 8,192,408 B2 | 6/2012 | Nazzaro et al. |
| 8,197,435 B2 | 6/2012 | Prausnitz et al. |
| 8,197,443 B2 | 6/2012 | Sundar et al. |
| 8,221,353 B2 | 7/2012 | Cormier et al. |
| 8,235,967 B2 | 8/2012 | Chevallier et al. |
| D667,111 S | 9/2012 | Robinson |
| 8,287,494 B2 | 10/2012 | Ma |
| D672,506 S | 12/2012 | Szymanski |
| 8,323,227 B2 | 12/2012 | Hamatake et al. |
| 8,328,772 B2 | 12/2012 | Kinast et al. |
| 8,337,421 B2 | 12/2012 | Freeman et al. |
| 8,337,509 B2 | 12/2012 | Schieber et al. |
| 8,348,924 B2 | 1/2013 | Christian et al. |
| 8,430,862 B2 | 4/2013 | Peyman et al. |
| 8,460,242 B2 | 6/2013 | Paques et al. |
| 8,506,515 B2 | 8/2013 | Burns et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,545,554 B2 | 10/2013 | Novakovic et al. |
| 8,562,545 B2 | 10/2013 | Freeman et al. |
| 8,571,802 B2 | 10/2013 | Robinson et al. |
| 8,574,214 B2 | 11/2013 | Kuhn et al. |
| 8,574,217 B2 | 11/2013 | Peyman |
| 8,602,959 B1 | 12/2013 | Park et al. |
| 8,617,121 B2 | 12/2013 | Lanin et al. |
| 8,632,589 B2 | 1/2014 | Helmy |
| 8,636,713 B2 | 1/2014 | Prausnitz et al. |
| 8,652,118 B2 | 2/2014 | Peyman |
| 8,663,167 B2 | 3/2014 | Bartha |
| 8,663,303 B2 | 3/2014 | Horvath et al. |
| 8,668,676 B2 | 3/2014 | Chang |
| 8,685,435 B2 | 4/2014 | Nivaggioli et al. |
| 8,702,659 B2 | 4/2014 | Lanin et al. |
| 8,747,365 B2 | 6/2014 | De Sausmarez Lintell |
| 8,795,226 B2 | 8/2014 | Kuhn et al. |
| 8,808,225 B2 | 8/2014 | Prausnitz et al. |
| 8,808,242 B2 | 8/2014 | Paques et al. |
| D713,958 S | 9/2014 | Srinivasan et al. |
| 8,821,870 B2 | 9/2014 | Robinson et al. |
| D715,125 S | 10/2014 | Hung |
| 8,852,137 B2 | 10/2014 | Horvath et al. |
| 8,864,740 B2 | 10/2014 | Schabbach et al. |
| D718,602 S | 12/2014 | Musser |
| D719,256 S | 12/2014 | Ohashi |
| 8,920,375 B2 | 12/2014 | Gonnelli |
| D726,908 S | 4/2015 | Yu et al. |
| D733,289 S | 6/2015 | Blanchard et al. |
| D740,098 S | 10/2015 | Kuo et al. |
| 9,180,047 B2 * | 11/2015 | Andino ............... A61M 5/347 |
| D750,223 S | 2/2016 | Andino et al. |
| 9,539,139 B2 | 1/2017 | Andino et al. |
| 9,636,253 B1 * | 5/2017 | Andino ............... A61M 5/347 |
| 9,770,361 B2 | 9/2017 | Andino et al. |
| 9,788,995 B2 | 10/2017 | Prausnitz et al. |
| 9,937,075 B2 | 4/2018 | Andino et al. |
| 9,956,114 B2 | 5/2018 | Andino et al. |
| 10,188,550 B2 | 1/2019 | Andino et al. |
| 2001/0008961 A1 | 7/2001 | Hecker et al. |
| 2001/0051798 A1 | 12/2001 | Hochman |
| 2002/0042594 A1 | 4/2002 | Lum et al. |
| 2002/0052580 A1 | 5/2002 | Ooyauchi |
| 2002/0082527 A1 | 6/2002 | Liu et al. |
| 2002/0082543 A1 | 6/2002 | Park et al. |
| 2003/0009113 A1 | 1/2003 | Olson |
| 2003/0050602 A1 | 3/2003 | Pettis et al. |
| 2003/0083645 A1 | 5/2003 | Angel et al. |
| 2003/0171722 A1 | 9/2003 | Paques et al. |
| 2003/0233070 A1 | 12/2003 | De La Serna et al. |
| 2004/0019331 A1 | 1/2004 | Yeshurun |
| 2004/0039253 A1 | 2/2004 | Peyman et al. |
| 2004/0106904 A1 | 6/2004 | Gonnelli et al. |
| 2004/0122359 A1 | 6/2004 | Wenz et al. |
| 2004/0141925 A1 | 7/2004 | Bosch et al. |
| 2004/0186084 A1 | 9/2004 | Alam et al. |
| 2004/0199130 A1 | 10/2004 | Chornenky et al. |
| 2004/0249404 A1 | 12/2004 | Haefliger |
| 2004/0265365 A1 | 12/2004 | Daddona et al. |
| 2005/0009910 A1 | 1/2005 | Hughes et al. |
| 2005/0033230 A1 | 2/2005 | Alchas et al. |
| 2005/0065137 A1 | 3/2005 | Jani et al. |
| 2005/0101582 A1 | 5/2005 | Lyons et al. |
| 2005/0101882 A1 | 5/2005 | Leira et al. |
| 2005/0101967 A1 | 5/2005 | Weber et al. |
| 2005/0137525 A1 | 6/2005 | Wang et al. |
| 2005/0148034 A1 | 7/2005 | Hariri et al. |
| 2005/0171507 A1 | 8/2005 | Christian et al. |
| 2005/0181017 A1 | 8/2005 | Hughes et al. |
| 2005/0209565 A1 | 9/2005 | Yuzhakov et al. |
| 2005/0244462 A1 | 11/2005 | Farooq |
| 2005/0244469 A1 | 11/2005 | Whitcup et al. |
| 2005/0245906 A1 | 11/2005 | Makower et al. |
| 2005/0256499 A1 | 11/2005 | Pettis et al. |
| 2005/0281862 A1 | 12/2005 | Karakelle et al. |
| 2006/0013859 A1 | 1/2006 | Yamada et al. |
| 2006/0036318 A1 | 2/2006 | Foulkes |
| 2006/0084942 A1 | 4/2006 | Kim et al. |
| 2006/0086689 A1 | 4/2006 | Raju |
| 2006/0089607 A1 | 4/2006 | Chen |
| 2006/0173418 A1 | 8/2006 | Rinaudo et al. |
| 2006/0178614 A1 | 8/2006 | Nemati |
| 2006/0189608 A1 | 8/2006 | Bingaman |
| 2006/0229562 A1 | 10/2006 | Marsh et al. |
| 2006/0233858 A1 | 10/2006 | Tzekov et al. |
| 2006/0259008 A1 | 11/2006 | Orilla |
| 2006/0271025 A1 | 11/2006 | Jones et al. |
| 2007/0060927 A1 | 3/2007 | Longson et al. |
| 2007/0073197 A1 | 3/2007 | Prausnitz et al. |
| 2007/0082841 A1 | 4/2007 | Higuchi et al. |
| 2007/0093877 A1 | 4/2007 | Beecham et al. |
| 2007/0202186 A1 | 8/2007 | Yamamoto et al. |
| 2007/0233037 A1 | 10/2007 | Gifford, III et al. |
| 2007/0260201 A1 | 11/2007 | Prausnitz et al. |
| 2007/0270745 A1 | 11/2007 | Nezhat et al. |
| 2007/0270768 A1 | 11/2007 | Dacquay et al. |
| 2007/0287985 A1 | 12/2007 | Estes et al. |
| 2008/0008762 A1 | 1/2008 | Robinson et al. |
| 2008/0033351 A1 | 2/2008 | Trogden et al. |
| 2008/0058704 A1 | 3/2008 | Hee et al. |
| 2008/0058717 A1 | 3/2008 | Spector |
| 2008/0071246 A1 | 3/2008 | Nazzaro et al. |
| 2008/0097346 A1 | 4/2008 | Charles |
| 2008/0097390 A1 | 4/2008 | Dacquay et al. |
| 2008/0131484 A1 | 6/2008 | Robinson et al. |
| 2008/0177239 A1 | 7/2008 | Li et al. |
| 2008/0228127 A1 | 9/2008 | Burns et al. |
| 2008/0234625 A1 | 9/2008 | Dacquay et al. |

(56) References Cited

U.S. PATENT DOCUMENTS

| | | |
|---|---|---|
| 2009/0030381 A1 | 1/2009 | Lind et al. |
| 2009/0076463 A1 | 3/2009 | Attinger |
| 2009/0081277 A1 | 3/2009 | Robinson et al. |
| 2009/0082321 A1 | 3/2009 | Edelman et al. |
| 2009/0105749 A1 | 4/2009 | De Juan et al. |
| 2009/0148527 A1 | 6/2009 | Robinson |
| 2009/0259180 A1 | 10/2009 | Choi |
| 2009/0287161 A1 | 11/2009 | Traub et al. |
| 2009/0312782 A1 | 12/2009 | Park |
| 2010/0010004 A1 | 1/2010 | Van emelen et al. |
| 2010/0010452 A1 | 1/2010 | Paques et al. |
| 2010/0015158 A1 | 1/2010 | Robinson et al. |
| 2010/0057011 A1 | 3/2010 | Charles |
| 2010/0074957 A1 | 3/2010 | Robinson et al. |
| 2010/0100054 A1 | 4/2010 | Cormier et al. |
| 2010/0152646 A1 | 6/2010 | Girijavallabhan et al. |
| 2010/0152667 A1 | 6/2010 | Kietzmann |
| 2010/0173866 A1 | 7/2010 | Hee et al. |
| 2010/0191176 A1 | 7/2010 | Ho et al. |
| 2010/0211079 A1 | 8/2010 | Aramant |
| 2010/0241102 A1 | 9/2010 | Ma |
| 2010/0312120 A1 | 12/2010 | Meier |
| 2011/0060310 A1 | 3/2011 | Prestrelski et al. |
| 2011/0112546 A1 | 5/2011 | Juan, Jr. et al. |
| 2011/0166531 A1 | 7/2011 | Stroumpoulis et al. |
| 2011/0202012 A1 | 8/2011 | Bartlett |
| 2011/0213317 A1 | 9/2011 | Chen et al. |
| 2011/0238075 A1 | 9/2011 | Clauson et al. |
| 2011/0282298 A1 | 11/2011 | Agian et al. |
| 2011/0295152 A1 | 12/2011 | Sasaki et al. |
| 2012/0004245 A1 | 1/2012 | May et al. |
| 2012/0024987 A1 | 2/2012 | Nagele Nacken |
| 2012/0029360 A1 | 2/2012 | Hendriks et al. |
| 2012/0035524 A1 | 2/2012 | Silvestrini |
| 2012/0078224 A1 | 3/2012 | Lerner et al. |
| 2012/0083727 A1 | 4/2012 | Barnett |
| 2012/0095414 A1 | 4/2012 | Lanin et al. |
| 2012/0095438 A1 | 4/2012 | Lanin et al. |
| 2012/0101475 A1 | 4/2012 | Wilmot et al. |
| 2012/0116306 A1 | 5/2012 | Heald et al. |
| 2012/0123351 A1 | 5/2012 | Lanin et al. |
| 2012/0123437 A1 | 5/2012 | Horvath et al. |
| 2012/0123440 A1 | 5/2012 | Horvath et al. |
| 2012/0123473 A1 | 5/2012 | Hernandez |
| 2012/0130207 A1 | 5/2012 | O'dea et al. |
| 2012/0136318 A1 | 5/2012 | Lanin et al. |
| 2012/0150128 A1 | 6/2012 | Zhao |
| 2012/0157880 A1 | 6/2012 | Haselby et al. |
| 2012/0165723 A1 | 6/2012 | Horvath et al. |
| 2012/0191064 A1 | 7/2012 | Conston et al. |
| 2012/0197208 A1 | 8/2012 | Bruggemann et al. |
| 2012/0259288 A1 | 10/2012 | Wagner et al. |
| 2012/0265149 A1 | 10/2012 | Lerner et al. |
| 2012/0271272 A1 | 10/2012 | Hammack et al. |
| 2013/0035662 A1 | 2/2013 | Decker et al. |
| 2013/0041265 A1 | 2/2013 | Sostek et al. |
| 2013/0060202 A1 | 3/2013 | Thorley et al. |
| 2013/0072900 A1 | 3/2013 | Colantonio |
| 2013/0079716 A1 | 3/2013 | Thorley et al. |
| 2013/0096533 A1 | 4/2013 | Freeman et al. |
| 2013/0102973 A1 | 4/2013 | Thorley et al. |
| 2013/0116523 A1 | 5/2013 | Jung et al. |
| 2013/0138049 A1 | 5/2013 | Kemp et al. |
| 2013/0140208 A1 | 6/2013 | Hemmann |
| 2013/0150803 A1 | 6/2013 | Shetty et al. |
| 2013/0190694 A1 | 7/2013 | Barrow-Williams et al. |
| 2013/0211335 A1 | 8/2013 | Paques et al. |
| 2013/0216623 A1 | 8/2013 | Yamamoto et al. |
| 2013/0218102 A1 | 8/2013 | Iwase et al. |
| 2013/0237910 A1 | 9/2013 | Shetty et al. |
| 2013/0237916 A1 | 9/2013 | Hanson et al. |
| 2013/0245600 A1 | 9/2013 | Yamamoto et al. |
| 2013/0253416 A1 | 9/2013 | Rotenstreich |
| 2013/0295006 A1 | 11/2013 | Christoforidis et al. |
| 2013/0331786 A1 | 12/2013 | Hofmann |
| 2013/0338612 A1 | 12/2013 | Smith et al. |
| 2014/0010823 A1 | 1/2014 | Robinson et al. |
| 2014/0012226 A1 | 1/2014 | Hochman |
| 2014/0031833 A1 | 1/2014 | Novakovic et al. |
| 2014/0039391 A1 | 2/2014 | Clarke et al. |
| 2014/0039413 A1 | 2/2014 | Jugl et al. |
| 2014/0088552 A1 | 3/2014 | Soni et al. |
| 2014/0094752 A1 | 4/2014 | Hiles |
| 2014/0107566 A1 | 4/2014 | Prausnitz et al. |
| 2014/0114243 A1 | 4/2014 | Smith et al. |
| 2014/0135716 A1 | 5/2014 | Clarke et al. |
| 2014/0200518 A1 | 7/2014 | Ekman et al. |
| 2014/0224688 A1 | 8/2014 | Slemmen et al. |
| 2014/0236098 A1 | 8/2014 | Mica et al. |
| 2014/0243754 A1 | 8/2014 | Clarke et al. |
| 2014/0249539 A1 | 9/2014 | Mica et al. |
| 2014/0257207 A1 | 9/2014 | Clarke et al. |
| 2014/0296802 A1 | 10/2014 | Geiger et al. |
| 2014/0309599 A1 | 10/2014 | Schaller |
| 2014/0323979 A1 | 10/2014 | Henley et al. |
| 2014/0323985 A1 | 10/2014 | Hourmand et al. |
| 2014/0330213 A1 | 11/2014 | Hourmand et al. |
| 2014/0350479 A1 | 11/2014 | Hourmand et al. |
| 2015/0013827 A1 | 1/2015 | Kuhn |
| 2015/0013835 A1 | 1/2015 | Cordes |
| 2015/0025474 A1 | 1/2015 | Riedel et al. |
| 2015/0038905 A1 | 2/2015 | Andino et al. |
| 2015/0045731 A1 | 2/2015 | Gupta et al. |
| 2015/0045744 A1 | 2/2015 | Gupta et al. |
| 2015/0051545 A1 | 2/2015 | Henderson et al. |
| 2015/0051581 A1 | 2/2015 | Andino et al. |
| 2015/0110717 A1 | 4/2015 | Distel et al. |
| 2015/0133415 A1 | 5/2015 | Whitcup |
| 2015/0209180 A1 | 7/2015 | Prausnitz et al. |
| 2015/0258120 A1 | 9/2015 | Zarnitsyn et al. |
| 2015/0320596 A1 | 11/2015 | Gifford, III et al. |
| 2016/0106584 A1 | 4/2016 | Andino et al. |
| 2016/0193080 A1 | 7/2016 | Hammack et al. |
| 2016/0206628 A1 | 7/2016 | Zarnitsyn et al. |
| 2016/0213662 A1 | 7/2016 | Zarnitsyn et al. |
| 2016/0310417 A1 | 10/2016 | Prausnitz et al. |
| 2018/0028358 A1 | 2/2018 | Andino et al. |
| 2018/0042765 A1 | 2/2018 | Noronha et al. |
| 2018/0325884 A1 | 11/2018 | Zarnitsyn et al. |
| 2018/0333297 A1 | 11/2018 | Andino et al. |
| 2019/0000669 A1 | 1/2019 | Hammack et al. |

FOREIGN PATENT DOCUMENTS

| | | |
|---|---|---|
| CN | 1604799 A | 4/2005 |
| CN | 1706365 | 12/2005 |
| CN | 1736474 | 2/2006 |
| CN | 101052434 A | 10/2007 |
| CN | 101351239 A | 1/2009 |
| CN | 201356711 Y | 12/2009 |
| CN | 101854891 A | 10/2010 |
| CN | 101959519 A | 1/2011 |
| CN | 103037802 A | 4/2013 |
| CN | 103209733 A | 7/2013 |
| CN | 103857431 A | 6/2014 |
| EA | 006961 | 6/2006 |
| EP | 1188456 A1 | 3/2002 |
| EP | 1568359 | 8/2005 |
| EP | 2193821 | 6/2010 |
| EP | 2307055 | 4/2011 |
| JP | 2001-525826 | 12/2001 |
| JP | 2007-510744 | 4/2007 |
| JP | 2007-518804 | 7/2007 |
| JP | 2009-183441 | 8/2009 |
| JP | 2009-531298 | 9/2009 |
| JP | 2010-234034 | 10/2010 |
| JP | 2013-543418 | 12/2013 |
| RU | 14351 U1 | 7/2000 |
| RU | 2344767 | 1/2009 |
| RU | 2353393 | 4/2009 |
| RU | 2428956 | 9/2011 |
| WO | WO 92/08406 | 5/1992 |
| WO | WO 92/20389 | 11/1992 |
| WO | WO 94/01124 | 1/1994 |

(56) References Cited

FOREIGN PATENT DOCUMENTS

| WO | WO 94/12217 | 6/1994 |
|---|---|---|
| WO | WO 96/09838 | 4/1996 |
| WO | WO 98/51348 | 11/1998 |
| WO | WO 2000/007530 | 2/2000 |
| WO | WO 2000/007565 | 2/2000 |
| WO | WO 2001/041685 | 6/2001 |
| WO | WO 2002/058769 | 8/2002 |
| WO | WO 2003/002094 | 1/2003 |
| WO | WO 2003/024507 | 3/2003 |
| WO | WO 2003/039633 | 5/2003 |
| WO | WO 2005/011741 | 2/2005 |
| WO | WO 2005/032510 | 4/2005 |
| WO | WO 2005/046641 | 5/2005 |
| WO | WO 2005/069831 | 8/2005 |
| WO | WO 2005/074942 | 8/2005 |
| WO | WO 2005/107845 | 11/2005 |
| WO | WO 2006/004595 | 1/2006 |
| WO | WO 2006/042252 | 4/2006 |
| WO | WO 2006/058189 | 6/2006 |
| WO | WO 2006/128034 | 11/2006 |
| WO | WO 2006/138719 | 12/2006 |
| WO | WO 2007/100745 | 9/2007 |
| WO | WO 2007/130105 | 11/2007 |
| WO | WO 2007/131050 | 11/2007 |
| WO | WO 2007/150018 | 12/2007 |
| WO | WO 2009/067325 | 5/2009 |
| WO | WO 2009/114521 | 9/2009 |
| WO | WO 2010/009034 | 1/2010 |
| WO | WO 2010/054660 | 5/2010 |
| WO | WO 2010/132751 | 11/2010 |
| WO | WO 2011/057065 | 5/2011 |
| WO | WO 2011/123722 | 10/2011 |
| WO | WO 2011/139713 | 11/2011 |
| WO | WO 2012/019136 | 2/2012 |
| WO | WO 2012/051575 | 4/2012 |
| WO | WO 2012/125869 | 9/2012 |
| WO | WO 2013/050236 | 4/2013 |
| WO | WO 2013/098166 | 7/2013 |
| WO | WO 2013/151904 | 10/2013 |
| WO | WO 2014/028285 | 2/2014 |
| WO | WO 2014/036009 | 3/2014 |
| WO | WO 2014/074823 | 5/2014 |
| WO | WO 2014/179698 | 11/2014 |
| WO | WO 2014/197317 | 12/2014 |
| WO | WO 2015/015467 | 2/2015 |
| WO | WO 2015/095772 | 6/2015 |
| WO | WO 2015/195842 | 12/2015 |
| WO | WO 2015/196085 | 12/2015 |
| WO | WO 2016/042162 | 3/2016 |
| WO | WO 2016/042163 | 3/2016 |

OTHER PUBLICATIONS

Office Action for U.S. Appl. No. 11/743,535, dated Dec. 29, 2009, 6 pages.
International Search Report and Written Opinion for International Application No. PCT/US2007/068055, dated Nov. 7, 2007, 13 pages.
Office Action for Canadian Application No. 2797258, dated Nov. 21, 2016, 3 pages.
Extended European Search Report for European Application No. 11777924.9, dated Feb. 4, 2015, 7 pages.
Office Action for Russian Application No. 2012147341, dated Feb. 26, 2015, 8 pages.
Office Action for U.S. Appl. No. 12/767,768, dated Jun. 10, 2011, 5 pages.
International Search Report and Written Opinion for International Application No. PCT/US2011/033987, dated Feb. 14, 2012, 7 pages.
Office Action for Japanese Application No. 2016-068174, dated Mar. 1, 2017, 8 pages.
Office Action for U.S. Appl. No. 13/447,246, dated Oct. 28, 2013, 5 pages.
Office Action for U.S. Appl. No. 13/453,407, dated Mar. 20, 2013, 5 pages.
Office Action for U.S. Appl. No. 14/136,657, dated Dec. 16, 2016, 7 pages.
Extended Search Report for European Application No. 13833318.2, dated Apr. 1, 2016, 7 pages.
Office Action for U.S. Appl. No. 14/424,685, dated Jun. 10, 2016, 10 pages.
Office Action for U.S. Appl. No. 14/424,685, dated Dec. 12, 2016, 15 pages.
International Search Report and Written Opinion for International Application No. PCT/US2013/056863, dated Nov. 26, 2013, 8 pages.
First Office Action for Chinese Application No. 201380069089.0, dated Nov. 28, 2016, 30 pages.
Office Action for Eurasian Application No. 201590902, dated Apr. 4, 2017, 2 pages.
Office Action for Eurasian Application No. 201590902, dated Feb. 26, 2019, 1 page.
Supplementary Partial European Search Report for European Application No. 13853777.4, dated Jul. 4, 2016, 6 pages.
Extended European Search Report for European Application No. 13853777.4, dated Nov. 4, 2016, 12 pages.
Office Action for Israeli Application No. 238432, dated Dec. 7, 2017, 4 pages.
First Examination Report for New Zealand Application No. 707291, dated Jun. 15, 2018, 7 pages.
Search Report and Written Opinion for Singapore Application No. 11201503637S, dated Jun. 23, 2016, 9 pages.
Office Action for U.S. Appl. No. 14/441,151, dated Sep. 9, 2016, 18 pages.
International Search Report and Written Opinion for International Application No. PCT/US2013/069156, dated Mar. 10, 2014, 11 pages.
Office Action for U.S. Appl. No. 15/001,610, dated Sep. 8, 2016, 12 pages.
Office Action for U.S. Appl. No. 15/086,485, dated Jul. 28, 2016, 9 pages.
Office Action for U.S. Appl. No. 15/830,727, dated Mar. 7, 2019, 13 pages.
Supplementary European Search Report for European Application No. 14808034.4, dated Jan. 23, 2017, 7 pages.
Office Action for U.S. Appl. No. 14/894,161, dated Dec. 27, 2016, 17 pages.
International Search Report and Written Opinion for International Application No. PCT/US2014/040254, dated Oct. 31, 2014, 9 pages.
Examination Report No. 1 for Australian Application No. 2014259694, dated May 24, 2018, 2 pages.
First Office Action for Chinese Application No. 201480025034.4, dated Apr. 24, 2018, 10 pages.
Office Action for Eurasian Application No. 201592109, dated Apr. 1, 2016, 4 pages.
Office Action for Eurasian Application No. 201592109, dated Jan. 31, 2018, 2 pages.
Extended Search Report for European Application No. 14791646.4, dated Nov. 21, 2016, 6 pages.
Office Action for European Application No. 14791646.4, dated Dec. 4, 2017, 5 pages.
Office Action for European Application No. 14791646.4, dated Sep. 17, 2018, 5 pages.
Notice of Reasons for Rejection for Japanese Application No. 2016-512068, dated Mar. 26, 2018, 4 pages.
Office Action for New Zealand Application No. 714172, dated Feb. 1, 2018, 4 pages.
Office Action for New Zealand Application No. 714172, dated Jul. 24, 2018, 4 pages.
Office Action for New Zealand Application No. 714172, dated Dec. 12, 2018, 3 pages.
Search Report and Written Opinion for Singapore Application No. 11201509051V, dated Nov. 2, 2016, 6 pages.
Examination Report for Singapore Application No. 11201509051V, dated Feb. 1, 2017, 4 pages.

(56) References Cited

OTHER PUBLICATIONS

International Search Report and Written Opinion for International Application No. PCT/US2014/036590, dated Dec. 10, 2014, 10 pages.
Office Action for U.S. Appl. No. 14/268,687, dated May 19, 2016, 6 pages.
Partial European Search Report for European Application No. 18176172.7, dated Oct. 30, 2018, 13 pages.
Extended European Search Report for European Application No. 18176172.7, dated Feb. 6, 2019, 11 pages.
Office Action for U.S. Appl. No. 14/523,243, dated Feb. 27, 2015, 14 pages.
Examination Report No. 1 for Australian Application No. 2015277133, dated Mar. 29, 2019, 6 pages.
First Office Action for Chinese Application No. 201580044250.8, dated Apr. 24, 2018, 14 pages.
Second Office Action for Chinese Application No. 201580044250.8, dated Jan. 2, 2019, 7 pages.
Office Action for U.S. Appl. No. 15/319,045, dated Jul. 13, 2018, 13 pages.
Office Action for U.S. Appl. No. 15/319,045, dated Apr. 2, 2019, 14 pages.
International Search Report and Written Opinion for International Application No. PCT/US2015/036299, dated Nov. 10, 2015, 11 pages.
Extended European Search Report for European Application No. 15810459.6, dated Apr. 16, 2018, 11 pages.
Notice of Reasons for Rejection for Japanese Application No. 2016-574090, dated Mar. 4, 2019, 18 pages.
Office Action for Russian Application No. 2017101660, dated Mar. 5, 2019, 7 pages.
International Search Report and Written Opinion for International Application No. PCT/US2015/036715, dated Jan. 19, 2016, 9 pages.
Office Action for Canadian Application No. 162010, dated Aug. 25, 2015, 1 page.
International Search Report and Written Opinion for International Application No. PCT/US2014/071623, dated Jun. 25, 2015, 18 pages.
Office Action for Brazilian Application No. PI 0708133-2, dated Feb. 26, 2019, 11 pages.
Office Action for Chinese Application No. 200780014501.3, dated Mar. 11, 2010, 6 pages.
Office Action for Chinese Application No. 200780014501.3, dated Aug. 26, 2010, 10 pages.
Office Action for European Application No. 07751620.1, dated Sep. 13, 2013, 7 pages.
Extended European Search Report for European Application No. 07751620.1, dated Jan. 15, 2013, 10 pages.
Office Action for European Application No. 07751620.1, dated Dec. 11, 2014, 5 pages.
Invitation pursuant to Article 94(3) and Rule 71(1) for European Application No. 07751620.1, dated Feb. 29, 2016, 3 pages.
Summons to Attend Oral Proceedings Pursuant to Rule 115(1) EPC for European Application No. 07751620.1, dated Jun. 13, 2017, 8 pages.
Office Action for Japanese Application No. 2008-556462, dated Jul. 24, 2012, 15 pages.
Office Action for India Application No. 3345/KOLNP/2008, dated May 21, 2015, 3 pages.
Office Action for Singapore Application No. 200805936-2, dated Oct. 15, 2012, 7 pages.
Search Report and Written Opinion for Singapore Application No. 200805936-2, dated Jun. 8, 2010, 13 pages.
Supplementary Search Report for Singapore Application No. 200805936-2, dated May 6, 2011, 8 pages.
Supplementary Search Report for Singapore Application No. 200805936-2, dated May 26, 2011, 8 pages.
Office Action for U.S. Appl. No. 11/709,941, dated Jun. 24, 2014, 11 pages.

Office Action for U.S. Appl. No. 11/709,941, dated Mar. 23, 2011, 9 pages.
Office Action for U.S. Appl. No. 11/709,941, dated Feb. 11, 2015, 14 pages.
Office Action for U.S. Appl. No. 11/709,941, dated Oct. 27, 2011, 8 pages.
Office Action for U.S. Appl. No. 11/709,941, dated Apr. 12, 2016, 25 pages.
Office Action for U.S. Appl. No. 11/709,941, dated Dec. 27, 2016.
Office Action for U.S. Appl. No. 11/709,941, dated Dec. 14, 2018, 17 pages.
International Search Report and Written Opinion for International Application No. PCT/US2007/004874, dated Jun. 4, 2008, 6 pages.
Office Action for Chinese Application No. 201110093644.6, dated Mar. 26, 2012, 11 pages.
Office Action for Chinese Application No. 201110093644.6, dated Sep. 7, 2012, 8 pages.
Office Action for Chinese Application No. 201110093644.6, dated Dec. 14, 2012, 3 pages.
Extended European Search Report for European Application No. 18176149.5, dated Jan. 22, 2019, 11 pages.
Office Action for U.S. Appl. No. 13/842,218, dated Jul. 5, 2016, 11 pages.
Office Action for U.S. Appl. No. 13/842,288, dated Oct. 6, 2015, 10 pages.
First Office Action for Chinese Application No. 201180060268.9, dated Oct. 10, 2014, 9 pages.
Second Office Action for Chinese Application No. 201180060268.9, dated Jun. 18, 2015, 4 pages.
Third Office Action for Chinese Application No. 201180060268.9, dated Feb. 5, 2016, 6 pages.
Fourth Office Action for Chinese Application No. 201180060268.9, dated Oct. 9, 2016, 6 pages.
Examination Report for European Application No. 11776049.6, dated Oct. 25, 2016, 4 pages.
Office Action for Japanese Application No. 2013-534049, dated Sep. 1, 2015, 11 pages.
Office Action for U.S. Appl. No. 13/273,775, dated Feb. 12, 2015, 13 pages.
Office Action for U.S. Appl. No. 13/273,775, dated Jul. 3, 2014, 12 pages.
International Search Report and Written Opinion for International Application No. PCT/US2011/056433, dated Apr. 25, 2012, 17 pages.
Office Action for Chinese Application No. 201510144330.2, dated Apr. 5, 2016, 17 pages.
International Search Report and Written Opinion for International Application No. PCT/US2017/065796, dated Apr. 12, 2018, dated Apr. 12, 2018, 9 pages.
Abbott Laboratories Inc., Abbott Park, Illinois, USA, Abbott Medical Optics, "HEALON5 OVD," 2004, [online]. Retrieved from the Interent: <URL: http://abbottmedicaloptics.com/products/cataract/ovds/healon5-viscoelastic>. Retrieved from the Internet on: Aug. 16, 2016, 5 pages.
Anthem, USA, "Medical Policy. Suprachoroidal Injection of a Pharmacologic Agent," Last Review Date: Nov. 14, 2013, [online]. Retrieved from the Internet: <URL: http://www.anthem.com/medicalpolicies/policies/mp_pw_b076412.htm>. Retrieved from the Internet on: Oct. 24, 2014, American Medical Association, 3 pages.
Beer, P. J. et al., "Photographic Evidence of Vitreous Wicks After Intravitreal Injections," Retina Today, 2(2):24-39 (Mar. 2007).
Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lypholization Techniques," Invest Ophthalmol Vis Sci., 51:E—Abstract 5330 (2010), 2 pages.
Careforde Inc., Careforde Healthcare, Chicago, IL, "B Braun Glass Loss-Of-Resistance Syringes # 332155—5cc Glass Loss-Of-Resistance Syringe, Luer Lock Metal Tip, 10/cs," [online]. Retrieved from the Internet: <http://careforde.com/b-braun-glass-loss-of-resistance-syringes-332155-5cc-glass-loss-of-resistance-syringe-luer-lock-metal-tip-10-cs/>. Retrieved from the Internet on: Oct. 16, 2014, (2014), 2 pages.

(56) References Cited

OTHER PUBLICATIONS

Careforde Healthcare, B Braun Glass Loss-Of-Resistance Syringes # 332158—10cc Glass Loss-Of-Resistance Syringe, Luer Slip Metal Tip, 10/cs, (2014), 2 pages.
Careforde Inc., Careforde Healthcare, Chicago, IL, "B Braun Perifix Plastic Loss-Of-Resistance Syringes # 332152—8cc Plastic Luer Lock Loss-of-Resistance Syringe, 50/cs," [online]. Retrieved from the Internet: <http://careforde.com/b-braun-perifix-plastic-loss-of-resistance-syringes-332152-8cc-plastic-luer-lock-loss-of-resistance-syringe-50-cs/>. Retrieved from the Internet on: Oct. 16, 2014, (2014), 2 pages.
Cho, S. W. et al., "Drug delivery to the suprachoroidal space," Chap. 12 in: Ocular Drug Delivery Systems: Barriers and Application of Nanoparticulate Systems, Thassu, D. et al. (eds.), CRC Press, pp. 235-258 (2012).
Choy, Y. B. et al., "Mucoadhesive microdiscs engineered for ophthalmic drug delivery: effect of particle geometry and fomulation on preocular residence time," Investigative Ophthalmology & Visual Science, 49:4808-4815 (2008).
Dinning, W. J., "Steroids and the eye-indications and complications," Postgraduate Medical Journal, vol. 52, 1976, pp. 634-638.
Doncaster and Bassetlaw Hospitals, NHS Foundation Trust, Department of Ophthalmology, "Intravitreal injection of triamcinolone," Jul. 2010, [online]. Retrieved from the Internet: <URL: http://www.dbh.nhs.uk/Library/Patient_Information_Leaflets/WPR32110%20IIT%20No%20crops.pdf>, 2 pages.
Edwards, A. et al., "Fiber matrix model of sclera and corneal stroma for drug delivery to the eye," AIChE Journal, 44(1):214-225 (1998).
Einmahl, S. et al., "Evaluation of a novel biomaterial in the suprachoroidal space of the rabbit eye," Invest. Ophthalmol. Vis. Sci., 43(5):1533-1539 (2002).
Einmahl, S. et al., "Ocular biocompatibility of a poly(ortho ester) characterized by autocatalyzed degradation," J. Biomed. Mater. Res., 67(1):44-53 (2003).
"Epidural," Wikipedia [online], retrieved from the internet on Sep. 3, 2014, <URL: http:/en.wikipedia.org/wiki/Ebidural>, 21 pages.
Falkenstein, I. A. et al., "Comparison of visual acuity in macular degeneration patients measured with Snellen and Early Treatment Diabetic Retinopathy study charts," Ophthalmology 115(2):319-323 (Feb. 2008).
Feldkamp, L. A. et al., "Practical cone-beam algorithm," J. Opt. Soc. Am. A, 1(6):612-619 (1984).
Furrer, P. et al., "Ocular tolerance of preservatives and alternatives," European Journal of Pharmaceutics and Biopharmaceutics, 53(3):263-280 (2002).
Geroski, D. H. et al., "Drug delivery for posterior segment eye disease," Invest. Ophthalmol. Vis. Sci., 41(5):961-964 (2000).
Gilger, B. C. et al., "Treatment of acute posterior uveitis in a porcine model by injection of triamcinolone acetonide into the suprachoroidal space using microneedles," Investigative Ophthalmology & Visual Science, 54(4):2483-2492 (2013).
Hanekamp, S. et al., "Inhibition of Corneal and Retinal Angiogenesis by Organic Integrin Antagonists After Intrascleral or Intravitreal Drug Delivery," Invest Ophthalmol Vis. Sci., 43: E—Abstract 3710, ARVO (2002), 2 pages.
Heller, J., Ocular delivery using poly(ortho esters), Adv. Drug. Deliv. Rev., 57(14):2053-2062 (2005).
Haller, J. A., "Intraocular Steroids in the Office. New formulations offer preservative-free triamcinolone without relying on compounding pharmacies," Retinal Physician [online]. Retrieved from the Internet: <URL: https://www.retinalphysician.com/supplements/2009/february-2009/special-edition/intraocular-steroids-in-the-office>, Feb. 1, 2009, 4 pages.
Hogan et al., Chapter Eight, Choroid, In Histology of the Human Eye, 9 pages (1971).
Jain, A., "Pseudo loss of resistance in epidural space localization: A complication of subcutaneous emphysema or simply a faulty technique," Saudi J. Anaseth, 5(1):108-109 (2011) (Abstract).

Jiang, J. et al., "Measurement and Prediction of Lateral Diffusion within Human Sclera," Investigative Ophthalmology & Visual Science, 47(7):3011-3016 (2006).
Jiang, J. et al., "Coated Microneedles for Drug Delivery to the Eye," Investigative Ophthalmology & Visual Science, 48(9):4038-4043 (2007).
Jiang, J. et al., "Intrascleral drug delivery to the eye using hollow microneedles," Pharmaceutical Research, 26(2):395-403 (2009).
Kadam, R. S. et al., "Suprachoroidal delivery in a rabbit ex vivo eye model: influence of drug properties, regional differences in delivery, and comparison with intravitreal and intracameral routes," Molecular Vision, 19:1198-1210 (May 2013).
Karim, R. et al., "Interventions for the treatment of uveitic macular edema: a systematic review and meta-analysis," Clinical Ophthalmology, 7:1109-1144 (2013).
Lee, S-B et al., "Drug delivery through the sclera: effects of thickness, hydration and sustained release systems," Experimental Eye Research, 78:599-607 (2004).
Lee et al., "Thixotropic property in pharmaceutical formulations," Journal of Controlled Release (2009) 136:88-98.
Lindfield, D. et al., "Suprachoroidal Devices in Glaucoma. The Past, Present, and Future of Surgery for Suprachoroidal Drainage," Cataract & Refractive Surgery Today Europe, [online], Oct. 2013, Retrieved from the Internet: <URL: http://bmctoday.net/crstodayeurope/2013/10/article.asp?f=suprachoroidal-devices-in-glaucoma>. Retrieved from the Internet on: Oct. 24, 2014, Bryn Mawr Communications LLC, Wayne, PA, USA, 3 pages.
Loewen, N., "The suprachoroidal space in glaucoma surgery," Jul. 2012, 4 pages.
Maurice, D., "Review: Practical Issues in Intravitreal Drug Delivery," J. Ocul. Pharmacol. Ther., 17(4):393-401 (2001).
McAllister, D. V. et al., "Microfabricated needles for transdermal delivery of macromolecules and nanoparticles: Fabrication methods and transport studies," Proc. Nat'l Acad. Sci USA, 100(24):13755-13760 (2003).
Norman, D., Epidural analgesia using loss of resistance with air versus saline: Does it make a difference? Should we reevaluate our practice?, AANA Journal, 71(6):449-453 (Dec. 2003).
Olsen, T. W. et al., "Cannulation of the Suprachoroidal Space: A Novel Drug Delivery Methodology to the Posterior Segment," American J. Opthamology, 142(5):777-787 (2006).
Olsen, , T., "Drug Delivery to the Suprachoroidal Space Shows Promise," Retina Today, pp. 36-39 (Mar./Apr. 2007).
Ozkiris, A., "Intravitreal Triamcinolone Acetonide Injection for the Treatment of Posterior Uveitis," Ocular Immunology and Inflammation, vol. 14, Issue 4, pp. 233-238 (May 2006), Published online: Jul. 8, 2009 (Abstract).
Patel, S. R. et al., "Targeted administration into the suprachoroidal space using a microneedle for drug delivery to the posterior segment of the eye," Investigative Ophthalmology & Visual Science, 53(8):4433-4441 (Jul. 2012).
Patel, S. et al., "Suprachoroidal Drug Delivery Using Microneedles," Invest. Ophthalmol. Vis. Sci., 49:E—Abstract 5006 (2008), 2 pages.
Patel, S. et al., "Drug Binding to Sclera," Invest Ophthalmol Vis Sci., 50:E—Abstract 5968 (2009), 2 pages.
Patel, S. R. et al., "Intraocular Pharmacokinetics of Suprachoroidal Drug Delivery Administered Using Hollow Microneedles," Invest Ophthalmol Vis Sci., 51:E—Abstract 3796 (2010), 2 pages.
Patel, S. R. et al., "Suprachoroidal drug delivery to the back of the eye using hollow microneedles," Pharmaceutical Research, 28(1):166-176 (2011). Published online: Sep. 21, 2010.
Penkov, M. A. et al., "A ten-year experience with usage of the method of supra-choroidal administration of medicinal substances," Oftalmol. Zh., 35(5):281-285 (1980) (Translated from Russian).
Prausnitz, M. R. et al., "Permeability of cornea, sclera and conjunctiva: A literature analysis for drug delivery to the eye," Journal of Pharmaceutical Sciences, 87(12):1479-1488 (1998).
Prausnitz, M. R. et al., "Measurement and prediction of transient transport across sclera for drug delivery to the eye," Industrial and Engineering Chemistry Research, 37(8):2903-2907 (1998).
Prausnitz, M. R., "Microneedles for Ocular Drug Delivery," Review of Olsen, T., Drug Delivery to the Suprachoroidal Space Shows Promise, Retina Today, Mar./Apr. 2007, p. 39.

(56) References Cited

OTHER PUBLICATIONS

Rowe-Rendleman, C. L. et al., "Prophylactic Intra-Scleral Injection of Steroid Compounds in Rabbit Model of Retinal Neovascularization," Invest Ophthalmol Vis. Sci.,43:E—Abstract 3872, ARVO (2002), 2 pages.

Saberski, L. R. et al., "Identification of the epidural space: Is loss of resistance to air a safe technique? A review of the complications related to the use of air," Regional Anesthesia, 22(1):3-15 (1997).

Sallam, A. et al., "Repeat intravitreal triamcinolone acetonide injections in uveitic macular oedema," Acta Ophthalmologica, 90(4):e323-e325 (2012).

Scott, I. U. et al., "Baseline characteristics and response to treatment of participants with hemiretinal compared with branch retinal or central retinal vein occlusion in the standard care vs. corticosteroid for retinal vein occlusion (SCORE)," Arch. Ophthalmol., 130(12):1517-1524 (Dec. 2012).

Shuler, R. K. et al., "Scleral Permeability of a Small, Single-Stranded Oligonucleotide," Journal of Ocular Pharmacology and Therapeutics, 20(2):159-168 (2004) (Abstract).

Wang, P. M. et al., "Minimally Invasive Extraction of Dermal Interstitial Fluid for Glucose Monitoring Using Microneedles," Diabetes Technology & Therapeutics, 7(1):131-141 (2005).

You, X. D. et al., "Chitosan drug delivery system implanting into suprachoroidal space for perforating ocular injury in rabbits," International Journal of Ophthalmology, 5(1):74-76 (2005) [English Abstract].

Office Action for Canadian Application No. 2,882,184, dated May 1, 2019, 3 pages.

Office Action for Israeli Application No. 242395, dated May 7, 2019, 7 pages.

Notice of Reasons for Rejection for Japanese Application No. 2018-142345, dated Jun. 6, 2019, 6 pages.

Office Action for U.S. Appl. No. 15/946,838, dated Jun. 27, 2019, 7 pages.

Haller, J. A. et al., "Evaluation of the safety and performance of an applicator for a novel intravitreal dexamethasonedrug delivery system for the treatment of macularedema," Retina, 2009;29:46-51.

\* cited by examiner

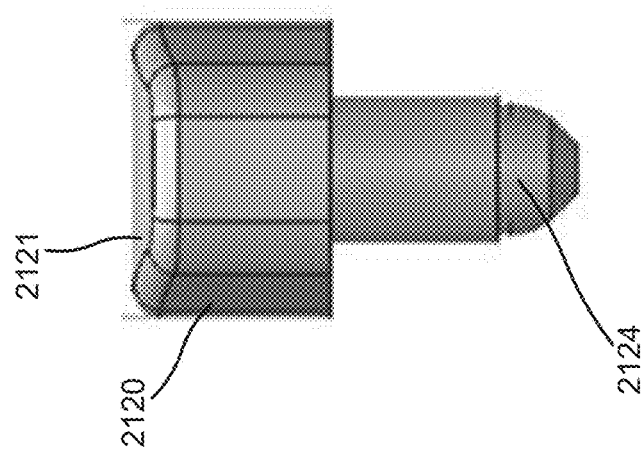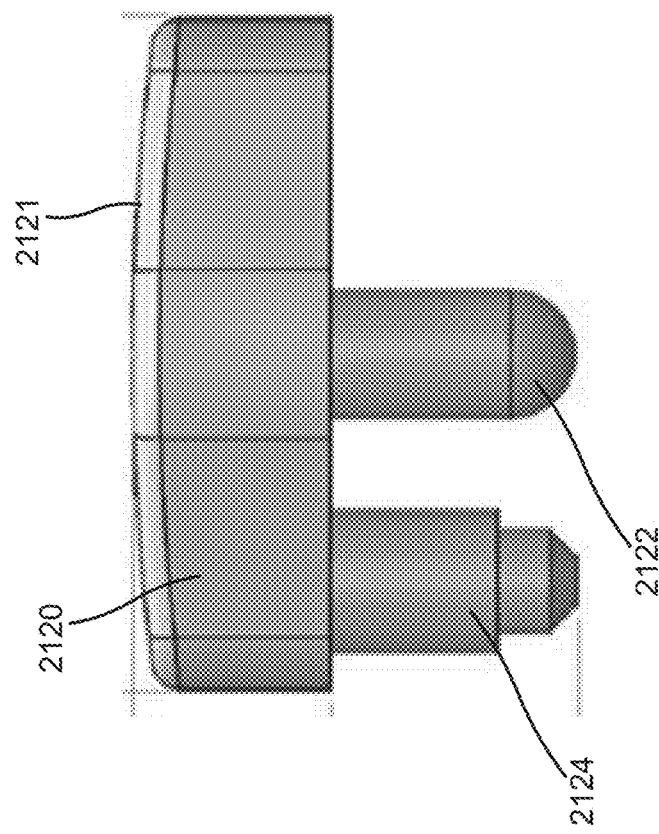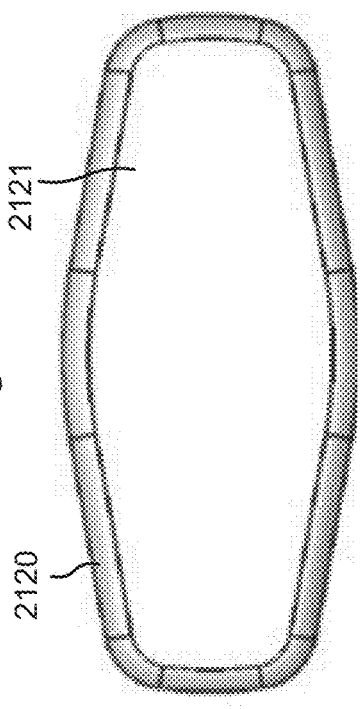

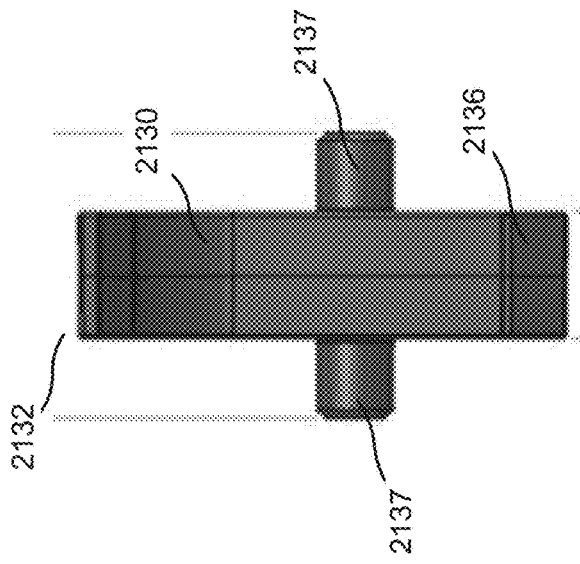
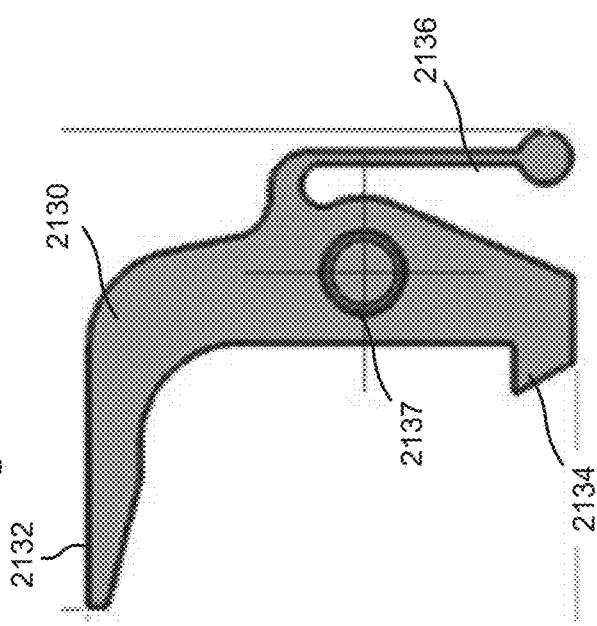
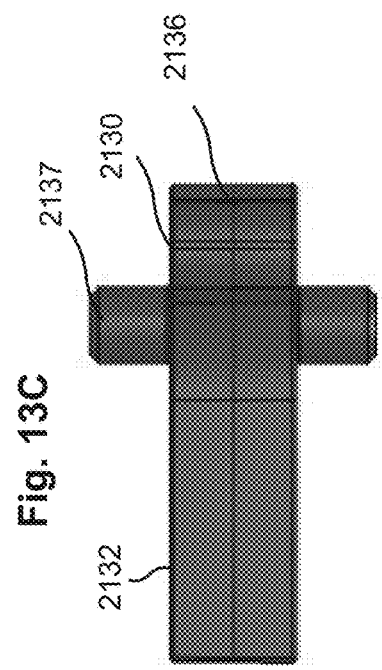

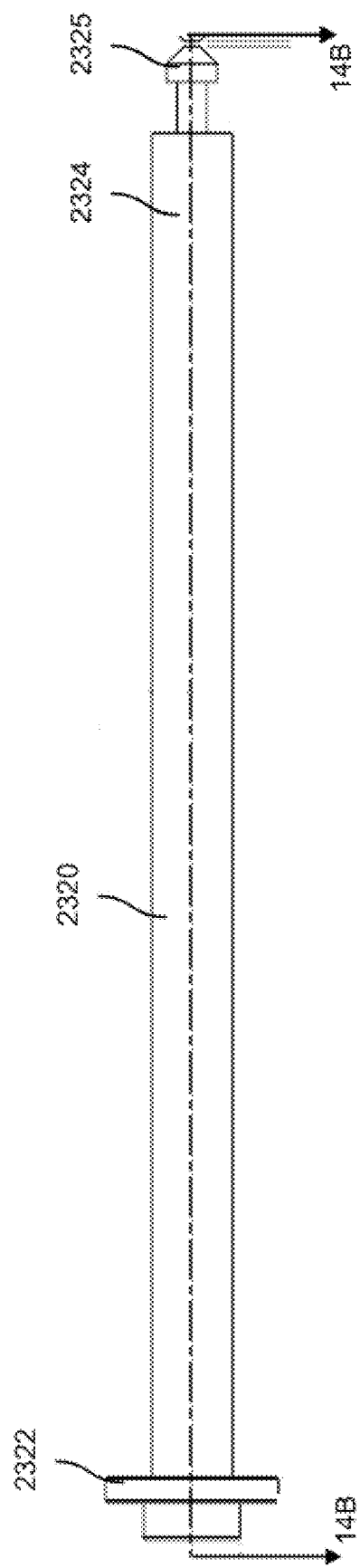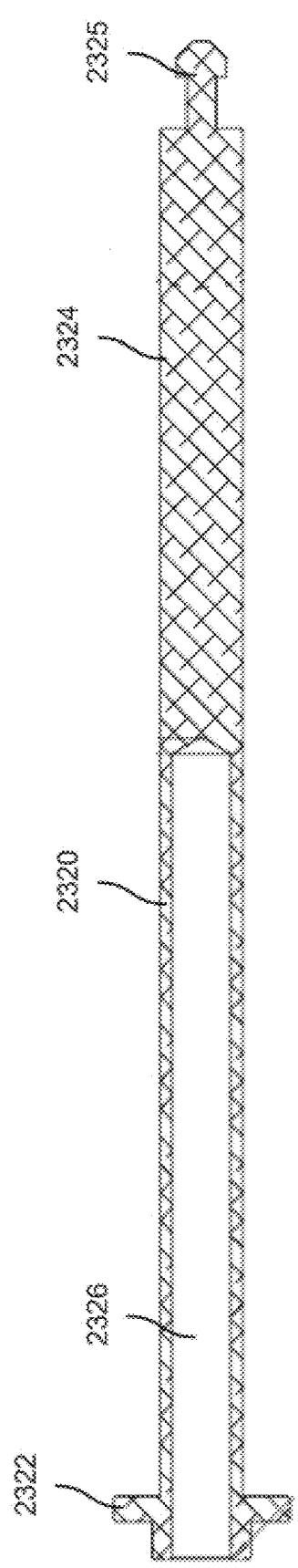

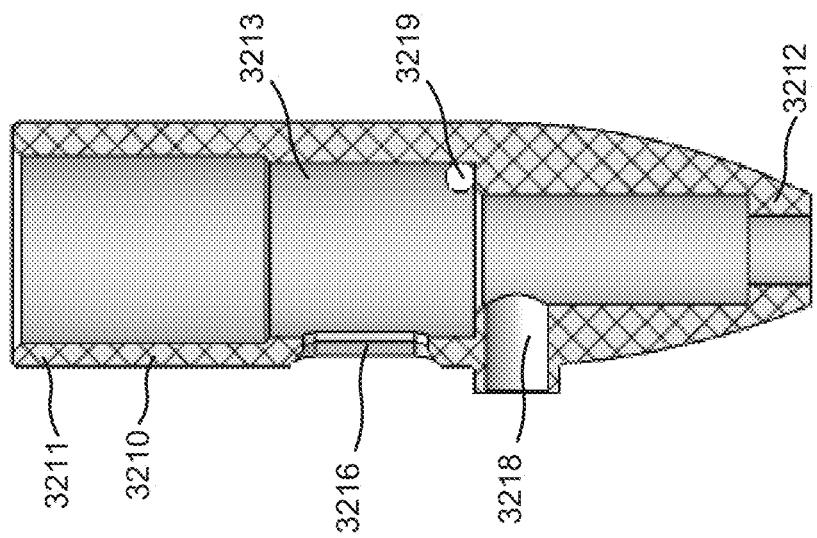
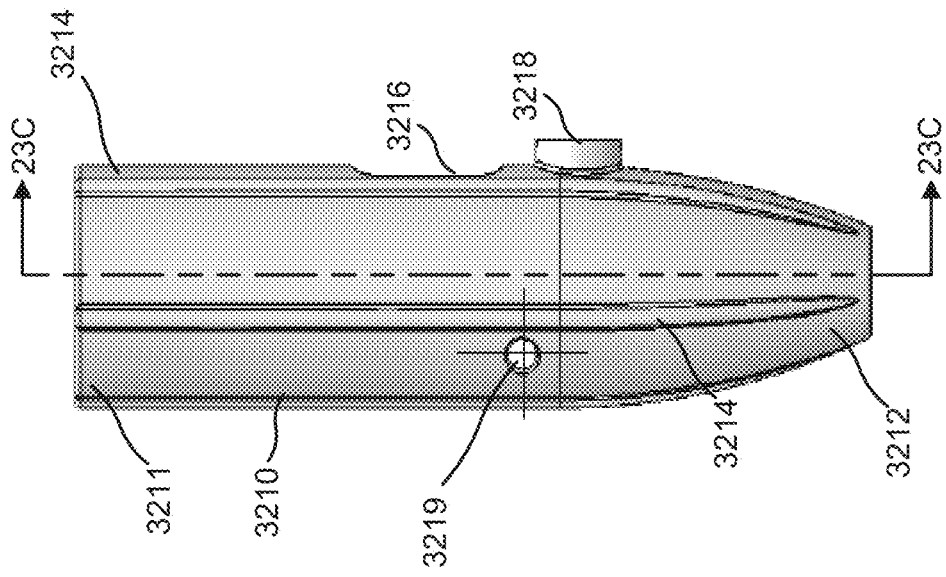
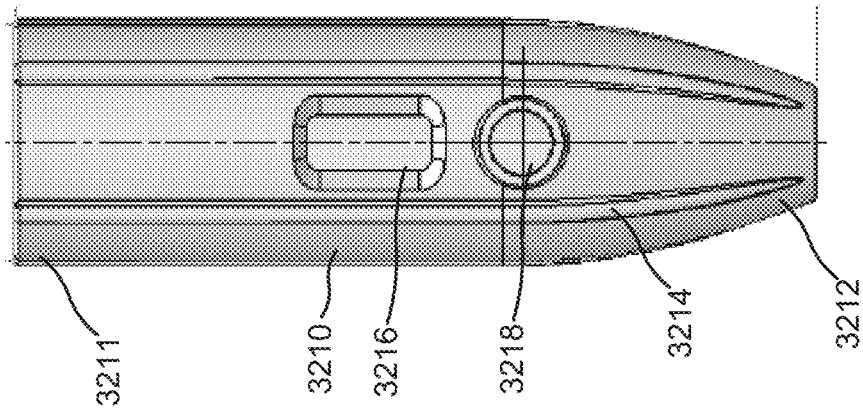

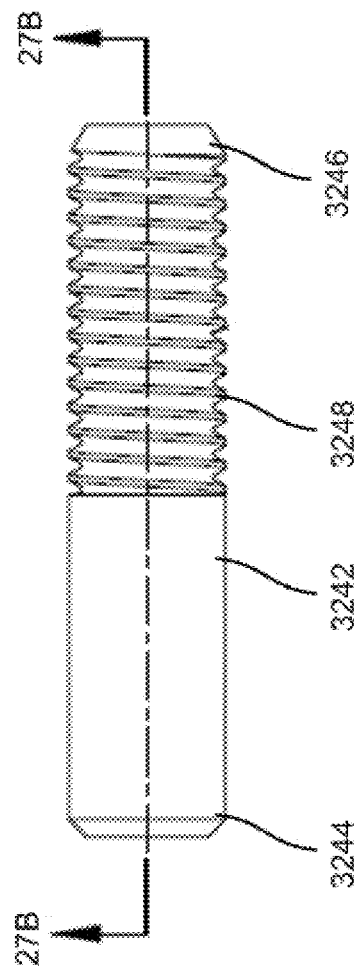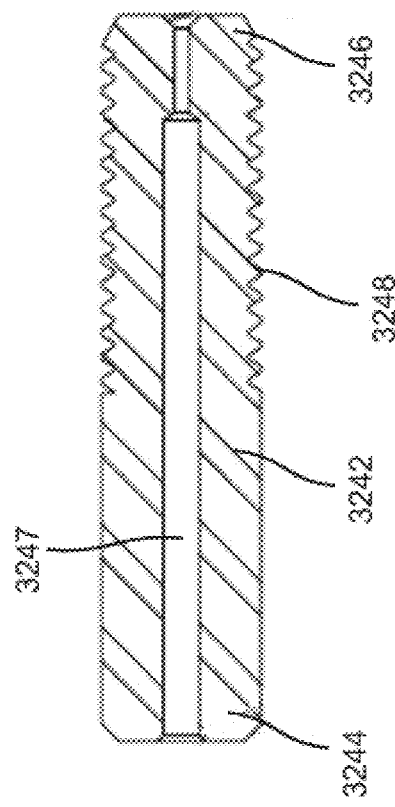
Fig. 27A
Fig. 27B

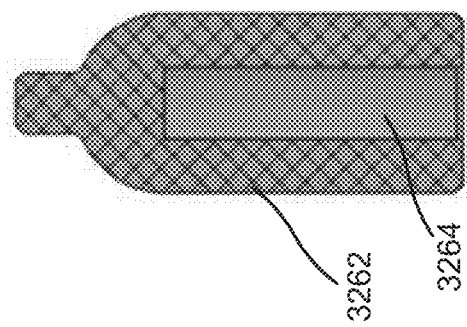
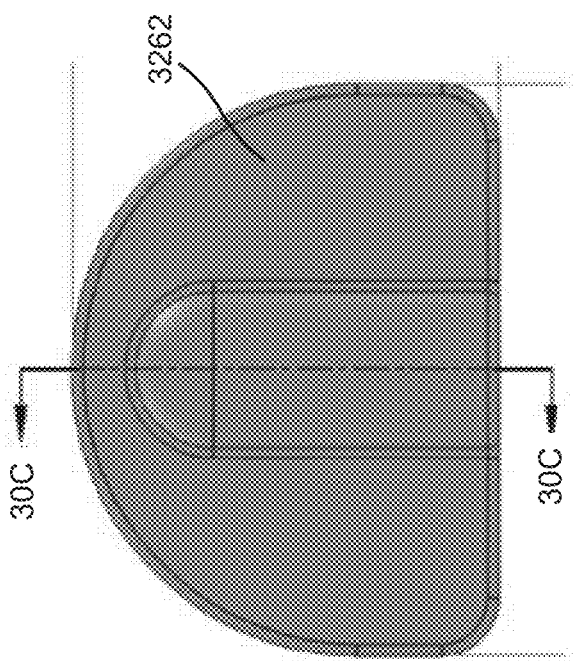
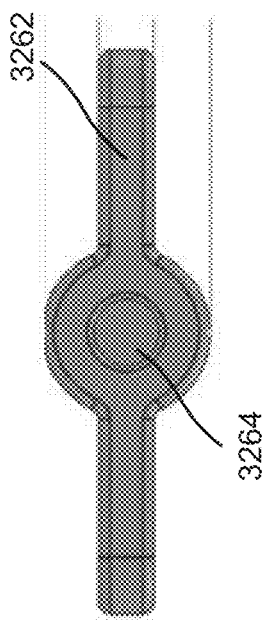

Fig. 41A
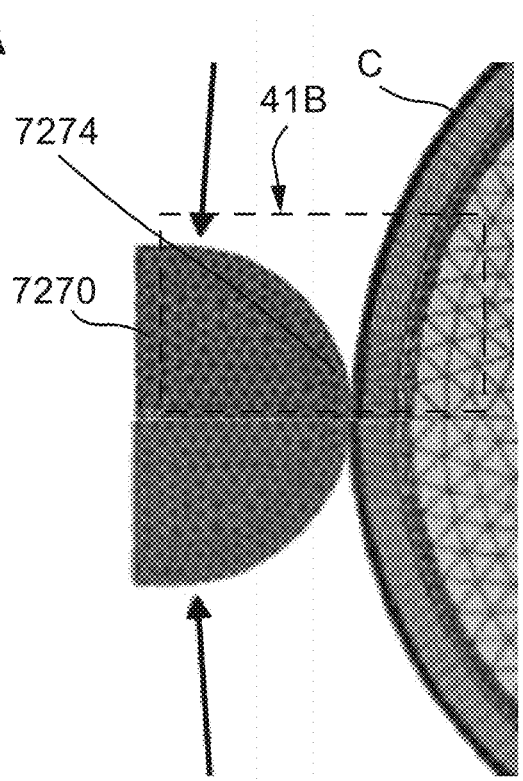
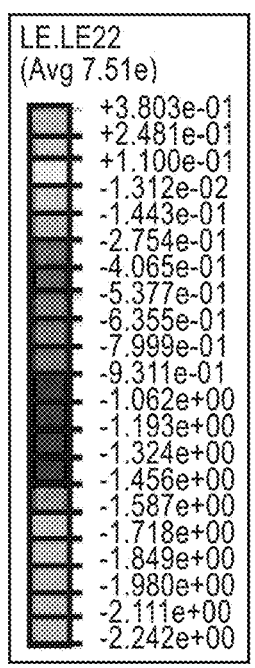
Fig. 41B
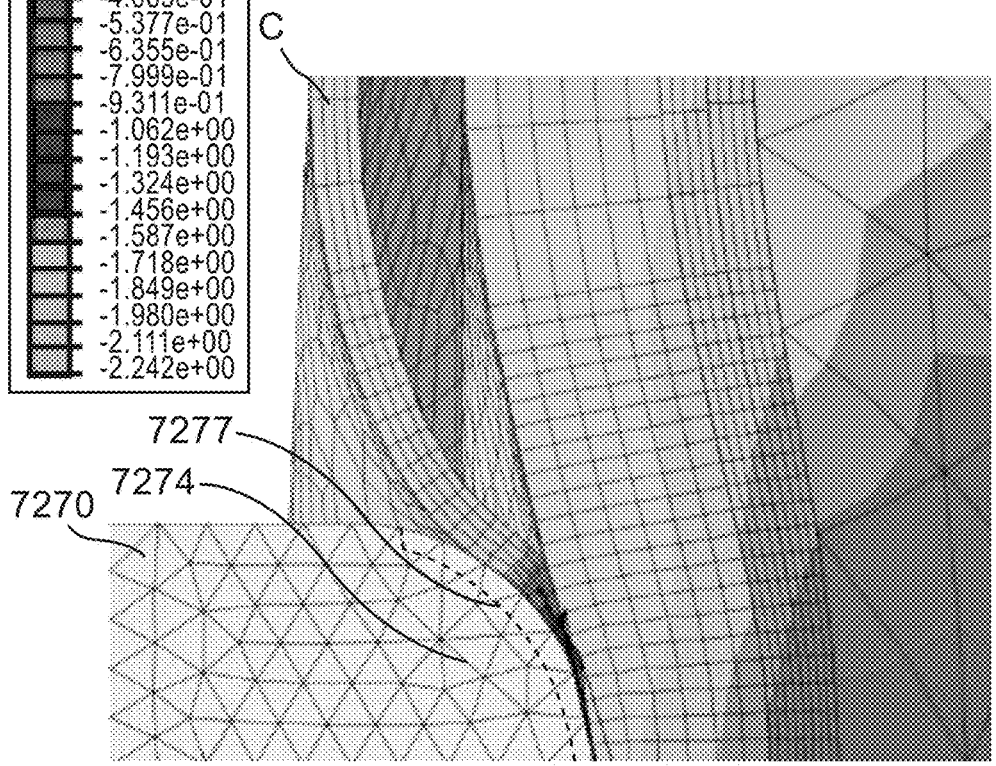

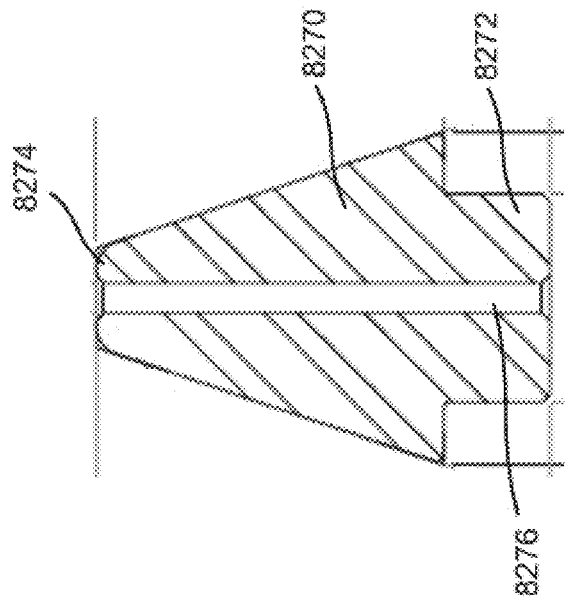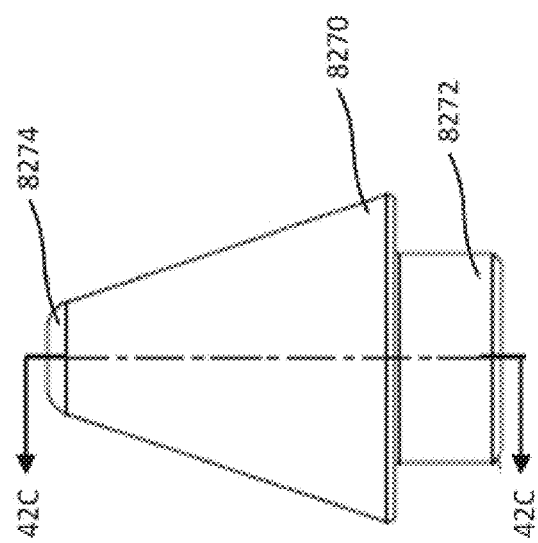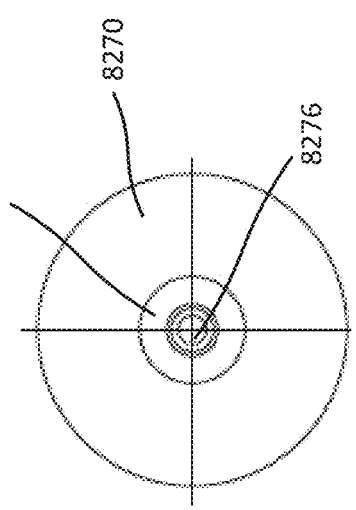

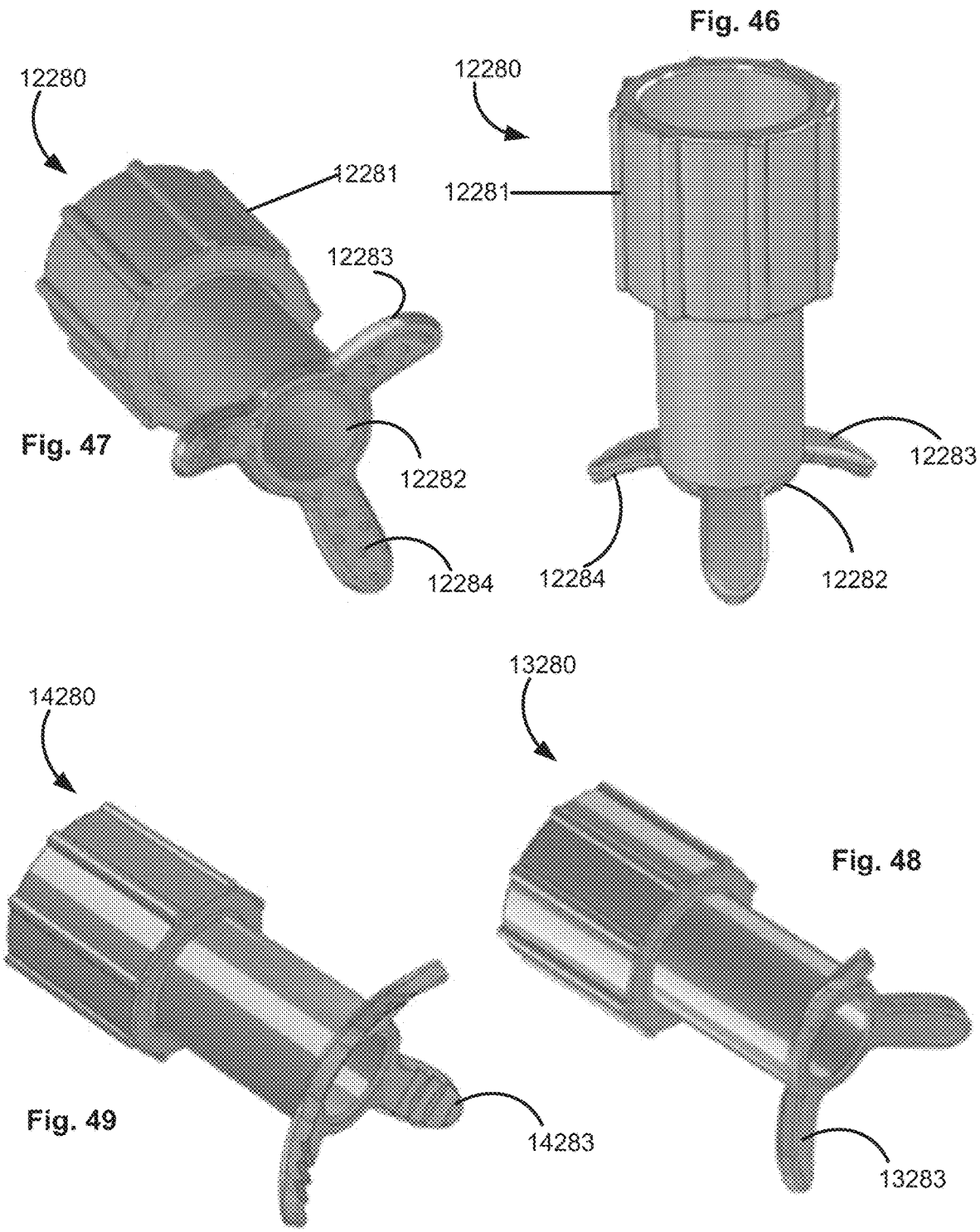

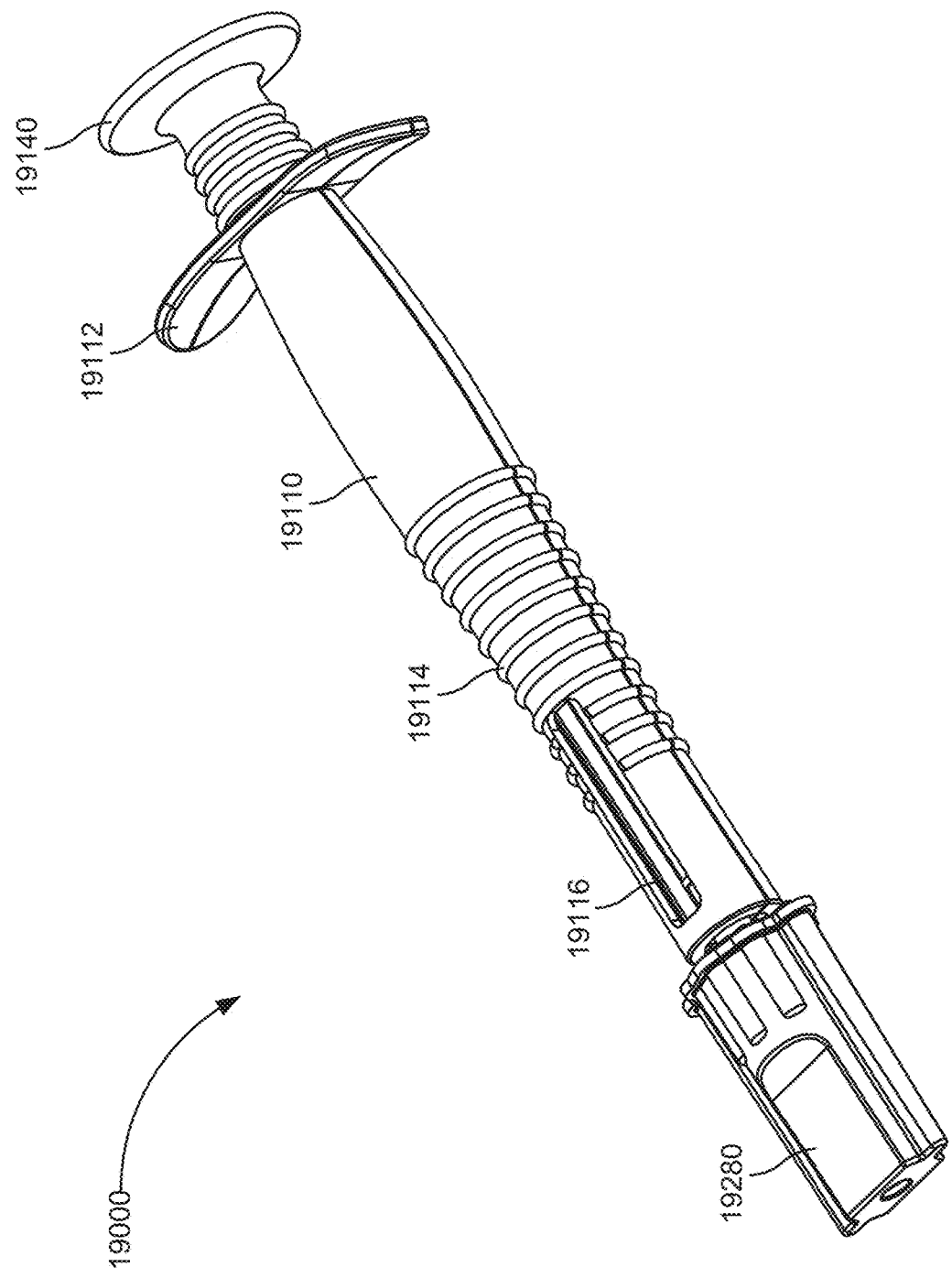

Fig. 66
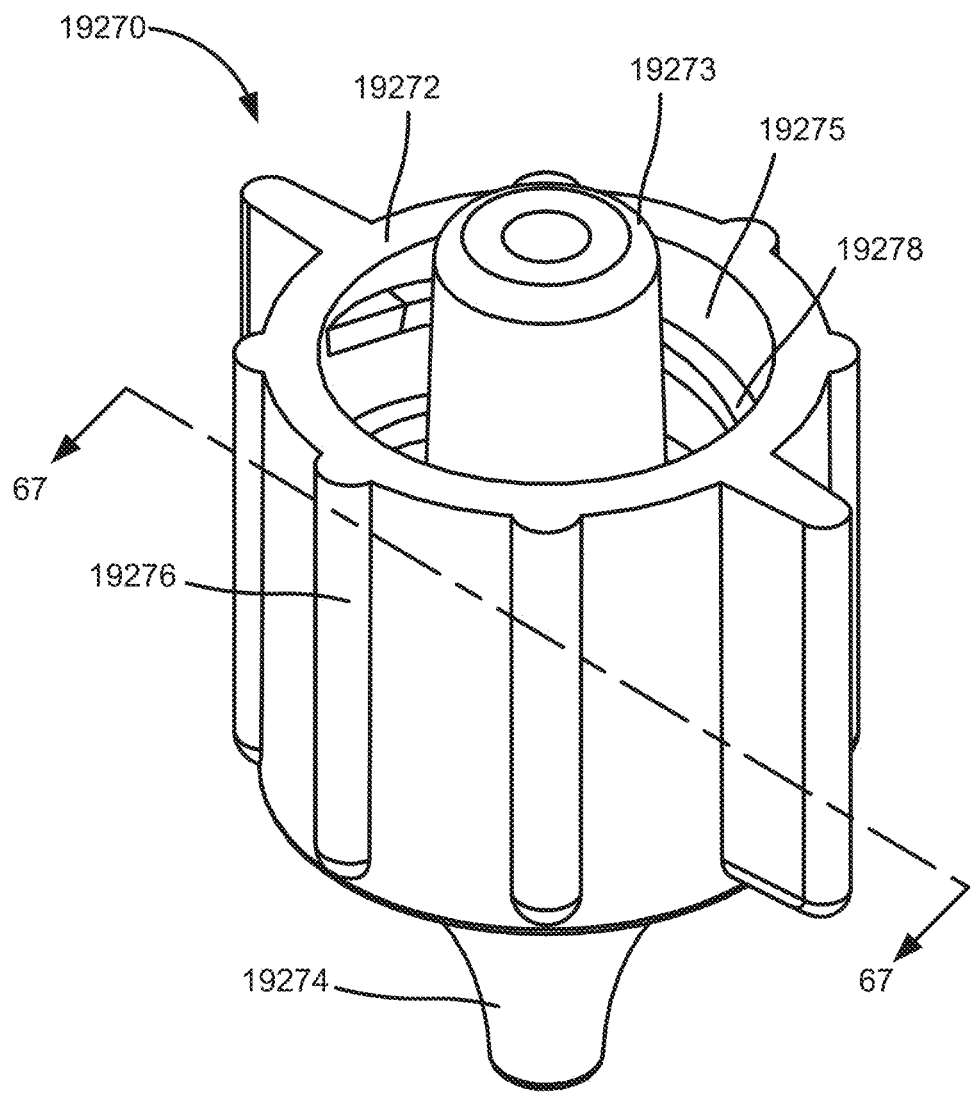
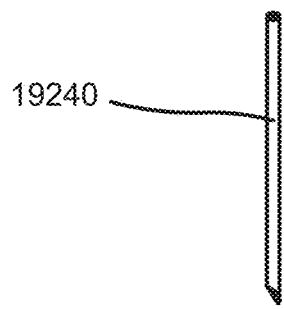

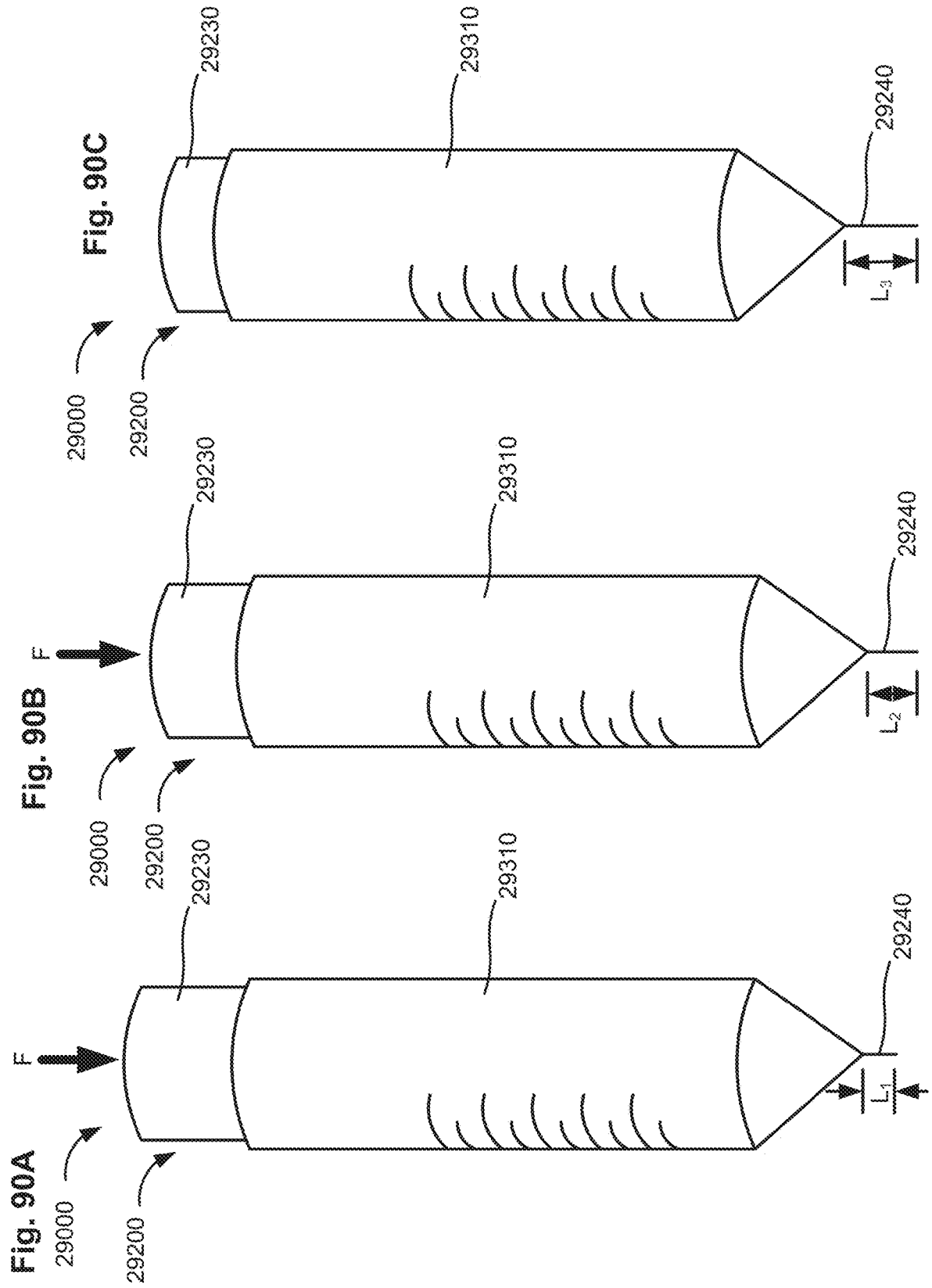

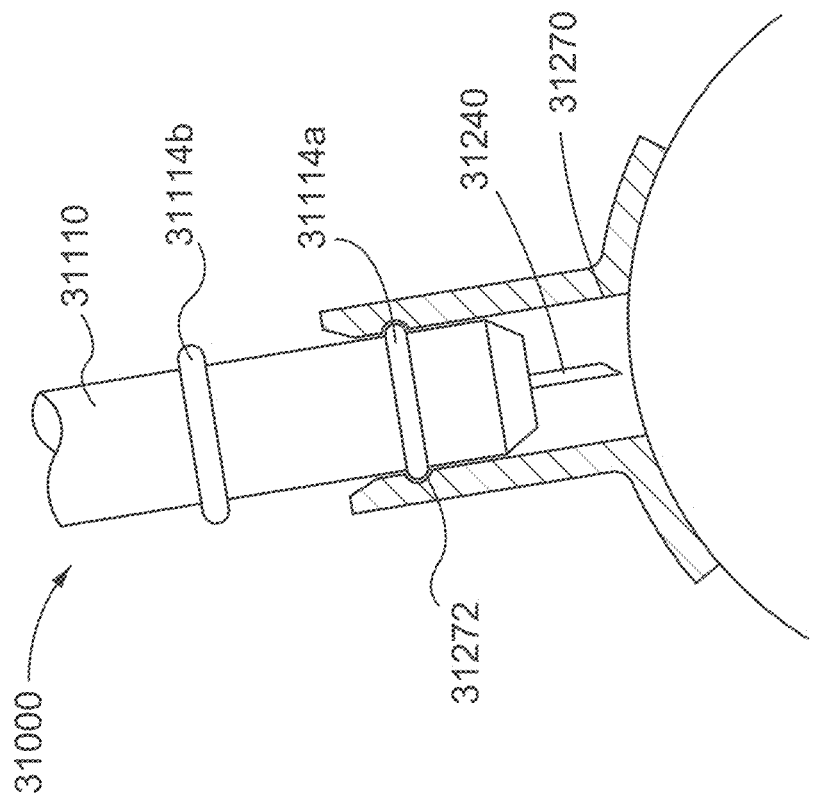
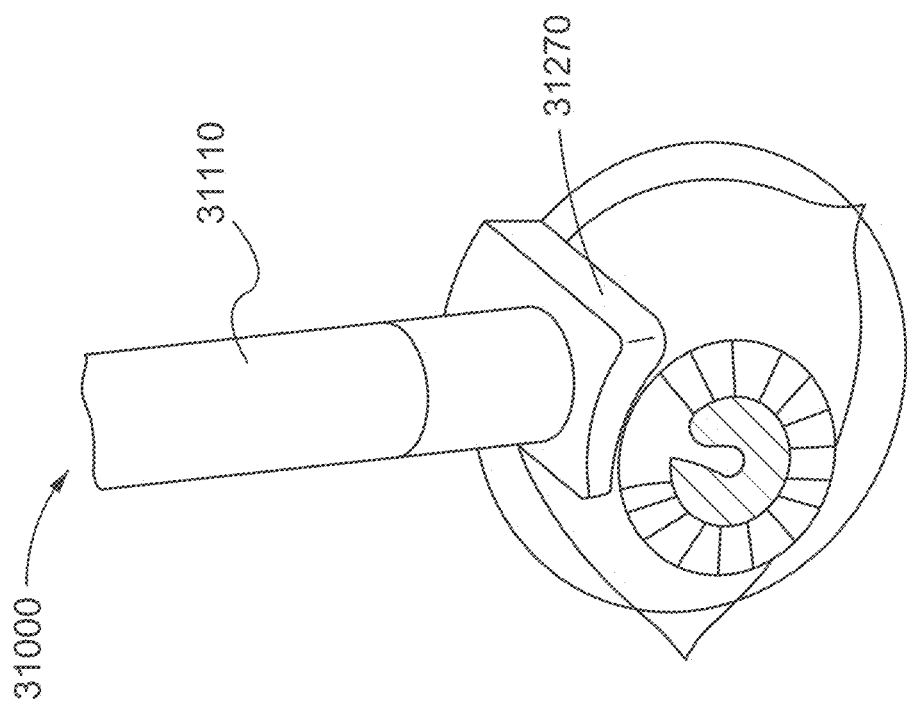

APPARATUS AND METHODS FOR OCULAR INJECTION

CROSS REFERENCE TO RELATED APPLICATIONS

This application is a continuation of U.S. patent application Ser. No. 15/946,838, entitled "Apparatus and Methods for Ocular Injection," filed Apr. 6, 2018, which is a continuation of U.S. patent application Ser. No. 15/714,441, entitled "Apparatus and Methods for Ocular Injection," filed Sep. 25, 2017 (now U.S. Pat. No. 9,937,075), which is a continuation of U.S. patent application Ser. No. 15/472,551, entitled "Apparatus and Methods for Ocular Injection," filed Mar. 29, 2017 (now U.S. Pat. No. 9,770,361), which is a continuation of U.S. patent application Ser. No. 15/399,239, entitled Apparatus and Methods for Ocular Injection, filed Jan. 5, 2017 (now U.S. Pat. No. 9,636,253), which is a continuation of U.S. patent application Ser. No. 14/268,687 entitled Apparatus and Methods for Ocular Injection, filed May 2, 2014 (now U.S. Pat. No. 9,539,139), which claims priority to and benefit of U.S. Provisional Patent Application No. 61/953,147, entitled "Apparatus and Methods for Ocular Injection," filed Mar. 14, 2014, U.S. Provisional Patent Application No. 61/944,214, entitled "Apparatus and Methods for Controlling the Insertion Depth of a Needle," filed Feb. 25, 2014, U.S. Provisional Patent Application No. 61/827,371, entitled "Apparatus and Methods for Ocular Injection," filed May 24, 2013, U.S. Provisional Patent Application No. 61/819,052, entitled "Apparatus and Methods for Delivering a Drug to Ocular Tissue," filed May 3, 2013, and U.S. Provisional Patent Application No. 61/819,048, entitled "Apparatus and Methods for Controlling the Insertion Depth of a Needle," filed May 3, 2013, the disclosures of each of which are incorporated herein by reference in their entirety.

BACKGROUND OF THE INVENTION

The embodiments described herein relate generally to the field of ophthalmic therapies and more particularly to the use of a microneedle for delivery and/or removal of a substance, such as a fluid therapeutic agent into and/or from ocular tissues for treatment of the eye.

Although needles are used in transdermal and intraocular drug delivery, there remains a need for improved microneedle devices and methods, particularly for delivery of substances (e.g., drugs) into the posterior region of the eye. Many inflammatory and proliferative diseases in the posterior region (or other regions) of the eye require long-term pharmacological treatment. Examples of such diseases include macular degeneration, diabetic retinopathy, and uveitis. It is often difficult to deliver effective doses of a drug to the back of the eye using conventional delivery methods such as topical application or an intravitreal administration (IVT), which has poor efficacy, and systemic administration, which often causes significant side effects. For example, while eye drops are useful in treating conditions affecting the exterior surface of the eye or tissues at the front of the eye, the eye drops are often not sufficiently conveyed to the back of the eye, as may be required for the treatment of some of the retinal diseases listed above.

Although there have been advances in the past decade regarding the utilization of systemically delivered substances, there are obstacles to wide spread adoption of such methods. For example, in certain situations, direct injection into the eye (e.g., into the vitreous) using conventional 27 gauge or 30 gauge needles and syringes can be effective. Direct injection, however, can be associated with significant safety risks, and physicians often require professional training to effectively perform such methods. Moreover, in some instances, targeted injection of a therapeutic agent is desirable. In such instances, however, the relatively small anatomic structures of the eye often result in significant challenges to placing a needle at a target location using known devices and methods, especially as they pertain to placing the distal end of the needle at the desired depth within the eye. Furthermore, IVT administration can have side effects such as increased intraocular pressure or faster onset of cataract formation.

In addition, many known methods of direct injection of a drug into the eye include inserting a needle or a cannula at an acute angle relative to a surface of the eye, which can make controlling the depth of insertion challenging. For example, some such methods include controlling the angular orientation of the needle such that the injected substance exits the needle at a particular location. Moreover, some known methods of injecting substances into ocular tissue include using complicated visualization system or sensors to control the placement of the needle or cannula.

Known devices for ocular injection do not provide the mechanism for adjusting needle length so that the needle can be inserted into the eye to the desired depth. Known systems also do not provide a reliable mechanism for determining when the needle tip is in the desired location, for example, the suprachoroidal space (SCS) of the eye. Such shortcomings in known systems and methods are exacerbated because the size and thickness of various layers included in the eye can vary substantially from one person to another. For example, the thickness of the conjunctiva and the sclera can be substantially different and their true value cannot easily be predetermined via standard techniques. Furthermore, the thickness of these layers can also be different in different portions of the eye and at different times of the day in the same eye and location. Therefore, using known systems and methods it can be challenging to determine and/or adjust the length of the needle for puncturing the eye, such that a tip of the needle is at the desired depth, for example, the SCS. Too short a needle might not penetrate the sclera, and too long a needle can traverse beyond the SCS and damage the retina of the eye. Further, known systems do not provide a convenient way to detect the position of the needle tip within the eye.

Because of the sensitivities associated with intraocular injection (e.g., the sensitivity of the tissue, the potential impact on intraocular pressure and the like), many known systems involve manual injection. More particularly, many known devices and methods include the user manually applying a force (e.g., via pushing a plunger with their thumb or fingers) to expel a fluid (e.g., a drug) into the eye. Because of the small needle size and/or the characteristics of the injected drug, some such devices and methods involve the use of force levels higher than that which users are comfortable with applying. For example, some studies have shown that users generally do not like to apply more than 2N force against the eye during ocular injection. Accordingly, in certain situations a user may not properly deliver the medicament using known systems and methods because of their reluctance to apply the force to fully expel the medicament.

Moreover, injection into different target layers of the eye can cause variability in the amount of the force required for insertion of the needle and/or injection of the medicament. Different layers of the eye can have different densities. For example, the sclera generally has a higher density than the conjunctiva or the SCS. Differences in the density of the target region or layer can produce different backpressure against the needle exit, i.e., the tip of the needle from which the fluid emerges. Thus, injection into a relatively dense ocular material such as sclera requires more motive pressure to expel the medicament from the needle than is required when injecting a medicament into the SCS.

Furthermore, the injection force to expel the medicament also depends on the density and viscosity of the liquid medicament, length of the needle, and diameter of the needle. To inject certain medicaments into the eye via desired needles (e.g., 27 gauge, 30 gauge, or even smaller) can require more force than many practitioners are comfortable applying.

Intraocular injection can also lead to leakage of intraocular fluids (e.g., aqueous and vitreous humour) or the medicament from a delivery passageway formed by the needle penetrating into the ocular tissue. By way of example, if the medicament is delivered to the sclera instead of the target ocular tissue layer, for example, the SCS, the high backpressure of the sclera can force the medicament to leak from the insertion site. Known systems do not provide a convenient way to prevent leakage from insertion site, which can lead to discomfort and loss of medicament. This can prolong treatment as well as increase costs associated with the treatment.

Thus, a need exists for improved devices and methods, which can assist in determining if the needle is at the correct depth, can facilitate injection of the medicament into ocular tissue, and/or can prevent leakage of ocular fluids and/or medicament form the insertion site.

SUMMARY OF THE INVENTION

The embodiments described herein relate generally to the field of ophthalmic therapies and more particularly to the use of a microneedle for delivery and/or removal of a substance, such as a fluid therapeutic agent into and/or from ocular tissues for treatment of the eye.

In some embodiments, an apparatus includes a housing configured to be coupled to a medicament container. The medicament container is configured to be coupled to a needle. An injection assembly is disposed within the housing and includes an energy storage member and an actuation rod. A distal end portion of the actuation rod is configured to be disposed within the medicament container. The energy storage member is configured to produce a force on a proximal end portion of the actuation rod. The force is sufficient to move the distal end portion of the actuation rod within the medicament container to convey at least a portion of a substance from the medicament container via the needle when a distal tip of the needle is disposed within a first region of a target location. Furthermore, the force is insufficient to move the distal end portion of the actuation rod within the medicament container when the distal tip of the needle is disposed within a second region of the target location. In some embodiments, the first region of the target location has a first density and the second region of the target location has a second density, higher than the first density. In some embodiments, the first region of the target location produces a first backpressure and the second region of the target location produces a second backpressure, higher than the first backpressure.

In some embodiments, an apparatus includes a housing configured to receive a portion of a medicament container, and an adjustment member. A proximal end portion of the adjustment member is configured to be coupled to the medicament container. A distal end portion of the adjustment member is coupled to a needle. The adjustment member is movably disposed within the housing such that when the adjustment member is rotated relative to the housing, the needle is moved through a plurality of discrete increments along a longitudinal axis of the housing. In some embodiments, the adjustment member defines a lumen configured to place the medicament container in fluid communication with the needle.

In some embodiments, an apparatus includes a hub configured to be coupled to a medical injector. The hub defines a passageway configured to receive a needle therethrough. The hub has a convex distal end surface that is configured to contact a target surface of a target tissue when a substance is conveyed through the needle into the target tissue. In some embodiments, the distal end surface includes a sealing portion configured to define a substantially fluid-tight seal with the target surface when the distal end surface is in contact with the target surface. In such embodiments, the sealing portion can be symmetrical about the centerline of the passageway.

BRIEF DESCRIPTION OF THE DRAWINGS

FIG. 12A shows a side view, FIG. 12B shows a front view, and FIG. 12C shows a top view of an actuating member included in the system of FIG. 9.

FIG. 13A shows a side view, FIG. 13B shows a front view, and FIG. 13C shows a top view of a pawl included in the system of FIG. 9.

FIG. 14A shows a side view of an actuator included in the system of FIG. 9. FIG. 14B shows a side cross-section view of the actuator of FIG. 14A taken along the line 14B-14B.

FIG. 23A, shows a top view, FIG. 23B shows a side view, and FIG. 23C shows a side cross-section view (taken along the line 23C-23C) of a housing of the needle assembly of FIG. 22.

FIG. 27A shows a side view of the lead screw included in the needle assembly of FIG. 22. FIG. 27B shows a cross-section view of the lead screw of FIG. 27A taken along the line 27B-27B.

FIG. 30A shows a side view and FIG. 30B shows a front view of a tab coupled to the locking pin included in the needle assembly of FIG. 22. FIG. 30C shows a cross-section view of the tab of FIG. 30A taken along the line 30C-30C.

FIG. 41A shows a finite element analysis (FEA) model of the hub of FIG. 40 A-D, pressed against the conjunctiva of an eye with a 1N force. FIG. 41B shows an enlarged view of a portion shown by the arrow 41B shown in FIG. 41A.

FIG. 42A shows a side view and FIG. 42B shows a front view of a hub that includes a convex distal end, according to an embodiment. FIG. 42C shows a cross-section view of the hub of FIG. 42A taken along the line 42C-42C.

FIGS. 46 and 47 are perspective views of a portion of a delivery device according to an embodiment.

FIG. 48 is a perspective view of a portion of a delivery device according to an embodiment.

FIG. 49 is a perspective view of a portion of a delivery device according to an embodiment.

FIG. 56 shows a perspective view of a delivery device, according to an embodiment.

FIG. 66 shows a top perspective view of a hub included in the delivery device of FIG. 56.

FIGS. 90A-C show a schematic illustrations of a delivery device that includes a needle assembly in a first, second and third configuration, according to an embodiment.

FIG. 92A shows a perspective view and FIG. 92B shows a side cross-section view of a delivery device that includes a hub, according to an embodiment.

DETAILED DESCRIPTION OF THE INVENTION

Figure 1:
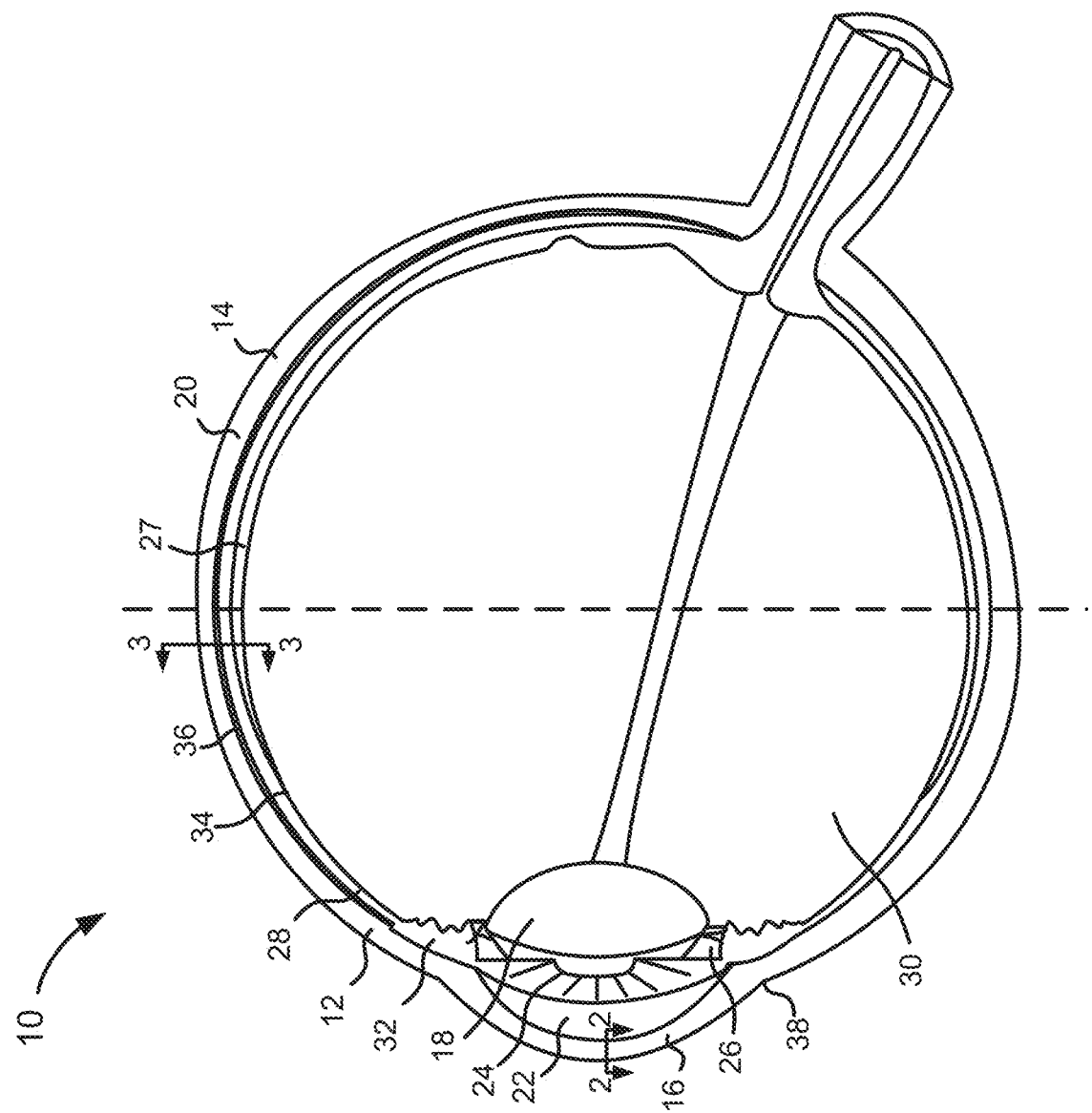
FIG. 1 is a cross-sectional view of an illustration of the human eye.

The embodiments described herein relate to systems and devices for delivering a fluid (e.g., a drug) or extracting a fluid into the sclera of an eye. Furthermore, embodiments described herein are related to systems, devices, and methods to assist in the insertion of a delivery member, for example, a needle or microneedle into the eye, and/or assist in injecting a medicament into a target ocular tissue. Embodiments described herein are also related to systems, devices, and methods for controlling the insertion depth of a delivery member, such as, for example, a microneedle, into the eye to deliver a therapeutic agent to, for example, a posterior region of the eye (e.g., via the suprachoroidal space). Embodiments, described herein are also related to systems, devices and methods to form a substantially fluid-tight seal around a delivery passageway formed by insertion of a delivery member, for example, a microneedle, into the eye to prevent leakage of the substance and/or ocular fluid from the insertion site.

In some embodiments, the microneedles included in the embodiments described herein include a bevel, which allows for ease of penetration into the sclera and/or suprachoroidal space with minimal collateral damage. Moreover, in some embodiments, the micro needles disclosed herein can define a narrow lumen (e.g., gauge size greater than or equal to 30 gauge, 32 gauge, 34 gauge, 36 gauge, etc.) to allow for suprachoroidal drug delivery while minimizing the diameter of the needle track caused by the insertion of the microneedle. In some embodiments, the lumen and bevel aspect ratio of the microneedles described herein are distinct from standard 27 gauge and 30 gauge needles, which are now commonly used for intraocular injection. For example, the microneedles included in the embodiments described herein can be any of those described in International Patent Application Publication No. WO2014/036009, entitled, "Apparatus and Methods for Drug Delivery Using Microneedles," filed on Aug. 27, 2013, the disclosure of which is incorporated by reference herein in its entirety (referred to henceforth as the "'009 PCT application").

In some embodiments, an apparatus includes a housing configured to be coupled to a medicament container. The medicament container is configured to be coupled to a needle. An injection assembly is disposed within the housing and includes an energy storage member and an actuation rod. A distal end portion of the actuation rod is configured to be disposed within the medicament container. The energy storage member is configured to produce a force on a proximal end portion of the actuation rod. The force is sufficient to move the distal end portion of the actuation rod within the medicament container to convey at least a portion of a substance from the medicament container via the needle when a distal tip of the needle is disposed within a first region of a target location. Furthermore, the force is insufficient to move the distal end portion of the actuation rod within the medicament container when the distal tip of the needle is disposed within a second region of the target location. In some embodiments, the first region of the target location has a first density and the second region of the target location has a second density, higher than the first density. In some embodiments, the first region of the target location produces a first backpressure and the second region of the target location produces a second backpressure, higher than the first backpressure.

In some embodiments, an apparatus includes a housing configured to receive at least a portion of a medicament container. The medicament container is configured to be coupled to a needle. An injection assembly is disposed within the housing. The injection assembly includes an energy storage member, an actuation rod, and a release member. A distal end portion of the actuation rod is configured to be disposed within the medicament container. The release member is configured to maintain a position of the actuation rod relative to the housing when the release member is in a first position such that the movement of the housing relative to the medicament container moves the distal end portion of the actuation rod within the medicament container. The release member is configure to release the actuation rod when moved from the first position to a second position such that a force produced by the energy storage member moves the distal end portion of the actuation rod relative to the housing within the medicament container. This conveys at least a portion of a substance from the medicament container via the needle. In some embodiments, the force is sufficient to move the distal end portion of the actuation rod within the medicament container when a distal tip of the needle is disposed within a first region of a target location. The force however, is insufficient to move the distal end portion of the actuation rod within the medicament container when the distal tip of the needle is disposed within a second region of the target location.

In some embodiments, a method includes inserting a distal tip of a needle of a medical injector, which includes a medicament container and an injection assembly, a first distance into a target tissue. The medicament container is in fluid communication with the needle. The injection assembly includes an actuation rod and an energy storage member that is configured to produce a force on a proximal end portion of the actuation rod. The method further includes releasing the actuation rod of the injection assembly to allow a distal end portion of the actuation rod to move within the medicament container in response to the force. Finally, the method includes inserting, after releasing, the distal tip of the needle of the medical injector a second distance into the target tissue if the distal end portion of the actuation rod moves less than a threshold injection distance within the medicament container in response to the force, the second distance greater than the first distance. In some embodiments, the distal end portion of the actuation rod moves a first injection distance within the medicament container in response to the force. In such embodiments, the method can further include moving the injection assembly relative to the medicament container to move the distal end portion of the actuation rod a second injection distance, greater than the first injection distance, within the medicament container.

In some embodiments, an apparatus includes a housing configured to receive a portion of medicament container and an adjustment member. A proximal end portion of the adjustment member is configured to be coupled to the medicament container. A distal end portion of the adjustment member is coupled to a needle. The adjustment member is movably disposed within the housing such that when the adjustment member is rotated relative to the housing, the needle is moved through a plurality of discrete increments along a longitudinal axis of the housing. In some embodiments, the adjustment member defines a lumen configured to place the medicament container in fluid communication with the needle.

In some embodiments, an apparatus includes a housing configured to receive a portion of a medicament container and an adjustment member. A proximal end portion of the adjustment member is configured to be coupled to the medicament container. A distal end portion of the adjustment member is coupled to a needle. The adjustment member defines a plurality of detents such that a protrusion of the housing is configured to be removably disposed within each detent from the plurality of detents when the adjustment member is moved relative to the housing to move the needle relative to the housing through a plurality of discrete increments. In some embodiments, the protrusion can be a bearing movably coupled within the housing. In such embodiments, the bearing is configured to be removably disposed within each detent from the plurality of detents when the adjustment member is moved relative to the housing to move the needle through the plurality of discrete increments. Furthermore, the apparatus can also include a bias member configured to maintain the bearing within a detent from the plurality of detents.

In some embodiments, an apparatus includes a hub configured to be coupled to a medical injector. The hub defines a passageway configured to receive a needle therethrough. The hub has a convex distal end surface, which is configured to contact a target surface of a target tissue when a substance is conveyed through the needle into the target tissue. In some embodiments, the distal end surface includes a sealing portion configured to define a substantially fluid-tight seal with the target surface when the distal end surface is in contact with the target surface.

In some embodiments, a method includes inserting a distal end portion of a needle of a medical injector into a target tissue to define a delivery passageway within the target tissue. This is followed by placing a convex distal end surface of a hub of the medical injector into contact with a target surface of the target tissue to fluidically isolate the delivery passageway. Next, the method includes conveying, after the placing, a substance into the target tissue via the needle. In some embodiments, the target tissue is an eye and the target surface is the conjunctiva of the eye. In some embodiments, the delivery passageway extends through a sclera of the eye and the conveying includes conveying the substance into at least one of a suprachoroidal space or lower portion of the sclera. In such embodiments, the method can further include adjusting, before the conveying, a length of the needle extending from the distal end surface of the hub.

In some embodiments, a method includes inserting a distal end portion of a needle of a medical injector into a target tissue to define a delivery passageway within the target tissue. The inserting is performed such that a centerline of the needle is substantially normal to a target surface of the target tissue. This is followed by placing a distal end surface of a hub of the medical injector into contact with a target surface of the target tissue to fluidically isolate the delivery passageway. Next, the method includes conveying, after the placing, a substance into the target tissue via the needle. In some embodiments, the delivery is performed such that a centerline of the delivery passageway and a surface line tangent to the target surface defines an angle of entry of between about 75 degrees and about 105 degrees.

As used herein, the singular forms "a," "an", and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to the direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the end of a microneedle described herein first inserted inside the patient's body would be the distal end, while the opposite end of the microneedle (e.g., the end of the medical device being manipulated by the operator) would be the proximal end of the microneedle.

As used herein, a "set" can refer to multiple features or a singular feature with multiple parts. For example, when referring to set of walls, the set of walls can be considered as one wall with distinct portions, or the set of walls can be considered as multiple walls.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the terms "delivery member", "puncture member", and "puncturing member" are used interchangeably to refer to an article configured to pierce tissue layers and deliver a substance to a target tissue layer, for example, a needle or a microneedle.

As used herein, the terms "medicament container", and "medicament containment chamber" are used interchangeably to refer to an article configured to contain a volume of a substance, for example, a medicament.

The term "fluid-tight" is understood to encompass both a hermetic seal (i.e., a seal that is gas-impervious) as well as a seal that is liquid-impervious. The term "substantially" when used in connection with "fluid-tight," "gas-impervious," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal. Thus, a "substantially fluid-tight" seal includes a seal that prevents the passage of a fluid (including gases, liquids and/or slurries) therethrough when the seal is maintained at a constant position and at fluid pressures of less than about 5 psig, less than about 10 psig, less than about 20 psig, less than about 30 psig, less than about 50 psig, less than about 75 psig, less than about 100 psig and all values in between. Similarly, a "substantially liquid-tight" seal includes a seal that prevents the passage of a liquid (e.g., a liquid medicament) therethrough when the seal is maintained at a constant position and is exposed to liquid pressures of less than about 5 psig, less than about 10 psig, less than about 20 psig, less than about 30 psig, less than about 50 psig, less than about 75 psig, less than about 100 psig and all values in between.

Figure 2:
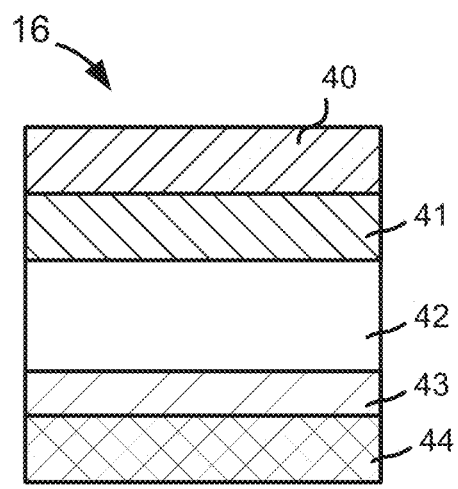
FIG. 2 is a cross-sectional view of a portion of the human eye of FIG. 1 taken along the line 2-2.
Figure 3:
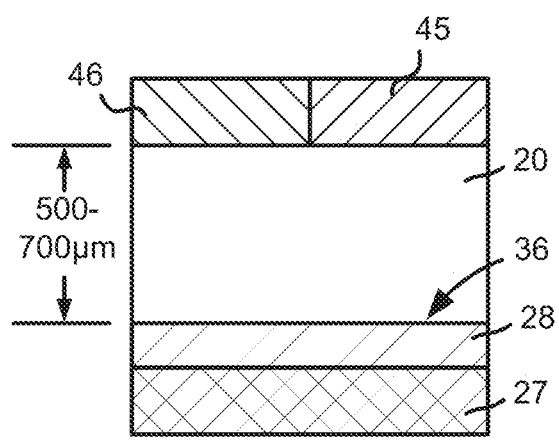
FIGS. 3 and 4 are cross-sectional views of a portion of the human eye of FIG. 1 taken along the line 3-3, illustrating the suprachoroidal space without and with, respectively, the presence of a fluid.
Figure 4:
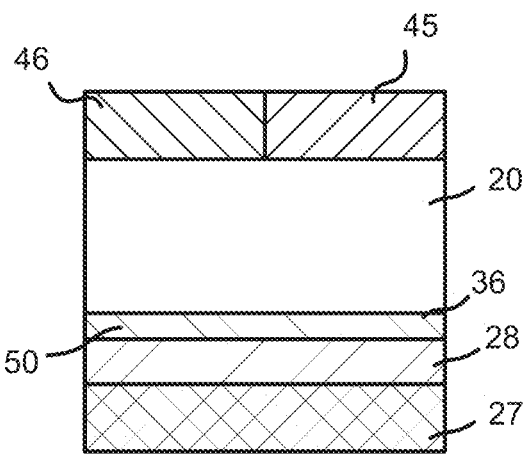

The embodiments and methods described herein can be used to treat, deliver substances to and/or aspirate substances from, various target tissues in the eye. For reference, FIGS. 1-4 are a various views of a human eye 10 (with FIGS. 2-4 being cross-sectional views). While specific regions are identified, those skilled in the art will recognize that the proceeding identified regions do not constitute the entirety of the eye 10, rather the identified regions are presented as a simplified example suitable for the discussion of the embodiments herein. The eye 10 includes both an anterior segment 12 (the portion of the eye in front of and including the lens) and a posterior segment 14 (the portion of the eye behind the lens). The anterior segment 12 is bounded by the cornea 16 and the lens 18, while the posterior segment 14 is bounded by the sclera 20 and the lens 18. The anterior segment 12 is further subdivided into the anterior chamber 22, between the iris 24 and the cornea 16, and the posterior chamber 26, between the lens 18 and the iris 24. The cornea 16 and the sclera 20 collectively form a limbus 38 at the point at which they meet. The exposed portion of the sclera 20 on the anterior segment 12 of the eye is protected by a clear membrane referred to as the conjunctiva 45 (see e.g., FIGS. 2 and 3). Underlying the sclera 20 is the choroid 28 and the retina 27, collectively referred to as retinachoroidal tissue. A vitreous humour 30 (also referred to as the "vitreous") is disposed between a ciliary body 32 (including a ciliary muscle and a ciliary process) and the retina 27. The anterior portion of the retina 27 forms an ora serrata 34. The loose connective tissue, or potential space, between the choroid 28 and the sclera 20 is referred to as the suprachoroid. FIG. 2 illustrates the cornea 16, which is composed of the epithelium 40, the Bowman's layer 41, the stroma 42, the Descemet's membrane 43, and the endothelium 44. FIG. 3 illustrates the sclera 20 with surrounding Tenon's Capsule 46 or conjunctiva 45, suprachoroidal space 36, choroid 28, and retina 27, substantially without fluid and/or tissue separation in the suprachoroidal space 36 (i.e., the in this configuration, the space is "potential" suprachoroidal space). As shown in FIG. 3, the sclera 20 has a thickness between about 500 µm and 700 µm. FIG. 4 illustrates the sclera 20 with the surrounding Tenon's Capsule 46 or the conjunctiva 45, suprachoroidal space 36, choroid 28, and retina 27, with fluid 50 in the suprachoroidal space 36.

As used herein, the term "suprachoroidal space," or SCS which is synonymous with suprachoroid, or suprachoroidia, describes the space (or volume) and/or potential space (or potential volume) in the region of the eye 10 disposed between the sclera 20 and choroid 28. This region primarily is composed of closely packed layers of long pigmented processes derived from each of the two adjacent tissues; however, a space can develop in this region because of fluid or other material buildup in the suprachoroidal space and the adjacent tissues. The suprachoroidal space can be expanded by fluid buildup because of some disease state in the eye or because of some trauma or surgical intervention. In some embodiments, the fluid buildup is intentionally created by the delivery, injection and/or infusion of a drug formulation into the suprachoroid to create and/or expand further the suprachoroidal space 36 (i.e., by disposing a drug formulation therein). This volume may serve as a pathway for uveoscleral outflow (i.e., a natural process of the eye moving fluid from one region of the eye to the other through) and may become a space in instances of choroidal detachment from the sclera.

The dashed line in FIG. 1 represents the equator of the eye 10. In some embodiments, the insertion site of any of the microneedles and/or methods described herein is between the equator and the limbus 38 (i.e., in the anterior portion 12 of the eye 10) For example, in some embodiments, the insertion site is between about two millimeters and 10 millimeters (mm) posterior to the limbus 38. In other embodiments, the insertion site of the microneedle is at about the equator of the eye 10. In still other embodiments, the insertion site is posterior the equator of the eye 10. In this manner, a drug formulation can be introduced (e.g., via the microneedle) into the suprachoroidal space 36 at the site of the insertion and can flow through the suprachoroidal space 36 away from the site of insertion during an infusion event (e.g., during injection).

Figure 5:
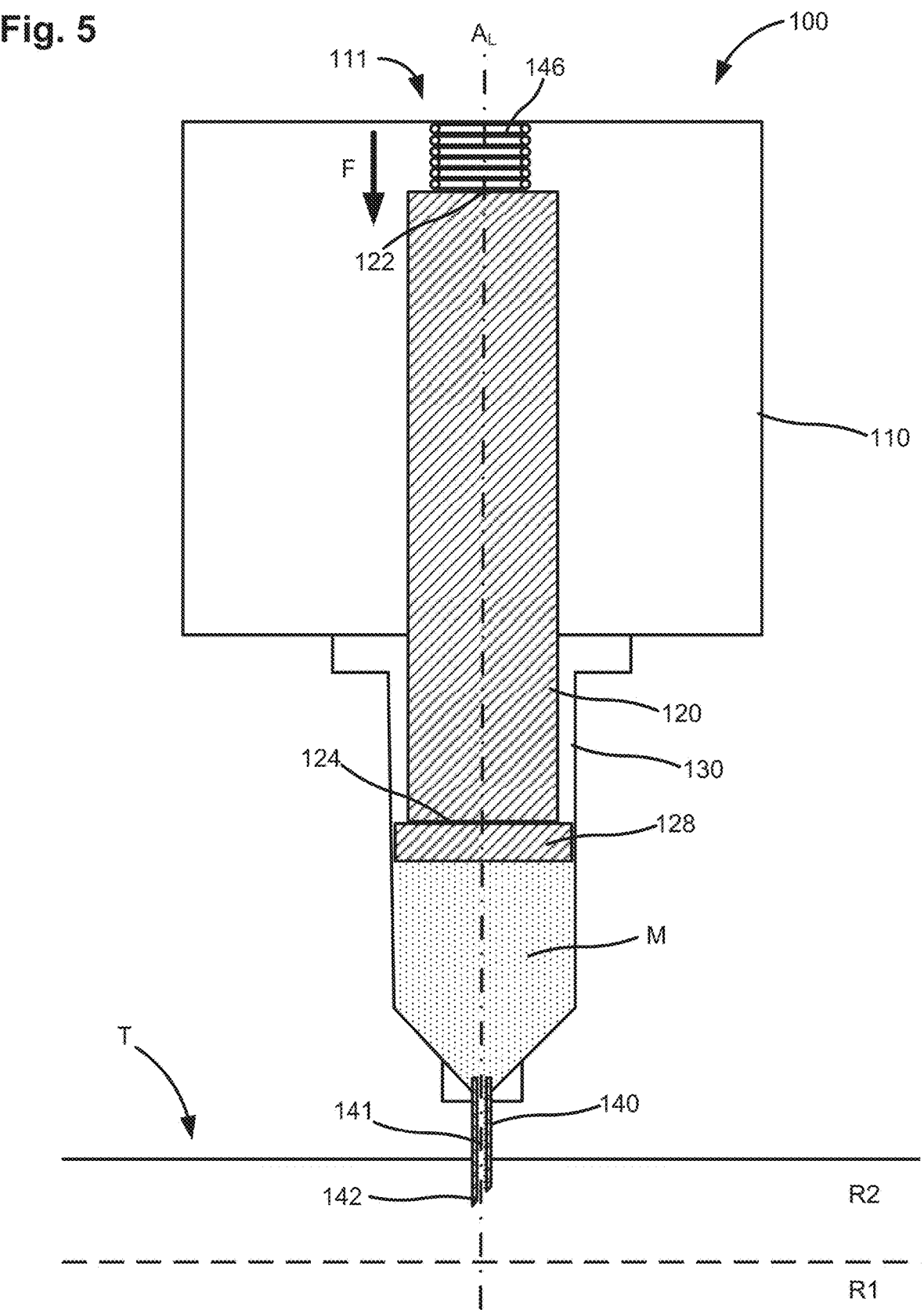
FIG. 5 is a schematic illustration of an apparatus that includes a housing and an injection assembly in a first configuration, according to an embodiment.
Figure 6:
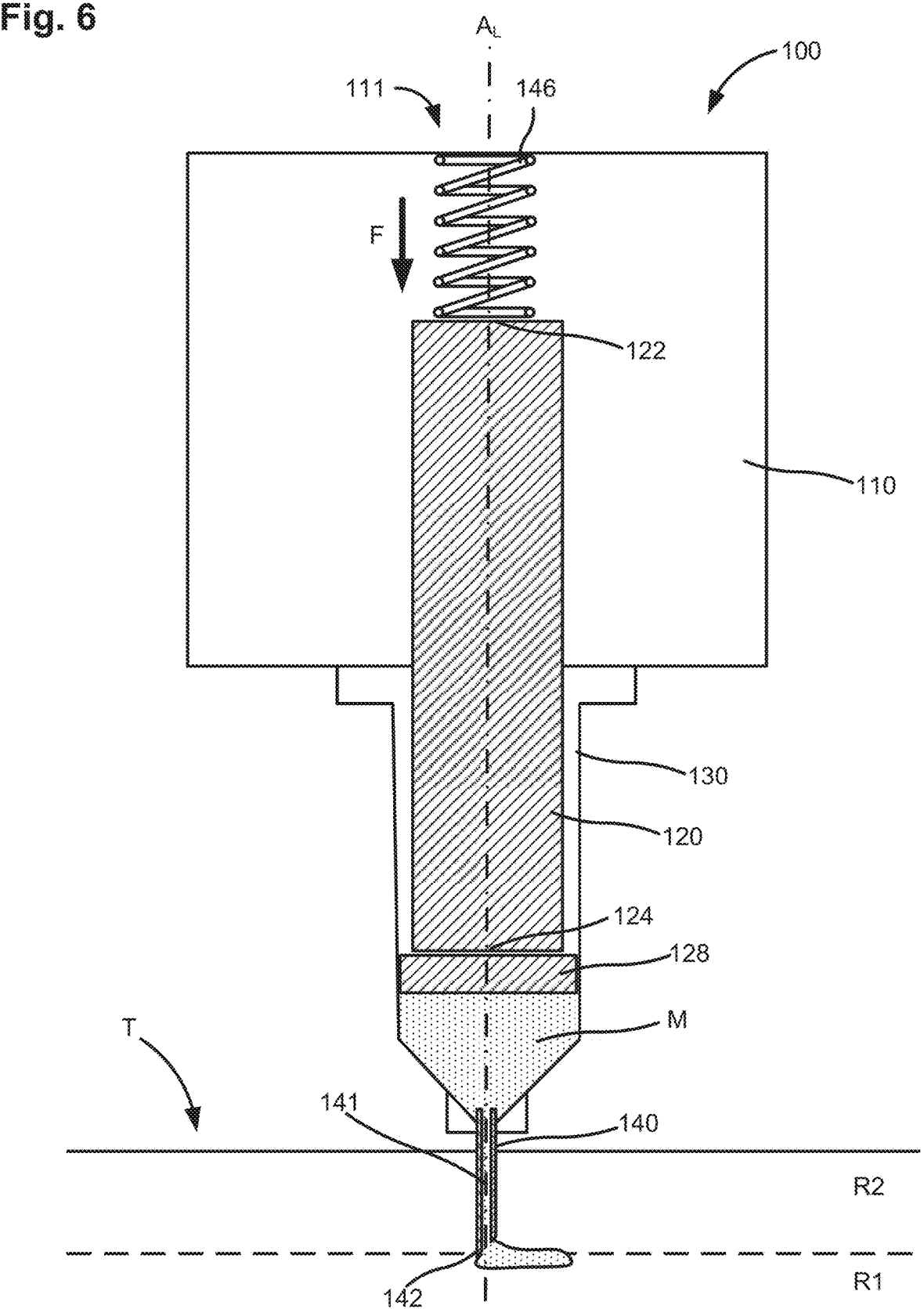
FIG. 6 shows the apparatus of FIG. 5 in a second configuration, according to an embodiment.

In some embodiments, a system for ocular injection can include a medicament container at least a portion of which is disposed in a housing that includes an injection assembly. The injection assembly can facilitate delivery of a substance disposed in a medicament container to a target tissue, for example, the SCS. For example, FIGS. 5-6, show a system 100, according to an embodiment. The system 100 includes a housing 110, an injection assembly 111, a medicament container 130, and a needle 140, in a first configuration and a second configuration, respectively. The system 100 can be configured to deliver a medicament to region and/or a layer of a target location, for example, an eye of a patient, (e.g., to the SCS of the eye), as described herein.

The housing 110 is configured to be coupled to the medicament container 130, and the medicament container 130 is configured to be coupled to the needle 140. For example, in some embodiments, at least a portion of the medicament container 130 can be disposed within an internal volume defined by the housing 110. In some embodiments, the medicament container 130 can be slidably disposed within the housing 110. The housing 110 can be a monolithic housing or include two or more portions which can be joined together to form the housing 110. As shown, the housing 110 defines an internal volume within which the injection assembly 111 is disposed. Mounting features, for example, mounts, notches, grooves, indents, guide rods, slots, or any other suitable mounting features can be disposed in the interval volume defined by the housing 110 configured to secure at least a portion of the components included in the injection assembly 111.

The injection assembly 111 includes an energy storage member 146 and an actuation rod 120. In some embodiments, the energy storage member 146 can be a spring, for example, helical spring, compression, extension, spring washers, Belleville washer, tapered, any other type of spring. In other embodiments, the energy storage member 146 can include a compressed gas container, or a container containing a propellant. The energy storage member 146 is operatively coupled to a proximal end portion 122 of the actuation rod 120, and produces a force on the proximal end portion 122 of the actuation rod 120.

A distal end portion 124 of the actuation rod 120 is disposed within the medicament container 130. The distal end portion 124 can be coupled to and/or in contact with a plug 128 which is in fluidic communication with a substance M (e.g., a medicament such as, for example, VEGF, a VEGF inhibitor, a combination thereof, or any other medicament described herein) disposed within an internal volume defined by the medicament container 130. The distal end portion 124 of the actuation rod 120 is configured to be displaced within the internal volume defined by the medicament container 130, for example, due to the force produced by the energy storage member 146, as described herein. In this manner, the actuation rod 120 can displace the plug 128 within the medicament container 130 to draw in or expel the substance M from the distal tip 142 of the needle 140, as described herein. The sidewalls of the plug 128 can be configured to contact the sidewalls of the medicament container 130 such that the plug 128 forms a substantially fluid-tight seal with the side wall of the medicament container 130, for example, to prevent leakage of the substance M. The plug 128 can be made of an inert and/or biocompatible material which is rigid but soft. Example materials include rubber, silicone, plastic, polymers, any other suitable material or combination thereof. In some embodiments, the plug 128 can be monolithically formed with the actuation rod 120.

The needle 140 can be coupled to the medicament container 130 using any suitable coupling features, for example, Luer connectors, threads, snap-fit, latch, lock, friction fit, or any other suitable coupling features. The needle 140 can include any suitable needle described herein, for example, a micro needle (e.g., a 27 gauge, 30 gauge, or even smaller needle). The distal tip 142 of the needle 140 can define a sharp tip such that the needle 140 is configured to pierce a target location T, for example, a bodily tissue (e.g., ocular tissue). In this manner, the distal tip 142 can be disposed within a first region R1 and/or a second region R2 of the target location T, as described herein. The needle 140 defines a lumen 141, which is in fluidic communication with the substance M disposed within the internal volume defined by the medicament container 130. In this manner, the needle 140 is configured to establish fluid communication between the medicament container 130 and the target location T, for example, the first region R1 of the target location T, as described herein. In some embodiments, the first region R1 of the target location T can have a first density and the second region R2 can have a second density, which is higher than the first density. In some embodiments, the first region R1 of the target location T produces a first backpressure on the distal tip 142 of the needle 140, and the second region R2 produces a second backpressure on the distal tip 142 of the needle 140, which is higher than the first backpressure. In other words, the first region R1 of the target location T produces a first pressure that resists and/or opposes flow from the distal tip 142 of the needle 140, and the second region R2 produces a second pressure that resists and/or opposes flow from the distal tip 142 of the needle 140, which is higher than the first pressure. In some embodiments, the target location T can be an eye such that the first region R1 is a suprachoroidal space of the eye, and the second region R2 is a sclera of the eye.

The force produced on the proximal end portion 122 of the actuation rod 120 by the energy storage member 146 can be sufficient to move the distal end portion 124 of the actuation rod 120 within the medicament container 130 to convey at least a portion of the substance M from the medicament container 130 via the needle 140 when the distal tip 142 of the needle 140 is disposed within the first region R1 (e.g., an SCS of the eye) of the target location T. Furthermore, the force can be insufficient to move the distal end portion 124 of the actuation rod 120 within the medicament container 130 when the distal tip 142 of the needle 140 is disposed within the second region R2 (e.g., the sclera of the eye) of the target location T. Said another way, the injection assembly 111 can be configured to assist a user in delivering at least a portion of the substance M to the region R1, while be configured or "calibrated" to limit and/or prevent delivery to the region R2. In some embodiments, the injection assembly 111 can be configured to inform the user when the distal tip 142 of the needle 140 is in the target region of the target location T, for example, the region R1, such that the substance M can be delivered to the target region with high confidence.

Expanding further, FIG. 5 shows the apparatus 100 in the first configuration in which the distal tip 142 of the needle 140 is disposed in the second region R2. When the apparatus is actuated, the energy storage member 146 exerts a force in a direction shown by the arrow F on the proximal end portion 122 of the actuation rod 120. The force F exerted, however, is insufficient to move the distal end portion 124 of the actuation rod 120 within the medicament container 130. For example, the second region R2 (e.g., the sclera of the eye) can produce a second backpressure which overcomes the force F, thereby preventing and/or limiting delivery of the substance M to the second region R2. In other words, the apparatus 100 is specifically configured or "calibrated" such that the force F is insufficient to convey the substance M to the second region R2.

In the second configuration shown in FIG. 6, the distal tip 142 of the needle is now disposed in the first region R1 (e.g., the SCS of the eye). Because of the anatomical differences and/or the differences in material properties between the first region R1 and the second region R2, the force F is sufficient to move the distal end portion 124 of the actuation rod 120 an injection distance within the medicament container 130. For example, the force F can be sufficient to overcome a first backpressure produced by the first region R1. In this manner, the injection assembly 111 can be configured to ensure that the injection is initiated only when the distal tip 142 of the needle is in the first region R1 such that the substance M (e.g., a medicament such as, for example, VEGF, a VEGF inhibitor, a combination thereof, or any other medicament described herein) can be delivered only to the region R1. In some embodiments, the force F exerted by the energy storage member 146 can be between about 2 N and about 6 N, for example, about 3 N, about 4 N, or about 5 N, inclusive of all ranges therebetween. In some embodiments, the actuation rod 120 and the medicament container 130 can be collectively configured such that the force produces an injection pressure within the medicament container 130 of between about 100 kPa and about 500 kPa. For example, in some embodiments, the injection pressure can be about 100 kPa, 110 kPa, 120 kPa, 130 kPa, 140 kPa, 150 kPa, 160 kPa, 170 kPa, 180 kPa, 190 kPa, 200 kPa, 220 kPa, 240 kPa, 260 kPa, 280 kPa, 300 kPa, 320 kPa, 340 kPa, 360 kPa, 380 kPa, 400 kPa, 420 kPa, 440 kPa, 460 kPa, or about 480 kPa, inclusive of all ranges and values therebetween. The injection pressure can be sufficient to overcome the backpressure produced by region R1, but insufficient to overcome the backpressure produced by region R2. For example, the force F can be varied (e.g., by varying the energy storage member 146) depending on the diameter of the medicament container 130 and/or the actuation rod, the viscosity of the substance M, and/or the material of the medicament container 130 and/or the actuation rod 120. In this manner, regardless of the variations in the actuation rod 120, the medicament container 130, and/or the substance M, the injection assembly 111 produces an injection pressure within the medicament container of between about 100 kPa and about 500 kPa.

In some embodiments, the injection assembly 111 can be configured to be engaged or disengaged by a user reversibly on demand. For example, the injection assembly 111 can include an ON/OFF switch which can be engaged by the user to activate or deactivate the injection assembly and/or the energy storage member 146. By way of example, in such embodiments, the injection assembly 111 can be activated by the user (e.g., by turning the injection assembly ON) to release the energy storage member 146 such that the energy storage member 146 exerts the force on the proximal end portion 122 of the actuation rod 120 (e.g., as shown in FIG. 6) to move the distal end portion 124 of the energy storage member 146 within the medicament container 130. The user can then deactivate the injection assembly 111 (e.g., by turning the injection assembly OFF). The disengaging can result in the force exerted on the proximal end portion 122 of the actuation rod 120 to be removed (e.g., to stop any further movement of the actuation rod 120 within the medicament container 130) or reduced. In some embodiments, the injection assembly 111 can be configured such that the direction of the force F can be reversed or the actutation rod 120 and/or the energy storage member 146 can be moved in an opposite direction of the arrow F (FIG. 5). In this manner, the medical injector 100 can be returned to the first configuration such that, for example, the energy storage member 146 and/or the actuation rod 120 can be secured. This can, for example, allow more flexiblity to the user to perform dry runs or correct a mistake, for example, inadvertent activation of the injection assembly 111 (e.g., during transportation to the target tissue), or injection in an incorrect insertion site (e.g., an undesired location on an eye). In such embodiments, the energy storage member 146 can include any suitable engagement member which can be reversibly engaged or disengaged by the user such as, for example, a valve (e.g., a flap valve, a butterfly valve, or the likes), a diaphragm, a mechanical actuator (e.g., a rack and pinion actuator, a lead screw and nut actuator, a cam, etc.), a hydraulic actuator (e.g., a hydraulic piston), an electromechanical actuator (e.g., a piezo electric actuator), a magnetic actuator, or any other suitable energy storage member 146 which can be reversibly engaged by the user. Such an energy storage member 146 can, for example, allow the medical injector 100 to be moved between the first configuration and the second configuration on demand.

In some embodiments, the injection assembly 111 can be configured such that injection distance traversed by the actuation rod 120 is sufficient to deliver substantially all of the desired dose of the substance M into the first region R1. In other embodiments, the injection assembly 111 can be configured such that the injection distance traversed by the actuation rod 120 is sufficient to deliver only a portion of the desired dose of the substance M into the first region R1. In such embodiments, the injection assembly 111 can be configured to initiate delivery of the substance M into the first region R1, for example, to inform the user that the distal tip 142 of the needle 140 is disposed within the first region R1 (e.g., the user would see or otherwise detect that the actuation rod 120 has moved, thus indicating the desired positioning of the needle 140). Said another way, the injection assembly 111 can assist the user in determining whether the distal tip 142 of the needle 140 is within the region R1 or not by initiating delivery of the substance M. In such embodiments, the injection distance can be a first injection distance. The user can then move the distal end portion 124 of the actuation rod 120 a second injection distance, for example, by applying a manual force on the actuation rod 120 (e.g., by moving the housing 110 relative to the medicament container 130, as described herein). In some embodiments, any suitable delivery mechanism (e.g., a mechanical actuator or a pump) can be used to move the distal end portion 122 of the actuation rod 120 the second injection distance such that substantially all of the desired dose of the substance M is delivered to the first region R1.

In some embodiments, the proximal end portion 122 of the actuation rod 120 moves relative to the housing 110 to move the distal end portion 124 of the actuation rod 120 within the medicament container 130, for example, when the distal tip 142 of the needle 140 is disposed within the first region R1 (e.g., the SCS of the eye) of the target location T. For example, in some embodiments, the proximal end portion 122 of the actuation rod 120 can be configured to move freely within the housing 110 such that, distal end portion 124 can move within the medicament container 130 without the housing 110 and the medicament container 130 moving relative to each other. This can, for example, ensure that force F exerted by the energy storage member 146 does not move the housing relative to the medicament container 130. In this manner, substantially all of the force F can be transferred to the proximal end portion 122 of the actuation rod 120. In such embodiments, the housing 110 and/or the medicament container 130 can include features, for example, ribs, notches, grooves, indents, locks, latches, high friction, or any other suitable mechanism, sufficient to prevent the housing 110 and the medicament container 130 from moving relative to each other due to the force F.

In some embodiments, the injection assembly 111 can include a release member (not shown) configure to selectively limit movement of the actuation rod 120 relative to the housing 110. In such embodiments, the housing 110 can be configured to move relative to the medicament container 130 to move the distal end portion 124 of the actuation rod 120 within the medicament container 130 independently from the force F. In this manner, the release member can be configured to lock or otherwise secure the actuation rod 120, for example, the proximal end portion 122 of the actuation rod 120, and/or the energy storage member 146 in the first configuration. This can, for example, bias the energy storage member 146 to exert the force F on the distal end portion 122 of the actuation rod 120. In this manner, the movement of the actuation rod 120 can be substantially limited within the housing 110 such that any movement of the housing 110 relative to the medicament container 130 also displaces the distal end portion 124 of the actuation rod 120 within the medicament container 130. For example, the user can move the housing 110 relative to the medicament container 130 to move the distal end portion 124 of the actuation rod 120 within the medicament container 130. The relative motion can be used to draw the substance M into the medicament container 130 and/or move the distal end portion 124 the second injection distance to expel substantially all of the substance M in the first region R1 or any other target region of the target location, as described herein.

In some embodiments, the release member can be configured to move between a first position and a second position such that the release member is configured to release the energy storage member 146 when the release member is moved from the first position to the second position. The release member can include any suitable release member such as, for example, a pawl, lock, latch, or any other suitable release member. By way of example, in the first position the release member can secure or otherwise engage the proximal end portion 122 of the actuation rod 120, and/or the energy storage member 146, such that the energy storage member 146 is biased and/or the actuation rod 120 is locked within the housing 110, as described herein. Once the distal tip 142 of the needle 140 is disposed within the second region R2, the release member can be moved into the second position to release the energy storage member 146 and/or the actuation rod 120. Said another way, the release member can be configured to maintain a position of the actuation rod 120 relative to the housing 110 when the release member is in the first position such that the movement of the housing 110 relative to the medicament container 130 moves the distal end portion 124 of actuation rod 120 within the medicament container. Furthermore, the release member can be configured to release the actuation rod 120 when moved from the first position to the second position. This can allow the force F produced by the energy storage member 146 to move the distal end portion 124 of the actuation rod 120 relative to the housing 110 and within the medicament container 130 and, thereby convey at least a portion of the substance M from the medicament container 130 via the needle 140. In some embodiments, an actuation mechanism, for example, a button, a pull tab, or any other actuation mechanism can be coupled to the release member. The actuation mechanism can, for example, be configured to be engaged by the user to move the release member into the second position thereby releasing the actuation rod 120 and/or the energy storage member 146.

In some embodiments, the injection assembly 111 can also include a guide rod (not shown) fixedly coupled to the housing 110. The actuation rod 120 can be configured to slide about the guide rod when the energy storage member 146 is released. For example, in some embodiments, at least a portion of the guide rod can be disposed within a cavity defined in proximal end portion 122 of the actuation rod 120. In some embodiments, the guide rod can be a hollow rod within which the proximal end portion 122 of the actuation rod 120 is disposed. The guide rod can be configured to ensure that the actuation rod 120 moves within the housing 110 and/or medicament container 130 substantially along a center line $A_L$ of the apparatus 100. In this manner, the guide rod can prevent any sideways (or lateral) movement of the actuation rod 120.

Figure 7:
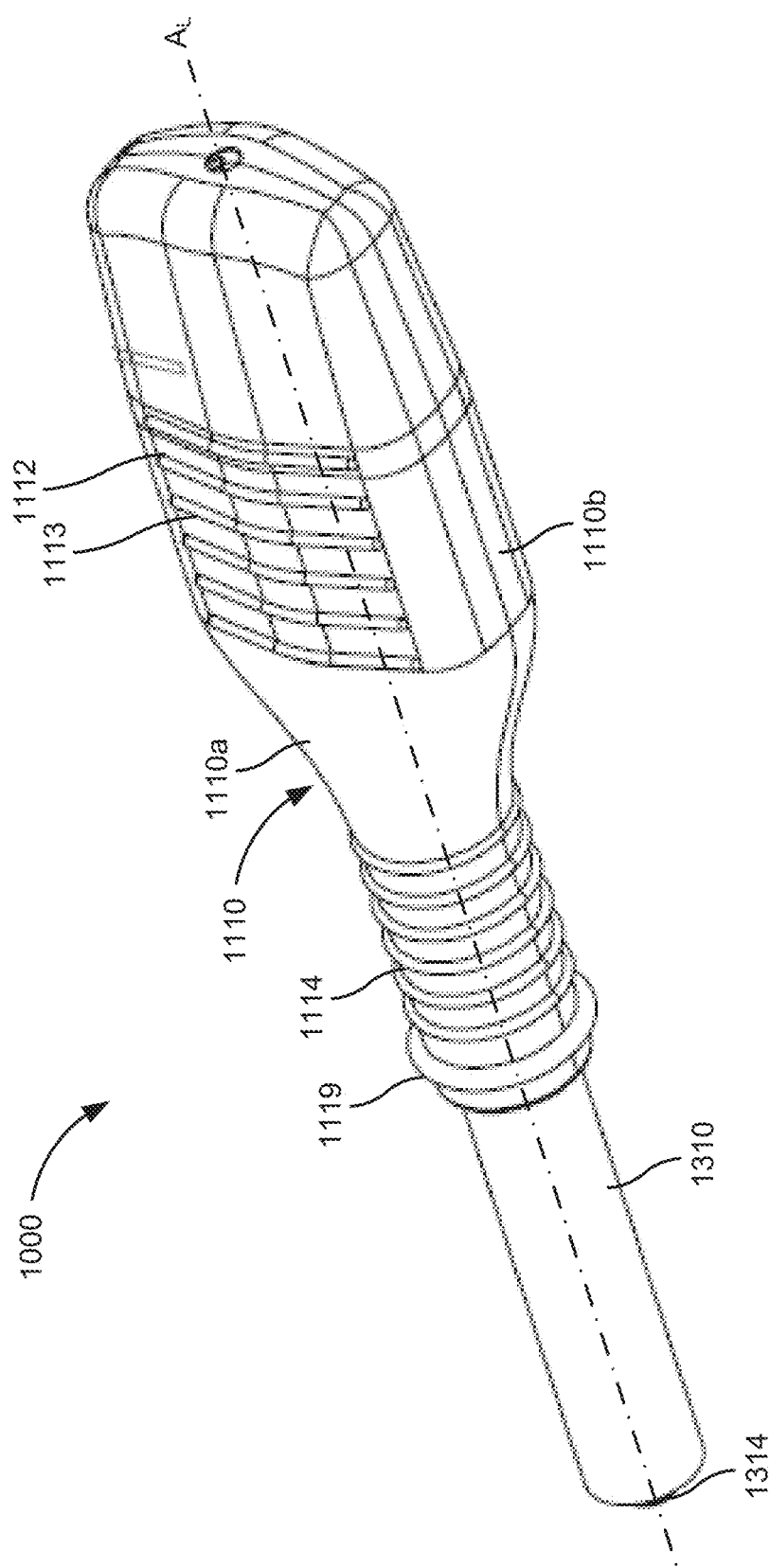
FIG. 7 is a perspective view of a system for delivering a medicament to an eye, according to an embodiment.
Figure 8:
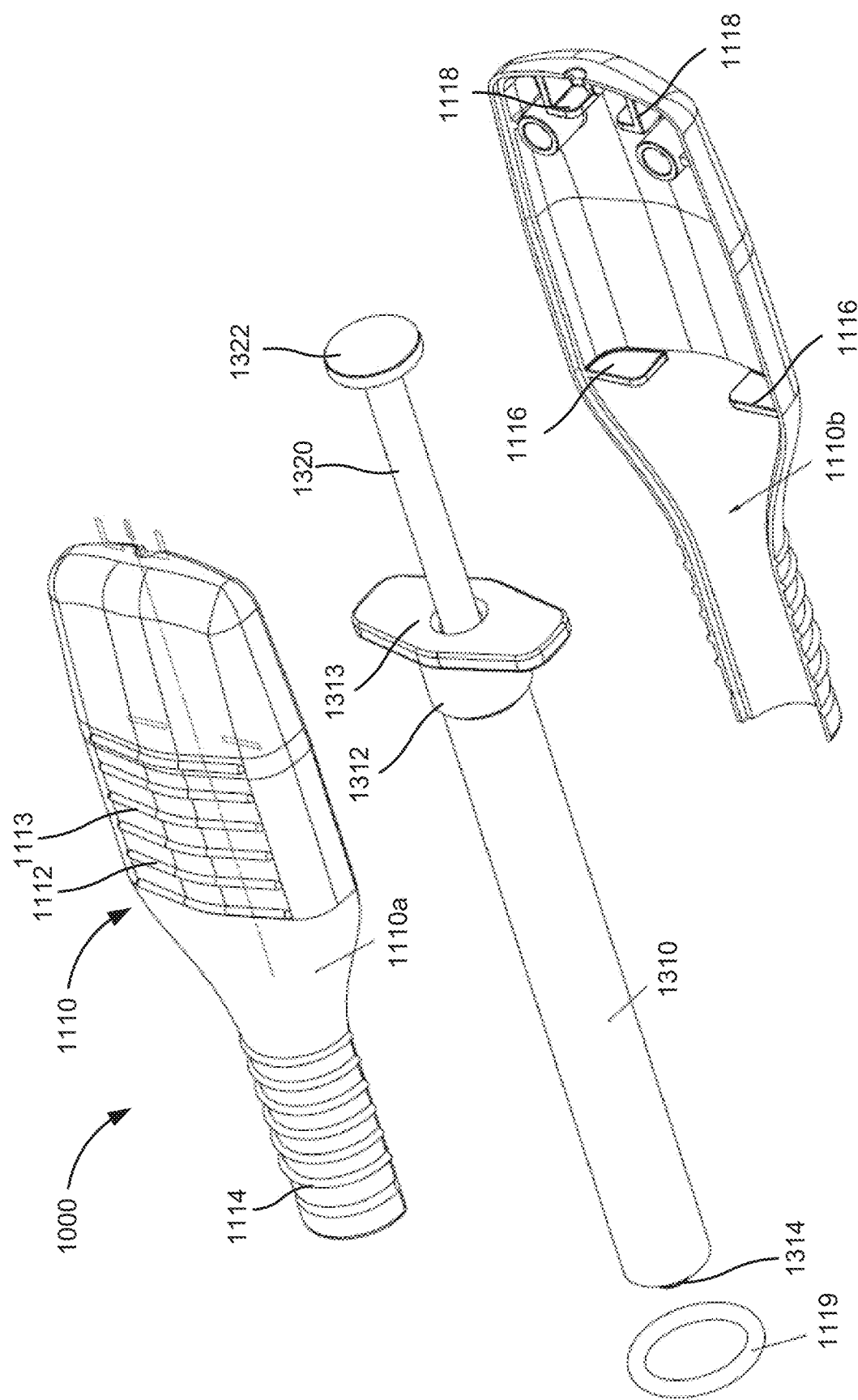
FIG. 8 is an exploded view of the system shown in FIG. 7.
Figure 9:
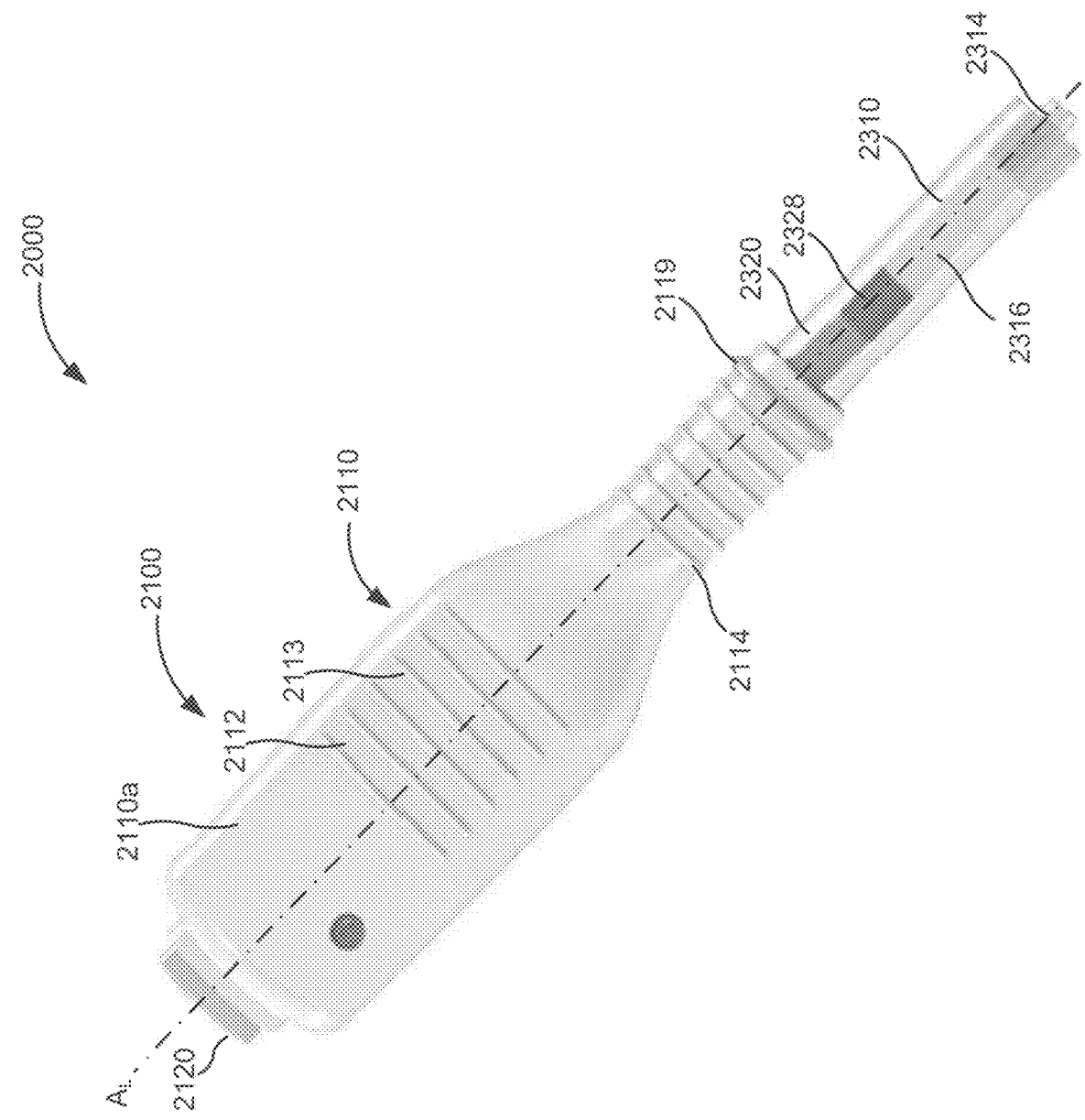
FIG. 9 is a perspective view of a system for delivering a medicament to an eye that includes an injector assembly, according to an embodiment.
Figure 10:
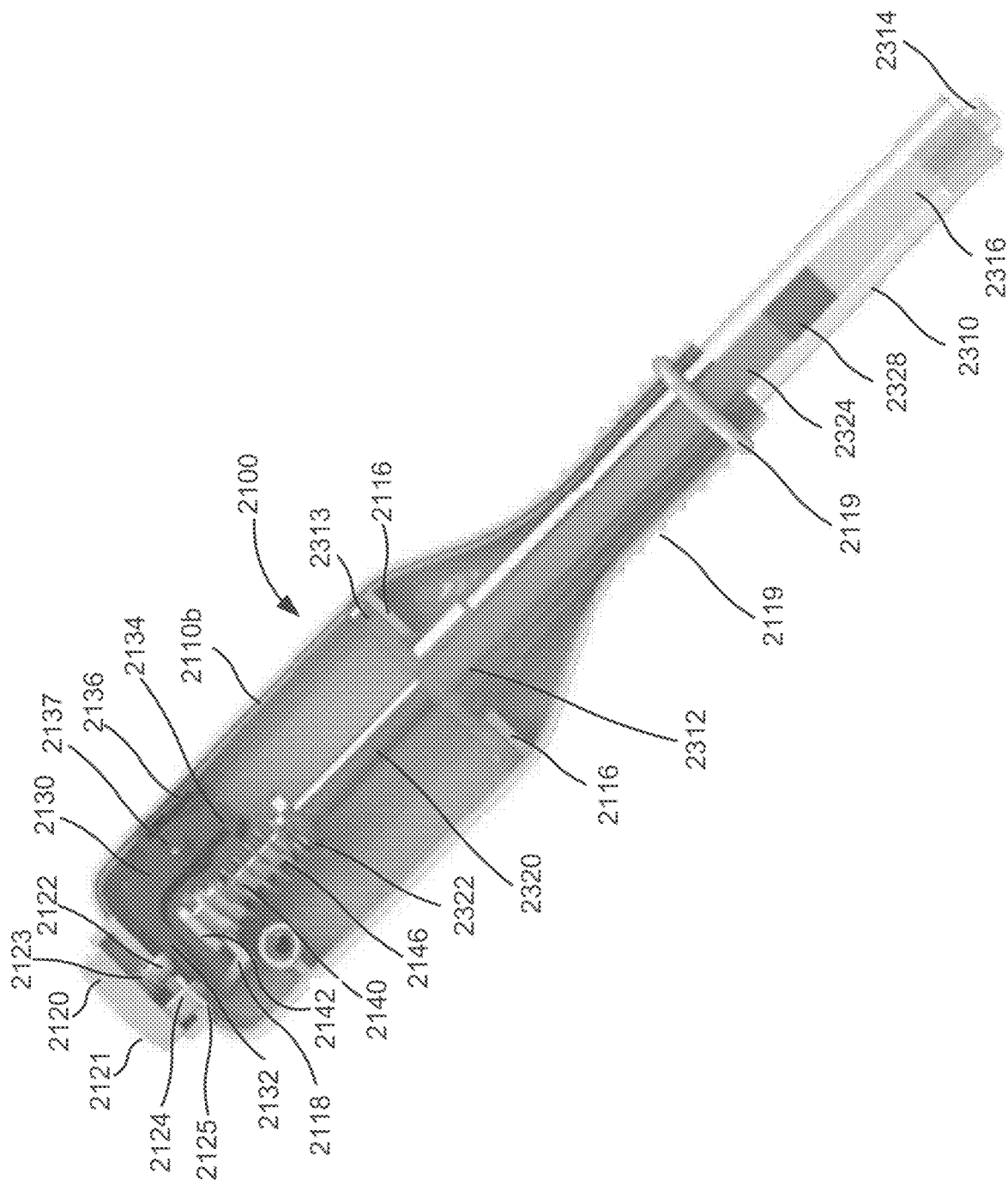
FIG. 10 shows the system of FIG. 9 with a first portion of a housing removed to show the injector assembly.
Figure 11:
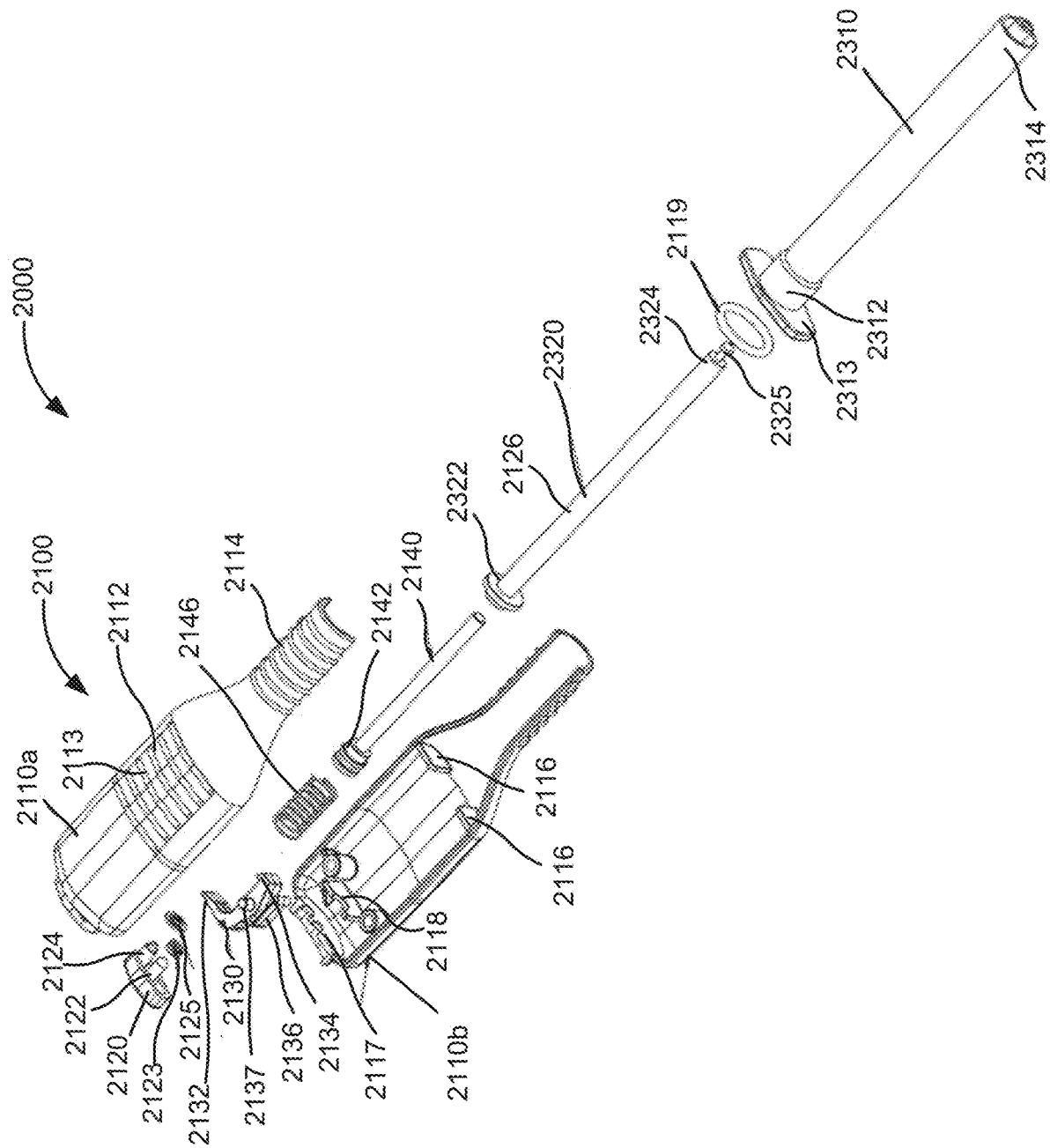
FIG. 11 shows an exploded view of the system of FIG. 10.
Figure 15:
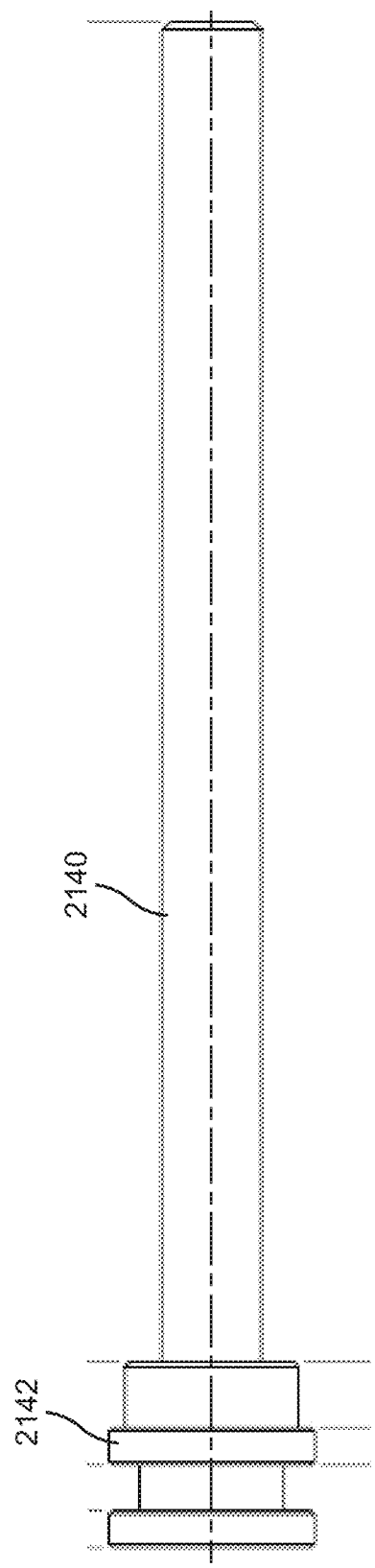
FIG. 15 shows a side view of a guide rod included in the system of FIG. 9.

In some embodiments, a system for ocular injection can include a medicament containment chamber at least a portion of which is disposed in a housing. Referring now to FIGS. 7-8, in some embodiments, a system 1000 includes at least a housing 1110, a medicament containment chamber 1310, and an actuator 1320. The system 1000 can be configured to deliver a medicament to a region and/or layer of an eye of a patient, for example, to the SCS of the eye.

The housing 1110 includes a first portion 1110a and a second portion 1110b, that can be coupled to define an internal volume for housing at least a portion of the medicament containment chamber 1310 and the actuator 1320. The first portion 1110a and the second portion 1110b can removably or fixedly coupled together using any suitable means, for examples, screws, nuts, bolts, rivets, adhesives, a snap-fit mechanism, notches, grooves, indents, lock, latch, or any other suitable coupling mechanism. The housing 1110 includes a gripping portion 1112. A plurality of ribs 1113 are disposed on the gripping portion 1112 to allow a user to easily grip the housing 1110, for example, between the user's index and/or middle finger, and thumb. A plurality of ridges 1114 are disposed on an outer surface of a distal portion of the housing 1110. The ridges 1114 can provide an additional gripping surface for the user to securely hold the housing 1110. For example, a user can grip the gripping portion 1112 with a first hand and grip the ridges 1114 with a second hand to limit any movement of the housing 1110 during injection of a medicament disposed in the medicament containment chamber 1310. A set of ribs (also referred to as sidewalls and/or protrusions) 1116 are disposed in the internal volume defined by the housing 1110. The ribs 1116 are configured to engage an engagement portion 1312 and/or a flange 1313 of the medicament containment chamber 1310, for example, to define a range of travel of the actuator 1320, as described herein. Similarly stated, the ribs 1116 are configured to limit movement of the actuator 1320 and/or the flange 1313 relative to the housing 1110 during use.

A set of mounts 1118 are disposed at a proximal end, within the interior region, of the housing. The mounts 1118 are configured to mount and/or retain an engagement portion 1322 of the actuator 1320, such that a linear translation of the housing 1110 along a longitudinal axis $A_L$ of the system 1000 urges the actuator 1320 to also translate along the longitudinal axis $A_L$ relative to the medicament containment chamber 1310. A securing member 1119 can be disposed over a distal end of the housing. The securing member 1119 can be a ring-like member formed from a relatively elastic material, for example, rubber, silicone, plastics, polymers, any other suitable material or combination thereof. The securing member 1119 can be configured to secure the first portion 1110a and the second portion 1110b of the housing 1110 to each other at a distal end of the housing 1110.

The medicament containment chamber 1310 defines an internal volume configured to house a medicament (e.g., triamcinolone acetonide, VEGF, VEGF inhibitor, or any other medicament described herein). The medicament containment chamber 1310 includes an engagement portion 1312 and a delivery portion 1314. The delivery portion 1314 can include any suitable coupling feature, for example, a luer connector, threads, a snap-fit, a latch, a lock, a friction fit coupling, or any other suitable coupling features. The coupling features can be configured to couple the delivery portion 1314 with a puncturing member (not shown), for example, a microneedle (e.g., a 27 gauge, a 30 gauge needle, or even smaller micro needle). The puncturing member can be any suitable puncturing member (such as those described in the '009 PCT application") configured to pierce a portion of a patient's body, for example, an eye, and to establish fluidic communication between the medicament containment chamber 1310 and the portion of the user's body (e.g., the eye).

The engagement portion 1312 is disposed proximate to the user and includes a flange 1313. The engagement portion 1312 is disposed in the housing 1110 such that the ribs 1116 are distal to the flange 1313, and interact with the flange 1313 to define a range of motion of the actuator 1320 and/or the medicament containment chamber 1310. In some embodiments, the medicament containment chamber 1310 can include a commercially available syringe such as, for example, a BD™ 1 CC syringe, or any other commercially available syringe.

The actuator 1320 includes an engagement portion 1322 and a plunger portion (not shown) movably disposed within the internal volume defined by the medicament containment chamber 1310. At least a portion of the actuator 1320 is slidably disposed in the internal volume defined by the medicament containment chamber 1310. Thus, the actuator 1320 can be displaced within the internal volume defined by the medicament containment chamber 1310 for drawing the medicament into or expelling the medicament from the internal volume defined by the medicament containment chamber 1310. The engagement portion 1322 is fixedly mounted in the mounts 1118 of the housing 1110. Thus, any linear displacement of the housing 1110 along the longitudinal axis $A_L$ of the system 1000 also urges the actuator 1320 to slide within the internal volume of the medicament containment chamber 1310.

In use, a user can grip the housing 1110, for example, at the gripping portion 1112 with one hand, and with the other hand grip a portion of the medicament containment chamber 1310 disposed outside the housing 1110. The user can then displace the housing 1110 relative to the medicament containment chamber 1310. Displacement of the housing 1110 also urges the actuator 1320 to slide within the internal volume defined by the medicament containment chamber 1310. The ribs 1116 can prevent the user from sliding the housing 1110 beyond a predetermined threshold to prevent the actuator 1320 from being separated from the medicament containment chamber 1310. Furthermore, the range of motion can also define a maximum dose of the medicament that can be drawn into the internal volume of the medicament containment chamber 1310. In this manner, the user can draw a medicament into the medicament containment chamber 1310, or inject the medicament into an ocular tissue, for example, the SCS of an eye.

In some embodiments, a system for injecting a medicament into ocular tissue can include an injector assembly configured to produce a force to assist in the delivery of a medicament. Referring now to FIG. 9 to FIGS. 16A-C, a system 2000 includes a housing 2110, an injector assembly 2100, a medicament containment chamber 2310, and an actuator 2320. The system 2000 can be configured to deliver a medicament to a desired layer and/or region of an eye of patient, for example, to the SCS of the eye.

The housing 2110 includes a first portion 2110a and a second portion 2110b, that can be coupled to define an internal region for housing the components of the injector assembly 2100 and at least a portion of the medicament containment chamber 2310 and/or the actuator 2320. The first portion 2110a and the second portion 2110b can removably or fixedly coupled together using any suitable means, for examples, screws, nuts, bolts, rivets, adhesives, a snap-fit mechanism, notches, grooves, indents, lock, latch, or any other suitable coupling mechanism. The housing 2110 includes a gripping portion 2112 A plurality of ribs 2113 are disposed on the gripping portion 2112 to allow a user to easily grip the housing 2110, for example, between the user's index and/or middle finger, and thumb. A plurality of ridges 2114 are also disposed on an outer surface of a distal portion of the housing 2110, for example to allow easy gripping of the housing 2110 by the user. For example, a user can grip the gripping portion 2112 with a first hand and grip the ridges 2114 with a second hand to limit any movement of the housing 2110 during injection of a medicament disposed in the medicament containment chamber 2310. A set of ribs 2116 are disposed in the internal region defined by the housing 2110. The ribs 2116 (also referred to as shoulders or protrusions) are configured to engage a flange 2313 included in an engagement portion 2312 of the medicament containment chamber 2310, for example, to define a range of travel of the actuator 2320 and/or the medicament containment chamber 2310, as described herein. A proximal end of the housing 2110 includes slots 2117 (see FIG. 11) configured to receive at least a portion of an actuating member 2120 included in the injector assembly 2100, as described herein. A set of mounts 2118 are disposed at a proximal end, within the interior region, of the housing. The mounts 2118, are configured to mount an engagement portion 2142 of a guide rod 2140 included in the injector assembly 2100. A securing member 2119 can be disposed over a distal end of the housing. The securing member 2119 can be a ring like member formed from a relatively elastic material, for example, rubber, silicone, plastics, polymers, any other suitable material or combination thereof. The securing member 2119 can be configured to secure the first portion 2110*a* and the second portion 2110*b* to each other at a distal end of the housing 2110.

The actuating member 2120 (FIGS. 12A-C) is disposed at the proximal end of the housing 2110 and is configured to actuate the injector assembly 2100, as described herein. The actuating member 2120 includes an engagement protrusion 2122 and a guide protrusion 2124. At least a portion of the engagement protrusion 2122 and the guide protrusion 2124 are slidably disposed in the slots 2117 (see FIG. 11). A user can engage an engagement surface 2121 of the actuating member 2120, and move the actuating member 2120 between a first configuration, in which the engagement protrusion 2122 and the guide protrusion 2124 are partially disposed within the internal volume defined by the housing 2110, and a second configuration, in which the engagement protrusion 2122 and the guide protrusion 2124 are substantially disposed within the internal volume defined by the housing 2110. Said another way, the actuating member 2120 can be moved relative to the housing 2110 between a first position (see FIG. 16D) and a second position (FIG. 16E).

Figure 16A:
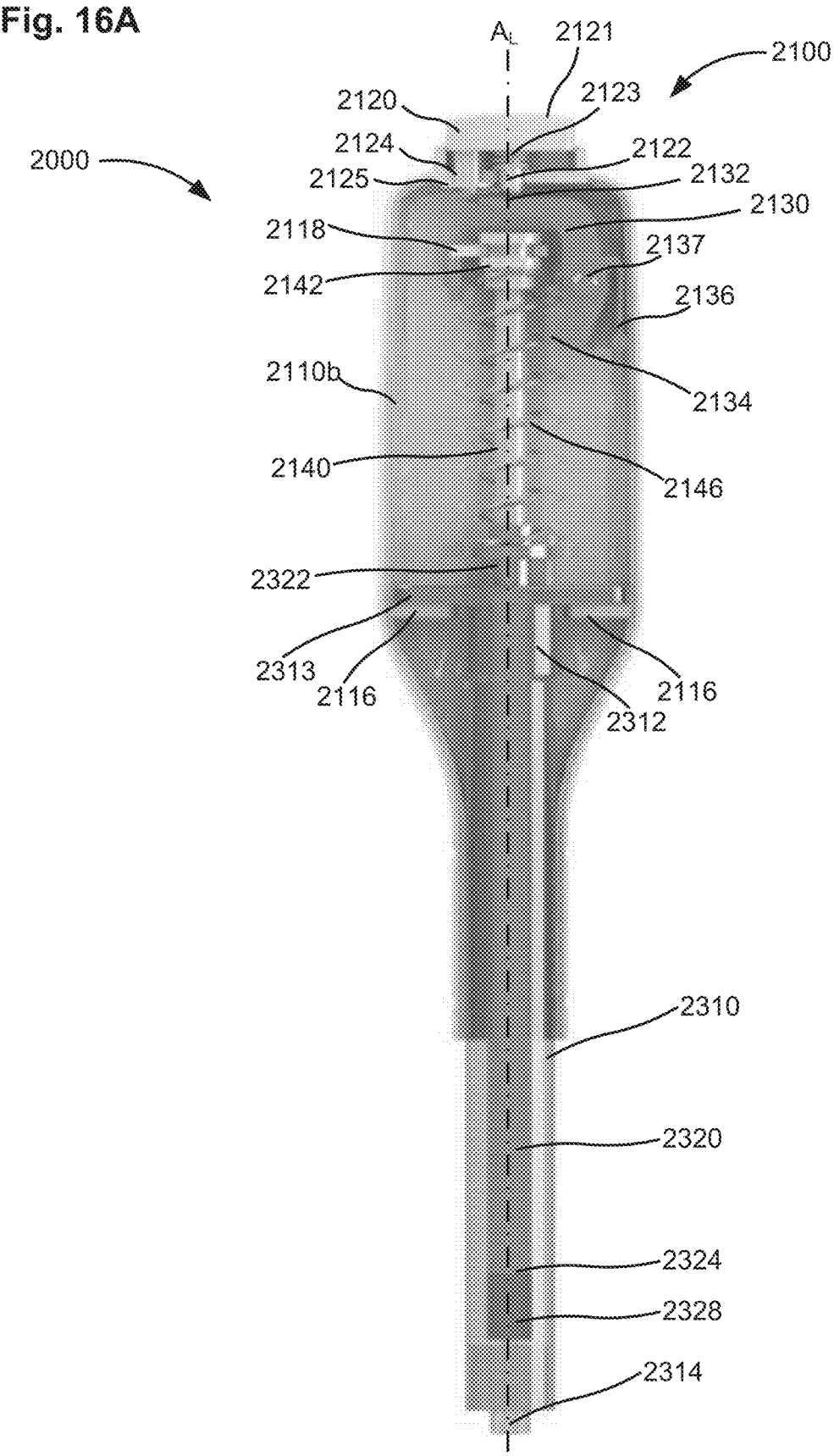
FIGS. 16A-E shows side views of the system of FIG. 9 with a first portion of the housing removed, the system shown in various states of operation.
Figure 16B:
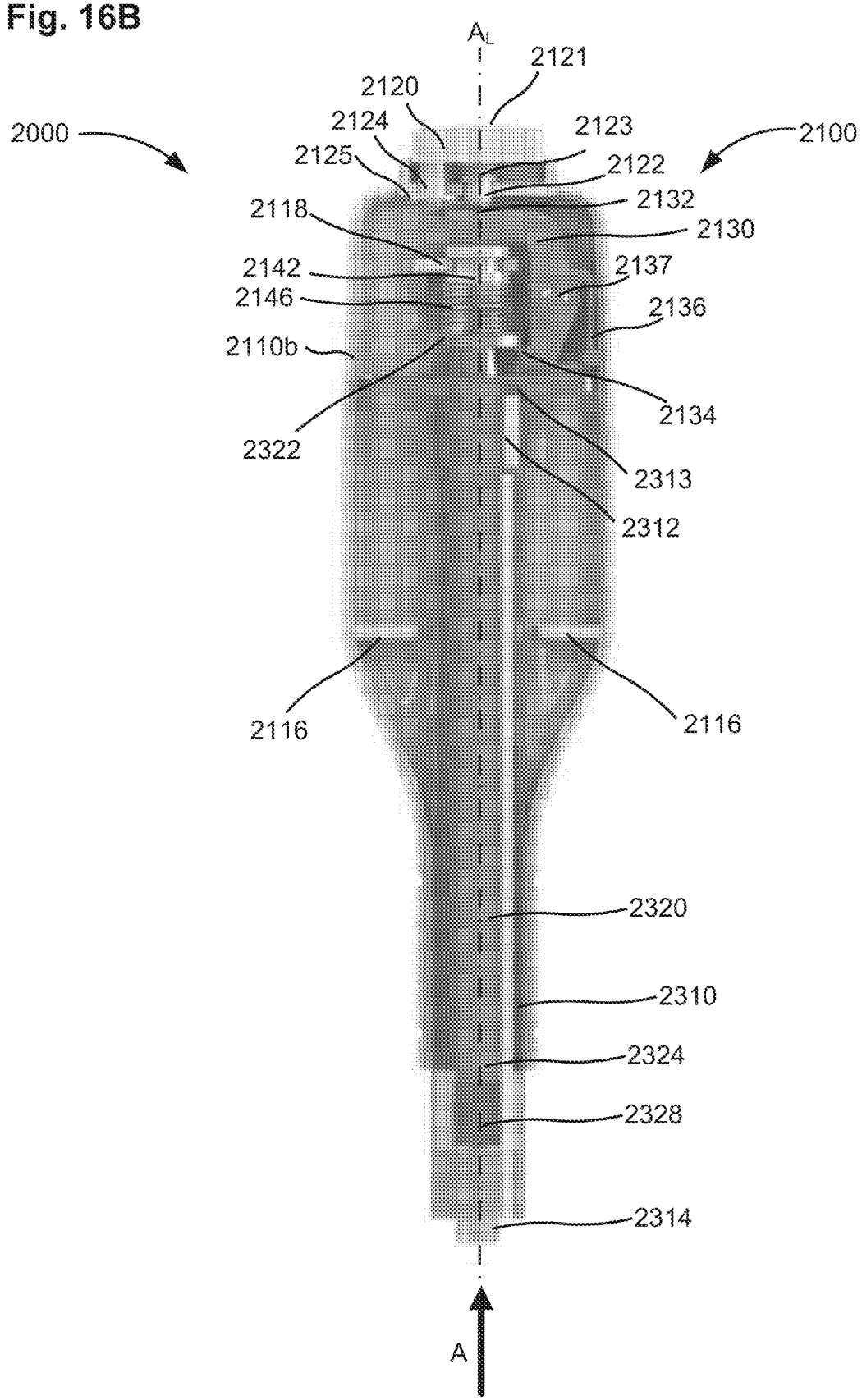
Figure 16C:
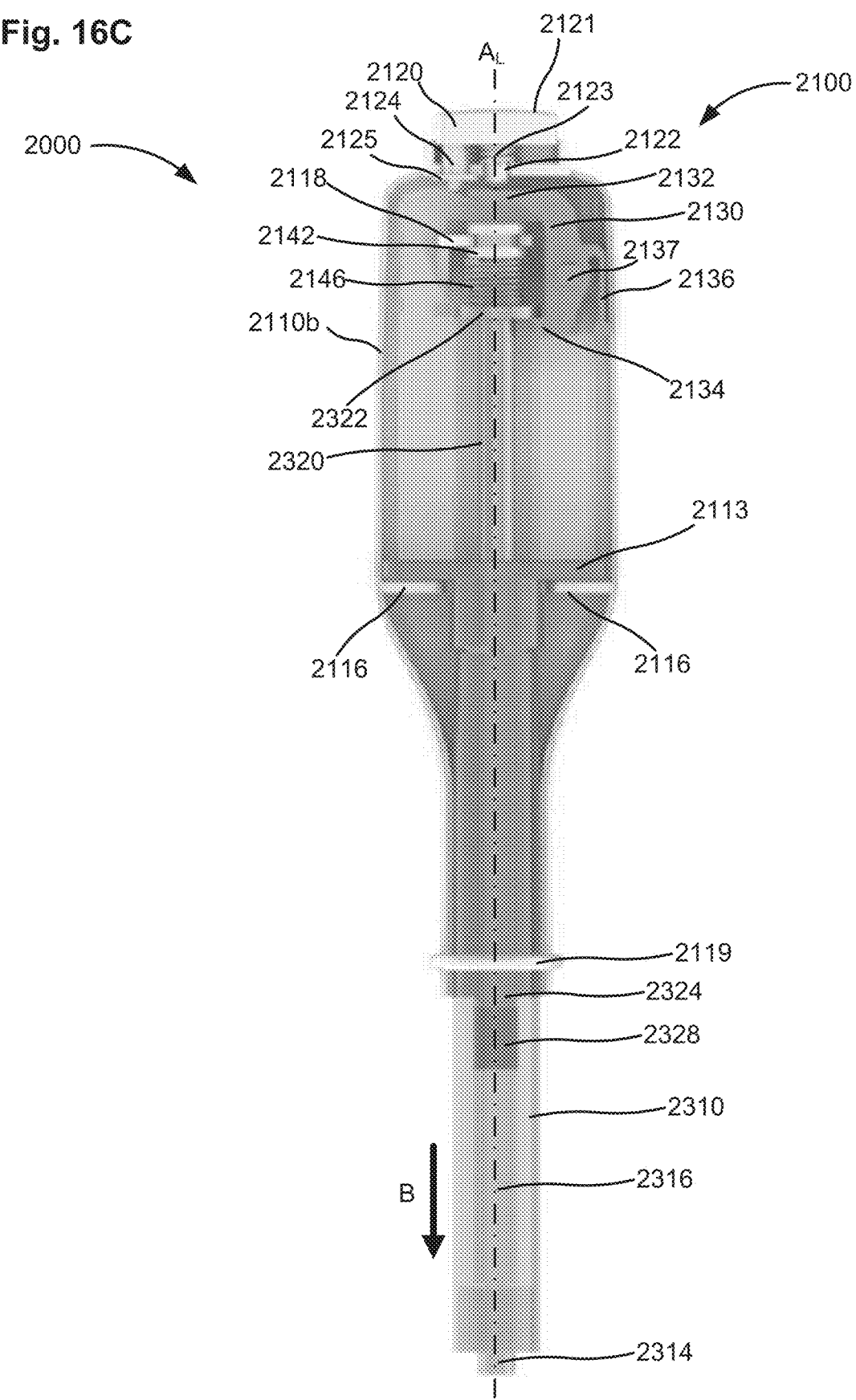
Figure 16D:
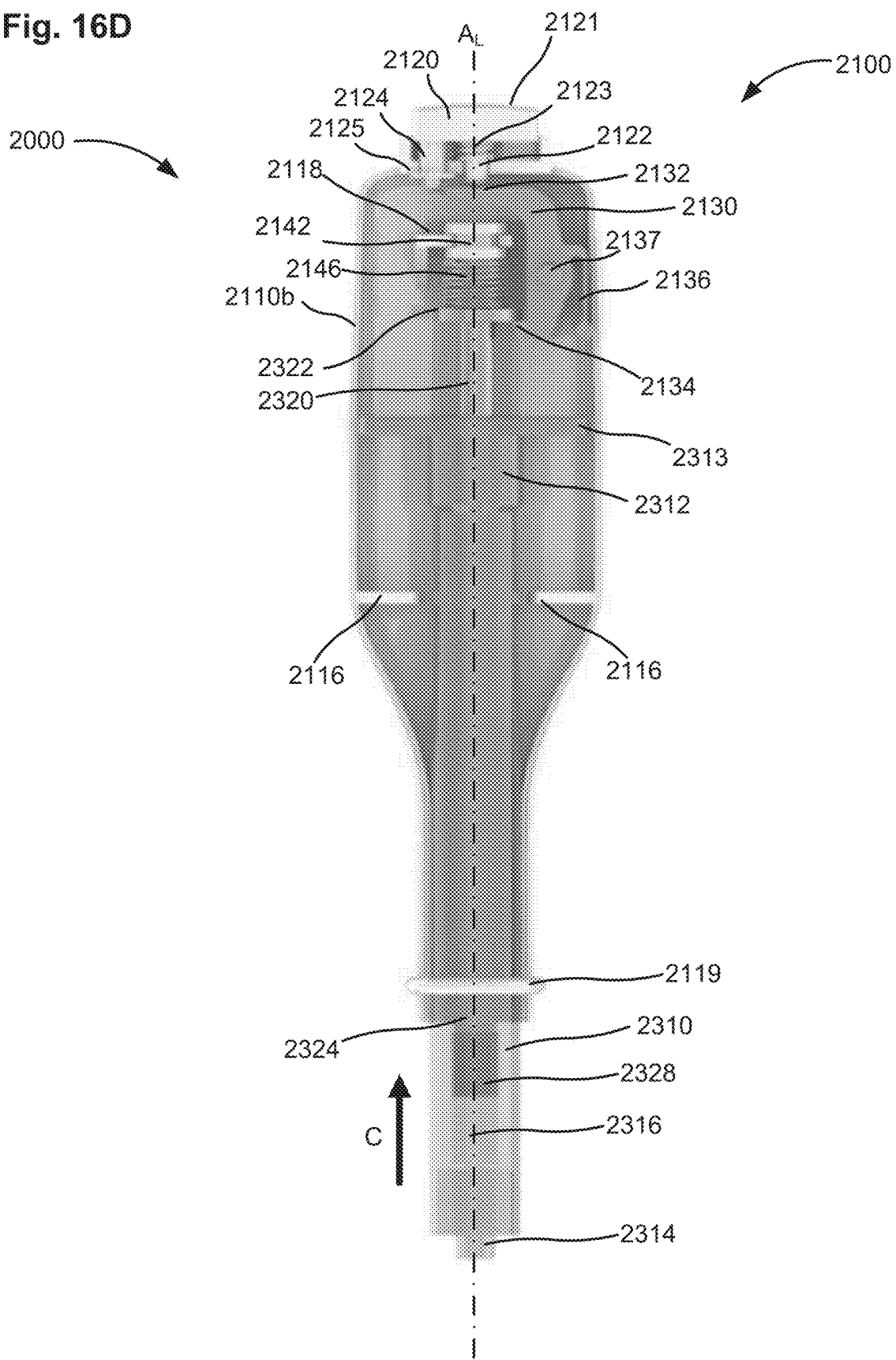
Figure 16E:
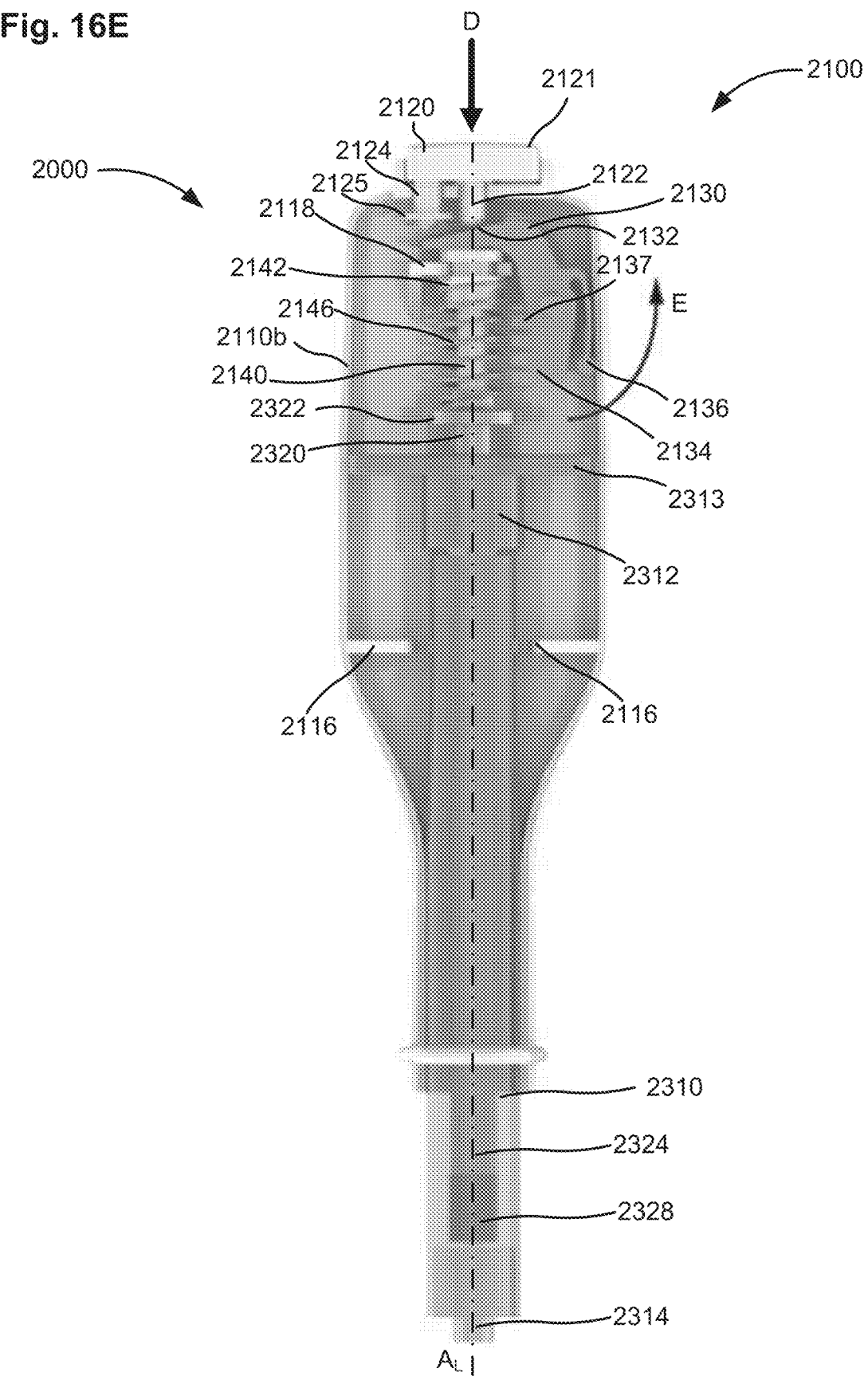

The engagement protrusion 2122 is configured to engage a pawl 2130 included in the injector assembly 2100 in the second configuration (or position), as described herein (see FIG. 16E). The guide protrusion 2124 is configured to slide within the slots 2117 along with the engagement protrusion 2122, to prevent any angular motion of the actuating member 2120 about the longitudinal axis $A_L$. A biasing member 2123, for example, a spring (e.g., helical spring, compression, extension, spring washers, Belleville washer, tapered, any other type of spring) is coupled to the engagement protrusion 2122, for example, disposed around the engagement protrusion 2122. The biasing member 2123 is configured to bias the actuating member 2120 in the first configuration (or position). A washer 2125 is coupled to a proximal end of the guide protrusion 2124 and is disposed inside the internal volume defined by the housing 2110. The washer 2125 has a diameter, or otherwise cross-section, which is substantially larger than the diameter or otherwise cross-section of the slots 2117, such that the washer 2125 prevents the actuating member 2120 from being removed from the housing 2100.

The pawl 2130 (FIGS. 13A-C) is disposed at the proximal end of the internal volume defined by the housing 2110. The pawl 2130 includes an engagement portion 2132, a latch 2134, and a biasing portion 2136. A set of protrusions 2137 are disposed on the pawl 2130. The protrusions 2137 are configured to pivotally mount the pawl 2130 in the internal volume defined by the housing 2110. This allows the pawl 2130 to rotate about the protrusions 2137 between a first configuration (or angular position) and a second configuration (or angular position) as described herein. The engagement portion 2132 defines a flat surface, which is configured to be engaged by the engagement protrusion 2122 of the actuating member 2120 (see e.g., FIG. 16E). More particularly, when the actuating member 2120 is moved from its first configuration (or position) to its second configuration (or position), the engagement protrusion 2122 can urge the pawl 2130 from the first configuration into the second configuration. The latch 2134 defines a ledge or shoulder configured to engage an engagement portion 2322 of the actuator (or push rod) 2320 in the first configuration, as described herein. The biasing portion 2136 includes a thin, beam-like structure configured to elastically bend in the second configuration. In this manner, the biasing member 2136 can urge the pawl 2130 into the first configuration, as described herein. For example, in the first configuration, the latch 2134 can engage the engagement portion 2322 of the actuator 2320 (see FIGS. 16B-16D) and the biasing portion 2136 can be in an extended position (i.e., maintaining the position of the pawl 2130). A user can engage the engagement portion 2121 of the actuating member 2120 and urge it into its second configuration (or position). In the second configuration of the actuating member 2120, the engagement protrusion 2122 can engage the engagement portion 2132 of the pawl 2130. This can urge the pawl 2130 to rotate about the protrusions 2137 and move into the second configuration. When the latch 2134 is in the second configuration, the latch 2134 can disengage from the engagement portion 2322 of the actuator 2320 such that the biasing portion 2136 is bent against the housing 2110 and is biased (or compressed). The user can then disengage the actuating member 2120. The biasing member 2123 coupled to the engagement protrusion 2122 can urge the actuating member 2120 back into the first configuration. This disengages the engagement protrusion 2122 from the engagement surface 2132 of the pawl 2130 such that the biasing portion 2136 can urge the pawl 2130 into the first configuration.

The guide rod 2140 (FIG. 15) includes a mounting portion 2142 that is immovably mounted on the mounts 2118 included in the housing 2110. Similarly stated, the guide rod 2140 is coupled within the housing 2110 such that movement (distal movement and proximal movement) is limited. At least a portion of the guide rod 2140 is disposed in a cavity 2326 defined within the actuator 2320. The guide 2140 rod is configured to prevent lateral motion of the actuator 2320 when the actuator 2320 slides in a linear direction along the longitudinal axis $A_L$ of the system 2000 within the housing 2110, as described in further detail herein. The guide rod 2140 also couples a biasing member 2146 (or energy storage member which is disposed around the guide rod 2140, see e.g. FIG. 16A) between the mounts 2118 and the actuator (or push rod) 2320. The biasing member 2146 can include, for example, a spring, (e.g., a helical spring, compression, extension, spring washers, Belleville washer, tapered, any other type of spring), any other suitable biasing member or combination thereof. A proximal end of the biasing member 2146 is coupled to and/or engaged with the mounting portion 2142 of the guide rod 2140, and a distal end of the biasing member 2146 is coupled to and/or engaged with the engagement portion 2322 of the actuator 2320. The biasing member 2146 is configured to bias the actuator 2320 when the engagement portion 2322 of the actuator 2320 is disposed relative to the mounting portion 2142 of the guide rod 2140 in the "readied" position (see e.g., FIGS. 16B-16D). In this manner, the biasing member 2146 can exert a predetermined biasing force on the actuator 2320 to enable or otherwise assist the actuator 2320 to expel a medicament from the medicament containment chamber 2310, as described in further detail herein.

The medicament containment chamber 2310 defines an internal volume 2316 configured to house a medicament (e.g., a VEGF, a VEGF inhibitor, triamcinolone acetonide, any other medicament described herein or a combination thereof). The medicament containment chamber 2310 includes an engagement portion 2312 and a delivery portion 2314. The delivery portion 2314 can include coupling features, for example, luer connectors, threads, snap-fit, latch, lock, friction fit, or any other suitable coupling features. The coupling features can be configured to couple the delivery portion 2314 with a puncturing member (not shown), for example, a microneedle (e.g., a 27 gage, or 30 gage, or even smaller needle). The puncturing member can be any suitable puncturing member (such as those described in the '009 PCT application) which is configured to pierce a portion of a patient's body, for example, an eye, and to establish fluidic communication between the medicament containment chamber 2310 and the portion of the user's body (e.g., the eye). The engagement portion 2312 includes a flange 2313. The engagement portion 2312 is disposed in the housing 2110 such that the ribs 2116 are distal to the flange 2313, and interact with the flange 2313 to define a range of motion of the actuator 2320 and/or the medicament containment chamber 2310. Said another way, the ribs 2116 and the flange 2313 can serve in combination as a locking mechanism to prevent the medicament containment chamber 2310 from moving beyond a threshold distance within the housing 2110. In some embodiments, the medicament containment chamber 2310 can include a commercially available syringe such as, for example, a BD™ 1CC syringe, or any other commercially available syringe.

The actuator (or actuation rod) 2320 (FIGS. 14A-B) includes an engagement portion 2322 and a plunger portion 2324. As described before, the engagement portion 2322 defines a cavity 2326 configured to receive at least a portion of the guide rod 2140. A proximal end of the engagement portion 2322 is coupled to and/or engaged with the biasing member 2146, as described before herein. At least a portion of the actuator 2320, for example, the plunger portion 2324, is slidably disposed in the internal volume 2316 defined by the medicament containment chamber 2310. Thus, the actuator 2320 can be displaced within the internal volume 2316 for drawing and/or expelling the medicament from the internal volume 2316 defined by the medicament containment chamber 2310.

As shown in FIGS. 14A and 14B, a protrusion 2325 is disposed at a distal end of the plunger portion 2324. The protrusion 2325 is configured to be inserted into a plug 2328 with close tolerance (e.g., friction-fit). The plug 2328 can be slidably disposed in the internal volume 2316 of the medicament containment chamber 2310. A distal end of the plug 2328 can be in fluid communication with the medicament disposed in the internal volume 2316 defined by the medicament containment chamber 2310. The sidewalls of the plug 2328 can be in contact with the sidewalls of the internal volume 2316 such that the plug forms a fluid tight seal to prevent leakage of the medicament. The plug 2328 can be made of an inert and/or biocompatible which is rigid but soft. Example materials include rubber, silicone, plastic, polymers, any other suitable material or combination thereof.

The injector assembly 2100 is configured to produce a force to inject or otherwise assist in injecting the medicament from the medicament containment chamber 2310 into the ocular tissue, for example, the SCS. Furthermore, the injector assembly 2100 can be configured to exert a predetermined force and/or a force within a desired range on the actuator 2320 sufficient to expel the medicament only when an outlet of a puncturing member (e.g., a needle such as a 27 gauge, a 30 gauge or any needle described herein) is within or otherwise near the target injection site, for example, the SCS. Similarly stated, the injector assembly 2100 can be configured to exert a predetermined force on the actuator (or push rod) 2320 and/or the plug 2328 such that the actuator 2320 and/or the plug 2328 move when the backpressure against the opening of a delivery member (e.g., a puncture member or needle, not shown) is below a desired level. As described below, the amount of backpressure against the delivery member can be a function of the tissue characteristics of the target tissue (e.g., tissue density, presence of voids, tissue type, etc.). Thus, the injector assembly 2100 can produce motive force when the opening of the delivery member is within a desired target location (e.g., the SCS). FIGS. 16A to 16E show the system 2000 that includes the injector assembly in various states of operation as described herein.

In a first state shown in FIG. 16A, a portion of the medicament containment chamber 2310 is disposed in the housing 2110 of the injector assembly 2100. The flange 2313 of the medicament containment chamber 2310 can be contiguous and/or in contact with the ribs 2116 of the housing 2110. The actuator 2320 is pushed into the medicament containment chamber 2310 such that the plunger portion 2324 of the actuator 2320 occupies substantially all of the internal volume 2316 of the medicament containment chamber 2310 and there is no medicament in the internal volume 2316. Additionally, the guide rode 2140 is disposed in a first relative position within the actuator (or push rod) 2320. In the first state, the biasing member 2146 is coupled to the engagement portion 2322 of the actuator 2320 and is unbiased (or in an expanded configuration). Said another way, the system 2000 is unarmed in the first state. Thus, in the first state (or configuration), the system 2000 can be shipped, stored or the like.

To move the system 2000 to the second state shown in FIG. 16B, the user moves the medicament containment chamber 2310 proximally relative to the injector assembly 2100. This can be achieved by applying a force on the housing 2110 and/or the medicament containment chamber 2310 such that the force pushes the medicament containment chamber 2310 into the housing 2110 in the direction shown by the arrow A. The housing 2110 is shaped and sized to prevent any rotational motion of the medicament containment chamber 2310 relative to the housing 2110. Motion of medicament containment chamber 2130 relative to the injector assembly 2100, also urges the actuator 2320 to slide over the guide rod 2140 and move relative to the injector assembly 2100. Thus, when the injector assembly 2100 is in the second state, the guide rod 2140 is disposed in a second relative position within the actuator (or push rod) 2320. Furthermore, the biasing member 2146 is biased (or compressed) when the injector assembly 2100 is in the second state. The force is maintained until the latch 2134 of the pawl 2130 engages and secures the engagement portion 2322 of the actuator 2320. The pawl 2130 includes an angled surface such that the engagement portion 2322 can slide past the latch 2134 in a proximal direction but cannot move past the latch 2134 in a distal direction. Thus, in the second state, the system 2000 is "armed" and is ready to be filled with a medicament.

The user can now couple a transfer needle, puncture member and/or delivery member (not shown) to the delivery portion 2314 of the medicament containment chamber 2310. The puncturing member can be inserted into a container of the medicament, for example, inserted through a septum of a vial containing the medicament. The system 2000 can then be moved into a third state (or configuration) to fill the medicament containment chamber 2310 with a substance. To move the injector assembly 2100 to the third state shown in FIG. 16C, a force can be applied on the medicament containment chamber 2310 and/or the housing 2110 to move the medicament containment chamber 2310 distally relative to the injector assembly 2100 in the direction shown by the arrow B. In this manner, the medicament containment chamber 2310 is drawn out of (moved distally relative to) the housing 2110. The engagement portion 2322 of the actuator 2320 remains secured by the latch 2134 of the pawl 2130 in the third state. Therefore, the relative motion of the medicament containment chamber 2310 to the housing 2110 urges the plunger portion 2324 of the actuator 2320 to slide within the internal volume 2316 of the medicament containment chamber 2310 until the plunger portion 2324 is proximate to the engagement portion 2312 of the medicament containment chamber 2310. The displacement of the actuator 2320 and the plug 2328 creates a suction force within the internal volume 2316 of the medicament containment chamber 2310, which draws the medicament into the internal volume 2316.

To place the injector assembly 2100 in a fourth state (shown in FIG. 16D), the user can move the medicament containment chamber 2310 proximally relative to the injector assembly 2100 such that the medicament containment chamber 2310 moves into the housing 2110 as shown by the arrow C. In the fourth state, the medicament containment chamber 2310 is partially drawn into the housing 2110. Since the actuator 2320 is still secured by the pawl 2130 in the fourth state, moving the housing 2310 urges the plunger portion 2324 of the actuator 2320 (and thus the plug 2328) to also slide in the internal volume 2316 proximally relative to the medicament containment chamber 2310. In this manner, the plunger portion 2324 of the actuator 2320 expels a portion of the medicament from the internal volume 2316. Said another way, the user can expel air from the internal volume 2316 and/or adjust a dose of the medicament in the fourth state.

Prior to injecting the medicament (i.e., moving the injector assembly 2000 to a fifth state shown in FIG. 16E), a puncturing member (e.g., a 27 gauge needle, a 30 gauge needle, or any other puncturing members described herein), or a needle assembly (e.g., the needle assembly 3200 or any other needle assembly described herein) can be coupled to the delivery portion 2314 of the medicament containment chamber 2310. While not shown, a hub can also be coupled to the delivery portion 2314, which is configured to contact an ocular tissue. The hub can include a hub that includes a convex distal end, a flat distal end, features for aligning the system 2000 on a surface (e.g., conjunctiva) of the eye, or any other hub described herein. For example, in some embodiments, the hub can include a convex distal end surface configured to form a substantially fluid-tight seal with a target surface around the insertion site (see e.g., hub 7270 included in the medical injector 7000).

The user can insert the puncturing member into an eye, until an outlet of the puncturing member is in or otherwise near a target delivery layer, for example, the SCS. The user can manually adjust the insertion depth of the puncturing member or a needle assembly to increase or decrease the insertion depth of the puncturing member (e.g., as described in further detail with reference to needle assembly 3200). To initiate injection (i.e., to move the injector assembly 2100 to the fifth configuration), the user can then exert a force on the engagement surface 2121 of the actuating member 2120 in the direction shown by the arrow D. This urges the engagement protrusion 2122 to slide in the slot 2117 distally to the user into the housing 2110 and engage the engagement surface 2132 of the pawl 2130. The engagement protrusion 2122 can urge the pawl 2130 to rotate about the protrusions 2137, such the biasing portion 2136 is biased and the latch 2134 disengages from the engagement portion 2322 of the actuator 2320. The biasing member 2146 exerts a force on the engagement portion 2322 of the actuator 2320 and urges the actuator 2320 to displace proximally relative to the medicament containment chamber 2310. Thus, the plunger portion 2324 of the actuator slides an injection distance within the internal volume 2316 of the medicament containment chamber 2310 and expels the medicament into the eye via the puncturing member. The housing 2110 and/or the medicament containment chamber 2310 can be configured to prevent the housing 2110 from displacing distally relative to the medicament containment chamber 2310 in the fifth state. For example, in some embodiments, the flange 2313 of the medicament containment chamber 2310 and/or an inner surface of the housing 2110 can have a high friction surface. The flange 2313 and the inner surface of the housing 2110 can contact each other to yield a high friction interface which can prevent the housing 2110 from displacing distally relative to the medicament containment chamber 2310 in the fifth state. In some embodiments, notches, grooves, indents, or any other features can be defined in the internal volume of the housing 2110, and/or the flange 2313. In some embodiments, a locking mechanism, for example, a twist lock mechanism, a push pin, a latch, a ledge, or any other suitable locking mechanism can be included in the housing 2110. In such embodiments, the user can engage the locking mechanism (e.g., twist the housing 2110 relative to the medicament containment chamber 2310, depress a pin, etc.) such that the housing 2110 can be prevented from displacing distally relative to the medicament containment chamber 2310 in the fifth state. In this manner, the force exerted by the biasing member 2146 is applied to move the actuator (or actuation rod) 2320 distally relative to (and/or within) the medicament containment chamber 2310, as opposed to being applied to move the entirety of the medicament containment chamber 2310 relative to the housing 2110.

In some embodiments, the injector assembly 2100 can be used as an injection-assist assembly to enable a user to inject the medicament into a desired tissue of the eye, for example, the SCS. In such embodiments, the biasing member 2146 can be configured to exert a predetermined force on the actuator 2320, for example a force of less than about 6N, less than about 5 N, less than about 4N, less than about 3 N, or less than about 2 N, inclusive of all ranges therebetween. The force can be sufficient to expel the medicament from the medicament containment chamber 2310 when the backpressure, existing or applied at an outlet of the puncturing member, is below a certain threshold. As described before herein, different layers of the eye can have different densities, for example, the sclera is much denser then the SCS. Therefore, a puncturing member inserted into the sclera will experience a much higher backpressure than a puncturing member near or within the SCS. The biasing member 2146 can be configured to exert a force, which is only sufficient to overcome the backpressure experienced in the target layer, for example, the SCS, but is not sufficient to overcome the backpressure of any other layer, for example, the sclera. In this manner, the biasing member 2146 urges the actuator 2320 to expel the medicament only into the target layer, for example, the SCS. The backpressure experienced by the actuator can vary based on the medicament used, the size of the puncturing member, the target ocular tissue layer, and/or thickness of the target layer. If the force delivered by the biasing member 2146 is too high, injection can occur in the incorrect target layer, for example, the sclera. Conversely, if the biasing force is too small, injection might not occur even when the outlet of the puncturing member is within or near the target layer, for example, the SCS. To overcome this, the biasing member 2146 can be tailored based on the medicament used, the needle size, the size of the medicament containment chamber 2310, the actuator 230, and/or target layer. In some embodiments, the actuator 2320 and the medicament containment chamber 2310 can be collectively configured such that the force exerted by the biasing member 2146 produces an injection pressure within the internal volume 2316 of the medicament containment chamber 2310 of between about 100 kPa and about 500 kPa. For example, the system 2000 can be configured such that the same injection pressure is produced within the medicament containment chamber 2310, regardless of the size (e.g., diameter or otherwise cross-section) of the medicament containment chamber 2310 and/or the actuator 2320, the material of the actuator 2320 or the medicament containment chamber 2310, the volume of the medicament, the viscosity of the medicament, and/or the size of the puncture member. In some embodiments, the pressure produced in the medicament containment chamber 2310 can be about 100 kPa, 110 kPa, 120 kPa, 130 kPa, 140 kPa, 150 kPa, 160 kPa, 170 kPa, 180 kPa, 190 kPa, 200 kPa, 220 kPa, 240 kPa, 260 kPa, 280 kPa, 300 kPa, 320 kPa, 340 kPa, 360 kPa, 380 kPa, 400 kPa, 420 kPa, 440 kPa, 460 kPa, or about 480 kPa, inclusive of all ranges and values therebetween.

Furthermore, in some embodiments, the injector assembly 2100 can also be used to inform the user when the puncturing member is within or near the target layer. For example, the housing 2110 can be transparent such that the user can see the actuator 2320 and/or the medicament containment chamber 2310. The user can insert the puncturing member into the eye and engage the actuating member 2120 such that the latch 2134 disengages the engagement portion 2322 of the actuator 2320. If the puncturing member is within or near the target layer, for example, the SCS, the biasing member 2146 overcomes the backpressure exerted by the target layer and displaces the actuator 2320 to move the injection distance and initiate injection of the medicament into the target layer. The user can visibly observe the actuator 2320 and/or the plug 2328 displacing within the housing 2110 and can be informed that the puncturing member is within or otherwise near the target layer, for example, the SCS. If the puncturing member is in a layer other than the target layer, for example, the sclera, the biasing member 2146 will not overcome the backpressure of the other layer and the actuator 2320 will not displace proximally relative to the medicament containment chamber 2310. This can inform the user that the puncturing member is not within or near the target layer. The user can then manipulate the puncturing member to reach within or near the target layer and initiate injection of the medicament. In some embodiments, any other communication mechanism, for example, audible alarm, LED light, a message, a display, a tactile alert, or any other communication mechanism can be used to inform the user about the location of the puncturing member. In some embodiments, the biasing member 2146 can be configured to exert a force sufficient to expel substantially all of the medicament into the target layer, for example, the SCS. In some embodiments, the biasing member 2146 can be configured to exert a force sufficient to initiate injection but not enough to expel all of the medicament into the target layer. In such embodiments, the injection distance can be a first injection distance. Once the injection is initiated, the user can then move the injection assembly 2100 and thereby the actuator 2320 a second injection distance proximally relative to the medicament containment chamber 2310. In this manner, the remaining medicament can be delivered to the target layer of the eye.

Figure 17:
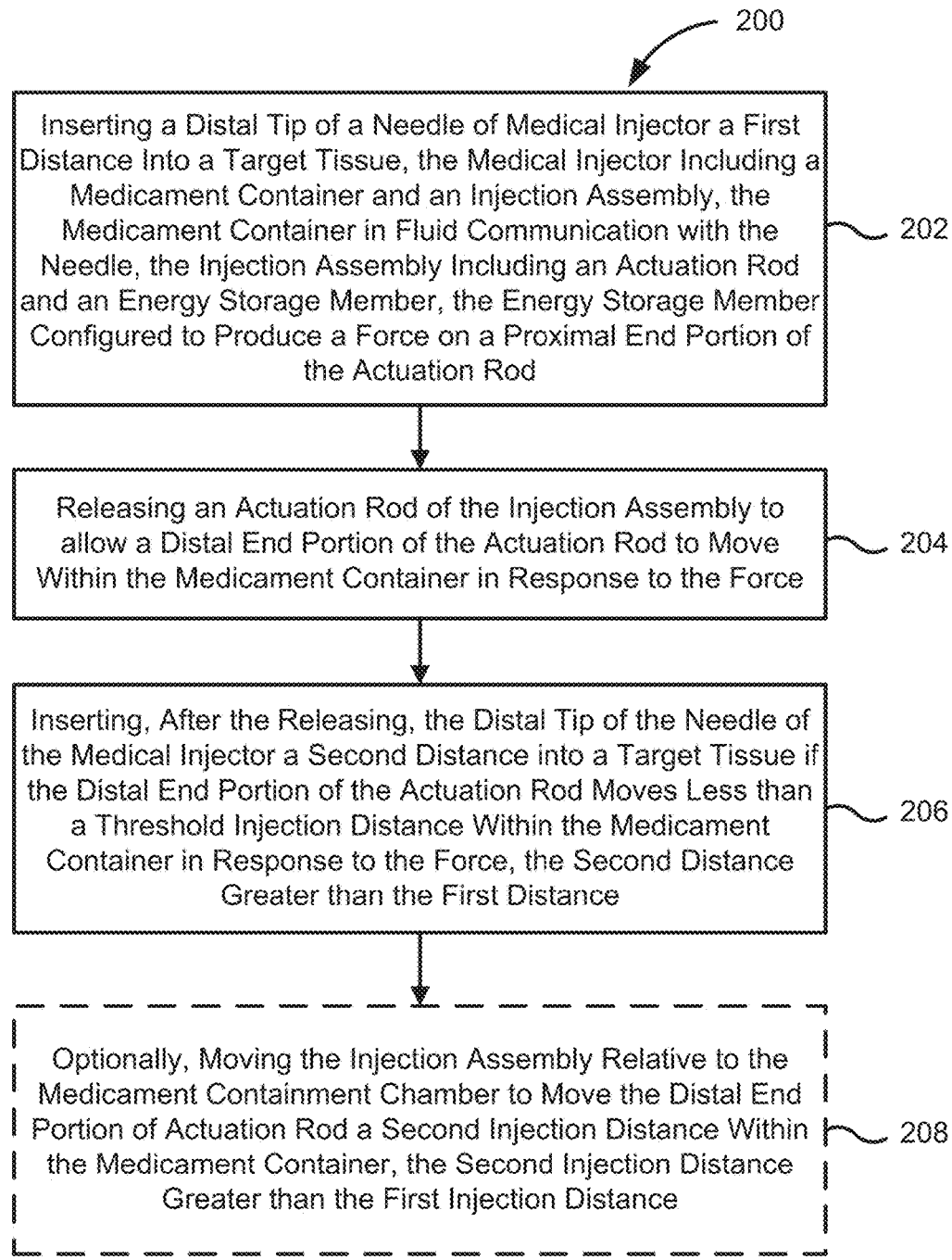
FIG. 17 show a flow diagram of a method for determining the insertion depth in a target tissue of a needle included in a medicament delivery device using an injection assembly, according to an embodiment.

FIG. 17 shows a schematic flow diagram of a method 200 of delivering a medicament to a target layer of a target tissue (or at a predetermined distance within the target tissue) using a medical injector that includes an injection assembly. The method 200 includes inserting a distal tip of a needle of a medical injector (e.g., the system 100, 1000, 2000, or any other system described herein) a first distance into a target tissue, at 202. The needle can include any suitable needle, for example, the needle 140 or any other needle described herein. The medical injector includes a medicament container (e.g., the medicament container 130, 1310, 2310, or any other medicament container described herein) and an injection assembly (e.g., the injection assembly 111, 2100, or any other injection assembly described herein). The medicament container is in fluid communication with the needle. The injection assembly includes an actuation rod (e.g., the actuation rod 120, the actuator 2320, or any other actuator described herein) and an energy storage member (e.g., the energy storage member 146, 2146, or any other energy storage member described herein). The energy storage member is configured to produce a force on a proximal end portion of the actuation rod.

The method 200 further includes releasing the actuation rod of the injection assembly allowing a distal end portion of the actuation rod to move within the medicament container in response to the force, at 204. For example, a proximal end portion of the actuation rod can be secured or otherwise engaged by a release member, for example, a pawl (e.g., the pawl 2130) or any other release member described herein. The release member can, for example, be moved from a first position in which the actuation rod is secured to a second position in which the actuation rod is released. As described herein, in certain situations the force will be insufficient to overcome the viscous forces, tissue backpressure, frictional losses or the like within the fluid delivery path defined by the medicament container, the needle and the target tissue when the needle at the first distance within the tissue. Thus, the actuation rod may not move, or may move less than a threshold "injection distance."

Accordingly, the distal tip of the needle included in the medical injector can be inserted, after the releasing, a second distance greater than the first distance into the target tissue (e.g., the ocular tissue of an eye) if the distal end portion of the actuation rod moves less than a threshold injection distance within the medicament container in response to the force, at 206. The injection distance can be a distance that the distal end portion of the actuation rod moves within the medicament container after the releasing. In some embodiments, the injection distance is less than about 1 cm. In this manner, the lack of movement and/or the limited movement of the actuation rod in operation 204 provides an indication to the user that additional movement and/or repositioning of the needle tip is desirable. Conversely, when the distal end portion of the actuation rod moves through the injection distance within the medicament container, the user is aware that the needle tip is in a suitable region of the target tissue.

In some embodiments, the distal end portion of the actuation rod can move a first injection distance within the medicament container in response to the force, for example, to deliver a portion of the medicament to the target tissue, for example, the SCS. In such embodiments, the method 200 can further include moving the injection assembly relative to the medicament container to move the distal end portion of the actuation rod a second injection distance greater than the first injection distance within the medicament container 208. For example, the force can move the actuation rod the first injection distance once the distal tip of the needle is disposed within or near a desired region of the target tissue. This can indicate to a user that the distal tip of the needle is disposed within or near a desired region of the target tissue. The actuation rod can then be moved proximally relative to the medicament container such that the actuation rod moves the second injection distance within the medicament container. In some embodiments, the distal end portion of the actuation rod can be moved the second injection distance manually by a user, for example, by moving the housing proximally to the medicament container. In other embodiments, the medical injector can include an automated delivery mechanism (e.g., a mechanical actuator, a pump, or any other suitable automated delivery mechanism) configured to move the actuation rod the second injection distance and deliver substantially all of the medicament to the target tissue.

In some embodiments, the target tissue can be an eye. In such embodiments, the inserting of the distal tip of the needle of the medical injector the second distance into the eye includes inserting at least a portion of the distal tip into a suprachoroidal space of the eye. In some embodiments, inserting the distal tip of needle of the medical injector the second distance includes contacting a surface of the eye with a hub coupled to the needle. The hub can include the hub 7270, 8270, 9270 or any other hub described herein in further detail below.

Figure 18:
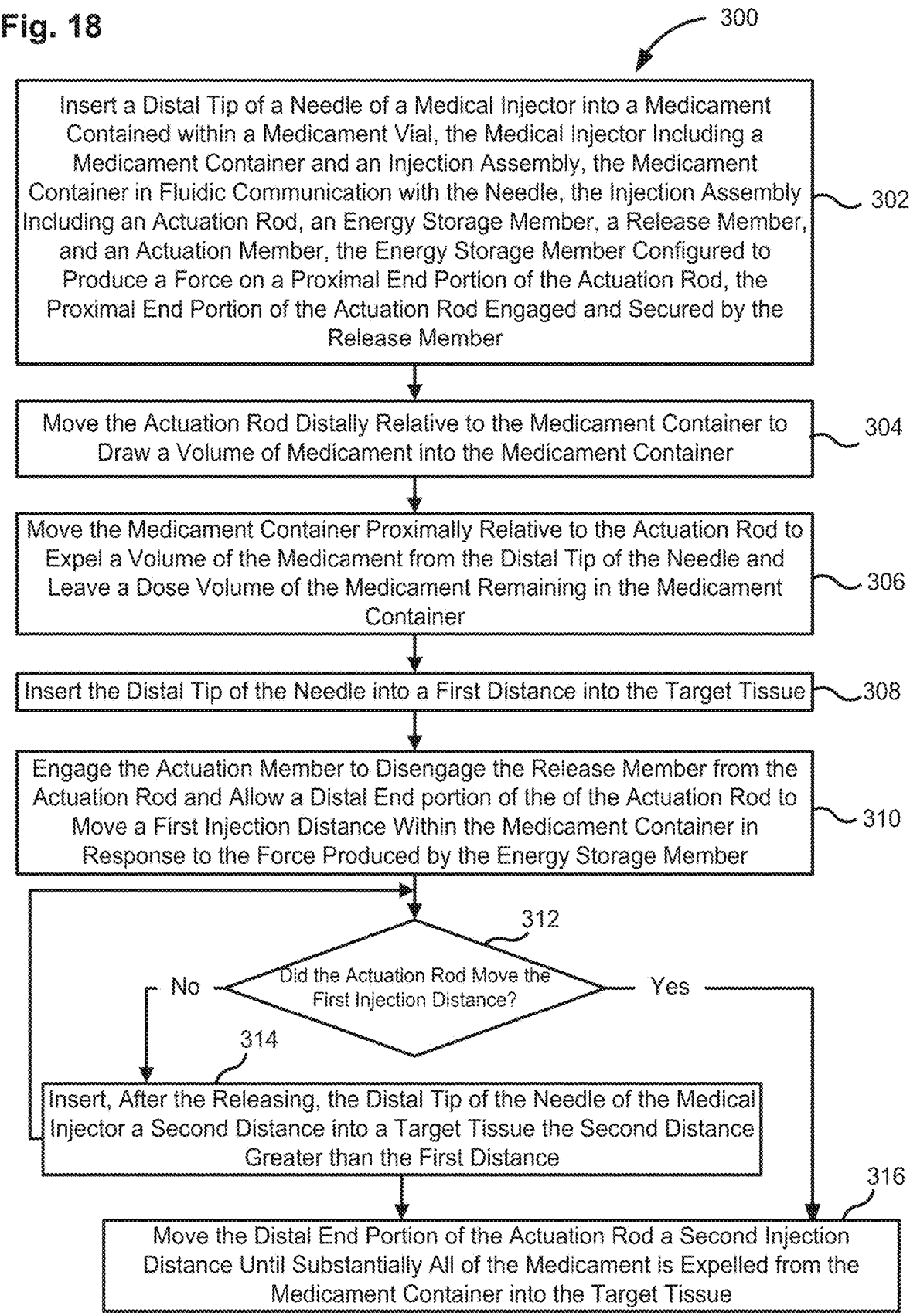
FIG. 18 show a flow diagram of a method for assisting a user in determining the insertion depth in a target tissue of a needle included in a medicament delivery device, and assisting the user in medicament delivery using an injection assembly, according to an embodiment.

FIG. 18 shows a schematic flow diagram of a method 300 for delivering a medicament to a target layer of a target tissue or a predetermined distance within the target tissue using a medical injector that includes an injection assembly. The method 300 includes inserting a distal tip of a needle of a medical injector (e.g., the medical injector 100, 1000, 2000 or any other medical injector described herein, into a medicament contained within a medicament vial 302. The medicament vial can be any suitable commercially available medicament vial, bottle, container, or any other vessel housing a medicament. The medicament can include any suitable medicament (e.g., VEGF, a VEGF inhibitor, a combination thereof, or any other medicament described herein) formulated to be delivered to a target tissue (e.g., the SCS of the eye). The medical injector includes a medicament container and an injection assembly, and is in fluidic communication with the needle. The injection assembly includes an actuation rod, and energy storage member, a release member and an actuation member. In some embodiments, the injection assembly and the components of the injection assembly described herein can be substantially similar to the components of the injection assembly 111, 2100, or any other injection assembly described herein. The energy storage member (e.g., a spring, a compressed gas container, or a container containing a propellant) is configured to produce a force on a proximal end portion of the actuation rod. The proximal end portion of the actuation rod can be engaged and secured by the release member. For example, the securing can lock the movement of the actuation rod with respect to a housing within which the actuation rod, the injection assembly, and/or at least a portion of the medicament container is disposed. Said another way, the securing of the proximal end portion of the actuation rod by the release member prevents a distal end portion of the actuation rod from moving relative to the housing. Furthermore, any movement of the housing relative to the medicament container also urges the distal end portion of the actuation rod to move within the medicament container.

Next, the method includes moving the distal end portion of the actuation rod distally relative to the medicament container to draw a volume of the medicament within the medicament container, at 304. Then, the medicament container is moved proximally relative to the actuation rod to expel a volume of the medicament from the distal tip of the needle and leave a dose volume of the medicament remaining in the medicament container, at 306. Said another way, any excess medicament drawn into the medicament container can be expelled from the medicament container by moving the medicament container proximally relative to the actuation rod.

The distal tip of the needle is then inserted a first distance into a target tissue, for example, an ocular tissue, at 308. The actuation member is activated (e.g., by a user) to disengage the release member form the actuation rod, thereby releasing the proximal end portion of the actuation rod. This allows the distal end portion of the actuation rod to move a first injection distance within the medicament container in response to the force produced by the energy storage member, at 310. As described herein, the actuation rod will move the first injection distance (or a great amount) when the needle tip is disposed within a desired region of the target tissue. Conversely, when the needle tip is not disposed within a desired region of the target tissue, the force produced by the energy storage member is insufficient to move the actuation rod by the first injection distance.

The method 300 then includes determining if the actuation rod has moved a threshold injection distance, at 312, for example, the first injection distance. For example, a user can visually observe if the distal end portion of the actuation rod moved within the medicament container or not (e.g., through a transparent housing of the medical injector). If the actuation rod did not move, the distal tip of the needle of the medical injector is inserted, after the releasing, a second distance greater than the first distance into the target tissue, at 314. In this manner, the user can reposition the needle tip (e.g., by inserting further, or removing from the tissue) in response to the indication produced by the actuation rod.

For example, the first distance can correspond to a sclera of the eye, which has a backpressure that, in conjunction with the frictional losses, viscous loses and the like via the fluid flow path, cannot be overcome by the force of the energy storage member. Thus, the actuation member does move the first injection distance to deliver at least a portion of the medicament into the sclera. The distal tip of the needle is then moved the second distance which can correspond to a target region of the target tissue, for example, the SCS. The method then returns to operation 312 to determine if the actuation rod has moved the first injection distance. If the actuation rod has moved the first injection distance, this confirms that the distal tip of the needle is disposed in the desired target region. For example, the target region can be SCS, which has a lower backpressure than that produced by the sclera. The force exerted by the energy storage member can be configured to overcome this backpressure such that the distal end portion of the actuation rod can be moved the first injection distance and deliver at least a portion of the medicament into the target tissue via the distal tip of the needle. In some embodiments, the force can be between about 2 N to about 6 N. Finally, the distal end portion of the actuation rod is moved a second injection distance until substantially all of the medicament is expelled from the medicament container into the target tissue (e.g., the SCS) at 316, via the distal tip of the needle. For example, the user can manually move the distal end portion of the actuation rod, or use any suitable actuation mechanism included in the medical injector to move the distal end portion of the actuator the second injection distance.

Figure 19:
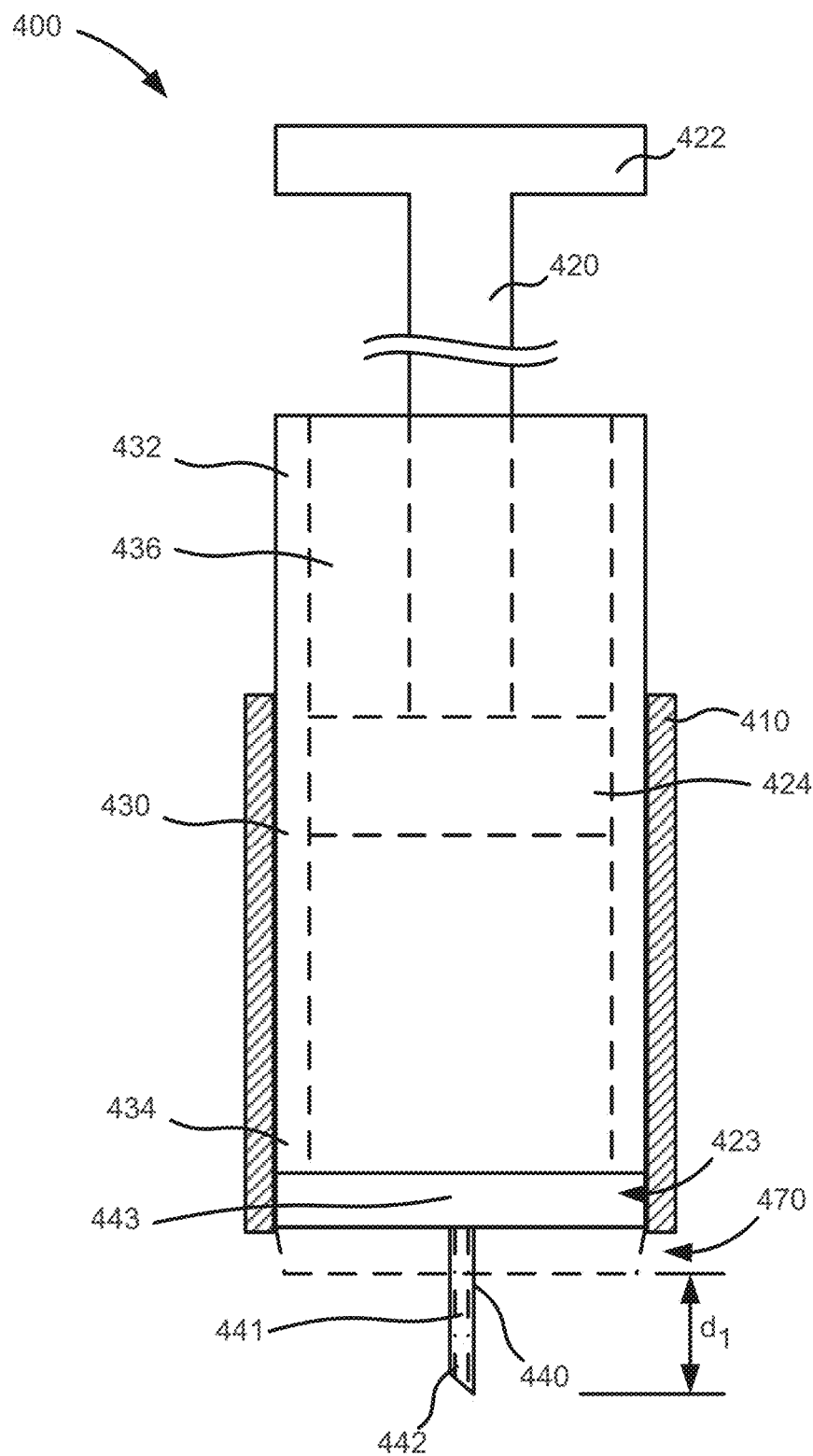
FIG. 19 shows a schematic illustration of a medical injector that includes an adjustment member in a first configuration, according to an embodiment.
Figure 20:
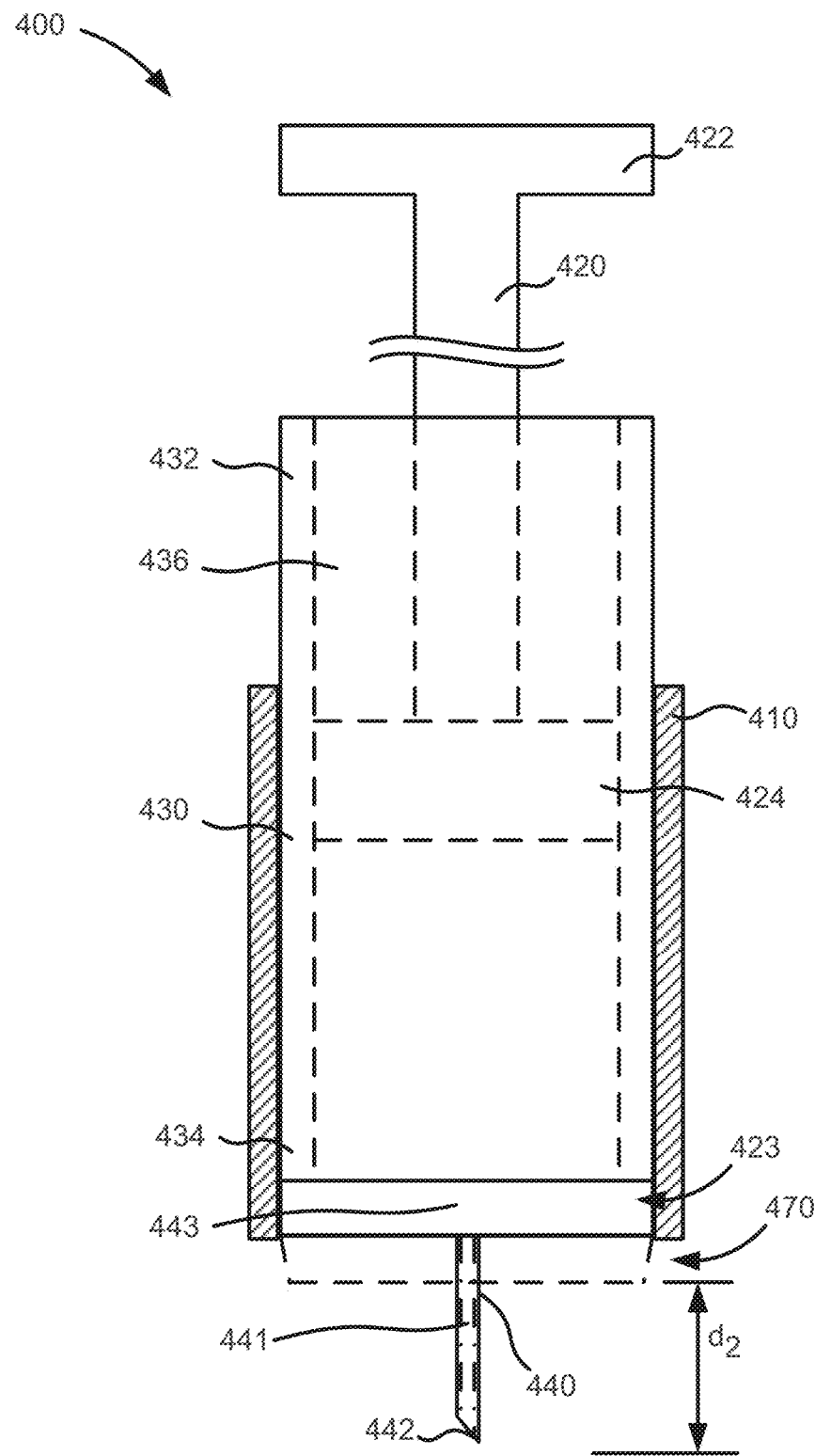
FIG. 20 shows the medical injector of FIG. 19 in a second configuration.
Figure 21:
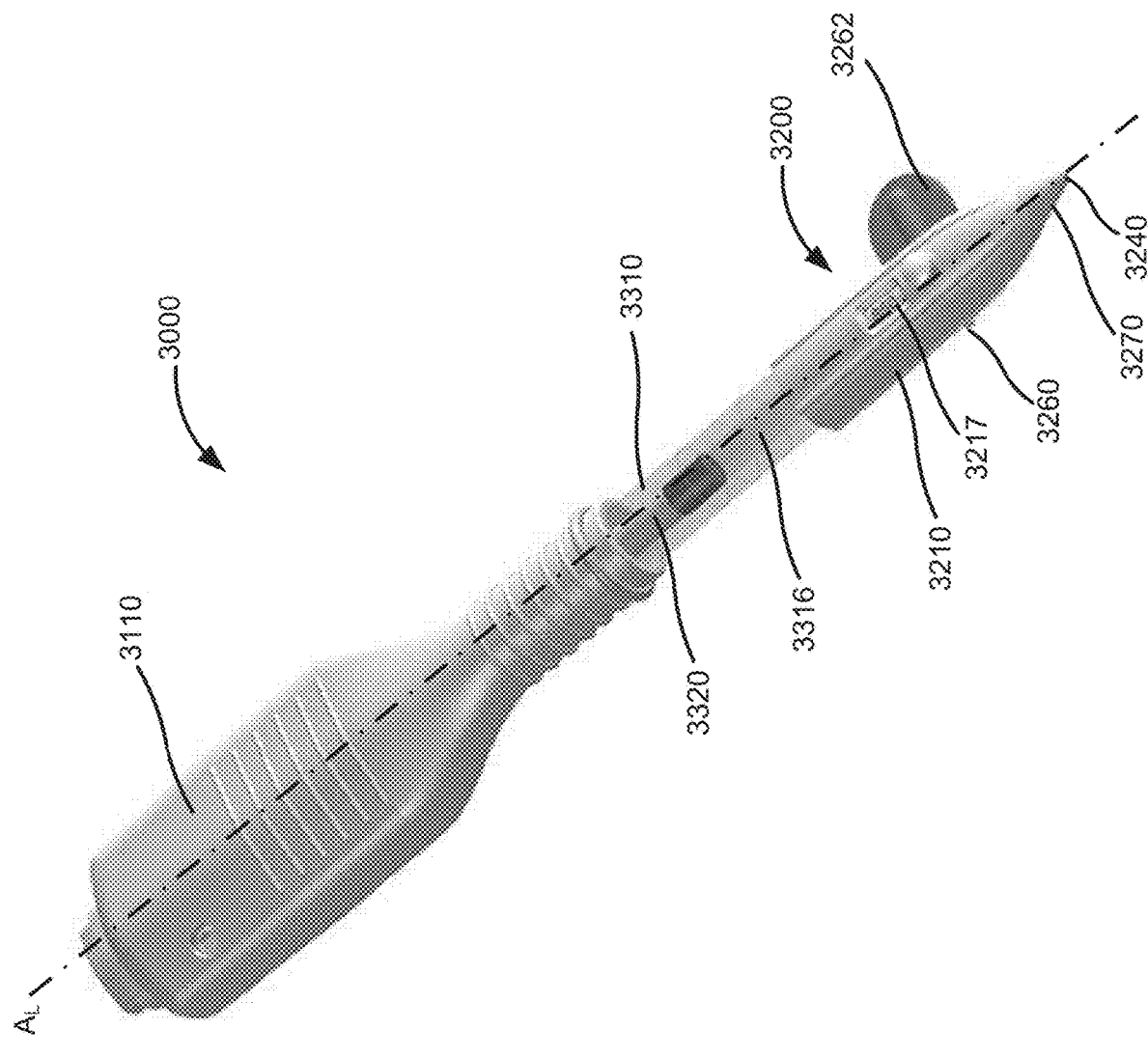
FIG. 21 shows a perspective view of a system for delivering a medicament to an eye that includes a needle assembly, according to an embodiment.

In some embodiments, a medical injector can include a needle assembly configured to adjust the length of a needle, for example, to adjust a distance the needle penetrates into a target tissue, for example, an ocular tissue. FIGS. 19 and 20 are schematic illustration of a medical injector 400 in a first configuration and a second configuration, according to an embodiment. The medical injector 400 includes a housing 410, an actuator rod 420, a medicament container 430, a needle 440, and an adjustment member 423. Optionally, the medical injector 400 can also include a hub 470 coupled to the housing 410. The housing 410 is configured to receive a portion of the medicament container 430. The housing 410 can include any suitable housing, for example, the housing 3210, or any other housing described herein with respect to a needle assembly.

The needle 440 can be any suitable puncture member configured to puncture a target tissue. For example, the needle 440 can be a microneedle configured to puncture ocular tissue. In some embodiments, the needle 440 can be a 32-gauge microneedle or a 34-gauge microneedle. In some embodiments, such a microneedle can be substantially similar to or the same as the microneedles described in the '009 PCT application incorporated by reference above. In some embodiments, the shape and/or size of the needle 440 can correspond, at least partially, with at least a portion of a target tissue. For example, in some embodiments, the length of the needle 440 can correspond with a thickness of a portion of ocular tissue such that when the needle 440 is inserted into the ocular tissue, at least a portion of the needle 440 is disposed within the sclera or suprachoroidal space of the eye, as described in further detail herein. The needle 440 defines a lumen 441 that extends through a proximal end portion 443 and a distal end portion 442 of the needle 440. The distal end portion 442 of the needle 440 can include a bevel or a sharpened tip configured to puncture a target tissue. At least a portion of the proximal end portion of the needle 440 can be disposed in a passageway defined by the hub 470, as described herein.

The medicament container 430 of the medical injector 400 has a proximal end portion 432 and a distal end portion 434. The medicament container 430 defines an inner volume 436 that can store, house, and/or otherwise contain a substance (e.g., a medicament, a prophylactic agent, a therapeutic agent, and/or a diagnostic agent). For example, in some embodiments, a cartridge or the like containing a drug formulation can be disposed within the inner volume 436 of the medicament container 430. In other embodiments, a drug formulation can be disposed directly within the inner volume 436 (e.g., without a cartridge or other intermediate reservoir). In some embodiments, the inner volume 436 can contain a drug formulation with a volume of about 0.5 mL or less. In other embodiments, the inner volume 436 can contain a drug formulation with a volume of about 0.1 mL. In still other embodiments, the inner volume 436 can contain a drug formulation with a volume greater the about 0.5 mL. In some embodiments, the medicament container 430 can be substantially similar to the medicament container 1310, 2310, 3310, or any other medicament container described herein.

The proximal end portion 432 of the medicament container 430 is substantially open to receive the actuation rod 420. More specifically, a distal end portion 424 of the actuation rod 420 is disposed within the inner volume 436 and can be moved between a first position (e.g., a proximal position) and a second position (e.g., a distal position). Said another way, the distal end portion 424 of the actuation rod 420 can move an injection distance within the inner volume 426. A sealing member such as, for example, a plug can be coupled to the distal end portion 424 of the actuation rod 420. The sealing member can be configured to form a friction fit with one or more surfaces of the medicament container 430 that define the inner volume 436. In this manner, the seal member and the medicament container 430 can form a fluidic seal that substantially isolates a portion of the inner volume 436 that is distal to the seal member from a portion of the inner volume 436 that is proximal to the seal member. Said another way, the medicament container 430 and the actuation rod 420 form at least a portion of a syringe.

In some embodiments, the distal end portion 434 of the medicament container 430 is physically and fluidically coupled to the hub 470. For example, in some embodiments, the hub 470 and the distal end portion 434 of the medicament container 430 can form a press fit, a snap fit, a threaded coupling, and/or the like. In other embodiments, the hub 470 can be monolithically formed with the medicament container 430. The hub 470 can define a passageway configured to receive the needle 440 therethrough such that the distal end portion 442 of the needle 440 extends past a distal end surface of the hub 470 by a distance, for example, a first distance $d_1$ (see e.g., FIG. 19) that can change, for example, to a second distance $d_2$ (see e.g., FIG. 20) or any other distance, when the needle is moved through a plurality of discrete increments along the longitudinal axis of the housing 410, as described herein. In some embodiments, the hub 470 can also be configured to limit movement of the adjustment member 422 within the housing 410.

A proximal end portion of the adjustment member 423 is configured to be coupled to the medicament container 430. The coupling can be performed using any suitable coupling mechanism, for example, a Luer lock, threads, snap-fit, friction-fit, or any other suitable coupling mechanism. A distal end portion of the adjustment member 423 is coupled to the needle 440, for example, to the proximal end portion 443 of the needle 440. In some embodiments, the adjustment member 423 can define a lumen configured to place the medicament container 430 in fluid communication with the needle 440. In some embodiments, the proximal end portion of the adjustment member 423 can also include a flange configured to be removably coupled to the medicament container 430. The adjustment member 420 is configured to transition between a first configuration (FIG. 19) and a second configuration (FIG. 20) to adjust the distance that the distal end portion 442 of the needle 440 extends past the distal end surface of the hub 470. For example, the adjustment member 423 can be movably disposed within the housing 410 such that when the adjustment member 423 is rotated relative to the housing 410, the needle 440 is moved through a plurality of discrete increments along a longitudinal axis of the housing 410. In this manner, the adjustment member 423 can adjust the effective length of the needle 440 in the plurality of discrete increments. Said another way, the adjustment member 423 can allow digital adjustment of the length of the needle 440. While not shown, in some embodiments, the adjustment member 423 and/or the housing 410 can include a plurality of detents. The detents can be configured such that each increment from the plurality of discrete increments is associated with a corresponding detent from the plurality of detents defined by at least one of the adjustment member 423 and/or the housing 410. For example, the housing 410 can include a protrusion configured to be removably disposed within each detent from the plurality of detents when the adjustment member 423 is rotated relative to the housing 410 to move the needle 440 through the plurality of discrete increments. As another example, in some embodiments, a bearing can be coupled within the housing 410 and configured to be removably disposed within each detent from the plurality of detents when the adjustment member 422 is rotated within the housing 410 to move the needle through the plurality of discrete increments. In such embodiments, a bias member can also be disposed in the housing 410 and configured to maintain the bearing within a detent from the plurality of detents. In some embodiments, the medical injector 400 can also include a lock member, for example, a lock, a latch, a tab, a rod, or any other suitable lock member removably coupled to the housing 410. The lock member can be configured to engage the adjustment member 423 to limit movement of the adjustment member 423 relative to the housing 410. In some embodiments, at least a portion of the adjustment member 423 can include an indication portion, for example, a portion including a plurality of markings. The markings can be configured to indicate a distance that the needle 440 extends beyond the housing 410 (e.g., extends beyond the distal end surface of the hub 470). In such embodiments, the housing 410 can define a window such that the indication portion is visible through the window. For example, a user can view the indication portion through the window to determine the distance that the needle 440 extends beyond the housing 410 and estimate an insertion depth of the distal end 442 of the needle 440 into a target tissue.

As shown in FIG. 19, in the first configuration of the adjustment member 423, the distal end portion 442 of the needle 440 can be spaced apart from a distal end surface of the hub 470 by a first distance $d_1$. The adjustment member 423 can then be moved into a second configuration by moving (e.g., rotating, translating or rotating and translating) the adjustment member 423 within the housing 410. This urges the needle 440 to move in a discrete increment such that distal end portion 442 of the needle 440 extends a second distance $d_2$, larger than $d_1$, beyond the distal end surface of the hub 470, as shown in FIG. 20. In this manner, a length of the needle 440 extending beyond the distal edge surface of the hub 470 can be adjusted.

In use, an operator (e.g., a doctor, technician, nurse, physician, ophthalmologist, etc.) can manipulate the delivery device 400 to insert the needle 440 into, for example, an ocular tissue. In this manner, the distal end portion 442 of the needle 440 can be advanced within the target tissue to pierce the sclera and place the hub 470 in contact with an outer surface of the sclera. Moreover, with the adjustment member 422 in the first configuration, the first distance $d_1$ between the distal end surface of the hub 470 and the distal end portion 442 of the needle 440 can substantially correspond to the thickness of the sclera. In this manner, a distal tip of the needle 440 can be disposed within the sclera (e.g., the sclera 20 of the eye 10 in FIG. 1).

The adjustment member 423 can be transitioned from the first configuration to the second configuration by moving, translating or rotating the adjustment member 423 within the housing 410. In some embodiments, the moving of the adjustment member 423 can be performed by moving (e.g., rotating) the medicament container 430 relative to the housing 410. This can increase the distance between the distal end surface of the hub 470 and the distal end portion 423 of the needle 440 from the first distance $d_1$ to the second distance $d_2$ (as described above). In this manner, when the adjustment member 422 is in the second configuration, the distal tip of the needle 440 can be moved further proximally relative to the ocular tissue to place the lumen 441 of the needle 440 in fluid communication with the suprachoroidal space (e.g., the suprachoroidal space 36 of the eye 10 in FIG. 1). With the lumen 441 of the needle 440 in fluid communication with the suprachoroidal space, the actuation rod 420 can be moved relative to the medicament container 430 from its first position to its second position. With the distal end portion 424 of the actuation rod 420 forming a substantially fluidic seal (i.e., a substantially hermetic seal) with an inner surface of the medicament container 430, the movement of the actuation rod 420 to its second position expels the drug formulation (contained within the inner volume of the medicament container 430) through the lumen 441 of the needle 440. Thus, the medical injector 400 can deliver the drug formulation to the SCS of the eye and the drug formulation can flow within the suprachoroidal space to be delivered to, for example, the posterior region of the eye.

By adjusting the distance between the distal edge surface of the hub 470 and the distal end portion 442 of the needle 440 in discrete increments using the adjustment member 423, the distal end portion 442 of the needle 440 can be placed within the SCS with more accuracy and precision than would otherwise be achieved with a fixed distance therebetween. For example, in some instances, the adjustment member 423 can be arranged such that the first distance $d_1$ between the distal end surface of the hub 470 and the distal end portion 442 of the needle 440 is less than the thickness of the sclera. Thus, the adjustment member 423 can be moved to the second configuration to increase the distance between the distal edge surface of the hub 470 and the distal end portion 442 of the needle 440 (e.g., to the second distance $d_2$) that is greater than the thickness of the sclera, thereby placing the distal end portion 442 of the needle 440 in contact with the SCS. Moreover, the second distance $d_2$ can be less than a combined thickness of the sclera and the SCS such that when the adjustment member 423 is moved to the second configuration, the distal end portion 442 of the needle 440 does not pierce the choroid (e.g., the choroid 28 of the eye 10 in FIG. 1).

The arrangement of the adjustment member 423, the needle 440, and the hub 470 allows for control of the effective length of the needle 440. Accordingly, the medical injector 400 can be used for procedures involving different portions of a target tissue (e.g., the eye) having different thicknesses. Moreover, control over the effective length of the needle 440, as described herein, allows the medical injector 400 to be used on a variety of patients having a range of anatomical differences (e.g., the device can be used in adult applications and pediatric applications).

The transition of the adjustment member 423 (and any of the needle assemblies described herein) between the first configuration and the second configuration can be performed at any suitable time before and/or during a procedure. For example, in some embodiments, the adjustment member 423 can be transitioned to the second configuration to set and/or adjust the effective length of the needle 440 before insertion of the needle 440 into the target tissue. The desired effective length of the needle 440 in such embodiments can be based on the known thickness of the sclera based on pre-operation measurements or the like. In other embodiments, however, the adjustment member 422 can be transitioned to the second configuration after the needle 440 has been inserted into the target tissue. In this manner, the adjustment member 422 can provide the operator with a mechanism for adjusting the effective length of the needle 440 in discrete increments during the procedure (e.g., based on tactile feedback, optical feedback or the like).

The medical injector 400 is shown in FIGS. 19-20 by way of example to provide context to the proceeding discussion. In this manner and for simplicity, only portions of a medical injector according to specific embodiments are shown. It should be understood that any of the embodiments described herein can be disposed in a similar arrangement as described above with reference to FIGS. 19-20. Moreover, while the delivery device 400 is shown and described with reference to FIGS. 19-20 as having a particular arrangement, the embodiments described herein can be used with any suitable delivery mechanism or device.

In some embodiments, a system for injecting a medicament into ocular tissue can include a needle assembly configured to perform any of the functions described herein. In other embodiments, a needle assembly can be configured to adjust the length and/or insertion depth of the needle. Referring now to FIGS. 21-33 a system 3000 can include at least a housing 3110, a medicament containment chamber 3310, an actuator 3320, and a needle assembly 3200. The needle assembly 3200 can be configured to adjust a length of a puncturing member 3240 (also referred to as a delivery member and/or a needle) included in the needle assembly 3200, as described herein. The system 3000 can be configured to deliver a medicament to a layer or region of an eye of patient, for example, to the SCS of the eye.

The housing 3110 can include any of the housings described herein and is configured to receive at least a portion of the medicament containment chamber 3310. In some embodiments, the housing 3110 can be substantially similar to the housing 1110 described with respect to the system 1000. In such embodiments, the housing 3110 can be configured for manual manipulation of the actuator 3320 to inject the medicament. In some embodiments, an injector assembly can be disposed in the housing 3110. The injector assembly can be substantially similar to the injector assembly 2100 or any other injector assembly described herein, and is therefore not described in further detail herein.

The medicament containment chamber 3310 defines an internal volume 3316 configured to house a medicament (e.g., a VEGF, a VEGF inhibitor, triamcinolone acetonide, any other medicament described herein, or a combination thereof). The medicament containment chamber 3310 includes an engagement portion disposed inside the internal volume defined by the housing 3110. The medicament containment chamber 3310 also includes a delivery portion disposed outside the internal volume defined by the housing 3110 and coupled to the needle assembly 3200. The medicament containment chamber 3310 can be substantially similar to the medicament containment chamber 1310, 2310 or any other medicament containment chamber described herein, and is therefore not described in further detail herein.

The actuator 3320 includes an engagement portion and a plunger portion. The plunger portion is slidably disposed inside the internal volume 3316 defined by the medicament containment chamber 3310 and is configured to draw the medicament into or expel the medicament from the internal volume 3316 defined by the medicament containment chamber 3310. The actuator 3320 can be substantially similar to the actuator 1320, 2320 or any other actuator described herein, and is therefore not described in further detail herein.

Figure 22:
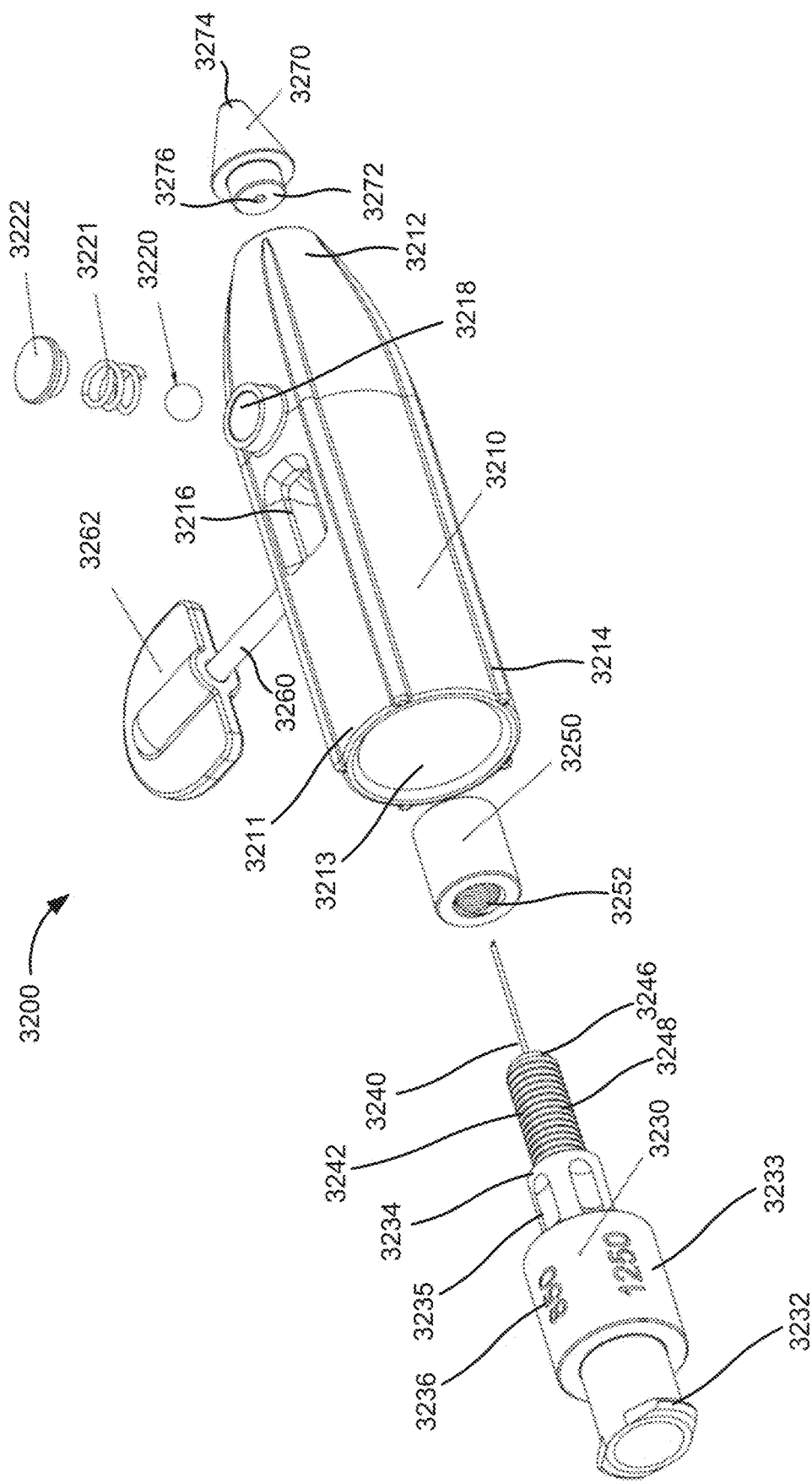
FIG. 22 shows an exploded view of the needle assembly included in the system of FIG. 21.
Figure 24A:
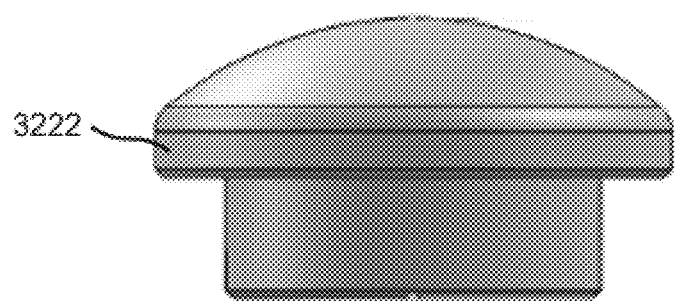
FIG. 24A shows a side view and FIG. 24B shows a top view of a plug included in the needle assembly of FIG. 22.
Figure 24B:
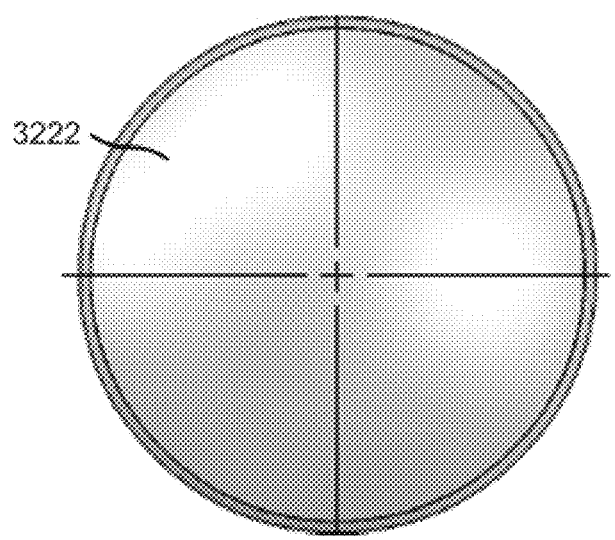
Figure 25:
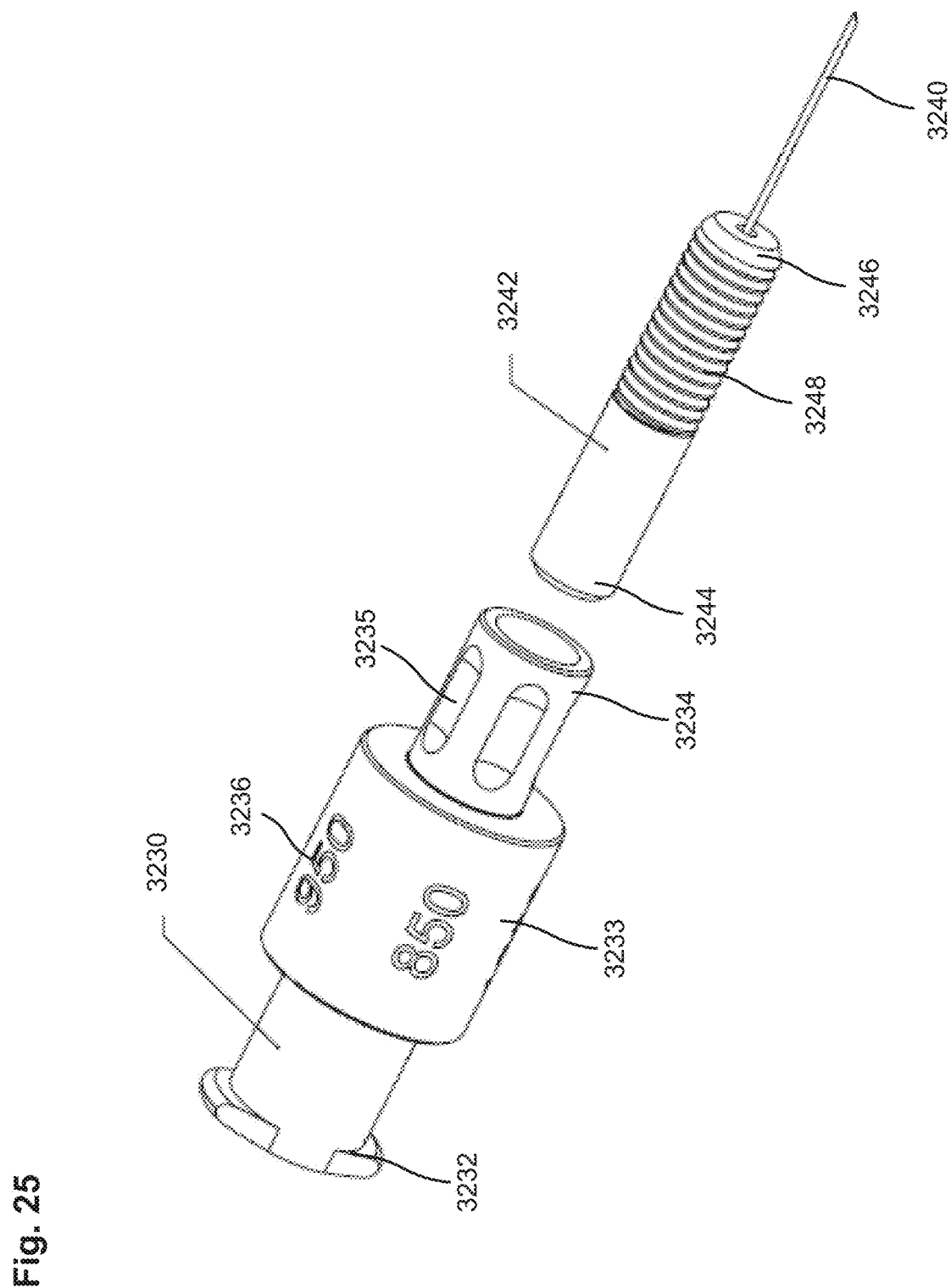
FIG. 25 shows a perspective view of an adjustment member, a lead screw and a puncturing member included in the needle assembly of FIG. 22.
Figure 26A:
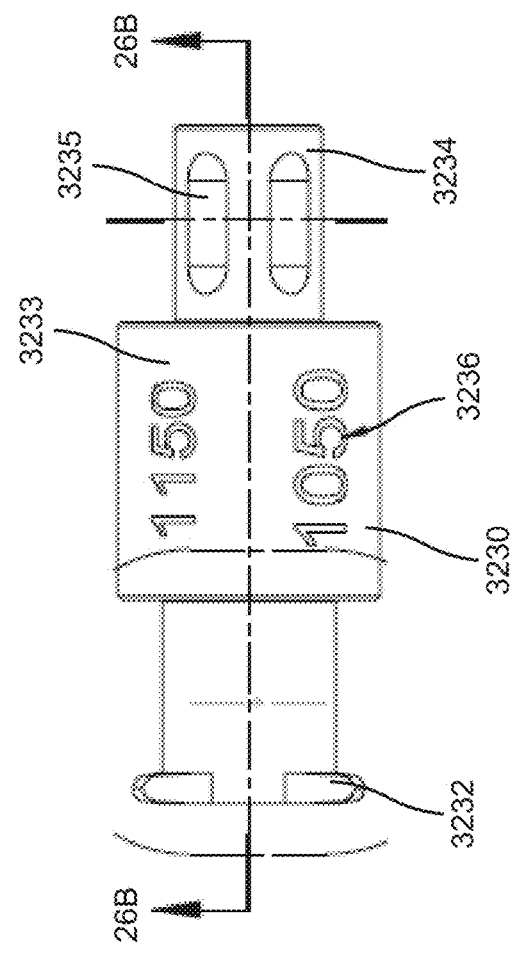
FIG. 26A shows a side view of the adjustment member included in the needle assembly of FIG. 22.
Figure 26B:
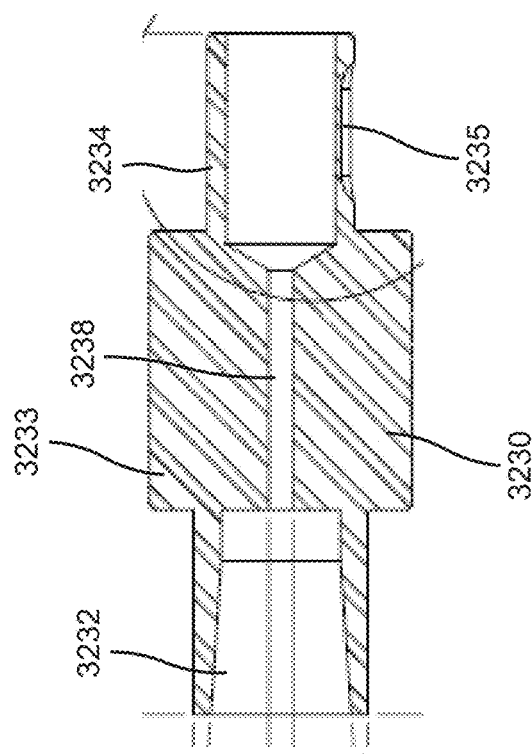
FIG. 26B shows a side cross-section of the adjustment member of FIG. 26A taken along the line 26B-26B.
Figure 28B:
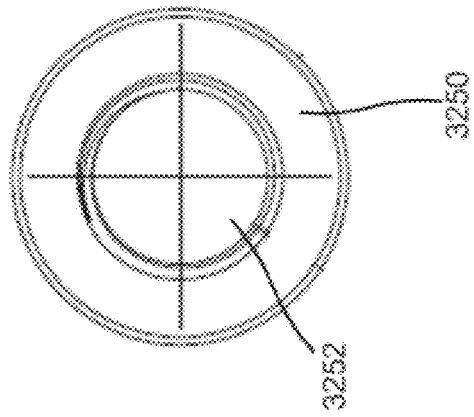
FIG. 28A shows a side view and FIG. 28B shows a front view of a bushing included in the needle assembly of FIG. 22.
Figure 28A:
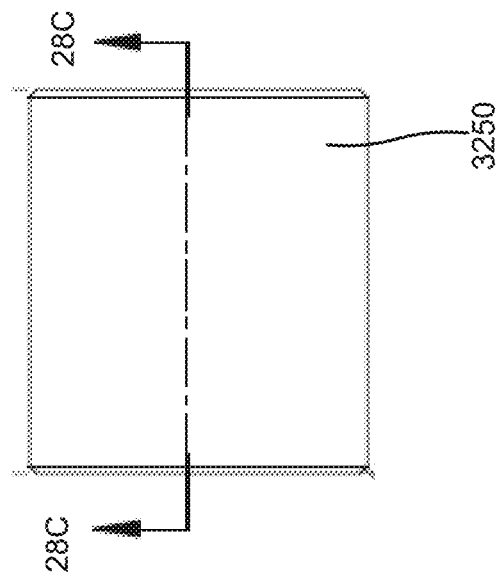
Figure 28C:
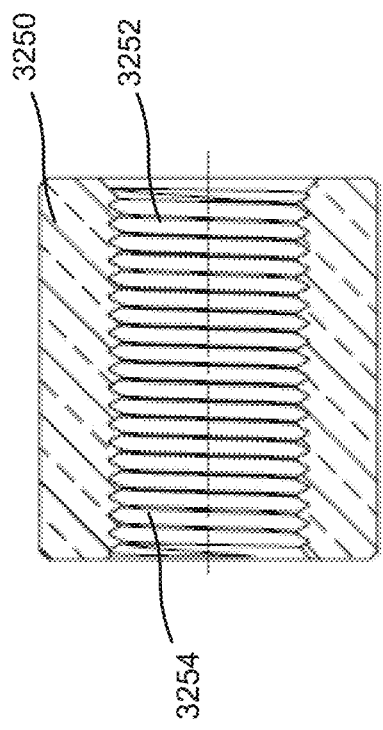
FIG. 28C shows a cross-section view of the bushing of FIG. 28A taken along the line 28C-28C.
Figure 29:
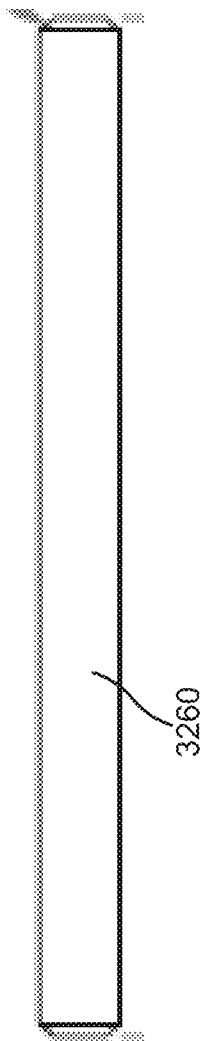
FIG. 29 shows a side view of a locking pin included in the needle assembly of FIG. 22.
Figure 31C:
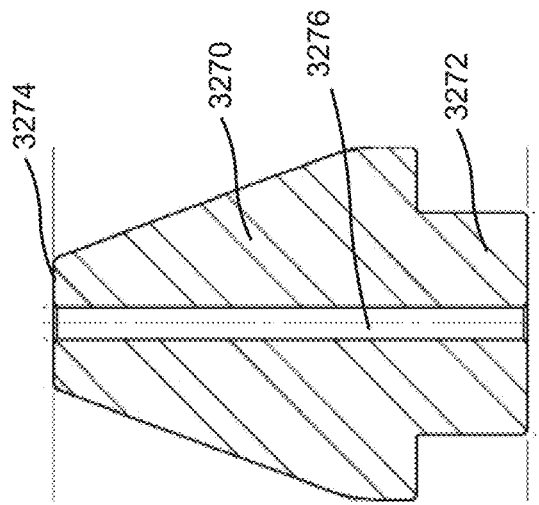
FIG. 31C shows a cross-section view of the hub of FIG. 31A taken along the line 31C-31C.
Figure 31A:
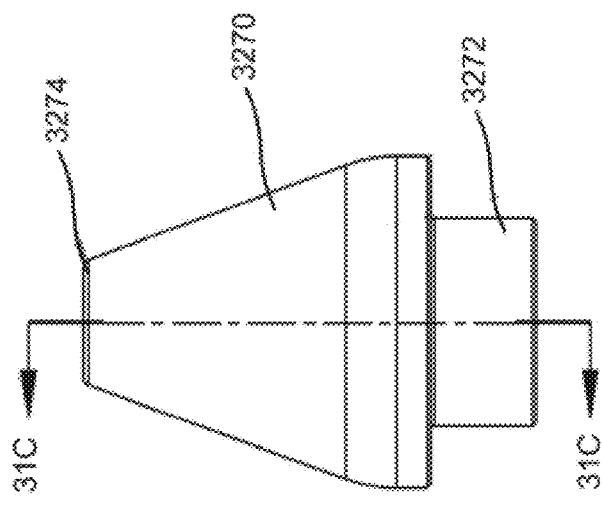
FIG. 31A shows a side view and FIG. 31B shows a front view of a hub included in the needle assembly of FIG. 22, according to an embodiment.
Figure 31B:
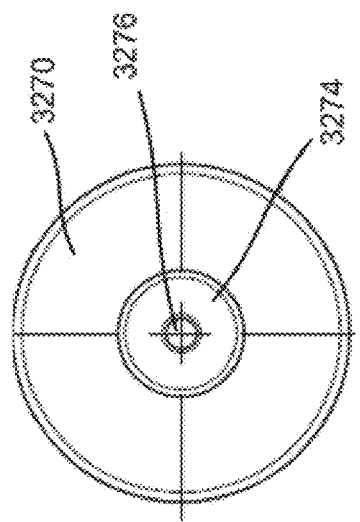

As shown in FIG. 22, the needle assembly 3200 includes a housing 3210, a bearing (or lock ball) 3220, an adjustment member 3230, a puncturing member 3240, a lead screw 3242, a bushing 3250, a locking pin 3260, and a hub 3270.

The needle assembly 3200 is configured to enable linear translation of the puncturing member 3240 in fixed and/or discrete increments to allow a user to insert the puncturing member to a desired depth within the eye, for example, insertion to the depth of the SCS.

The housing 3210 (FIGS. 23A-C, FIGS. 32 and 33) includes a proximal portion 3211 and a distal portion 3212. The housing 3210 can be substantially cylindrical in shape and tapers towards the distal portion 3212. The housing 3210 defines an internal 3213 volume within which the bearing 3220, the adjustment member 3230, at least a portion of the puncturing member 3240, the lead screw 3242, the bushing 3250, and at least a portion of the locking pin 3260 can be disposed. The internal volume 3213 defines a substantially circular cross-section to allow one or more components, for example, the adjustment member 3230 and/or the lead screw 3242 to rotate about a longitudinal axis $A_L$ of the system 3000 within the internal volume 3213. A delivery portion of the medicament containment chamber 3310 can also be disposed in the internal volume 3213. The distal portion 3212 of the housing 3210 is configured to receive a proximal end 3272 of the hub 3270 (see FIGS. 31A-31C) or any other hub described herein. Coupling features can be included in the distal portion 3212 to removably or fixedly couple the proximal end 3272 of the hub 3270. Suitable coupling features can include, for example, a friction fit mechanism, threads, a Luer assembly, adhesive, lock, latch, groove, indents, detents, a snap-fit mechanism, or any other suitable coupling mechanism. A multiplicity of ridges 3214 are disposed on an outer surface of the housing 3210. The ridges 3214 can be configured to allow the user to ergonomically grip the housing 3210, for example, when performing an injection of a medicament into the eye. A window 3216 is defined in the housing 3210. The window 3216 is configured to align with an intermediate portion 3233 of the adjustment member 3230, such that the user can see a set of markings 3236 defined on an outer surface of the intermediate portion 3233. The markings 3236 can indicate a length of the puncturing member 3240 protruding from a distal end 3274 of the hub 3270, which can correspond to the insertion depth of the puncturing member 3240 (e.g., a distance that a distal tip of the puncturing member 3240 traverses into the ocular tissue). A cavity 3218 is defined in the housing 3210. The cavity 3218 is configured to receive the bearing 3220, a biasing member 3221 and a plug 3222, as described in further detail herein. A set of through holes 3219 are defined in the sidewall of the housing 3210. The locking pin 3260 is inserted through the through holes 3219, such that the locking pin passes through the internal volume 3213 defined by the housing 3210, and at least a portion of the locking pin 3260 is disposed within the internal volume 3213.

The bearing (or lock ball) 3220 is disposed in the cavity 3218 of the housing 3210. The bearing can be any suitable bearing, for example, a metallic, plastic, or wooden bearing, a contoured cylindrical member, or any other suitable bearing. A first end of the biasing member 3221 is coupled and/or engaged with to the bearing 3220, and a second end of the biasing member 3221 is coupled to the plug 3222. The biasing member 3221 can include a spring, for example, helical, compression, extension, spring washers, Belleville washers, tapered, any other type of spring, or any other suitable biasing member. At least a portion of the plug 3222 (FIGS. 24A-B) is disposed within the cavity such that the plug 3222 secures the biasing member 3221 and the bearing 3220 inside the cavity 3218. The plug 3222 can include a dome shaped surface with rounded edges. In some embodiments, the plug 3222 can be fixedly coupled to the cavity 3218, for example, via adhesives. In some embodiments, the plug 3222 can be removably coupled to the cavity 3218 using a suitable coupling mechanism such as, for example, friction-fit, threads, grooves, indents, detents, any other suitable coupling mechanism or combination thereof. The plug 3222 can be configured to exert a force on and/or maintain a position of the biasing member 3221 such that the biasing member 3221 exerts a force against the bearing 3220. The bearing (or lock ball) 3220 is configured to engage at least one of a set of detents 3235 disposed on a distal portion 3234 of the adjustment member 3230. The biasing member 3221 biases the bearing 3220 inward relative to the detents 3235 such that the bearing 3220 prevents the adjustment member 3230 from rotating freely relative to the housing 3210 about the longitudinal axis $A_L$ of the system 3000. In this manner, the bearing 3220 allows a digital length adjustment of a length of the puncturing member 3240, as described in further detail herein. Similarly stated, the engagement of the bearing 3220 in the detents 3235 allows the rotational position of the adjustment member 3230 (and thus the effective length of the puncturing member 3240) to be adjusted in discrete increments.

The adjustment member 3230 (FIGS. 25, FIGS. 26A-B, FIG. 33) includes a proximal portion 3232, an intermediate portion 3233, and a distal portion 3234. The proximal portion 3232 is configured to couple to a delivery portion of the medicament containment chamber 3310. The proximal portion 3232 can include coupling features, for example, Luer lock connectors, threads, grooves, notches, indents, snap-fit, friction-fit, lock, latch, any other suitable coupling features or combination thereof. In this manner, the distal end portion of the medicament containment chamber 3310 can be coupled to the adjustment member 3230. In some embodiments, the delivery portion of the medicament containment chamber 3310 can be fixedly coupled to the proximal portion 3232, for example, by an adhesive. In other embodiments, the delivery portion of the medicament containment chamber 3310 can be removably coupled to the proximal portion 3232, for example, to allow the user to replace the medicament containment chamber 3310 to reuse the needle assembly 3200. In some embodiments, a locking feature (not shown), for example, a lock, a latch, or a friction fit, can be included in the proximal portion 3232. The locking feature can be configured to prevent uncoupling of the delivery portion of the medicament containment chamber 3310 from the proximal portion 3232 of the adjustment member 3230 due to a rotation of the medicament containment chamber 3310 (e.g., because of a rotation of the housing 3310 by the user). For example, a user can rotate the housing 3310 about the longitudinal axis $A_L$ of the system 3000 urging the medicament containment chamber 3310 and thereby, the adjustment member 3230 to also rotate about the longitudinal axis $A_L$. In this manner, the adjustment member 3230 can be configured to vary the length of the puncturing member 3240 protruding through the distal end of the 3274 of the hub 3270, as described in further detail herein.

The intermediate portion 3233 of the adjustment member 3230 includes markings 3236 corresponding to the length of the puncturing member 3240 protruding through distal end 3274 the hub 3270. The intermediate portion 3233 is aligned with the window 3216 included in the housing 3210 such that the user can see the markings 3236 through the window 3216 and determine the protruding length of the puncturing member 3240. This can, for example, indicate the insertion depth of the puncturing member 3240 into the eye. In some embodiments, the markings 3236 can indicate a length in the range of about 850 microns, 950 microns, 1050 microns, 1150 microns, or about 1250 microns. In such embodiments, the length interval can be about 100 microns. The intermediate portion 3233 also includes a fluidic channel 3238 defined therethrough. The fluidic cannel 3238 can be in fluidic communication with the internal volume 3316 of the medicament containment chamber 3310.

The distal portion 3234 is fixedly coupled to a proximal portion 3244 of the lead screw 3242. For example, the proximal portion 3244 of the lead screw 3242 can be welded, bonded, adhered, bolted, riveted, or fixedly mounted using any other coupling mechanism to the distal portion 3234 of the adjustment member 3230. In this manner, a rotation of the adjustment member 3230 can also rotate the lead screw 3242 about the longitudinal axis $A_L$ of the system 3000. The set of detents 3235 are defined on the outer surface of the distal portion 3234 and are configured to be engaged by the bearing 3220, as described herein. Although the lead screw 3242 and the adjustment member 3230 are shown and described as being separate components that are joined together, in other embodiments, the lead screw 3242 and the adjustment member 3230 can be monolithically formed.

The lead screw 3242 (FIGS. 22, 25, 27A-B, 33) includes the proximal portion 3244 and a distal portion 3246. The proximal portion 3244 is fixedly coupled to distal portion 3234 of the adjustment member 3230, as described herein. The distal portion 3246 is coupled to a proximal end of the puncturing member 3240 coupled thereto. The puncturing member 3240 can be a needle (e.g., a 27 gauge, a 30 gauge, or even smaller needle), or any other puncturing member described herein. The puncturing member 3240 defines a lumen 3241 (FIG. 33) configured to fluidically communicate the medicament to a target tissue of the eye, for example, the SCS. The puncturing member 3240 is fixedly coupled to the lead screw 3242 by any suitable mechanism. In this manner, a rotation of the adjustment member 3230 and lead screw 3242 about the longitudinal axis $A_L$, which causes a linear translation of the lead screw 3242 along the longitudinal axis $A_L$, also urges the puncturing member 3240 to rotate about or translate along the longitudinal axis $A_L$, respectively. The lead screw 3242 defines a lumen 3247 therethrough. The lumen 3247 is in fluidic communication with the fluidic channel 3238 of the adjustment member 3230 and the lumen 3241 of the puncturing member 3240. Thus, the fluidic channel 3238 of the adjustment member 3230, and the lumen 3247 of the lead screw 3242 provide a fluidic path for the medicament to be communicated between the internal volume 3316 of the medicament containment chamber 3310 and the lumen 3241 of the puncturing member 3240, for example, delivered to a target layer (e.g., the SCS) of the eye.

At least a portion of the outer surface of the lead screw 3242, for example, the distal portion 3246, includes threads 3248. The threads 3248 are configured to mate with mating threads 3254 included in the bushing 3250. The bushing 3250 (FIGS. 22, 28A-C, FIG. 33) is fixedly disposed inside the internal volume 3213 defined by the housing 3210. The bushing 3250 defines a lumen 3252 configured to receive the distal portion 3246 of the lead screw 3242 such that the threads 3248 of the lead screw 3242 are mated with the mating threads 3254 disposed along the surface of the lumen 3252 of the bushing 3250. Because the bushing 3250 is fixedly disposed in the housing 3210, a rotation of the adjustment member 3230 and the lead screw 3242 relative to the housing 3210 about the longitudinal axis $A_L$ urges the lead screw 3242 to move linearly relative to the housing

3210 along the longitudinal axis $A_L$ of the system 3000. Each full rotation of the lead screw 3242 can correspond to a predetermined translation distance of the lead screw 3242 and thereby, the puncturing member 3240, along the longitudinal axis $A_L$ of the system 3000. In this manner, the adjustment member 3230 can be rotated (e.g., by rotating the housing 3110) to rotate the lead screw 3230 and thereby, advance or retract a predetermined length of the puncturing member 3240 from the distal end 3274 of the hub 3270.

The locking pin 3260 (FIG. 29) is coupled to a tab 3262. As shown in FIGS. 30A-C, the tab 3262 includes a cavity 3264 configured to receive at least a portion of the locking pin 3260. In some embodiments, the tab 3262 can be removably coupled to the locking pin 3260, for example via, threads, grooves, notches, indents, detents, friction fit, or coupled using any other suitable coupling mechanism. In some embodiments, the tab 3262 can be fixedly coupled to the locking pin 3260, for example, via adhesives. At least a portion of the tab 3262 can be substantially flat. Although the locking pin 3260 is shown as being substantially cylindrical, in other embodiments, the locking pin can define a circular, oval, square, rectangular, polygonal, or any other suitable cross section. The locking pin 3260 is configured to be inserted through and/or within the through holes 3219 of the housing 3210, such that at least a portion of the locking pin 3260 is disposed in the internal volume 3213 defined by the housing 3210.

The locking pin 3260 is configured to be moved from a first configuration (or position) and a second configuration (or position). In the first configuration, the locking pin 3260 is inserted through the through holes 3219 and at least a portion of the locking pin 3260 is disposed in proximity of the intermediate portion 3233 of the adjustment member 3230. In the first configuration, the locking pin 3260 is configured to prevent a rotation of the adjustment member 3230 relative to the housing 3210, and thereby, the lead screw 3242. Thus, when the locking pin 3260 is in the first configuration, movement of the puncturing member 3240 along the longitudinal axis $A_L$ of the system 3000 distally relative to the medicament containment chamber 3310, for example, because of the rotation of the adjustment member 3260, is limited. In a second configuration, the user can pull the tab 3262 and thereby the locking pin 3260 out of the through holes 3219 and the internal volume 3213. Thus, in the second configuration the adjustment member 3230 can be free to rotate relative to the housing 3210, and thus move linearly along the longitudinal axis $A_L$, for example, to advance a length of the puncturing member 3240 from a distal end 3274 of the hub 3270. Said another way, the locking pin 3260 can serve as a safety mechanism to prevent accidental activation of the needle assembly 3200 and prevent advancement of the puncturing member 3260 out of the distal end 3274 of the hub 3270.

The hub 3270 includes a proximal portion 3272 and a distal portion 3274. The proximal portion 3272 is configured to be coupled to the distal portion 3214 of the housing 3210 (or any other housing defined herein) using any suitable coupling mechanism, for example, friction-fit, threads, snap-fit, notches, grooves, indents, detents, any other suitable coupling mechanism or combination thereof. The hub 3270 defines a lumen 3276 therethrough. At least a portion of the puncturing member 3240 (or any other puncturing member described herein) can be disposed in the lumen 3276, and can be configured to advance through the lumen 3276 out of the distal end 3274. The distal end 3274 of the hub 3270 is substantially flat, and is configured to contact an outer surface of the conjunctiva of the eye. Although the hub 3270 is shown and described as having a flat distal end (or "contact") surface, in some embodiments, a distal portion of a hub can define substantially convex or curved surface, as described in further detail herein.

Figure 32:
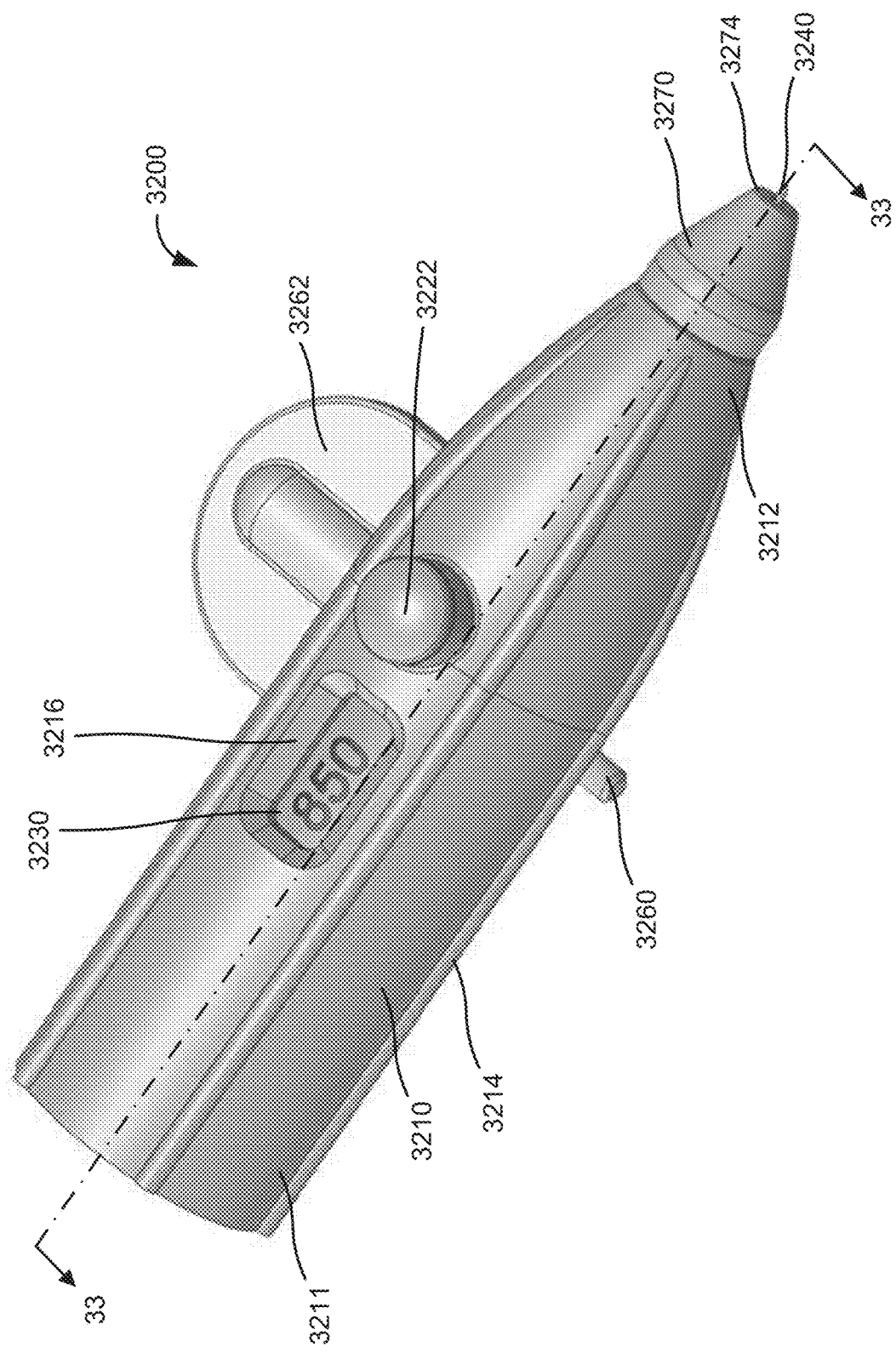
FIG. 32 shows a perspective view of the needle assembly of FIG. 22.
Figure 33:
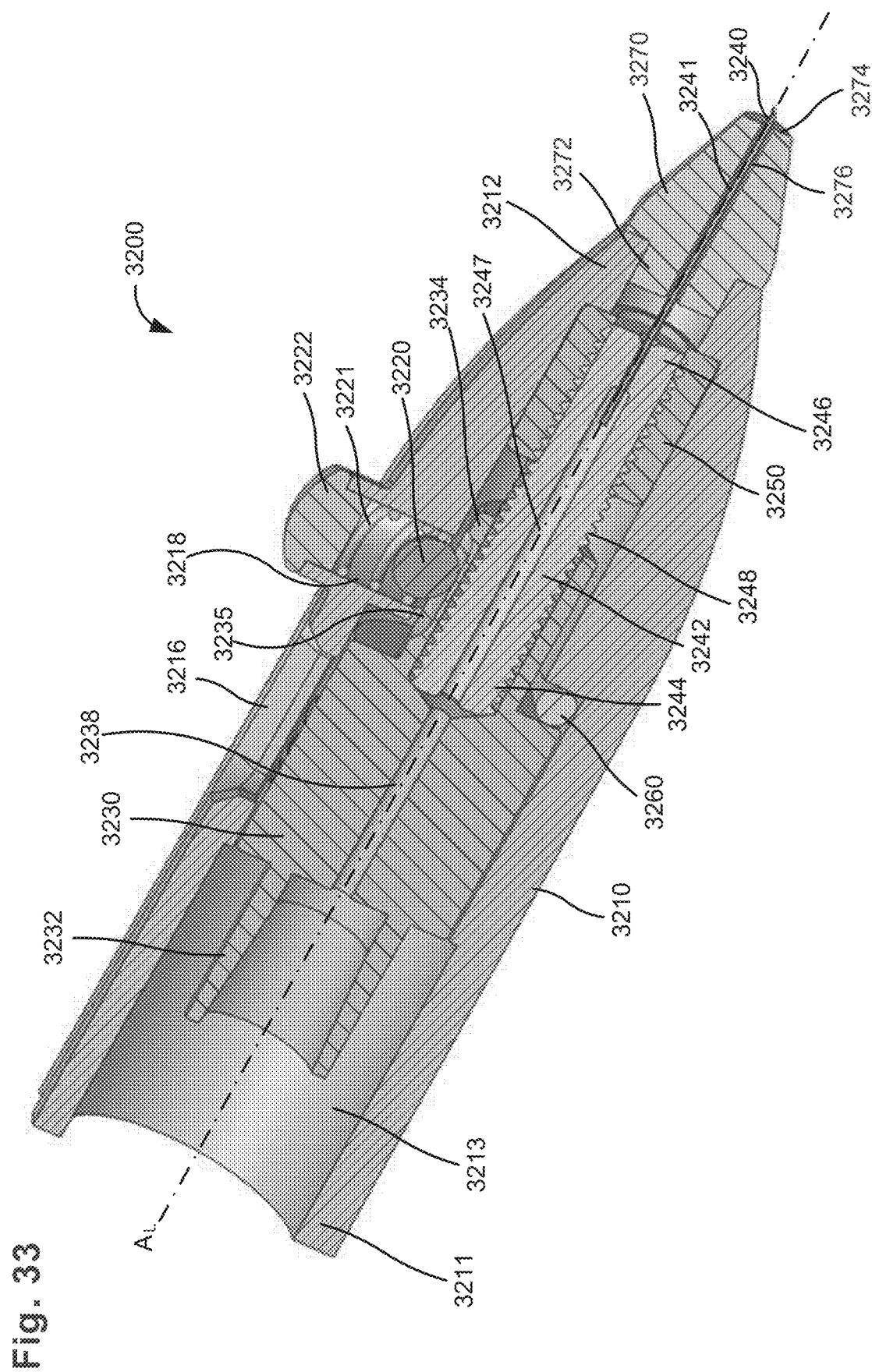
FIG. 33 shows a side cross-section view of the needle assembly of FIG. 32 taken along the line 33-33.

In operation, the needle assembly 3200 is configured to allow a user to adjust a length of the puncturing member 3240 emerging from the distal end of the hub 3270. FIG. 32 shows a perspective view of the needle assembly 3200 and FIG. 33 shows a cross-section of the needle assembly 3200 taken along the line 33-33. While shown as including the hub 3270, any other hub can be coupled to the distal end 3212 of the housing 3210, for example, the hub 7270, 8270, 9270, or any other hub described herein. The proximal portion 3232 of the adjustment member 3230 can be coupled to the delivery portion 3314 of the medicament containment chamber 3310. In a first configuration, a first length of the puncturing member 3240 can be protruding from the distal end 5274 of the hub 5270, for example, about 850 microns. This information can be communicated to the user via the markings 3236 visible to the user through the window 3216. At least a portion of the bearing 3220 is disposed in a first indent 3235 defined on the outer surface of the distal portion 3234 of the adjustment member 3230. The bearing 3220 is biased against the first indent 3235 by the biasing member 3221, and prevents any inadvertent rotation of the adjustment member 3270, thus maintaining the position of adjustment member 3230. In the first configuration, the puncturing member 3240 can protrude a known distance from the distal end 3274 of the hub, for example a length of about 850 microns.

To enable actuation of the needle assembly 3200, the user can remove the locking pin 3260 by pulling on the tab 3262 to remove the locking pin 3260 from the housing 3210. The user then disposes the distal end 3274 of the hub 3270 against the outer surface of the conjunctiva of the eye, which results in the initial length of the puncturing member 3240 being inserted into the eye. Similarly stated, the user can apply a distal force on the system 3000 such that a distal end of the puncturing member 3240 pierces the conjunctiva and is disposed in an ocular tissue layer below the conjunctiva, for example, the sclera. The user can then determine, using any suitable technique, if a distal end of the puncturing member 3240 is within or otherwise near a target layer, for example, the SCS of the eye. In some embodiments, the user can determine that the distal end of the puncturing member 3240 is not in a target layer of the eye, for example, the SCS. For example, in some embodiments, a relative thickness of the ocular tissue layers can be known to the user via prior visualization techniques. In other embodiments the system 3000 can include an injection assembly, for example, the injection assembly 111, 2100, or any other injection assembly described herein, which can be activated and thereby inform the user that the distal end of the puncturing member 3240 is not in the target layer, as described before herein. More particularly, because the injection assembly provides an "injection assist" force within a predetermined range, when the end of the puncturing member 3240 has not reached the SCS, actuation of the injection assembly will not result in movement of the plug within the medicament containment chamber. Thus, the user will receive feedback that the puncturing member 3240 is not in the target region (i.e., by not seeing any movement of the plug).

To move the needle assembly 3200 to a second configuration, the user can apply a first torque to rotate or otherwise twist the medicament containment chamber 3310 such that the adjustment member 3230 rotates relative to the housing 3210 about the longitudinal axis $A_L$. The first torque can urge the bearing 3220 to slide out of the first indent 3235 such that the adjustment member 3230 is free to rotate by application of a second torque substantially smaller than the first torque. The rotation of the adjustment member 3230 urges the lead screw 3242 to also rotate in the bushing 3250. Since the bushing 3250 is fixedly disposed in the internal volume 3213 of the housing 3210, the lead screw 3242 translates linearly along the longitudinal axis $A_L$. This urges the puncturing member 3240 to also translate and advance deeper into the ocular tissue layers. The adjustment member 3230 can be rotated until the bearing 3220 approaches a second indent 3235 of the set of the indents 3235. At least a portion of the bearing 3220 moves into the second indent 3235 and thus prevents further rotation of the adjustment member 3230 by the second torque. Each indent 3235 can correspond to predetermined length of the puncturing member 3240 protruding through the distal end 3274 of the hub 3270. For example, the second indent 3235 can correspond to a protrusion length of the puncturing member 3240 of about 950 microns. A third indent 3235 can correspond to a protrusion length of the puncturing member 3240 of about 1050 microns, and so on. Thus, in some embodiments, each indent 3235 can correspond to a difference in protrusion length of the puncturing member 3240 of about 100 microns. Since, in the second configuration, the bearing 3220 is disposed in the second indent 3235, the adjustment member 3230 can no longer be rotated by application of the second torque. The user can now apply a third torque, greater than the second torque (e.g., substantially equal to the first torque) to further rotate the adjustment member 3230, thereby increasing the protrusion length or otherwise insertion depth of the puncturing member 3240. In this manner, the needle assembly 3200 can serve as a digital length adjustment mechanism to allow the user to adjust a protrusion length or otherwise insertion depth of the puncturing member 3240 in discrete increments, reliably and repeatably. Furthermore, the different torques required for rotation of the adjustment member 3240 at different positions of the bearing 3220 relative to the indents 3235, also provide a tactile feedback to the user in adjusting the protruding length or otherwise insertion depth of the puncturing member 3240.

Figure 34:
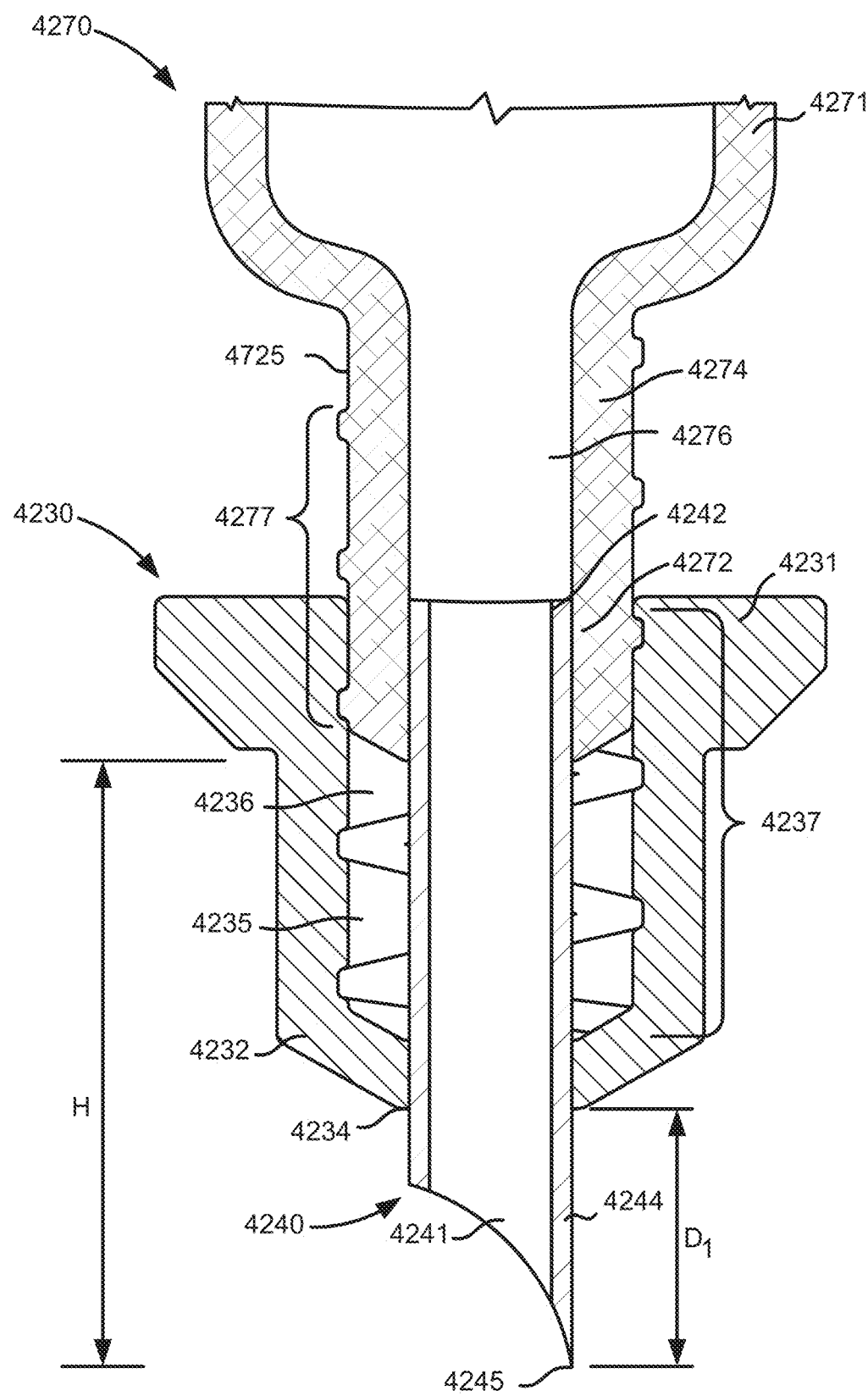
FIG. 34 is a cross-sectional view of a portion of a delivery device according to an embodiment.
Figure 35:
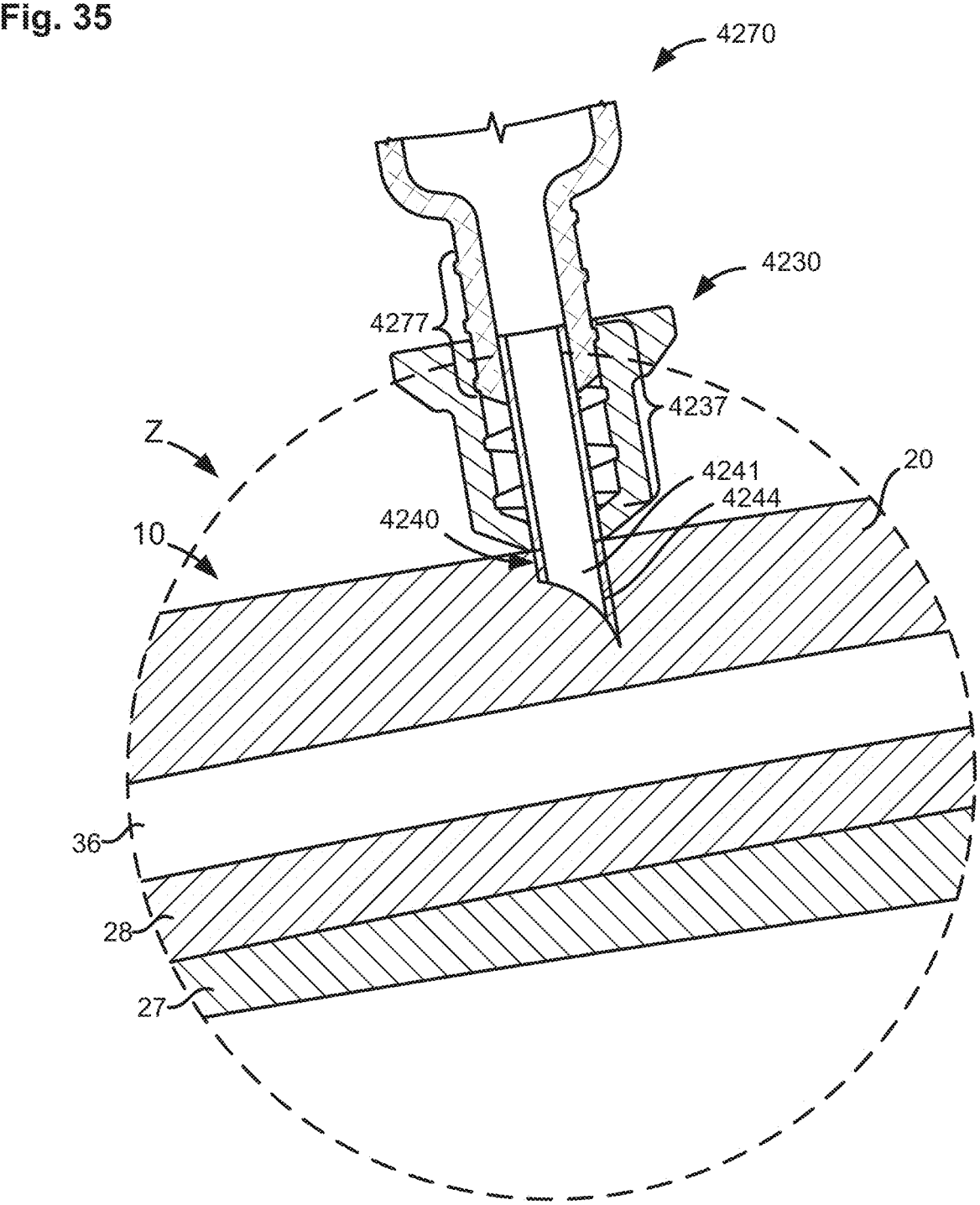
FIG. 35 is an enlarged portion of the eye identified in FIG. 1 as region Z and the portion of the delivery device of FIG. 34 in use, in a first configuration.
Figure 36:
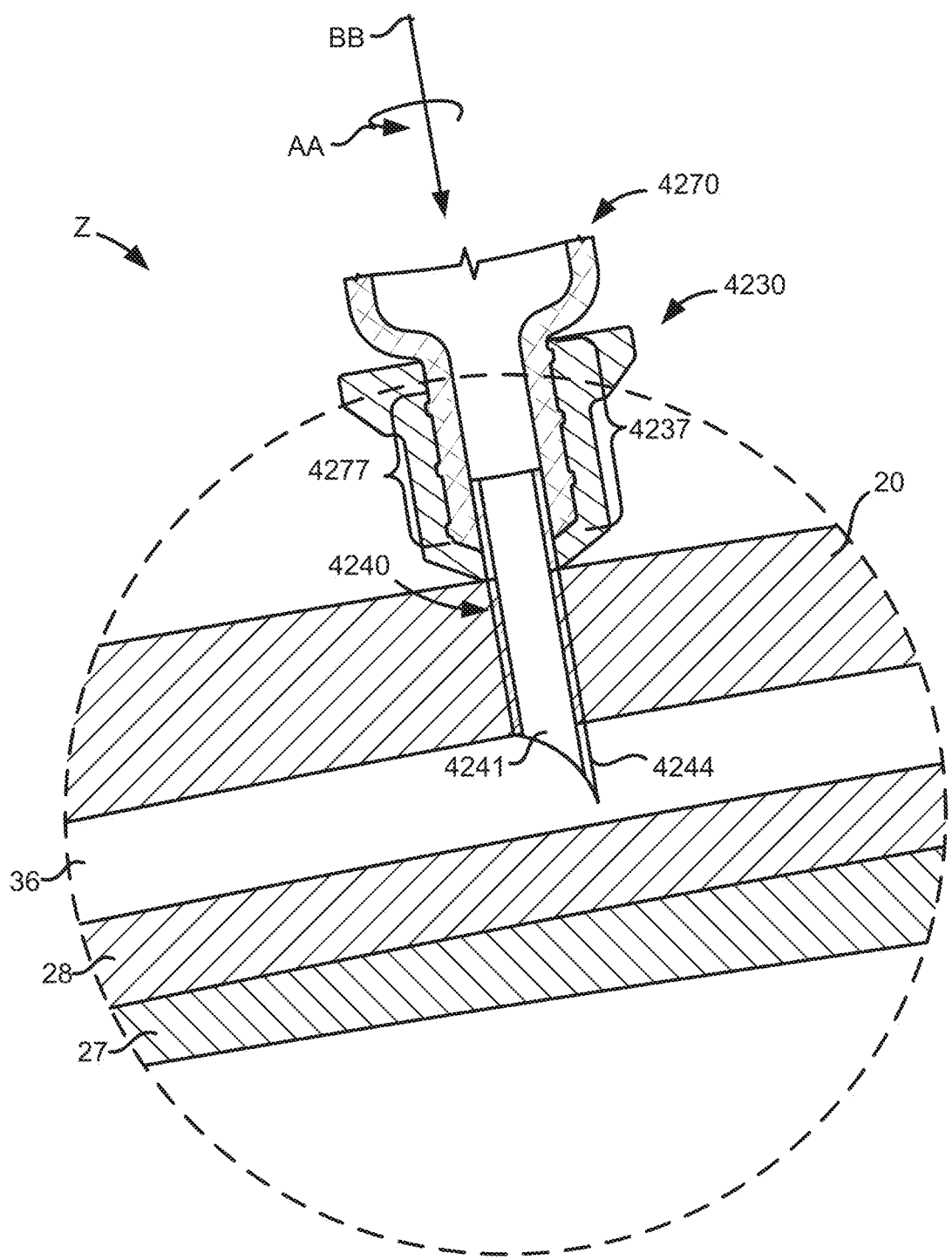
FIG. 36 is the enlarged portion of the eye identified in FIG. 1 as region Z and the portion of the delivery device of FIG. 34 in use, in a second configuration.

In some embodiments, a device includes an adjustment member configured to move relative to a hub and/or a puncture member. Moreover, although being described above as transitionable between a first configuration and a second configuration, in some embodiments, an adjustment member can be transitionable between any number of configurations and/or positions. For example, FIGS. 34-36 are schematic illustrations of a portion of a delivery device according to an embodiment. As shown in FIG. 34, a hub 4270 is coupled to a puncture member 4240 and an adjustment member 4230. The hub 4270 has a proximal end portion 4271 and a distal end portion 4272. The proximal end portion 4271 can be physically and fluidically coupled to a fluid reservoir such as, for example, the housing 4230 of the delivery device 400, 100, 1000, 2000, 3000, or any other delivery device or medical injector described herein). Although not shown in FIGS. 34-36, the proximal end portion 4271 of the hub 4270 can be coupled to a housing of a delivery device using any suitable coupling method such as, for example, a press fit, a snap fit, a threaded coupling, a Luer connection, a mechanical fastener, an adhesive, and/or the like. In other embodiments, the hub 4270 can be monolithically formed with a housing of a delivery device. For example, the hub 4270 can be included in and/or form a distal end portion of a housing (e.g., the medical containment chamber 1310, 2310, 3310, or any other medical containment chamber described herein). Thus, an inner volume of the hub 4270 can be placed in fluid communication with a drug formulation contained within a fluid reservoir (e.g., a medicament container or the like not shown in FIGS. 34-36).

As shown in FIG. 34, the distal end portion 4272 of the hub 4270 includes a substantially elongate portion that includes a set of annular walls 4274. As described in further detail herein, the annular walls 4274 have an outer surface 4275 that includes and/or forms a set of threads 4277 that are configured to engage a portion of the adjustment member 4230. The annular walls 4274 define a lumen 4276 that extends through the distal end portion 4272 of the hub 4270. The lumen 4276 is configured to receive a portion of the puncture member 4240 to physically and fluidically couple the puncture member 4240 to the hub 4270.

The puncture member 4240 (also referred to herein as "microneedle") can be configured to puncture and/or penetrate a portion of the eye to deliver a drug formulation to, for example, the suprachoroidal space. In some embodiments, the puncture member 4240 can be a 32-gauge microneedle or a 34-gauge microneedle. The microneedle 4240 has a proximal end portion 4242 and a distal end portion 4244, and defines a lumen 4241. As shown in FIG. 34, the proximal end portion 4242 is disposed within the lumen 4276 of the hub 4270. For example, in some embodiments, the hub 4270 can be over-molded about the proximal end portion 4242 of the puncture member 4240. In other embodiments, the hub 4270 and the puncture member 4240 can be monolithically formed (e.g., the puncture member 4240 can be a microcatheter or the like that is unitarily formed with the hub 4270). Therefore, with the hub 4270 physically and fluidically coupled to a housing or fluid reservoir (as described above), the lumen 4241 of the puncture member 4240 can be placed in fluid communication with a drug formulation contained therein.

As described above, the lumen 4241 of the puncture member 4240 extends through the proximal end portion 4242 and the distal end portion 4244. In this manner, the lumen 4241 can be placed in fluid communication with a volume substantially outside the microneedle 4240. The distal end portion 4244 can be any suitable shape, size, or configuration. For example, in some embodiments, the distal end portion 4244 can form a bevel or the like. In some embodiments, the distal end portion 4244 can be substantially similar to or the same as those described in the '009 PCT application incorporated by reference above. In this manner, the distal end portion 4244 of the puncture member 4240 can be configured to pierce an ocular tissue while minimizing deformation of the tissue at the insertion site.

As shown, the microneedle 4240 extends from the distal end portion 4272 of the hub 4270 in the distal direction. In this manner, the microneedle 4240 can have a shaft length H between a distal edge 4245 of the puncture member 4240 and a distal surface of the hub 4270. The shaft length H can be any suitable length. For example, in some embodiments, the shaft length H can substantially correspond to at least a portion of the eye. In some embodiments, the shaft length H can be such that when the microneedle 4240 is inserted into the eye, the distal end portion 4244 of the microneedle 4240 is disposed within the suprachoroidal space without puncturing the choroid. By way of example, the shaft length H of the microneedle 4240 can be about 1000 μm or less, about 900 μm or less, about 850 μm or less, about 800 μm or less, about 750 μm or less, about 700 μm or less, about 650 μm or less, about 600 μm or less. In some embodiments, the shaft length H of the microneedle 4240 can be about 750 μm.

In other embodiments, the shaft length of the microneedle 4240 can be about 800 μm, or about 850 μm, or about 900 μm, or about 950 μm, or about 1 mm.

The adjustment member 4230 can be any suitable shape, size, or configuration and can be movably disposed about a portion of the hub 4270 and the puncture member 4240. The adjustment member 4230 has a proximal end portion 4231 and a distal end portion 4232 and defines an opening 4236 therethrough. Moreover, the adjustment member 4230 includes an inner surface 4235 includes and/or forms a set of threads 4237 that can matingly engage the threads 4277 of the hub 4270 (described above). In this manner, the distal end portion 4272 of the hub 4270 can be movably disposed within a portion of the opening 4236. For example, with the distal end portion 4272 of the hub 4270 disposed within the portion of the opening 4236, the adjustment member 4230 can be rotated relative to the hub 4270 to advance the threads 4237 of the adjustment member 4230 along a length of the threads 4277 of the hub 4270. Thus, the adjustment member 4230 can be moved between a first position relative to the hub 4270 (e.g., a distal position, see e.g., FIGS. 34 and 35) and a second position relative to the hub 4270 (e.g., a proximal position, see e.g., FIG. 36). Moreover, the adjustment member 4230 can be moved to any number of different positions relative to the hub 4270.

The arrangement of the hub 4270, the adjustment member 4230 and the puncture member 4240 is such that a portion of the puncture member 4240 is disposed within the opening 4236 defined by the adjustment member 4230 while the distal end portion 4244 of the puncture member 4240 extends beyond a distal surface 4234 of the adjustment member 4230. For example, as shown in FIG. 34, the distal end portion 4244 of the puncture member 4240 can extend a distance $D_1$ (also referred to as an effective length of the puncture member 310) from the distal surface 4234 of the adjustment member 4230. Similarly stated, the distal edge 4245 of the puncture member 4240 is spaced apart from the distal surface of the adjustment member 4230 by the distance $D_1$. Thus, when the adjustment member 4230 is moved a given distance relative to the hub 4270, the effective length of the puncture member 4240 (i.e., the distance $D_1$) is changed by a corresponding distance. By way of example, while the adjustment member 4230 is in the first position relative to the hub 4270 (e.g., the distal position), the distance $D_1$ can be, for example, 350 μm and when the adjustment member 4230 is moved to the second position relative to the hub 4270 (e.g., the proximal position), the distance $D_1$ can be increased to, for example, 650 μm. In other embodiments, the distance $D_1$ can be increased to, for example, 500 μm, 550 μm, 600 μm, 700 μm, 750 μm, 800 μm, 850 μm, 900 μm, 950 μm, or any suitable fraction thereof.

As shown in FIGS. 35 and 36, in use, a user (e.g., a doctor, technician, nurse, physician, ophthalmologist, etc.) can manipulate a delivery device (not shown) to insert the puncture member 4240 into, for example, a portion of the eye 10. In this manner, the distal end portion 4244 of the puncture member 4240 can be advanced through a portion of the sclera 20 until the distal surface 4234 of the adjustment member 4230 is placed in contact with an outer surface of the sclera 20. With the adjustment member 4230 in the first configuration, the distance $D_1$ (e.g., the first distance) between the distal surface 4234 of the adjustment member 4230 and the distal edge 4245 of the puncture member 4240 can substantially depend on and/or be associated with the thickness of the sclera 20. For example, in some embodiments, when the adjustment member 4230 is in the first configuration, the distance $D_1$ (FIG. 34) between the adjustment member 4230 and the distal edge 4245 can be about 450 μm. In other embodiments, the distance $D_1$ when the adjustment member 4230 is in the first configuration can be about 350 μm, 400 μm, 500 μm, 550 μm, 600 μm, 650 μm, 700 μm, 750 μm, or any fraction therebetween. In still other embodiments, the distance $D_1$ when the adjustment member 4230 is in the first configuration can be less than 350 μm. In this manner, the distal edge 4245 of the puncture member 4240 can be disposed within the sclera 20, as shown in FIG. 35. While shown in FIG. 35 as being disposed entirely in the sclera 20, in other embodiments, at least a portion of the distal edge 4245 can be disposed within the suprachoroidal space 36.

The adjustment member 4230 can be moved from its first position relative to the hub 4270 to its second position relative to the hub 4270 to increase the distance $D_1$ (FIG. 34) between the adjustment member 4230 and the distal edge 4245 of the puncture member 4240 from the first distance (FIG. 35) to a second distance, as shown in FIG. 36. For example, in some embodiments, a user can manipulate a grip portion (e.g., a textured finish and/or a set of handles, ribs, detents, grooves, etc.) of the adjustment member 4230 to rotate the adjustment member 4230 relative to the hub 4270, as indicated by the arrow AA in FIG. 36. In this manner, the threads 4237 of the adjustment member 4230 are advanced along a length of the threads 4277 of the hub 4270. Thus, the hub 4270 is moved in a distal direction relative to the adjustment member 4230 such that the adjustment member 4230 is placed its second position relative to the hub 4270, as indicated by the arrow BB in FIG. 36. The movement of the adjustment member 4230 can be performed at any suitable time, i.e., either before or while the puncture member 4240 is disposed within the sclera 20.

Expanding further, by rotating the adjustment member 4230 relative to the hub 4270 (as indicated by the arrow AA), the adjustment member 4230 is placed in its second position relative to the hub 4270. Thus, with the adjustment member 4230 in the second position, the distance $D_1$ (FIG. 34) is increased between the distal surface 4234 of the adjustment member 4230 and the distal edge 4245 of the puncture member 4240 (e.g., to the second distance). In some embodiments, the distance $D_1$ can be increased to about 600 μm. In other embodiments, the distance $D_1$ can be increased to about 650 μm, 700 μm, 750 μm, 800 μm, 850 μm, 900 μm, 950 μm, 1000 μm, or any fraction therebetween. In still other embodiments, the distance $D_1$ can be increased to less that 600 μm (e.g., such as, for example, in use on pediatric eyes).

As shown in FIG. 36, the distal movement of the hub 4270 can allow the distal end portion 4244 of the puncture member 4240 (e.g., in a distal direction) to be moved distally relative to the sclera 20 to place the lumen 4241 of the puncture member 4240 in fluid communication with the suprachoroidal space 36. With the lumen 4241 of the puncture member 4240 in fluid communication with the suprachoroidal space 36, a drug formulation (contained within a fluid reservoir that is in fluid communication with the lumen 4241, for example, as described above with reference to the medical injector 400 of FIGS. 19-20) can be expelled through the lumen 4241 of the puncture member 4240 and into the suprachoroidal space 36 of the eye 10. In this manner, the drug formulation can flow within the suprachoroidal space 36 to be delivered to, for example, the posterior region of the eye (e.g., the posterior region 14 of the eye 10 in FIG. 1). Moreover, with the adjustment member 4230 in the second configuration, the distance between the distal surface 4234 of the adjustment member 4230 and the distal edge 4245 of the puncture member 4240 (e.g., the distance $D_1$ in FIG. 34) can be less than a combined thickness of the sclera 20 and the suprachoroidal space 36 such that the distal end portion 4244 of the puncture member 4240 does not pierce the choroid 28.

In some embodiments, the relative position of the distal edge 4245 of the puncture member 4240 within the eye can be localized (e.g., determined, realized, etc.) via any suitable method. For example, in some instances, the amount of force exerted to advance the distal edge 4245 of the puncture member 4240 through the sclera 20 can be greater than an amount of force exerted to advance the distal edge 4245 through the suprachoroidal space 36. Thus, reduction in the amount of force that is exerted to advance the distal end portion 4244 of the puncture member 4240 can indicate to a user the relative position of the distal edge 4245 of the puncture member 4240 in the eye. In some instances, imagining techniques (e.g., fluoroscopy, X-ray Computed Tomography (CT) scans, or the like) can be used to provide an indication of the relative position of the distal edge 4245 with respect to the anatomy of the target tissue.

Although not shown in FIGS. 34-36, in some embodiments, the hub 4270 and/or the adjustment member 4230 can provide an indicator associated with the distance $D_1$ between the adjustment member 4230 and the distal edge 4245 of the puncture member 4240. In some embodiments, the indicator can be a visual indicator such as a measuring scale or the like. For example, in some embodiments, the puncture member 4240 can include indicia (e.g., lines, markings, tic marks, etc.) that represents a gradation of a length of the puncture member 4240 associated with the distance $D_1$ between the distal surface 4234 of the adjustment member 4230 and the distal edge 4245 of the puncture member 4240. In some embodiments, the markings can represent distances of 100 microns or less. In this manner, a user can view the indicia to determine, for example, a change in the distance $D_1$ that would otherwise be indeterminate. In other embodiments, the adjustment member 4230 and/or the hub 4270 can produce a audible or haptic indicator such as, for example, a "clicking" sound or the like.

Although the adjustment member 4230 is described above with reference to FIGS. 34-36 as rotating about the hub 4270 to change the distance (e.g., the distance $D_1$ in FIG. 34) between the distal surface 4234 of the adjustment member 4230 and the distal edge 4245 of the puncture member 4240, in other embodiments, an adjustment member can be transitioned relative to a hub in any suitable manner. For example, in some embodiments, an outer surface of a hub can include a set of protrusions that can engage a set of detents defined by an inner surface of an adjustment member (or vice versa). In such embodiments, the adjustment member can be moved linearly relative to the hub such that the detents of the adjustment member sequentially engage the protrusions of the hub.

Figure 37:
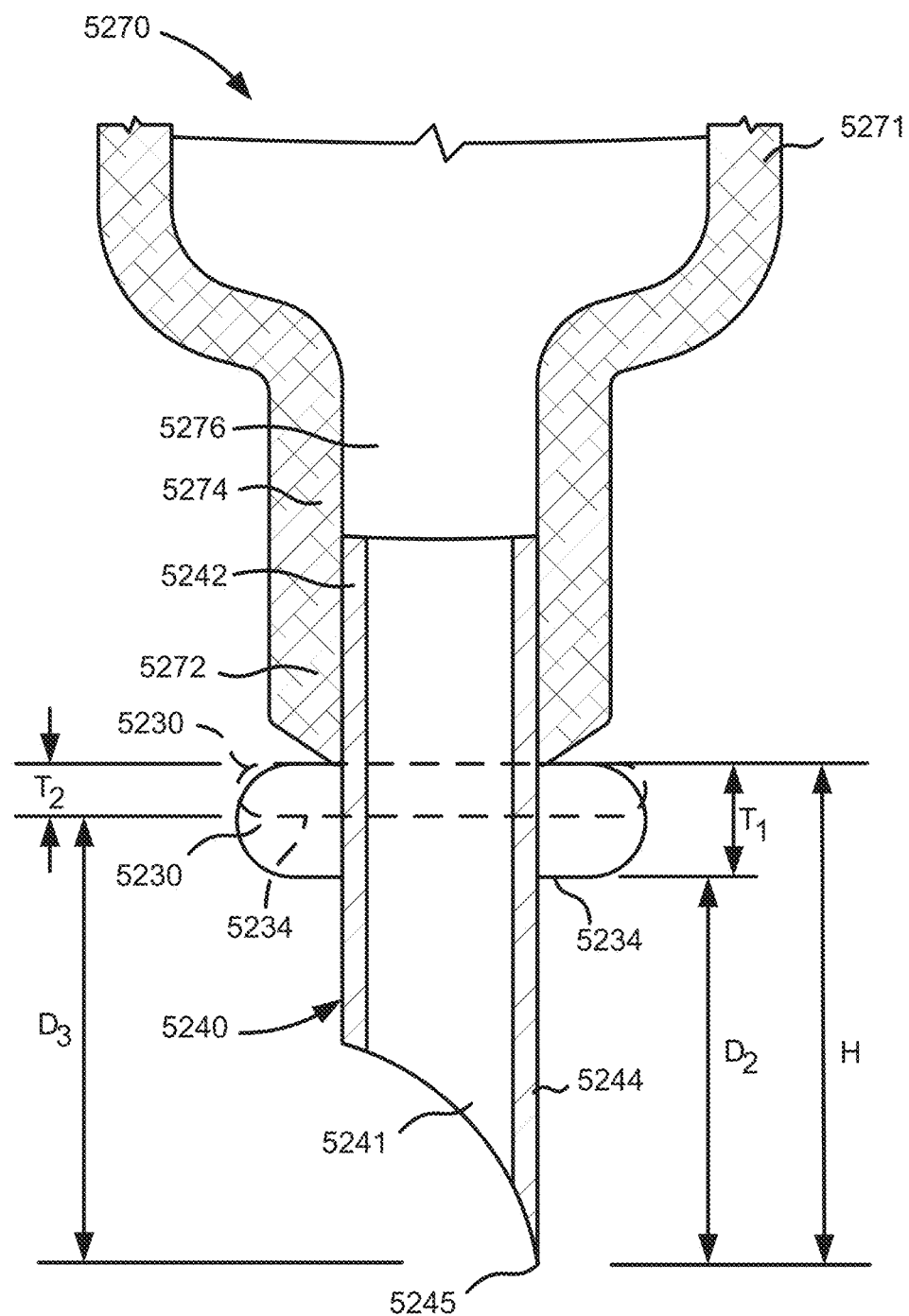
FIG. 37 is a cross-sectional view of a portion of a delivery device according to an embodiment.

FIG. 37 is a schematic illustration of a portion of a delivery device according to an embodiment. As shown, a hub 5270 is coupled to a puncture member 5240 and an adjustment member 5230. The hub 5270 has a proximal end portion 5271 and a distal end portion 5272. The proximal end portion 5271 can be physically and fluidically coupled to a fluid reservoir such as, for example, the medicament container 430 of the medical injector 400 described above with reference to FIGS. 19-20, or any other medicament container described herein. Although not shown in FIG. 37, the proximal end portion 5271 of the hub 5270 can be coupled to a housing (e.g., a medicament container) of a delivery device using any suitable coupling method such as, for example, a press fit, a snap fit, a threaded coupling, a Luer connection, a mechanical fastener, an adhesive, and/or the like. In other embodiments, the hub 5270 can be monolithically formed with a housing of a delivery device. For example, the hub 5270 can be included in and/or form a distal end portion of a housing (e.g., distal end portion 434 of the medicament container 430). Thus, an inner volume of the hub 5270 can be placed in fluid communication with a drug formulation contained within a fluid reservoir (e.g., a medicament container), as described above with reference to the hub 4270 of FIGS. 34-36. As shown in FIG. 37, the distal end portion 5272 of the hub 5270 can be a substantially elongate portion that includes and/or is formed from a set of annular walls 5274. As described in further detail herein, the annular walls 5274 define a lumen 5276 that extends through the distal end portion 5272 of the hub 5270. The lumen 5276 is configured to receive a portion of the puncture member 5240 to physically and fluidically couple the puncture member 5240 to the hub 5270.

The puncture member 5240 (also referred to herein as "microneedle") can be configured to puncture and/or penetrate a portion of the eye to deliver a drug formulation to, for example, the suprachoroidal space. The microneedle 5240 has a proximal end portion 5242 and a distal end portion 5244, and defines a lumen 5241. As shown in FIG. 37, the proximal end portion 5242 is disposed within the lumen 5276 of the hub 5270. For example, in some embodiments, the hub 5270 can be over-molded about the proximal end portion 5242 of the puncture member 5240. In other embodiments, the hub 5270 and the puncture member 5240 can be monolithically formed (e.g., the puncture member 5240 can be a microcatheter or the like that is unitarily formed with the hub 5270). Therefore, with the hub 5270 physically and fluidically coupled to a housing or fluid reservoir (as described above), the lumen 5241 of the puncture member 5240 can be placed in fluid communication with a drug formulation contained therein.

As shown, the microneedle 5240 extends from the distal end portion 5272 of the hub 5270 in the distal direction. In this manner, the microneedle 5240 can have a shaft length H between a distal edge 5245 of the puncture member 5240 and a distal surface of the hub 5270. In this manner, the puncture member 5240 can be substantially similar to or the same as the puncture member 4240 described above with reference to FIGS. 34-46. Thus, portions of the puncture member 5240 are not described in further detail herein.

The adjustment member 5230 can be any suitable shape, size, or configuration and is transitionable between a first configuration and a second configuration. The adjustment member 5230 is coupled to the distal end portion 5272 of the hub 5270. For example, in some embodiments, the adjustment member 5230 can be coupled to the hub 5270 via a press fit, a snap fit, a threaded coupling, mechanical fastener, an adhesive, and/or the like. In other embodiments, the adjustment member 5230 can be disposed about a portion of the puncture member 5240 such that a portion of the adjustment member 5230 is in contact with the distal end portion 5272 of the hub 5270 (e.g., adjacent to yet not coupled to the hub 5270). In this manner, the hub 5270 and the puncture member 5240 can be reusable (after sterilization) and can be temporarily coupled to a disposable adjustment member 5230. In some embodiments, the adjustment member 5230 and the hub 5270 can be monolithically formed. In some embodiments, the adjustment member 5230 can be over-molded about the distal end portion 5272 of the hub 5270. For example, in some embodiments, the hub 5270 can be formed from a relatively rigid material such as a metal or hard plastic and can act as a substrate about which the adjustment member 5230 is molded (e.g., from a relatively soft material such as an elastomeric material, thermoplastic, rubber, silicone, or the like). As shown in FIG. 37, when the adjustment member 5230 is in the first configuration, the adjustment member 5230 has a thickness $T_1$. In some embodiments, the thickness $T_1$ of the adjustment member 460 can be, for example, about 25 µm, 50 µm, 100 µm, 400 µm, or any suitable fraction therebetween. In other embodiments, the adjustment member 5230 can have a thickness $T_1$ that is greater than 400 µm. In other embodiments, the overall thickness $T_1$ of the adjustment member 5230 can be less than about 25 µm.

The adjustment member 5230 is removably disposed about a portion of the puncture member 5240. More specifically, the puncture member 5240 can extend in the distal direction from the hub 5270 such that a portion of the puncture member 5240 extends through the adjustment member 5230. For example, as shown in FIG. 37, the distal end portion 5244 of the puncture member 5240 can extend a distance (i.e., $D_2$ or $D_3$) from a distal surface 5234 of the adjustment member 5230. Similarly stated, the distal edge 5245 of the puncture member 5240 is spaced apart from the distal surface 5234 of the adjustment member 5230 by the distance $D_2$ (also referred to as an effective length of the puncture member 5240). As described above, the adjustment member 5240 can be transitioned between a first configuration and a second configuration. More specifically, the first configuration can be associated with the first thickness $T_1$ of the adjustment member 5230 and the second configuration can be associated with a second thickness $T_2$. Thus, when the adjustment member 5230 is moved from the first configuration to the second configuration (e.g., from the first thickness $T_1$ to the second thickness $T_2$), the effective length of the puncture member 5240 between the distal edge 5245 of the puncture member 5240 and the distal surface 5234 of the adjustment member 5230 is increased by a corresponding distance (e.g., increased from the first distance $D_1$ to a second distance $D_3$). Similarly stated, the nominal change in the thickness from the first thickness $T_1$ to the thickness $T_2$ substantially corresponds with (or is the same as) the nominal change in distance from the first distance $D_2$ to the second distance $D_3$. By way of example, while the adjustment member 5230 is in the first configuration, the first thickness $T_1$ can be, for example, 250 µm and the first distance $D_2$ can be, for example, about 450 µm. When the adjustment member 5230 is moved to the second configuration, the second thickness $T_2$ of the adjustment member 5230 can be, for example, 100 µm and the second distance $D_3$ can be, for example, about 600 µm.

In use, a user (e.g., a doctor, technician, nurse, physician, ophthalmologist, etc.) can manipulate a delivery device (not shown) to insert the puncture member 5240 into, for example, a portion of the eye (e.g., the eye 10 shown in FIG. 1). In this manner, the distal end portion 5244 of the puncture member 5240 can be advanced through a portion of the sclera until the distal surface 5234 of the adjustment member 5230 is placed in contact with an outer surface of the sclera. With the adjustment member 5230 in the first configuration, the distance $D_2$ (e.g., the first distance) between the distal surface 5234 of the adjustment member 5230 and the distal edge 5245 of the puncture member 5240 can substantially depend on and/or can be associated with the thickness of the sclera. For example, in some embodiments, when the adjustment member 5230 is in the first configuration, the distance $D_2$ between the distal surface 5234 of the adjustment member 5230 and the distal edge 5245 can be about 550 µm. In other embodiments, the distance $D_2$ when the adjustment member 5230 is in the first configuration can be about 350 µm, 400 µm, 450 µm, 500 µm, 600 µm, 650 µm, 700 µm, 750 µm, 800 µm, 850 µm, 900 µm, 950 µm, 1000 µm, or any fraction therebetween. In still other embodiments, the distance $D_2$ when the adjustment member 5230 is in the first configuration can be less than about 350 µm. In this manner, a distal edge 5245 of the puncture member 5240 can be disposed within the sclera (e.g., the sclera 20 of the eye 10 in FIG. 1).

The adjustment member 5230 can be moved from its first configuration to its second configuration to increase the distance between the distal surface 5234 of the adjustment member 5230 and the distal edge 5245 of the puncture member 5240 from the first distance $D_2$ to the second distance $D_3$. For example, in some instances, a user can exert a force (either directly or indirectly) on the hub 5270 to advance the puncture member 5240 relative to the eye. With the distal surface 5234 of the adjustment member 5230 in contact with an outer surface of the sclera, the force exerted on the hub 5270 can be operable in compressing the adjustment member 5230 from the first thickness $T_1$ to the second thickness $T_2$. Thus, the adjustment member 5230 is placed in the second configuration and the distance between the distal surface 5234 of the adjustment member 5230 is increased from the first distance $D_2$ to the second distance $D_3$. For example, in some instances, the second distance $D_3$ can be about 600 µm. In other embodiments, the second distance $D_3$ can be about 650 µm, 700 µm, 750 µm, 800 µm, 850 µm, 900 µm, 950 µm, 1000 µm, or any fraction therebetween. In still other embodiments, the second distance $D_3$ can be increased to less than about 600 µm (e.g., such as, for example, in use on pediatric eyes).

As described above with reference to FIG. 36, the movement of the adjustment member 5230 to the second configuration can be such that further movement of the puncture member 5240 (e.g., in a distal direction) relative to the sclera places the lumen 5241 of the puncture member 5240 in fluid communication with the suprachoroidal space (e.g., the suprachoroidal space 36 of the eye 10 in FIG. 1). Similarly stated, the increase in distance from the first distance $D_2$ to the second distance $D_3$ can be sufficiently large to extend the distal edge 5245 of the puncture member 5240 through the sclera such that the lumen 5241 is placed in fluid communication with the suprachoroidal space. With the lumen 5241 of the puncture member 5240 in fluid communication with the suprachoroidal space, a drug formulation (contained within a fluid reservoir as described above with reference to FIG. 36) can be expelled through the lumen 5241 of the puncture member 5240 and into the suprachoroidal space of the eye. In this manner, the drug formulation can flow within the suprachoroidal space to be delivered to, for example, the posterior region of the eye (e.g., the posterior region 14 of the eye 10 in FIG. 1). Moreover, with the adjustment member 5230 in the second configuration, the distance between the distal surface 5234 of the adjustment member 5230 and the distal edge 5245 of the puncture member 5230 (e.g., the second distance $D_3$) can be less than a combined thickness of the sclera and the suprachoroidal space such that the distal end portion 5244 of the puncture member 5240 does not pierce the choroid.

In addition to adjusting and/or controlling the effective length of the puncture member 5240 to enhance the likelihood that the lumen 5241 is placed in fluid communication with the desired region of the target tissue (e.g., the suprachoroidal space of the eye), in some embodiments, the adjustment member 5230 (and any of the adjustment members shown and described herein) can form a substantially fluid-tight seal and/or a substantially liquid-tight seal with the outer surface of the target tissue (e.g., the conjunctiva of the eye). In this manner, leakage of the injected medicament along the needle track during the injection event can be reduced and/or eliminated. Expanding further, in some embodiments, the anatomy of the target tissue and/or the arrangement of the delivery device can be such that, in use, a portion of the opening of the lumen 5241 may be placed in fluid communication with the suprachoroidal space 36 of the eye, while another portion of the opening of the lumen 5241 may be positioned within the sclera 20. Thus, when the drug formulation is conveyed into the eye via the puncture member 5240, a portion of the drug formulation may be prone to migrating away from the desired region (e.g., the suprachoroidal space 36) and out of the eye via the needle track. By forming a substantially fluid-tight seal and/or a substantially liquid-tight seal, the adjustment member 5230 can produce an area of high resistance to flow, thus minimizing and/or eliminating the flow migration and/or leakage.

Although the adjustment member 5230 is described above as being constructed from a relatively soft material, which can be well suited to forming a fluid-tight seal, in some embodiments, the adjustment member 5230 can be constructed from multiple materials. For example, in some embodiments, the distal end surface 5234 of the adjustment member 5230 can be constructed from and/or can include a layer or portion constructed from a material formulated to form a substantially fluid-tight seal with the outer surface of the target tissue (e.g., the conjunctiva).

Although not shown in FIG. 37, in some embodiments, the adjustment member 5230 and/or the puncture member 5240 can include a locking feature that can be configured to at least temporarily retain the adjustment member 5230 in the second configuration. For example, in some embodiments, the puncture member 5240 and/or hub 5270 can include one or more detents, grooves, protrusions, etc. that can matingly engage a portion of the adjustment member 5230 to retain the adjustment member 5230 in the second configuration. More specifically, in some embodiments, the adjustment member 5230 can include a set of protrusions (not shown) that extend from the adjustment member toward the puncture member 5240. In such embodiments, the adjustment member 5230 can be moved to the second configuration to decrease the thickness of the adjustment member (as described above). In this manner, the protrusions can move along a surface of the puncture member 5240 while the adjustment member 5230 is being moved to the second configuration. Once the adjustment member 5230 is in the second configuration, the protrusions can matingly engage a set of detents that can at least temporarily retain the protrusions therein. Thus, the adjustment member 5230 can be at least temporarily locked in the second configuration. In other embodiments, the adjustment member 5230 and the puncture member 5240 do not include a locking feature and a user can exert a substantially constant force to retain the adjustment member 5230 in the second configuration.

In some embodiments, the puncture member 5240 and/or the adjustment member 5230 can include a visual indicator that is associated with the distance between the distal surface 5234 of the adjustment member 5230 and the distal edge 5245 of the puncture member 5240. For example, in some embodiments, the puncture member 5240 can include a measurement indicator. In such embodiments, a user determine the distance between the distal surface 5234 of the adjustment member 5230 and the distal edge 5245 of the puncture member 5240 by visually inspecting the measurement indicator.

Figure 38:
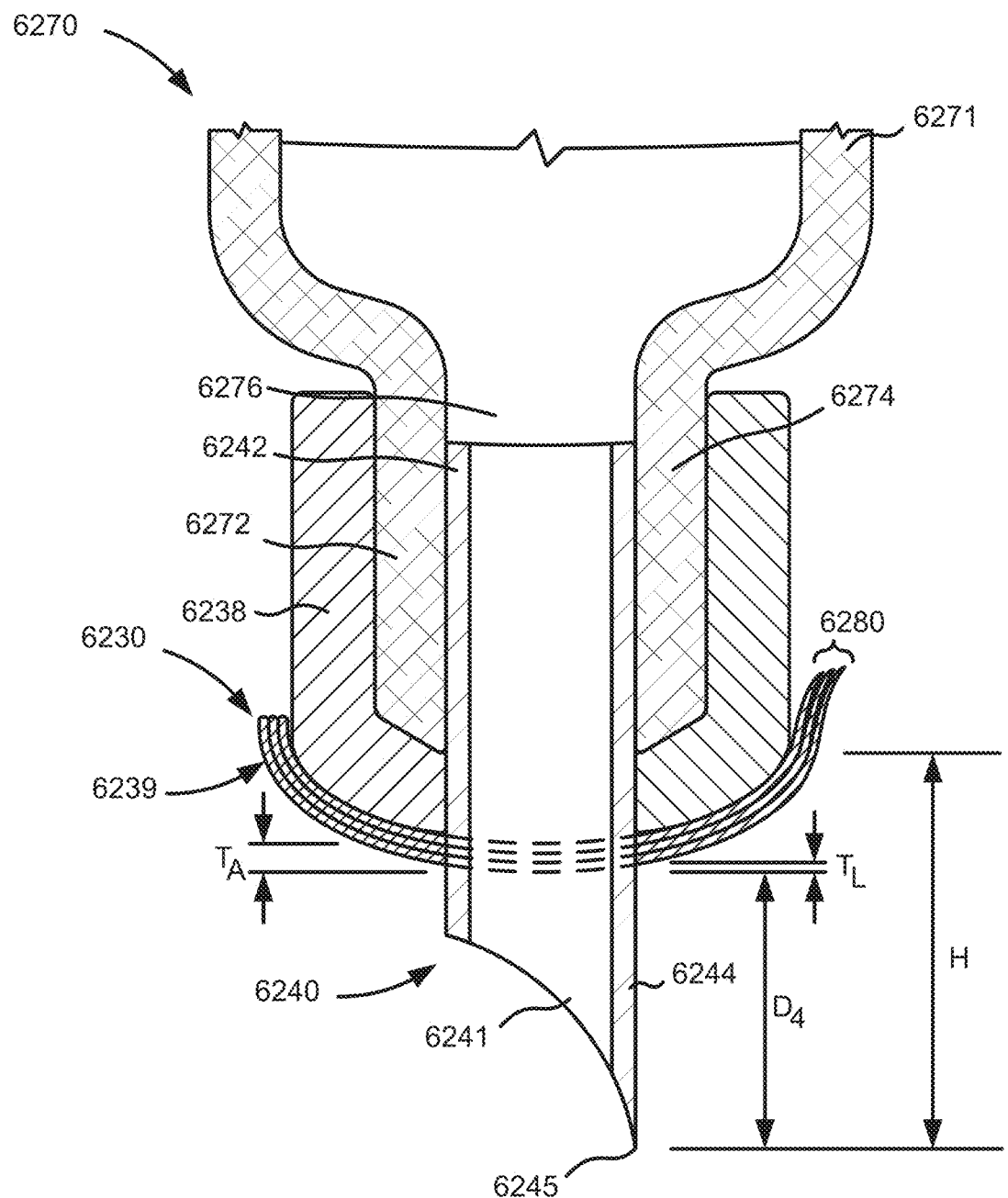
FIG. 38 is a cross-sectional view of a portion of a delivery device according to an embodiment.

FIG. 38 is a schematic illustration of a portion of a delivery device according to an embodiment. As shown, a hub 6270 is coupled to a puncture member 6240 and an adjustment member 6230. The hub 6270 has a proximal end portion 6271 and a distal end portion 6272. The proximal end portion 6271 can be physically and fluidically coupled to a fluid reservoir such as, for example, the medicament container 430 of the medical injector 400 described above with reference to FIGS. 19-20. Although not shown in FIG. 38, the proximal end portion 6271 of the hub 6270 can be coupled to a housing (e.g., a medicament container) of a delivery device using any suitable coupling method such as, for example, a press fit, a snap fit, a threaded coupling, a Luer connection, a mechanical fastener, an adhesive, and/or the like. In other embodiments, the hub 6270 can be monolithically formed with a housing of a delivery device. For example, the hub 6270 can be included in and/or form a distal end portion of a housing (e.g., the distal end portion 343 of the housing 430). Thus, an inner volume of the hub 6270 can be placed in fluid communication with a drug formulation contained within a fluid reservoir (e.g., a housing), as described above with reference to the hub 6270 of FIGS. 34-36. As shown in FIG. 38, the distal end portion 6272 of the hub 6270 can be a substantially elongate portion that includes and/or is formed from a set of annular walls 6274. The annular walls 6274 define a lumen 6276 that extends through the distal end portion 6272 of the hub 6270. The lumen 6276 is configured to receive a portion of the puncture member 6270 to physically and fluidically couple the puncture member 6270 to the hub 6270.

The puncture member 6240 (also referred to herein as "microneedle") can be configured to puncture and/or penetrate a portion of the eye to deliver a drug formulation to, for example, the suprachoroidal space. The microneedle 6240 has a proximal end portion 6242 and a distal end portion 6244, and defines a lumen 6241. As described above, the proximal end portion 6242 is disposed within the lumen 6276 of the hub 6270. For example, in some embodiments, the hub 6270 can be over-molded about the proximal end portion 6242 of the puncture member 6240. In other embodiments, the hub 6270 and the puncture member 6240 can be monolithically formed (e.g., the puncture member 6240 can be a microcatheter or the like that is unitarily formed with the hub 6270). Therefore, when the hub 6270 is physically and fluidically coupled to a housing or fluid reservoir (as described above), the lumen 6241 of the puncture member 6240 can be placed in fluid communication with a drug formulation contained therein.

As shown, the microneedle 6240 extends from the distal end portion 6272 of the hub 6270 in the distal direction. The microneedle 6240 has a shaft length H between a distal edge 6245 of the puncture member 6240 and a distal surface of the hub 6270. In this manner, the puncture member 6240 can be substantially similar to or the same as the puncture member 6240 described above with reference to FIGS. 34-36. Thus, portions of the puncture member 6240 are not described in further detail herein.

The adjustment member 6230 can be any suitable shape, size, or configuration and can be disposed about a portion of the hub 6270 and/or the puncture member 6240. For example, although some of the adjustment members are described herein as being monolithic, in other embodiments, such as here, an adjustment member can be constructed from multiple different components that are joined together. In particular, the adjustment member 6230 includes a base 6238 and a set of removable layers 6239. The base 6238 is coupled to the distal end portion 6272 of the hub 6270. For example, in some embodiments, the base 6238 can be removably coupled to the hub 6270 (e.g., via a press fit, a snap fit, a threaded coupling, mechanical fastener, and/or the like). In this manner, the hub 6270 can be reusable (after sterilization) and can be temporarily coupled to a disposable adjustment member 6230. In other embodiments, the base 6238 can be fixedly coupled to the hub 6270 (e.g., via an adhesive, ultrasonic welding, and/or the like).

The set of layers 6239 is comprised of relatively thin strips that are sequentially stacked on one another. More specifically, a first layer 6239 is removably coupled to the base 6238 and each subsequent layer 6239 is stacked on top of the preceding layer. In some embodiments, the layers 6239 can be relatively thin strips of a self-adhering flexible material such as sheets of polyethylene, polyvinylidene chloride, polypropylene, polyacrylate, or the like. In other embodiments, the layers 6239 can be at least temporarily retained to each other and/or to the hub via an adhesive. In such embodiments, the layers 6239 can be retained by one or more adhesive material having varying adhesive strengths. For example, in some embodiments, the adhesive strength between adjacent layers 6239 can increase from a first adhesive strength between the distal-most layer and its adjacent layer and a second adhesive strength between the proximal-most layer and its adjacent layer. In some embodiments, each layer can be adhered to an adjacent layer by a unique adhesive. In other embodiments, each layer can be adhered to an adjacent layer by the same adhesive with, for example, varying adhesive strengths. In yet other embodiments, the layers can be retained via a combination of an adhesive and one or more self-adhesive material. In this manner, one or more layers 6239 can be removed from the set of layers 6239 to transition the adjustment member 6230 from the first configuration to the second configuration. Moreover, by varying the properties of the adhesive, the user can more easily remove the desired layer(s) without inadvertently removing additional layers.

As shown in FIG. 38, each layer 6239 has a thickness $T_L$. In some embodiments, the thickness $T_L$ of each layer 6239 can be, for example, about 5 µm, 10 µm, 20 µm, 30 µm, 40 µm, 50 µm, 100 µm, or any suitable fraction therebetween. In other embodiments, a layer 6239 can have a thickness $T_L$ that is greater than 100 µm. Although each layer 6239 is shown and described as having substantially the same thickness $T_L$, in other embodiments, the layers 6239 can have varying thickness. As shown in FIG. 38, the set of layers 6239 can have an overall thickness $T_A$ that is the sum of the thicknesses $T_L$ of each stacked layer 6239. For example, in some embodiments, the overall thickness $T_A$ of the set of layers 6239 can be about 50 µm, 100 µm, 150 µm, 200 µm, 250 µm, 300 µm, 400 µm, 500 µm, 1000 µm, or any suitable fraction therebetween. In other embodiments, the overall thickness $T_A$ of the set of layers 6239 can be less than about 50 µm. In still other embodiments, the overall thickness $T_A$ of the set of layers 6239 can be greater than about 1000 µm. Although three removable layers 6239 are shown in FIG. 38, in other embodiments, an adjustment member can include any suitable number of removable layers (e.g., two layers, four layers, five layers, six layers, seven layers, eight layers, nine layers ten layers, or more).

As described above, the adjustment member 6230 is disposed about a portion of the hub 6270 and the puncture member 6270. More specifically, the puncture member 6240 can extend in the distal direction from the hub 6240 such that a portion of the puncture member 6240 extends through the adjustment member 6230 (e.g., through the base 6238 and the set of layers 6239). For example, as shown in FIG. 38, the distal end portion 6244 of the puncture member 6240 can extend a distance $D_4$ from the outermost layer 6239 of the adjustment member 6230 (also referred to as an effective length of the puncture member 6240). Similarly stated, the distal edge 6245 of the puncture member 6240 is spaced apart from a distal surface of the adjustment member 6230 (e.g., the outermost layer 6239) by the distance $D_4$. Thus, when a layer 6239 is removed from the set of layers 6239 of the adjustment member 6230, the effective length of the puncture member 6240 (e.g., the distance $D_4$) is increased by a distance that substantially corresponds to the thickness $T_L$ of the layer 6239 that was removed. By way of example, while the adjustment member 6230 is in the first configuration (e.g., where all the layers included in the set of layers 6239 are stacked), the distance $D_4$ can be, for example, about 550 µm and when the adjustment member 6230 is moved to the second configuration (e.g., when one or more layers are removed from the set of layers 6239), the distance $D_4$ can be increased to, for example, about 650 µm. In other embodiments, the effective length of the puncture member 6240 can be increased to 600 µm, 700 µm, 750 µm, 800 µm, 850 µm, 900 µm, 950 µm, 1000 µm, or any suitable fraction therebetween.

In use, a user (e.g., a doctor, technician, nurse, physician, ophthalmologist, etc.) can manipulate a delivery device (not shown) to insert the puncture member 6240 into, for example, a portion of the eye (e.g., the eye 10 shown in FIG. 1). In this manner, the distal end portion 6244 of the puncture member 6240 can be advanced through a portion of the sclera until an outermost layer of the set of layers 6239 included in the adjustment member 6230 is placed in contact with an outer surface of the sclera. With the adjustment member 6230 in the first configuration, the distance $D_4$ (e.g., a first distance) between the outermost layer 6239 of the adjustment member 6230 and the distal edge 6245 of the puncture member 6240 can substantially depend on and/or can be associated with the thickness of the sclera. For example, in some embodiments, when the adjustment member 6230 is in the first configuration, the distance $D_4$ between the outermost layer 6239 of the adjustment member 6230 and the distal edge 6245 can be about 450 µm. In other embodiments, the distance $D_4$ when the adjustment member 6230 is in the first configuration can be about 350 µm, 400 µm, 500 µm, 550 µm, 600 µm, 650 µm, 700 µm, 750 µm, or any fraction therebetween. In still other embodiments, the distance $D_4$ when the adjustment member 6230 is in the first configuration can be less than about 350 µm. In yet other embodiments, the distance $D_4$ when the adjustment member 6230 is in the first configuration can be greater than 750 µm. In this manner, a distal edge 6245 of the puncture member 6240 can be disposed within the sclera (e.g., the sclera 20 of the eye 10 in FIG. 1).

The adjustment member 6230 can be moved from its first configuration to its second configuration to increase the distance $D_4$ between the outermost layer 6239 of the adjustment member 6230 and the distal edge 6245 of the puncture member 6240 from the first distance to a second distance. For example, in some embodiments, a user can manipulate an engagement portion 6280 of one or more layers to remove (e.g., peel, tear, shear, break away, etc.) the one or more layers from the stack of layers 6239 (i.e., the set of layers). In this manner, the overall thickness $T_A$ of the set of layers 6239 is reduced by the combined thicknesses $T_L$ of each layer that is removed. Expanding further, by removing the one or more layers, the overall thickness $T_4$ of the set of layers 6239 is reduced, thereby placing the adjustment member in the second configuration. Thus, with the adjustment member 6230 in the second configuration, the distance $D_4$ is increased between the current outermost layer (e.g., the outermost layer after removing the one or more layers) and the distal edge 6245 of the puncture member 6240 (e.g., to a second distance). In some embodiments, the distance $D_4$ can be increased to about 600 µm. In other embodiments, the distance $D_4$ can be increased to about 650 µm, 700 µm, 750 µm, 800 µm, 850 µm, 900 µm, 950 µm, 1000 µm, or any fraction therebetween. In still other embodiments, the distance $D_4$ can be increased to less than about 600 µm (e.g., such as, for example, in use on pediatric eyes). By way of example, in some embodiments, the adjustment member 6230 can include a set of 10 layers 6239 with each layer having a thickness of about 50 µm. In such embodiments, the distance $D_4$ between the outermost layer 6239 and the distal edge 6245 can be, for example, about 450 µm. In some instances, three layers can be removed from the set of 10 layers 6239 to increase the distance $D_4$ to about 600 µm.

In addition to adjusting and/or controlling the effective length of the puncture member 6240 (e.g., by manipulating a layer from the stack of layers 6239) to enhance the likelihood that the lumen 6241 is placed in fluid communication with the desired region of the target tissue (e.g., the suprachoroidal space of the eye), in some embodiments, the adjustment member 6230 (and any of the adjustment members shown and described herein) can form a substantially fluid-tight seal and/or a substantially liquid-tight seal with the outer surface of the target tissue (e.g., the conjunctiva of the eye). In this manner, leakage of the injected medicament along the needle track during the injection event can be reduced and/or eliminated. Expanding further, in some embodiments, the anatomy of the target tissue and/or the arrangement of the delivery device can be such that, in use, a portion of the opening of the lumen 6241 may be placed in fluid communication with the suprachoroidal space 36 of the eye, while another portion of the opening of the lumen 6241 may be positioned within the sclera 20. Thus, when the drug formulation is conveyed into the eye via the puncture member 6240, a portion of the drug formulation may be prone to migrating away from the desired region (e.g., the suprachoroidal space 36) and out of the eye via the needle track. By forming a substantially fluid-tight seal and/or a substantially liquid-tight seal, the adjustment member 6230 can produce an area of high resistance to flow, thus minimizing and/or eliminating the flow migration and/or leakage.

Although the adjustment member 6230 is described above as being constructed from a relatively soft material, which can be well suited to forming a fluid-tight seal, in some embodiments, the adjustment member 6230 can be constructed from multiple materials. For example, in some embodiments, the adjustment member 6230 can include a set of layers 6239 with a first layer constructed from and/or including a portion constructed from a first material, and a second layer constructed from and/or including a portion constructed from a second material different from the first material. Further to this example, at least a portion of the first material and/or at least a portion of the second material can be constructed from and/or can include a layer or portion constructed from a material formulated to form a substantially fluid-tight seal with the outer surface of the target tissue (e.g., the conjunctiva).

Although not shown in FIG. 38, in some embodiments, the layers 6239 can provide and/or include an indicator associated with the distance $D_4$ between the outermost layer 6269 and the distal edge 6245 of the puncture member 6230. In some embodiments, the indicator can be indicia such as, for example, a value associated with the distance $D_4$ (e.g., 500 µm). In other embodiments, the layers 6239 can be color coded with each layer having a different color and each color being associated with an effective length of the puncture member 6240.

Although not shown in FIG. 38, in some embodiments, at least a portion of the layers 6239 can be disposed, at least temporarily, within a housing or the like. For example, in some embodiments, the layers 6239 can be coupled to the base 6238, as described above, and a housing can be disposed about at least a portion of the layers 6239 and the base 6238. Expanding further, in some embodiments, the housing can be movably disposed about the base and can define a window through which the engagement portion 6280 of the layers 6239 can extend. Thus, a user can manipulate the engagement portion 6280 of a layer 6239 to remove the layer 6239 from the adjustment member 6230. In some embodiments, the layer 6239 can be withdrawn through the window defined by the housing. In this manner, the housing can be moved in the proximal direction to be placed in contact with the outermost layer 6239, thereby allowing a shaft length of the puncture member 6240 between the distal edge 6245 and a distal surface of the housing to be increased. In some embodiments, the window can provide for visualization of the shaft length indicator (described above).

As described above with reference to FIG. 36, the increase in the distance $D_4$ can be such that further movement of the puncture member 6240 (e.g., in a distal direction) relative to the sclera places the lumen 6241 of the puncture member 6240 in fluid communication with the suprachoroidal space (e.g., the suprachoroidal space 36 of the eye 10 in FIG. 1). Similarly stated, the increase in the distance $D_4$ can be sufficiently large to extend the distal edge 6245 of the puncture member 6240 through the sclera such that the lumen 6241 is placed in fluid communication with the suprachoroidal space. Expanding further, by removing the one or more layers from the set of layers 6239 of the adjustment member 6230, the distance between the outermost layer 6239 of the adjustment member 6230 and the distal edge 6245 of the puncture member 6240 (e.g., the distance $D_4$) is increased and the user can move the hub 6270 (e.g., either directly or indirectly) place the current outermost layer in contact with the outer surface of the sclera.

With the lumen 6241 of the puncture member 6240 in fluid communication with the suprachoroidal space, a drug formulation (contained within a fluid reservoir as described above with reference to FIG. 36) can be expelled through the lumen 6241 of the puncture member 6240 and into the suprachoroidal space of the eye. In this manner, the drug formulation can flow within the suprachoroidal space to be delivered to, for example, the posterior region of the eye (e.g., the posterior region 14 of the eye 10 in FIG. 1). Moreover, with the adjustment member 6230 in the second configuration, the distance $D_4$ can be less than a thickness of the sclera and the suprachoroidal space such that the distal end portion 6244 of the puncture member 6240 does not pierce the choroid.

As described herein, a system, for example, the system 1000, 2000, 3000, or any other system described herein, can include a hub, for example, the hub 3270, 4270, 5270, or any other hub described herein. The hub can be configured to form a substantially fluid-tight zone around the insertion site of a puncturing member (e.g., the puncturing member 3240 or any other puncturing member described herein) into the eye. For example, in some embodiments, a system can include a hub or contact surface configured to contact a surface of a target tissue to produce the desired effects during medicament delivery (e.g., maintaining a position of the conjunctiva, forming a seal or the like).

Figure 39:
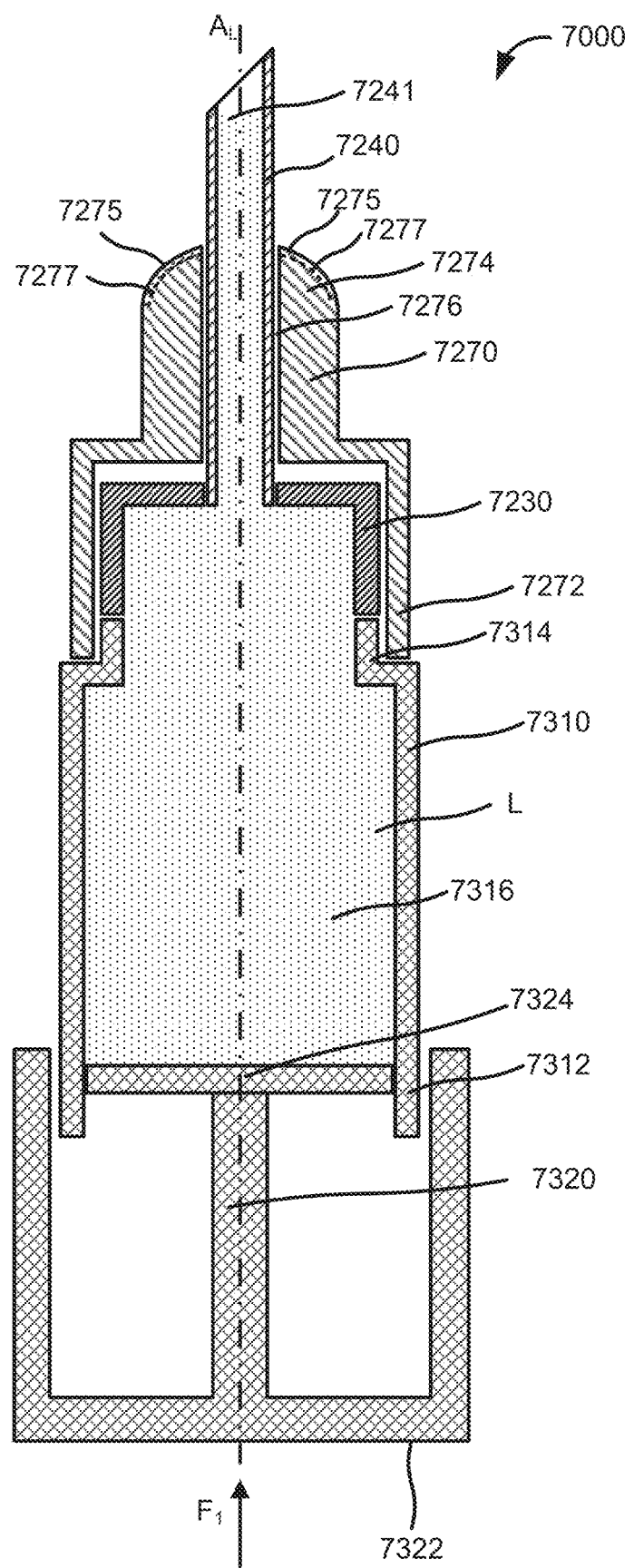
FIG. 39 shows a schematic illustration of a system for delivering a medicament to an eye that includes a hub including a sealing portion, according to an embodiment.

FIG. 39 shows an apparatus 7000 that includes a medical injector 7310, an actuation rod 7320, a needle 7240, and a hub 7270, and optionally a needle adjustment mechanism 7230. The system 7000 can be configured to deliver a medicament to a target layer of an eye of patient, for example, to the SCS of the eye.

The medical injector 7310 defines an internal volume 7316 configured to house a medicament L (e.g., a VEGF, a VEGF inhibitor, triamcinolone acetonide, any other medicament described herein or a combination thereof). The medical injector 7310 includes an engagement portion 7312 and a delivery portion 7314 coupled to the needle adjustment mechanism 7230. The medical injector 7310 can be substantially similar to the medicament containment chamber 1310, 2310, 3310, or any other medicament containment chamber described herein, and is therefore not described in further detail herein.

The actuation rod 7320 includes an engagement portion 7322 and a plunger portion 7324. The plunger portion 7324 is slidably disposed inside the internal volume 7316 defined by the medical injector 7310. The engagement portion 7322 is configured to be engaged by the user and urge the plunger portion 7324 to slide within the internal volume 7316 defined by the medical injector 7310. For example, the user can apply a force in the direction shown by the arrow $F_1$ on the engagement portion 7322 to move the plunger portion 7324 proximally relative to the medical injector 7310 thereby, expelling at least a portion of the medicament L through a lumen 7241 of the needle 7240. As shown, at least a portion of the actuation rod 7320 can be disposed around and concentric with the medical injector 7310. The plunger portion 7324 is configured to draw in the medicament L into or expel the medicament L from the internal volume 7316 defined by the medical injector 7310. In some embodiments, any other actuation rod can be included in the apparatus 7000, for example the actuator 1320, 2320, 3320 or any other actuator described herein.

The needle 7240 defines the lumen 7241 and is configured to pierce the eye and deliver the medicament L into a target tissue of the eye. The needle 7240 can be substantially similar to any of the puncturing members described herein, and is therefore not described in further detail herein. In some embodiments, the needle 7240 can be a microneedle movably disposed within a passageway 7276 of the hub 7270, as described herein. The needle adjustment mechanism 7230 can be coupled to the delivery portion 7314 of the medical injector 7310 and a proximal end of the needle 7240. In some embodiments, the needle adjustment mechanism 7230 is configured to move the needle 7240 within the passageway 7276 such that a distal end portion of the needle 7240 extends from the distal end surface 7275 of the hub 7270 by a predetermined amount. For example, the needle adjustment mechanism 7230 can urge the needle 7240 to translate linearly along the longitudinal axis $A_L$ and thereby adjust a length of the needle 7240 protruding through a distal end 7274 of the hub 6270. The needle adjustment mechanism 7230 can be substantially similar to the adjustment member 422, 3200, 4230, 5230, 6230, or any other adjustment mechanism or adjustment member described herein.

The hub 7270 is configured to be coupled to the medical injector 7230. The hub 7270 includes a proximal end 7272 and a distal end 7274. The proximal end 7272 is coupled to a distal end portion of the needle adjustment mechanism 7230. In some embodiments, the proximal end 7272 can be coupled to a housing (not shown) which can be included in the system 7000. The hub 7270 defines the passageway 7276 configured to receive at least a portion of the needle 7240 therethrough. In this manner, the needle 7240 is configured to pass through the lumen 7276 and into the eye. The distal end surface 7275 of the hub 7270 is configured to contact a target tissue (e.g., the conjunctiva of the eye) when the medicament L (or any other substance disposed within the medical injector 7230) is conveyed through the needle 7240 into the target tissue. In some embodiments, the distal end surface 7275 of the hub 7270 is configured to deform the target surface (e.g., the conjunctiva of the eye) when the distal end surface 7275 is contact with the target surface. At least a portion of the distal end surface 7275 can have a substantially convex shape, for example, a hemispherical shape such that at least a portion of distal end surface 7275 defines a sealing portion 7277. The sealing portion 7277 can be configured to define a substantially fluid-tight seal with the target surface when the distal end surface 7275 is in contact with the target surface. For example, the distal end surface 7275 can deform the target surface such that the sealing portion 7277 is contiguous with the target surface and forms the substantially fluid-tight seal. In some embodiments, the sealing portion 7277 can be symmetric about a center $A_L$ of the apparatus 7000 and hence the passageway. This can, for example, facilitate perpendicular approach of the needle 7240 into the target tissue (e.g., ocular tissue). Thus, the size of the insertion zone can be minimized reducing damage. Furthermore, the needle 7240 can use the shortest path to reach a target region of the target tissue (e.g., the SCS of the eye). While shown as being a cross-section, the hub 7270 can be substantially cylindrical, for example, have a circular cross-section and such that the convex shape of the distal end surface 7275 resembles, for example, a hemisphere. In such embodiments, the sealing portion 7277 can circumferentially surround the needle 7240 to form a hemispherical substantially fluid-tight seal with the target surface. In some embodiments, only a small portion of the sealing portion 7277 surrounding the needle 7240 needs to contact and form the substantially fluid-tight seal with the target surface. For example, in some embodiments, only a small band of the sealing portion 7277 surrounding the needle 7240 can contact and form the substantially fluid-tight seal with the target surface.

Figure 40A:
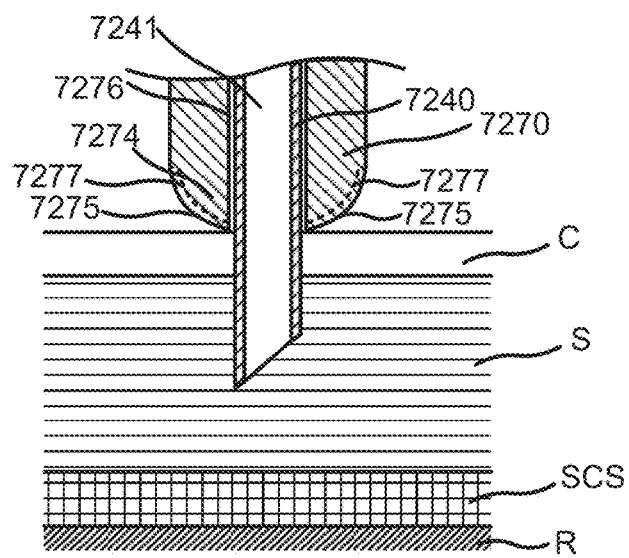
FIG. 40A shows a distal end surface of a hub included in the system of FIG. 39 in contact with a conjunctiva of an eye and a puncturing member included in the system of FIG. 39 inserted into the sclera of the eye.
Figure 40B:
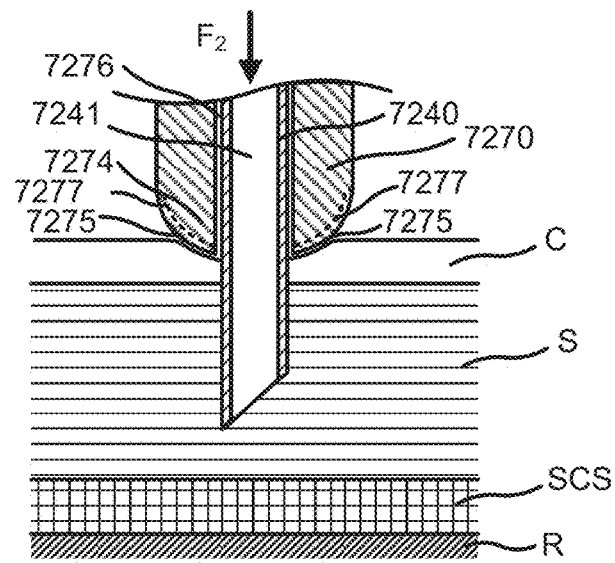
FIG. 40B shows the distal end of the hub compressing the conjunctiva.
Figure 40C:
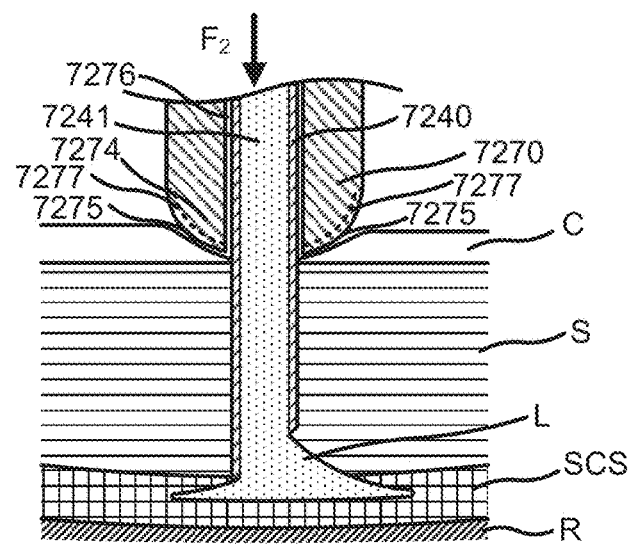
FIG. 40C shows the hub further compressing the conjunctiva, and the distal end of the puncturing member is disposed in proximity of a suprachoroidal space of the eye and is delivering a medicament to the suprachoroidal space, such that the sealing portion forms a substantially fluid tight seal with the conjunctiva.

In some embodiments, the target tissue is an eye and the target surface is a conjunctiva of the eye. For example, FIGS. 40A-C shows a portion of an eye which includes a conjunctiva C, the sclera S, the suprachoroidal space SCS (which can be the target layer), and a retina R. As shown in FIG. 40A, in a first configuration, the distal end 7274 of the hub 7270 is in contact with a conjunctiva C of an eye and a distal end of the needle 7240 is disposed in a sclera S of the eye. Further to this example, the curved shape of the distal end surface 7275 of the hub 7270 can allow for a desired distribution of force(s) to be applied to a portion of the eye, for example, the conjunctiva C. In some embodiments, the curved distal end surface 7275 of the hub 7270 can create a taut spherical injection site. For example, the hub 7274 can deform the conjunctiva C in a radial direction from the center point (i.e., away from where the needle 7240 penetrates) when the system 7000 moves from the first configuration to a second configuration (e.g., the second configuration shown in FIG. 40B). In this manner, the conjunctiva C can be moved into and/or held in a preferable position during the injection. In some instances, this can reduce the puncturing forces to penetrate the surface of the eye. In some embodiments, the "stretching" of the conjunctiva C can minimize and/or eliminate any "bunching" of the conjunctiva C that may otherwise occur, and instead can produce a surface layer (e.g., conjunctiva) having a substantially constant thickness. In some instances, the hub 7270 can, at least temporarily, adhere to a portion of the conjunctiva C. In this manner, the hub 7270 can cause movement of and/or stabilize at least a portion of the conjunctiva C such that at least the portion of the conjunctiva C is in a preferable position during the injection.

Figure 40D:
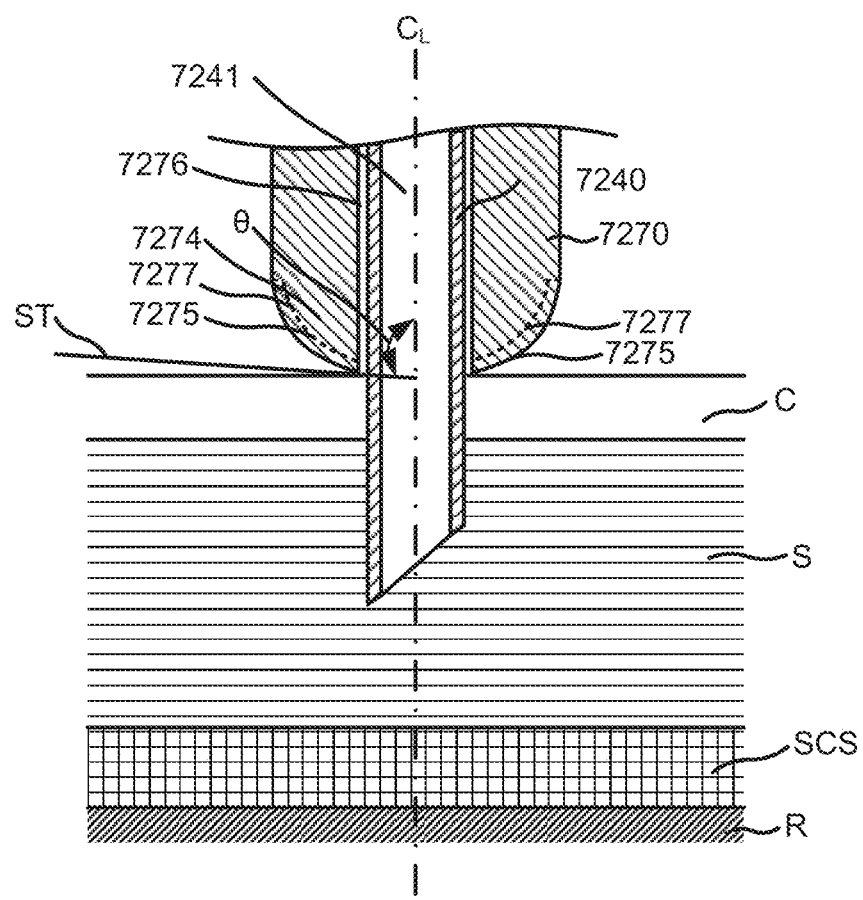
FIG. 40D shows an angle θ formed between a centerline of a delivery passageway formed by the insertion of the puncturing member into the sclera of the eye and a surface line tangent to the conjunctiva.

In some embodiments, the inserting of the needle 7240 into the target tissue (i.e., the conjunctiva and the sclera) can be performed such that a centerline of the delivery passageway and a surface line tangent to the target surface define an angle of entry of between about 75 degrees and about 105 degrees. For example, as shown in FIG. 40D, a centerline $C_L$ of the lumen 7241 of the needle 7240 can define an insertion angle θ with a surface line tangent ST formed relative to the surface of the conjunctiva C. The insertion angle θ can be in the range of between about 75 degrees and about 105 degrees, inclusive of all ranges therebetween. For example, in some embodiments, the insertion angle θ can be about 90 degrees. Said another way, the needle 7240 can be inserted into the target tissue (i.e., the conjunctiva C, and the sclera S) such that the centerline $C_L$ defined by the lumen 7241 of the needle 7240 is substantially perpendicular or otherwise normal to the surface of the target tissue. In this manner, the size of the insertion zone can be reduced thereby minimizing injury and inflammation, which can be caused by any lateral travel of the needle 7240 within the target tissue. Furthermore, normal insertion can also provide the shortest path for the distal tip of the needle 7240 to reach the target tissue (e.g., the SCS) thereby, reducing the time required to reach the target tissue (e.g., the SCS).

Referring back to FIGS. 40A-C, to initiate delivery of the medicament L the user can apply a force $F_2$ on the system 7000, for example, on the engagement portion 7322 of the actuation rod 7320. The force $F_2$ can urge the plunger portion 7324 to slide within the internal volume 7316 of the medical injector 7310 proximally relative to the medical injector 7310 and urge the system into a second configuration. While not shown, in some embodiments, the system 7000 can include an injection assembly, for example, the injection assembly 100, 2100 or any other injection assembly described herein configured to exert the force on the actuation rod 7320. In the second configuration, the hub 7270 is pressed against the conjunctiva C, such that the conjunctiva C compresses and conforms around the convex shape of the distal end surface 7275 of the hub 7270. This also pushes the needle 7240 further into the sclera S. Furthermore, at least a portion of the sealing portion 7277 defined by the distal end surface 7275 is contiguous with the deformed surface of the conjunctiva C such that the sealing portion 7277 defines a substantially fluid-tight seal with the conjunctiva C around the insertion site. In some embodiments, the sealing portion 7277 can be substantially symmetrical about the centerline $C_L$ of the needle 7240 (e.g., as shown in FIG. 40D). In some embodiments, only a circular band of the sealing portion 7277 can contact and form a substantially fluid-tight seal with the conjunctiva C surrounding the needle 7240. However, in the second configuration, the distal end of the needle 7240 can still be proximal relative to but not within the suprachoroidal space SCS, which can be the target layer for delivery of the medicament L.

In some embodiments, the hub 7270 can be a rigid member that has a stiffness substantially greater than the stiffness of the conjunctiva C (e.g., a stiffness substantially similar to a stiffness of stainless steel). In such embodiments, application of the force $F_2$ only deforms the conjunctiva C, without causing any substantial deformation of the hub 7270. In some embodiments, the hub 7270 can have a stiffness that is intermediate to the stiffness of the conjunctiva C and the sclera S. In such embodiments, application of the force $F_2$ can urge the hub 7270 to deform the conjunctiva C (FIGS. 40B and 40C) until the distal end surface 7275 of the hub 7270 is proximate to the sclera S. Since the stiffness of the hub 7270 is less than the stiffness of the sclera S, further application of the force $F_2$ will urge the distal end surface 7275 of the hub 7270 to deform without any substantial deformation of the sclera S. In this manner, the hub 7270 can prevent application of an excessive force from causing damage to or otherwise deformation and/or piercing of the internal layers of the eye.

In a third configuration shown in FIG. 40C, the user can then maintain the force $F_2$ and increase the length of the needle 7240 protruding into the eye, for example, using the needle adjustment mechanism 7230. The length of the needle 7240 can be increased until a distal tip or outlet of the needle 7240 is within or otherwise near the suprachoroidal space SCS. The force $F_2$ can further depress the distal end surface 7275 of the hub 7270 into the conjunctiva C. This can urge substantially all of the sealing portion 7277 of the distal end surface 7275 to be contiguous with the conjunctiva C further strengthening the substantially fluid-tight seal. In this manner, leakage of the injected medicament L along the needle 7240 track during the injection event can be reduced and/or eliminated. Expanding further, in some embodiments, the anatomy of the target tissue and/or the arrangement of the system 7000 can be such that, in use, a portion of the opening of the lumen 7241 of the needle 7240 may be placed in fluid communication with the suprachoroidal space SCS of the eye, while another portion of the opening of the lumen 7241 may be positioned within the sclera S. Thus, when the medicament L is conveyed into the eye via the needle 7240, a portion of the medicament L may be prone to migrating away from the desired region, i.e., the suprachoroidal space SCS and out of the eye via the needle 7240 track. By forming a substantially fluid-tight seal and/or a substantially liquid-tight seal, the hub 7270 can produce an area of high resistance to flow, thus minimizing and/or eliminating the flow migration and/or leakage.

While not shown, in some embodiments, the system 7000 can include an injection assembly, for example, the injection assembly 100, 2100 or any other injection assembly described herein. As described before herein, the injection assembly can be configured to exert a force on the medicament L disposed in the internal volume 7316 of the medicament containment chamber 7310. The force can be sufficient to overcome a backpressure of the suprachoroidal space SCS exerted upon the needle opening, but not the backpressure of the sclera S. In such embodiments, the user can insert the needle 7240 into the sclera S as shown in FIG. 40A and activate the injection assembly. The injection assembly can pressurize the medicament L but the backpressure of the sclera S can prevent the medicament L from delivery into the sclera S. As shown in FIG. 40B, the user can continue the insertion of the needle 7240, for example, by maintaining or increasing a magnitude of the force $F_2$.

This can urge the hub 7240 to deform the conjunctiva C and initiate the formation of the fluid tight seal around the insertion site, as described herein. The force $F_2$ can be maintained until a distal end of the needle 7240 is within or near the suprachoroidal space SCS. The force exerted by the injection assembly on the medicament L can now overcome the backpressure of the suprachoroidal space SCS thereby, initiating communication of the medicament L into or near the suprachoroidal space SCS as shown in FIG. 40C. In this manner, the injection assembly can assist the user in determining the location of the distal end of the needle 7240 such that the medicament L is delivered substantially only to the target layer (i.e., the suprachoroidal space SCS). Furthermore, over excursion of the puncturing member 7240 beyond the suprachoroidal space SCS (i.e., into the retina R) can be prevented.

In some embodiments, the needle adjustment mechanism 7230 can be used to ensure delivery to the target layer. In such embodiments, the user can insert the needle 7240 into the sclera S as shown in FIG. 40A and activate the injection assembly to pressurize the medicament L as described herein. While maintaining the force $F_2$, the user can use the needle adjustment mechanism 7230 to advance the needle 7240 in predetermined increments (e.g., about 100 μm increments) into the sclera S, for example, as described herein with reference to the needle assembly 422, 3200, or any other needle assembly describe herein. In this manner, the needle adjustment mechanism 7230 can be used to advance the needle 7240 through the sclera S until a distal end of the needle 7240 is within or near the suprachoroidal space SCS. The force exerted by the injection assembly on the medicament L can now overcome the backpressure of the suprachoroidal space SCS thereby, initiating communication of the medicament L into or near the suprachoroidal space SCS as shown in FIG. 40C. Thus, by allowing the user to advance the needle 7240 in known discrete increments, the needle adjustment mechanism 7230 can assist the user in preventing over excursion of the needle 7240 beyond the suprachoroidal space SCS (i.e., into the retina R). In this manner, the injection assembly can assist the user in determining the location of the distal end of the needle 7240 such that communication of the medicament into a layer of the eye other than the target layer (i.e., the suprachoroidal space SCS) can be prevented. Furthermore, the needle adjustment mechanism 7230 can assist the user in precisely controlling the excursion length of the needle 7240, thereby eliminating the use of excessive force and/or preventing over excursion of the needle 7240 beyond the target layer (i.e., the suprachoroidal space SCS).

In some embodiments, the hub 7270 or any of the hubs described herein can be constructed from a relatively soft material, which can be well-suited to forming a fluid-tight seal. For example, in some embodiments, the system 7000, or any other system described herein can be used to deliver a medicament through the skin of a user (e.g., for intravenous or intramuscular delivery of the medicament). In such embodiments, the hub 7270 or any other hub described herein can have a stiffness less than the stratum corneum that forms the top layer of the skin. The distal end surface 7275 of the hub 7270 or any other hub described herein can deform about the stratum corneum as a force is applied on the system 7000. In this manner, the sealing portion 7277 defined by the distal end surface 7275 of the hub 7270 can form a fluid tight seal around the stratum corneum thereby preventing leakage of the medicament, an interstitial fluid, and/or blood from the injection site. In yet other embodiments, the hub 7270 can be constructed from multiple materials. For example, in some embodiments, the distal end surface 7275 of the hub 7270 can be constructed from and/or can include a layer or portion constructed from a material formulated to form a substantially fluid-tight seal with the outer surface of the target tissue (e.g., the conjunctiva C).

FIGS. 41A and 41B show a finite element analysis (FEA) model of the distal portion 7274 of the hub 7270 compressed against the conjunctiva C of the eye. In this model, a force of 1N is exerted on the hub 7270. At this force, the conjunctiva C is compressed by about 2 mm, which is substantially equal to the total thickness of the conjunctiva C. Furthermore, the conjunctiva C conforms around the distal end surface 7275 of the distal end portion 7274 of the hub 7270. As shown, the sealing portion 7277 of the distal end surface forms a substantially fluid-tight seal around the injection site of the needle 7240. The hub 7270 was modeled as a rigid and inflexible member. However, the hub 7270 or any other hub described herein can have any suitable stiffness based on the material used to form the hub. In some embodiments, the hub 7270 or any other hub described herein can have a stiffness substantially similar to the stiffness of rubber, silicone, polymers, plastics (e.g., polyethylene, polypropylene, polycarbonate, polytetrafluoroethylene, high density polyethylene, etc.), metals (e.g., aluminum, stainless steel, metal alloys, etc.), or any other material described herein.

FIGS. 42A-C shows a hub 8270, according to an embodiment. The hub 8270 includes a proximal end portion 8272 and a distal end portion 8274. The proximal end portion 8272 can configured to be coupled to a distal end of a housing (e.g., a distal end 3212 of the housing 3210 of the needle assembly 3200, or any other housing described herein) using any suitable coupling mechanism, for example, friction-fit, threads, snap-fit, notches, grooves, indents, detents, any other suitable coupling mechanism or combination thereof. The hub 8270 defines a passageway 8276 therethrough. At least a portion of a needle (e.g., the puncturing member 3240, the needle 7240, or any other puncturing member described herein) can be disposed within the passageway 8276, and can be configured to advance through the passageway 8276 out of the distal end 8274. The distal end 8274 of the hub 8270 includes a contact surface that is curved, and for example, defines a convex or hemispherical shape. The contact surface of the distal portion 8274 is configured to (i.e., has a size and/or shape configured to) contact an outer surface of a conjunctive of the eye and define a sealing portion that forms a substantially fluid-tight seal around the insertion zone of the puncturing member 8240 into a target tissue, for example, the eye. Thus, the hub 8270 can prevent leakage of the medicament, and/or bodily fluid from the insertion site, as described in with respect to the hub 7270 included in the apparatus 7000.

Figure 43C:
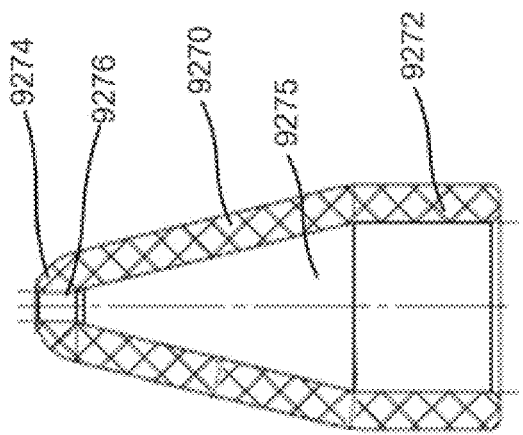
FIG. 43C shows a cross-section view of the hub of FIG. 43A taken along the line 43C-43C.
Figure 43A:
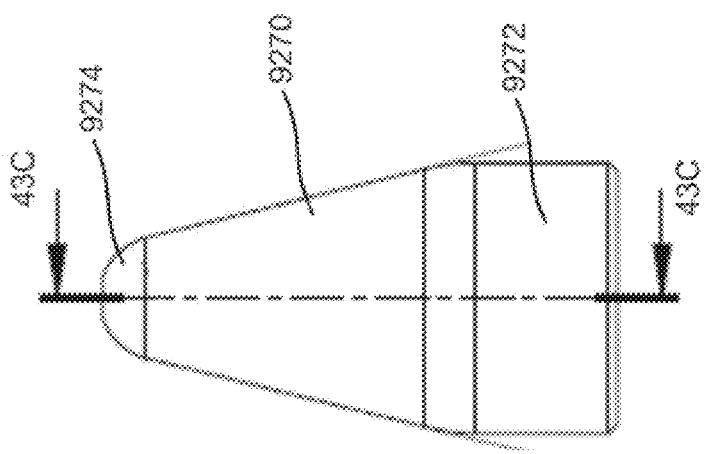
FIG. 43A shows a side view and FIG. 43B shows a front view of a hub that includes a convex distal end, according to an embodiment.
Figure 43B:
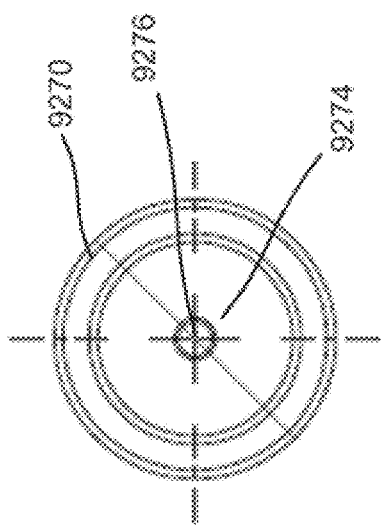

In some embodiments, a hub can be substantially hollow and/or can define an enlarged lumen therethrough. Referring now to FIGS. 43A-C, a hub 9270 includes a proximal end portion 9272, a distal end portion 9274, and defines an internal volume 9275. The proximal end portion 9272 can be configured to be coupled to a distal end of a housing (e.g., the distal end 3214 of the housing 3210 included in the needle assembly 3200, or any other housing included in a needle assembly described herein). For example, a portion of a distal end of a housing (e.g., the housing 3210) can be configured to slide into the internal volume 9275. At least a portion of a needle (e.g., the puncturing member 3240, the needle 7240, or any other puncturing member described herein) can be disposed in the internal volume 9275. In some embodiments, at least a portion of a needle assembly, for example, the lead screw 3242 included in the needle assembly 3200 or any other component or any other needle assembly, can also be disposed in the internal volume 9275. The distal end 9274 has a contact surface that is curved, for example, defines a convex or a hemispherical shape, such that the contact surface defines a sealing portion which can form a substantially fluid-tight seal around the insertion zone of the puncturing member (e.g., the puncturing member 3240, or the needle 7240), as described with respect to the hub 8270. The distal end 9274 defines an opening 9276 configured to enable at least portion of the puncturing member (e.g., the puncturing member 3240) to pass therethrough and into the ocular tissue of the eye.

Figure 44A:
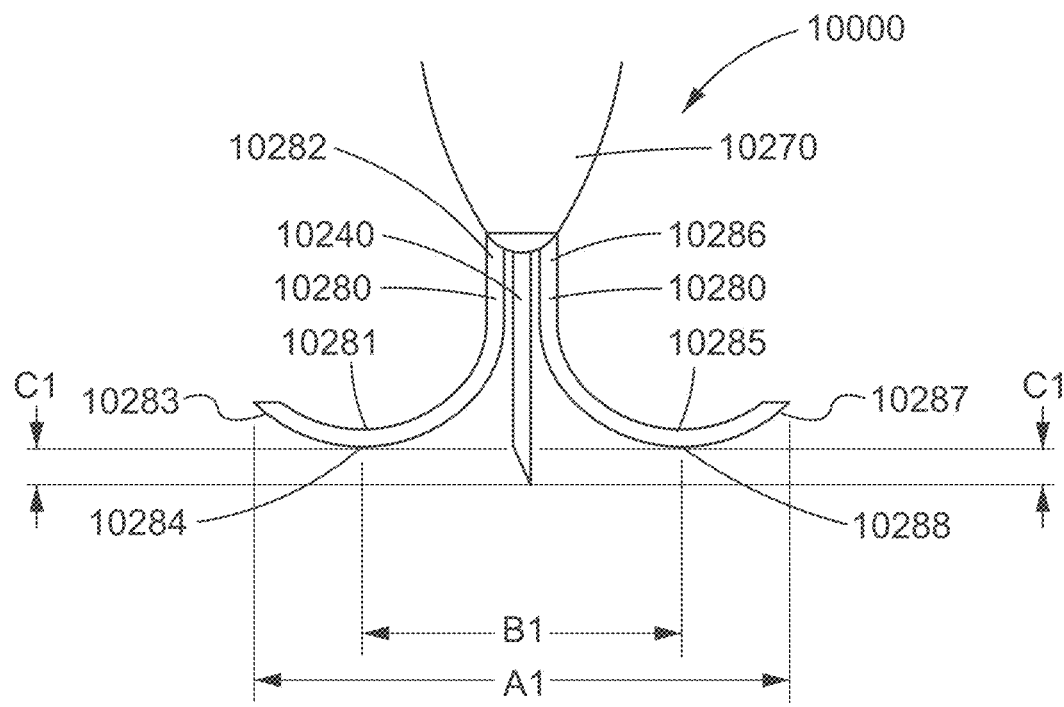
FIG. 44A-B show schematic illustrations of a hub included in a medicament delivery system in a first configuration and a second configuration respectively, according to an embodiment.
Figure 44B:
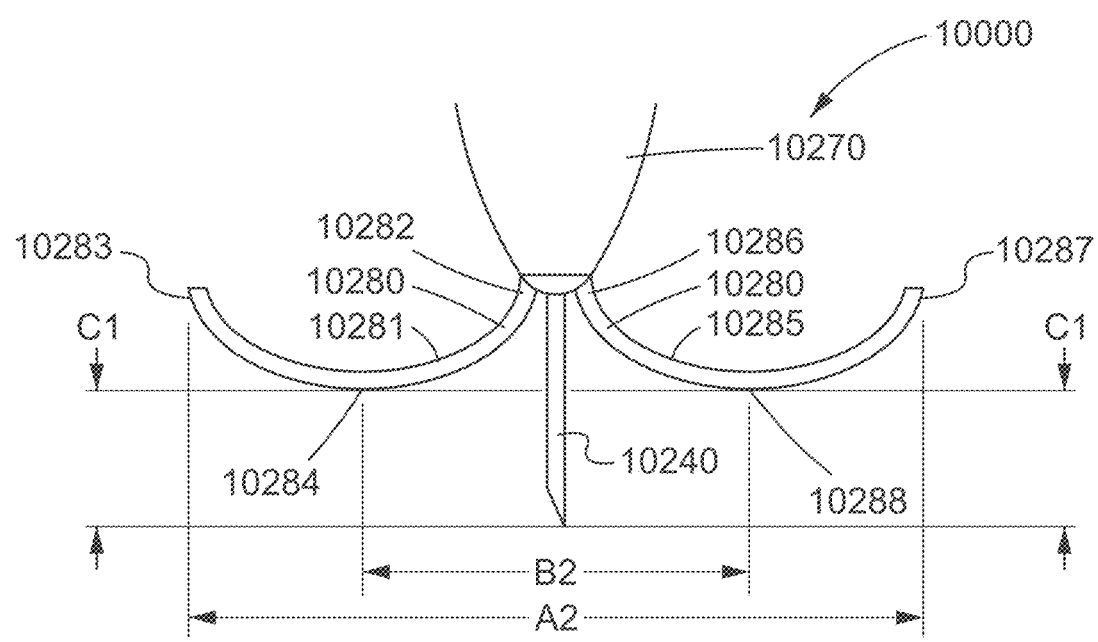

In some embodiments, a hub can include one or more engagement structures that cooperatively function to surround the puncture member and/or contact a surface of the target tissue. Moreover, in some embodiments, a hub can also be configured to induce deformation and/or movement of a portion of the target tissue when placed into contact with the target tissue. In such embodiments, the adjustment member can minimize "bunching" of the surface tissue (e.g., the conjunctiva). For example, FIGS. 44A and 44B are schematic illustrations of a portion of a delivery device 10000 in a first configuration and a second configuration, respectively, according to an embodiment. The delivery device 10000 includes a hub 10270, a puncture member 10240 (also referred to herein as a delivery member or a needle) and an engagement assembly 10280. The engagement assembly 10280 includes a first elongate member 10281 and a second elongate member 10285. The elongate members 10281, 10285 can be any suitable structure configured to engage the target tissue and deform (as described herein). For example, in some embodiments, the first elongate member 10281 and/or the second elongate member 10285 can be a thin structure (e.g., feeler gauge, wire, etc.). In some embodiments, the first elongate member 10281 and/or the second elongate member 10285 can be any suitable structure configured to grip, hold, and/or deform a portion of the target tissue (e.g., the conjunctiva). Although not shown, additional elongate members (or "sleds") can be coupled to the hub 10270. For example, in some embodiments, the hub 10270 can include three elongate members attached thereto. In other embodiments, for example, the hub 10270 can include more than three elongate members (e.g., four, five, or more elongate members) attached thereto.

As shown, a proximal end portion 10286 of the first elongate member 10281 is coupled to the hub 10270. The first elongate member 10281 has a contact portion 10284 (e.g., the portion where the first elongate member 10281 can contact a portion of the eye 10 shown in FIG. 1, during use). The first elongate member 10281 has a distal end portion 10283. At least a portion of the first elongate member 10281 can have a curved shape. The curved shape, for example, can be such that the contact portion 10284 is configured to contact a portion of the eye (e.g., the conjunctiva) along a line tangent to a portion of the first elongate member 10281. Further to this example, the curved shape of the portion of the first elongate member 10281 can allow for a desired distribution of force(s) to be applied to a portion of the eye during use. For example, in this manner the contact portion 10284 does not contact the surface of the eye at a single point, but rather along a surface that is less likely to puncture the eye.

A proximal end portion 10286 of a second elongate member 10285 is coupled to the hub 10270. The second elongate member 10285 has a contact portion 10288 (e.g., where the second elongate member 10285 contacts a portion of the eye 10 shown in FIG. 1). The second elongate member 10285 has a distal end portion 10287. At least a portion of the second elongate member 10285 can have a curved shape. The curved shape, for example, can be such that the contact portion 10288 is configured to contact a portion of the eye (e.g., the conjunctiva) along a line tangent to a portion of the second elongate member 10285. Further to this example, the curved shape of the portion of the second elongate member 10285 can allow for a desired distribution of force(s) to be applied to a portion of the eye, as discussed above with respect to the first elongate member 10281.

When the delivery device 10000 is in a first configuration, as shown in FIG. 44A, the distal end portion 10283 of the first elongate member 10281 and the distal end portion 10287 of the second elongate member 10285 are separated by a distance A1. Similarly, in the first configuration, the contact portion 10284 of the first elongate member 10281 and the contact portion 10288 of the second elongate member 10285 are separated by a distance B1. Moreover, when the delivery device 10000 is in the first configuration, the distal tip of the puncture member 10240 is spaced apart from the contact portion 10284 and/or the contact portion 10288 by a distance C1 taken along a center line of the puncture member 10240, as shown in FIG. 44A. In some embodiments, the distal tip of the puncture member 10240 is spaced apart from a line defined by the contact portion 10284 and the contact portion 10288 by a distance C1 taken along a center line of the puncture member 10240.

In use, a user (e.g., a doctor, technician, nurse, physician, ophthalmologist, etc.) can manipulate a delivery device 10000 to insert the puncture member 10240 into, for example, a portion of the eye (e.g., the eye 10 shown in FIG. 1). In this manner, the user can apply a distal force to move the delivery device 10000 from the first configuration to a second configuration. Similarly stated, when the puncture member 10240 is inserted into the eye, the first elongate member 10281 and the second elongate member 10285 can both move from the first configuration to the second configuration. When the delivery device 10000 is in the second configuration, as shown in FIG. 44B, the distal end portion 10283 of the first elongate member 10281 and the distal end portion 10287 of the second elongate member 10285 can be separated by a distance A2, A2 being greater than A1. In the second configuration, as shown in FIG. 44B, the contact portion 10284 of the first elongate member 10281 and the contact portion 10288 of the second elongate member 10285 can be separated by a distance B2, B2 being greater than B1. Moreover, when the delivery device 10000 is in the second configuration, the distal tip of the puncture member 10240 is spaced apart from the contact portion 10284 and/or the contact portion 10288 by a distance C2 taken along a center line of the puncture member 10240, as shown in FIG. 44B, C2 being greater than C1. In some embodiments, the distal tip of the puncture member 10240 is spaced apart from a line defined by the contact portion 10284 and the contact portion 10288 by a distance C2 taken along a center line of the puncture member 10240, C2 being greater than C1 when the delivery device 10000 is in the second configuration.

In some embodiments, when the delivery device 10000 is moved from the first configuration to the second configuration, the contact portion 10284 of the first elongate member 10281 and the contact portion 10288 of the second elongate member 10285 can cause a portion of the eye to move, or instead, prevent a portion of the eye from moving. Similarly stated, in some embodiments, the deformation of the first elongate member 10281 and/or the second elongate member 10285 can move (or alternatively maintain a position of) a portion of the target tissue. For example, is some uses, at least one of the contact portion 10284 or the contact portion 10288 can contact the conjunctiva of the eye. In this manner, at least one of the contact portions 10284, 10288 can stabilize, hold steady, grip, stretch, or mechanically fix a portion of the eye (e.g., the conjunctiva) when the device is moved from the first configuration to the second configuration.

In some embodiments, the contact portions 10284, 10288 can create a taught spherical injection site. For example, the first elongate member 10281 and/or the second elongate member 10285 can deform in a radial direction from the center point (i.e., away from where the puncture member 10280 penetrates) when the delivery device 10000 moves from the first configuration to the second configuration. In this manner, the conjunctiva can be held in a preferable position during the injection. In some instances, this can reduce the puncturing force to penetrate the surface of the eye. In some embodiments, the "stretching" of the conjunctiva can minimize and/or eliminate any "bunching" of the conjunctiva that may otherwise occur, and instead can produce a surface layer (e.g., conjunctiva) having a substantially constant thickness. In some instances, the contact portions 10284, 10288 can, at least temporarily, adhere to a portion of the surface layer (e.g., conjunctiva). In this manner, the contact portions 10284, 10288 can cause movement of and/or stabilize at least a portion of the surface layer such that at least the portion of the surface layer is in a preferable position during the injection.

In some embodiments, the elongate member 10281 and/or the elongate member 10285 can be attached to the hub 10270 in any suitable manner, as shown in FIGS. 44A and 44B. In yet other embodiments, the elongate member 10281 and/or the elongate member 10285 can be coupled to an elongate member holder or interface (not shown). The elongate member holder can be coupled to the hub 10270. In some embodiments, the elongate member holder (not shown) can be a ring.

The elongate members 10281, 10285 can be any suitable material (e.g., metallic or plastic). In some embodiments, the sleds can contain a plurality of different materials. For example, the contact portion 10284 of the first elongate member 10281 may contain a material not contained on a different portion of the first elongate member 10281. In some embodiments, for example, additional materials (e.g., a coating) can be applied to any portion of the elongate members 10281, 10285. Further to this example, the additional material can be configured to increase or decrease friction between the elongate members 10281, 10285 and a surface layer (e.g., conjunctiva). In some embodiments, a plurality of additional materials can be applied to the elongate members 10281, 10285. Each additional material (e.g., coating) from the plurality of additional materials, for example, can include relatively unique material properties (e.g., viscosity, density, surface tension, etc.).

In some embodiments, the elongate members 10281, 10285 can provide an indicator associated with at least one of the distance A1, A2, B1, B2, C1, and/or C2. In some embodiments, the indicator can be a visual indicator such as a measuring scale, graduated marking or the like. For example, in some embodiments, the first elongate member 10281 can include indicia (e.g., lines, markings, tic marks, etc.). In some embodiments, the markings can represent a change in location of the distal tip of the puncture member 10240 from the first configuration to the second configuration. In yet another embodiment, the markings can represent a portion of the eye where the distal tip of the puncture member 10240 is located. For example, the markings can indicate whether the distal tip of the puncture member 10240 is located in the sclera, choroid, suprachoroidal space, or retina of the eye. For another example, the markings can indicate by term the location of the distal tip of the puncture member 10240 (e.g., sclera, choroid, suprachoroidal space, retina, etc.), and can further indicate a location within the termed location (e.g., a location within the choroid). In this manner, the markings can indicate, for example, the location of the distal tip of the puncture member 10240 relative to the sclera and/or the choroid when the distal tip is located within the suprachoroidal space.

Figure 45A:
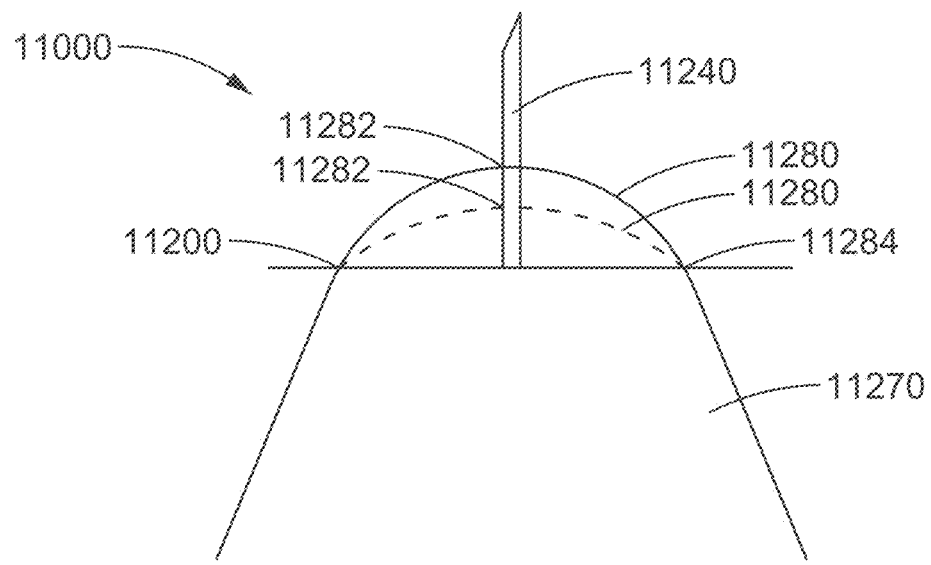
FIGS. 45A and 45B are schematic illustrations of a portion of a delivery device according to an embodiment.
Figure 45B:
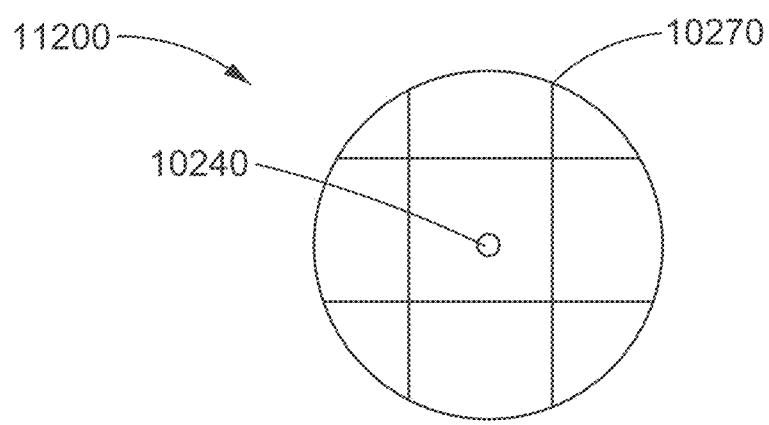

Although shown as including multiple, deformable elongate members, in other embodiments an engagement assembly and/or an adjustment assembly, for example, included or coupled to a hub, can include a single deformable member. For example, FIGS. 45A and 45B are schematic illustrations of a portion of a delivery device 11000, according to an embodiment. Specifically, FIG. 45A illustrates a portion of a delivery device 11000 in a first configuration and a second configuration (e.g., illustrated with dashed lines), and FIG. 45B illustrates a bottom view of the portion of the delivery device 11000. The delivery device 11000 includes a hub 11270, a puncture member 11240 (also referred to herein as a delivery member or a needle) and an engagement member 11280. The engagement member 11280 can be any suitable structure configured to engage the target tissue.

As shown, a proximal portion 11282 of the engagement member 11280 is coupled to the delivery device 11000. The engagement member 11280 is coupled to the delivery device 11000 via the hub 11270. In yet other embodiments, the engagement member 11280 can be coupled to an engagement member holder (not shown). The engagement member holder can then be coupled to the hub 11270. The engagement member 11280 has a contact portion 11284.

When the delivery device 11000 is in a first configuration, as shown, in FIG. 45A, a portion of the contact portion 11284 of the engagement member 11280 is spaced apart from the distal tip of the puncture member 11240 by a distance A1 taken along a center line of the puncture member 11240. In some embodiments, the distal tip of the puncture member 11240 is spaced apart from a line defined by the contact portion 11282 of the engagement member 11280 by a distance A1 taken along a center line of the puncture member 11240. In use, a user (e.g., a doctor, technician, nurse, physician, ophthalmologist, etc.) can manipulate a delivery device (not shown) to insert the puncture member 11240 into, for example, a portion of the eye (e.g., the eye 10 shown in FIG. 1). In this manner, the user can apply a distal force to move the delivery device 11000 from the first configuration to a second configuration. Similarly stated, when the puncture member 11240 is inserted into the eye, the engagement member 11280 can move from the first configuration to the second configuration, as illustrated by the dashed line in FIG. 45A. When the delivery device 11000 is in the second configuration, as shown in FIG. 44A, a portion of the contact portion 11284 of the engagement member 11280 and the distal tip of the puncture member 11240 are separated by a distance A2 (see the distance indicated from the dashed lines), A2 being greater than A1. In some embodiments, when the delivery device 11000 is in the second configuration, the distal tip of the puncture member 11240 is spaced apart from a line defined by the contact portion 11284 of the engagement member 11280 by a distance A2 taken along a center line of the puncture member 11240, A2 being greater than A1.

In some embodiments, when the delivery device 11000 is moved from the first configuration to the second configuration, the contact portion 11284 can cause a portion of the eye to move, or instead, prevent a portion of the eye from moving. Similarly stated, in some embodiments, the deformation of the engagement member 11280 can move (or alternatively maintain a position of) a portion of the target tissue. For example, in some uses, the contact portion 11282 of the engagement member 11280 can stabilize, hold steady, grip, stretch, or mechanically fix a portion of the eye (e.g., the conjunctiva) when the delivery device 11000 is moved from the first configuration into the second configuration.

Although the engagement member 11280 is shown and described above as including a contact portion 11284 that is curved in a convex manner (i.e., curved outwardly, or in a manner that resembles an outer surface of a sphere), in other embodiments, a hub and/or an engagement member can include a contact portion that is curved in a concave manner (i.e., curved inwardly, or in a manner that resembles an inner surface of a sphere).

In some embodiments, the engagement member 11280 can deform at a variable rate. For example, the engagement member 11280 can provide variable resistance when a user manipulates the delivery device 11000. In some embodiments, the engagement member 11280 can provide a hard stop (i.e., a user would be substantially prevented from further inserting the puncture member 11240 into a portion of the eye). In yet other embodiments, the engagement member 11280 can be configured to provide variable resistance based on its level of deformity. In this manner, the engagement member 11280 can be configured to provide a first level of resistance when the puncture member 11240 is in a first portion of the eye and a second level of resistance when the puncture member 11240 is in a second portion of the eye, the first level of resistance being different than the second level of resistance. In some embodiments, for example, the first portion of the eye can be the sclera and the second portion of the eye can be the suprachoroidal space.

In some embodiments, the engagement member 11000 can provide an indicator associated with at least one of the distance A1 or A2 (i.e., the depth of penetration of the puncture member 11240). In some embodiments, the indicator can be a visual indicator such as a measuring scale, graduated marking or the like. For example, in some embodiments, the engagement member 11280 can include indicia (e.g., lines, markings, tic marks, etc.). In some embodiments, the markings can represent a change in location of the distal tip of the puncture member 11240 from the first configuration to the second configuration. In yet other embodiments, the markings can represent a portion of the eye where the distal tip of the puncture member 11240 is located. For example, the markings can indicate whether the distal tip of the puncture member 11240 is located in the sclera, choroid, suprachoroidal space, or retina of the eye. For another example, the markings can indicate by the anatomical term the location of the distal tip of the puncture member 11240 (e.g., sclera, choroid, suprachoroidal space, retina, etc.) and can further indicate a location within the termed location (e.g., a location within the choroid). In this manner, the markings can indicate, for example, the location of the distal tip of the puncture member 11240 relative to the sclera and/or the choroid when the distal tip is located within the suprachoroidal space.

Although the engagement assembly 10000 is shown and described above as including two or more elongate members having contact portions that are curved in a convex manner (i.e., curved outwardly, or in a manner that resembles an outer surface of a sphere), in other embodiments, a hub, an engagement assembly and/or adjustment member can include a contact portion or surface that is curved in a concave manner (i.e., curved inwardly, or in a manner that resembles an inner surface of a sphere). Similarly stated, in some embodiments, a delivery device can include a hub, an engagement assembly and/or adjustment member having a surface that is configured to engage, fit and/or conform to the surface of the target tissue (e.g., the eye). As one example, FIGS. 46-47 are perspective views of a portion of a delivery device according to an embodiment. In particular, FIGS. 46-47 are perspective views of an engagement member 12280 configured to be used in conjunction with any of the delivery devices shown and described herein. The engagement member 12280 includes a proximal end portion 12281 and a distal end portion 12282 and defines a lumen or passageway therebetween.

The proximal end portion 12281 of the engagement member 12280 can be coupled to a delivery device (not shown in FIG. 46). In some embodiments, the proximal end portion 12281 of the engagement member 12280 can be coupled to the hub 10270 (not shown in FIGS. 45-46), or any other hub described herein. For example, in some embodiments, the engagement member 12280 can be threadedly coupled to a hub to control an effective length of a puncture member (also referred to as a delivery member or needle) as described above. In this manner, the engagement member 12280 can perform the function of a needle adjustment mechanism.

As shown in FIGS. 46 and 47, the distal end portion 12282 of the engagement member 12280 includes three contact members 12283. Each of the contact members 12283 has a surface that includes an inverse-dimpled or "beaded" traction pattern 12284. The contact members 12283 are configured to contact a surface of the target tissue (e.g., the conjunctiva of the eye) during use to facilitate insertion of a puncture member (not shown) and/or injection of a drug formulation into the target tissue. The distal end portion 12282 of the engagement member 12280 and/or the contact members 12283 can be any suitable structure configured to engage the target tissue (as described herein). For example, in some embodiments, the distal end portion 12282 of the engagement member 12280 and/or the contact members 12283 can be any suitable structure configured to grip, hold, and/or deform a portion of the target tissue (e.g., the conjunctiva of the eye). As shown, at least a portion of the distal end portion 12282 and/or the contact members 12283 have a curved shape. The curved shape, for example, can be such that the contact members 12283 are configured to contact a portion of the eye (e.g., the conjunctiva) along a line tangent to a portion of the contact members 12283. Further to this example, the curved shape of the portion of the contact members 12283 can allow for a desired distribution of force(s) to be applied to a portion of the eye.

In some embodiments, the contact members 12283 can create a taught spherical injection site. For example, the contact members 12283 can deform in a radial direction from the center point (i.e., away from where the puncture member penetrates) when the delivery device (not shown) moves from a first configuration to a second configuration. In this manner, the conjunctiva can be moved into and/or held in a preferable position during the injection. In some instances, this can reduce the puncturing forces to penetrate the surface of the eye. In some embodiments, the "stretching" of the conjunctiva can minimize and/or eliminate any "bunching" of the conjunctiva that may otherwise occur, and instead can produce a surface layer (e.g., conjunctiva) having a substantially constant thickness. In some instances, the contact members 12283 can, at least temporarily, adhere to a portion of the surface layer (e.g., the conjunctiva). In this manner, the contact members 12283 can cause movement of and/or stabilize at least a portion of the surface layer such that at least the portion of the surface layer is in a preferable position during the injection.

In some embodiments, the engagement member 12280 (and any of the engagement and/or adjustment members shown and described herein) can form a substantially fluid-tight seal and/or a substantially liquid-tight seal with the outer surface of the target tissue (e.g., the conjunctiva of the eye). In this manner, leakage of the injected medicament along the needle track during the injection event can be reduced and/or eliminated. Expanding further, in some embodiments, the anatomy of the target tissue and/or the arrangement of the delivery device can be such that, in use, a portion of the opening of the needle (not shown) may be placed in fluid communication with the suprachoroidal space (e.g., suprachoroidal space 36 in FIG. 1) of the eye, while another portion of the opening of the needle may be positioned within the sclera 20 (e.g., sclera 20 in FIG. 1). Thus, when the drug formulation is conveyed into the eye via the needle (not shown), a portion of the drug formulation may be prone to migrating away from the desired region (e.g., the suprachoroidal space 36 in FIG. 1) and out of the eye via the needle track. By forming a substantially fluid-tight seal and/or a substantially liquid-tight seal, the engagement member 12280 (e.g., the surface of the contact members 12283) can produce an area of high resistance to flow, thus minimizing and/or eliminating the flow migration and/or leakage.

In some embodiments, the engagement member 12280 can be constructed from a relatively soft material, which can be well-suited to forming a fluid-tight seal. In yet other embodiments, the engagement member 12280 can be constructed from multiple materials. For example, in some embodiments, the contact members 12283 of the engagement member 12280 can be constructed from and/or can include a layer or portion constructed from a material formulated to form a substantially fluid-tight seal with the outer surface of the target tissue (e.g., the conjunctiva). Although the contact members 12283 are shown and described above as including a beaded surface, in other embodiments, the contact members 883 can include any suitable surface features. For example, as shown in FIG. 48, in some embodiments, an engagement member 13280 can include a series of contact members 13283 having a smooth surface. As another example, as shown in FIG. 49, in some embodiments, an engagement member 14280 can include a series of contact members 14283 having a ridged and/or stepped surface. In other embodiments, for example, an engagement member can include a contact member having a ribbed surface (e.g., similar to that shown in FIG. 52).

In other embodiments, an engagement member and/or contact members can include any combination of suitable surface features. In this manner, for example, an engagement member can include a first contact member with a smooth surface and a second contact member with a ribbed surface. As another example, a contact member can include a first portion having a ribbed surface and a second portion having a beaded surface.

Figure 50:
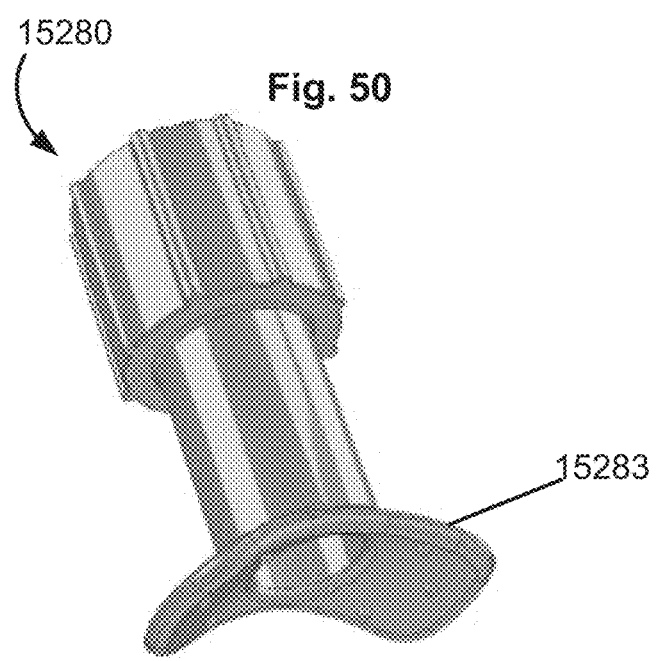
FIG. 50 is a perspective view of a portion of a delivery device according to an embodiment.
Figure 51:
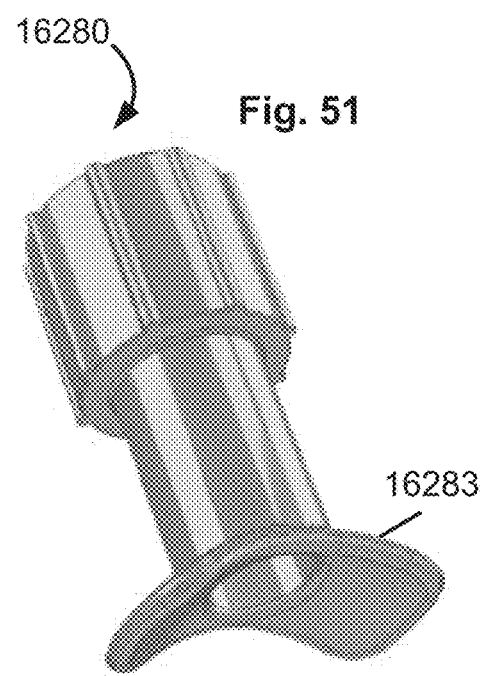
FIG. 51 is a perspective view of a portion of a delivery device according to an embodiment.
Figure 52:
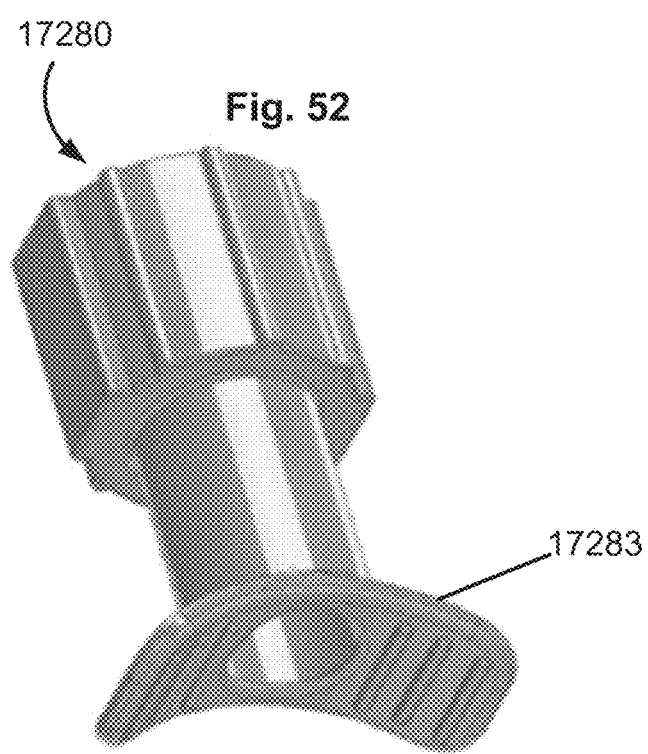
FIG. 52 is a perspective view of a portion of a delivery device according to an embodiment.
Figure 53:
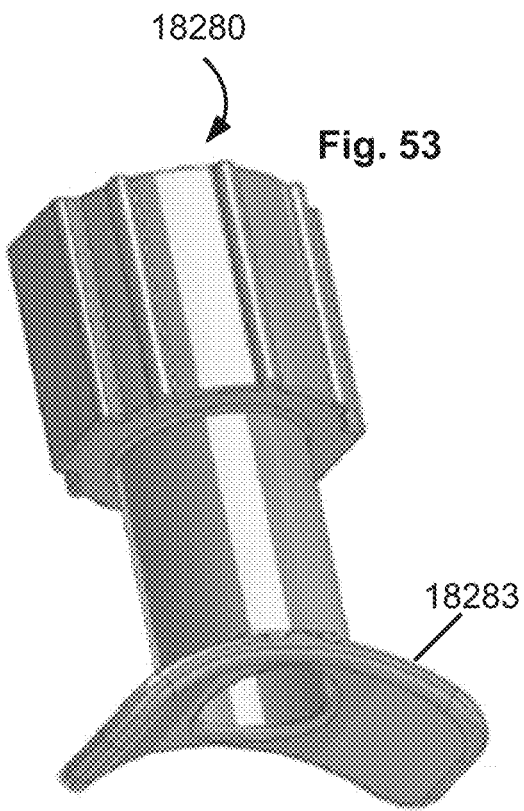
FIG. 53 is a perspective view of a portion of a delivery device according to an embodiment.
Figure 55:
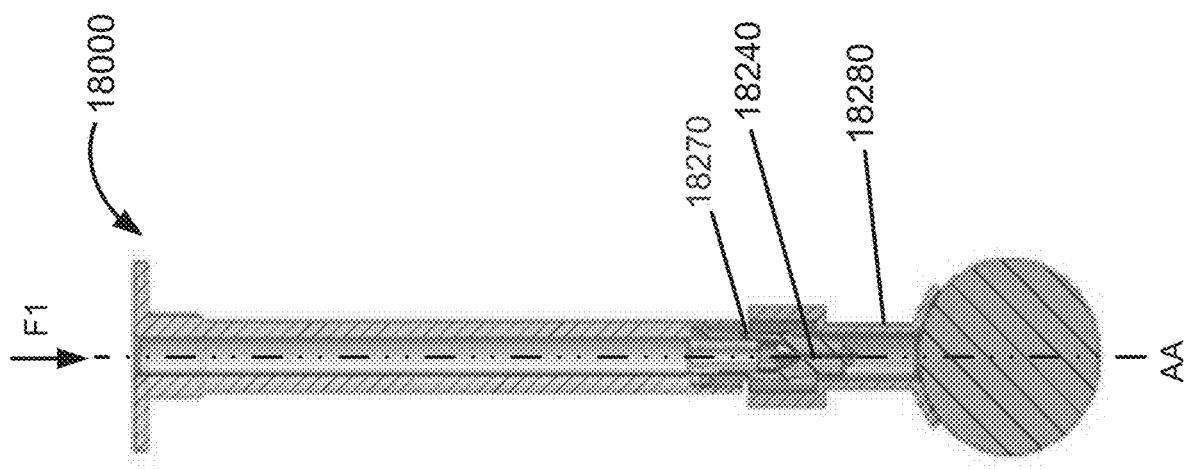
FIG. 55 is a cross-sectional view of the portion of the delivery device shown in FIG. 54.
Figure 54:
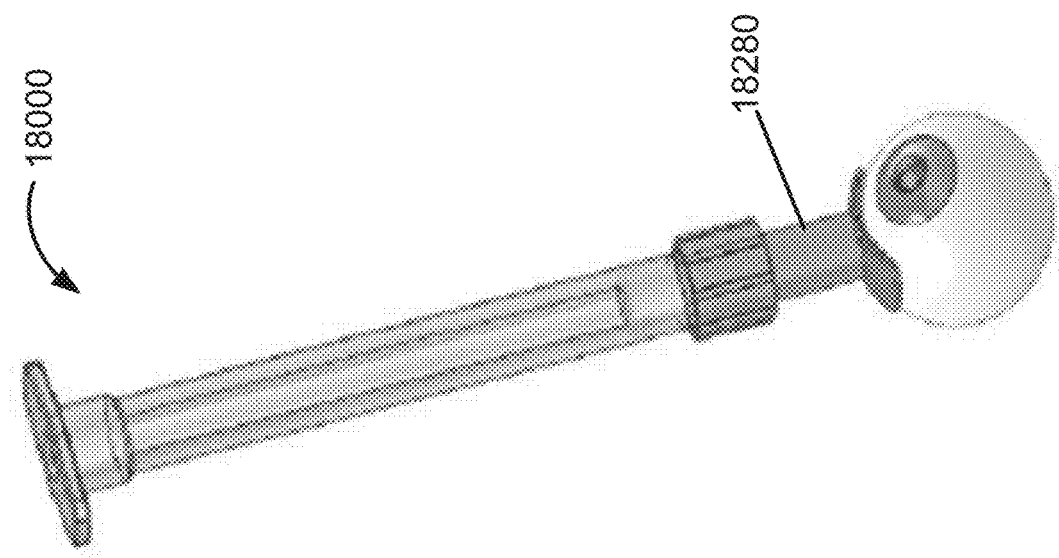
FIG. 54 is a perspective view of a portion of a delivery device being used to facilitate an ocular injection, according to an embodiment.

Although shown as including three contact members, in other embodiments, an engagement member, hub and/or adjustment member can include any number of contact members. For example, FIGS. 50-55 are illustrations of delivery devices according to various embodiments. In particular, FIG. 50 is a perspective view of an engagement member 15280 according to some embodiments. FIG. 51 is a perspective view of an engagement member 16280 according to some embodiments. As shown, for example in FIGS. 50 and 51, in some embodiments, the engagement member 15280, 16280 can include contact members 15283, 16283 that are curved in a spherical manner. Further to this example, in some embodiments, the contact member 15283 can include a dimpled surface (e.g., FIG. 50). In yet other embodiments, for example, the contact member 16283 can include a smooth surface (e.g., FIG. 51). FIG. 52 is a perspective view of an engagement member 17280 according to some embodiments. FIG. 53 is a perspective view of an engagement member 18280 according to some embodiments. As shown, for example in FIGS. 52 and 53, in some embodiments, the engagement member 17280, 18280 can include contact members 17283, 18283 that are curved in a planar manner. Further to this example, in some embodiments, the contact member 172823 can include a ribbed surface (e.g., FIG. 52). In yet other embodiments, for example, the contact member 18283 can include a smooth surface (e.g., FIG. 53). FIG. 54 shows a perspective view of the engagement member 18280 in use with a delivery device 18000 to engage an eye and/or deliver a medicament thereto, according to an embodiment. The delivery device can be similar to the delivery device 100, 400, 1000, 2000, 3000, 7000, or any other delivery device or medical injector described herein. FIG. 55 shows a cross-sectional view of the perspective view shown in FIG. 54. The delivery device 18000 includes a hub 18270, a puncture member 18240 (also referred to herein as a delivery member or a needle) and an engagement member 18280.

In use, a user (e.g., a doctor, technician, nurse, physician, ophthalmologist, etc.) can manipulate the delivery device 18000 to insert the puncture member 18240 into, for example, a portion of the eye (e.g., the eye 10 shown in FIG. 1). In this manner, the user can apply a distal force such that puncture member 18240 is advanced distally relative to and/or through the engagement member 18280 (e.g., as shown by arrow F1 along longitudinal axis AA in FIG. 55). In this manner, a portion of the puncture member 11080 can be advanced through a portion of the eye.

In some embodiments, a system for ocular injection can include any of the hubs described herein and/or a drug extraction device configured to matingly engage with a housing and/or a medicament delivery container. For example, referring now to FIGS. 56-71, in some embodiments, a system 19000 can include housing 19110, an actuator 19320, an actuating member 19140, a medicament containment chamber 19310, a hub 19270, a needle 19240, and a cap 19280. The system 19000 can be configured to deliver a substance, for example, a medicament to a target tissue, for example, the SCS of an eye.

The housing 19110 (FIG. 57) includes a first portion 19110*a*, and a second portion 19110*b* (collectively "19110") that can be coupled together to define an internal region for housing at least a portion of the medicament containment chamber 19310 and the actuator 19320. The housing 19110 includes a gripping portion 19112 to allow a user to grip the housing 19110 between his index and middle finger. The housing 19110 also includes ridges 19114 to allow easy gripping of the housing 19110 by the user. For example, the user can grip the gripping portion 19112 with one hand and grip the ridges 19114 with the fingers of a second hand during injection, for example, delivery of a medicament into a target tissue (e.g., ocular tissue). In this manner, the user any sideways movement of the system 19000 during medicament delivery can be reduced. A set of windows 19116 are defined in a sidewall of the housing 19110. The set of windows 19116 can be configured to allow the user to view the interior volume of the medicament containment chamber 19310, for example, to view a level of a medicament remaining in the medicament containment chamber 19310. The housing 19110 also include a set of slots 19118, each slot configured to slidably receive a rib 19323 included in an engagement portion 19322 of the actuator 19320, such that the set of slots are configured to keep the actuator 19320 aligned as the actuator 19320 is displaced within the housing 19110 and the medicament containment chamber 19310.

Figure 57:
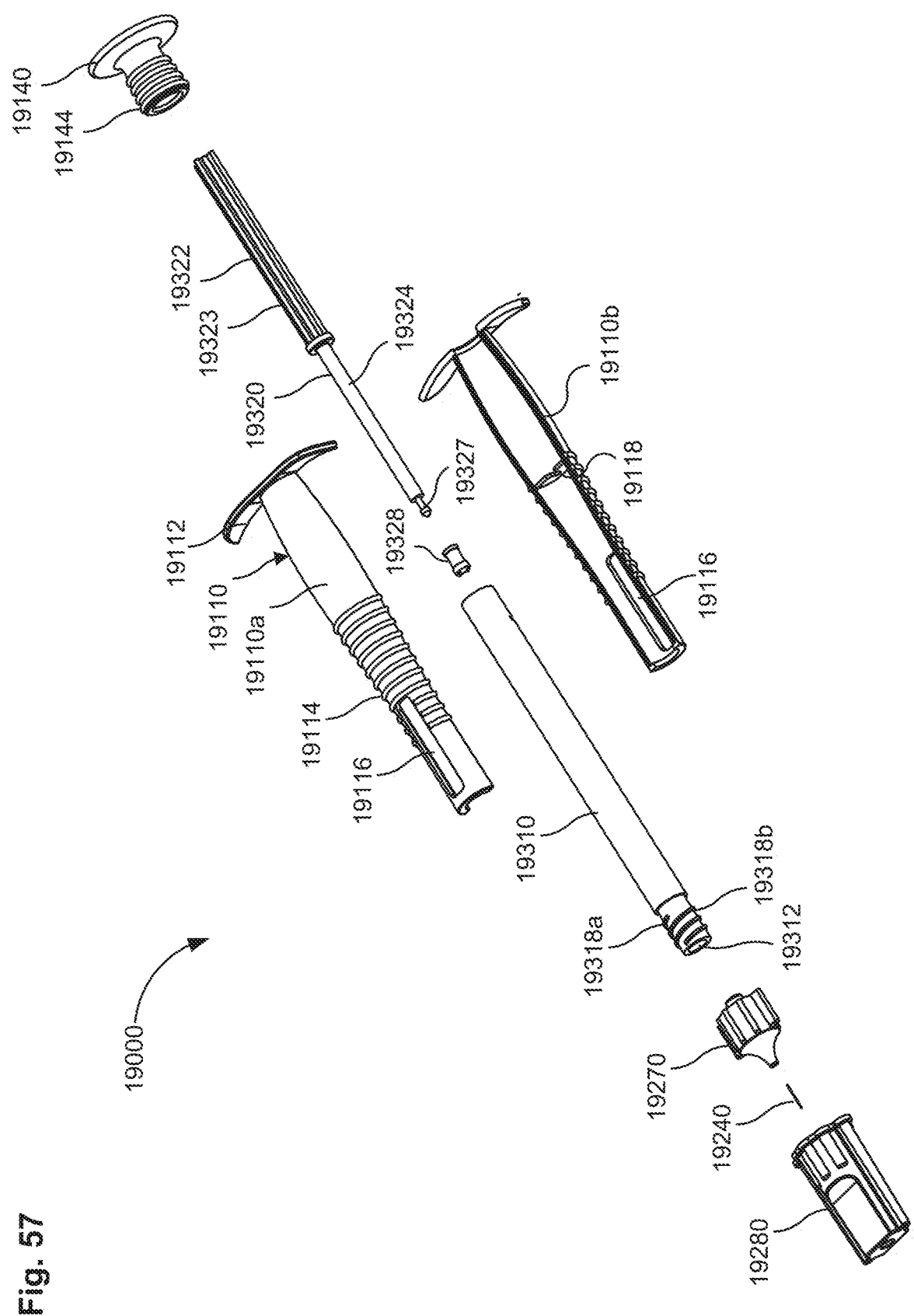
FIG. 57 shows an exploded view of the delivery device shown in FIG. 56.
Figure 58:
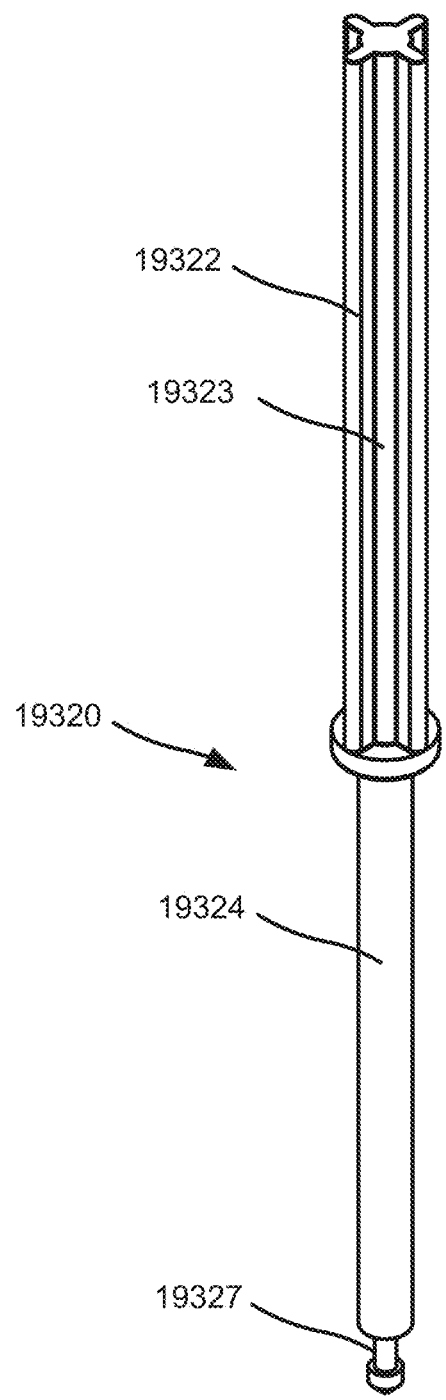
FIG. 58 shows a perspective view of an actuator rod included in the delivery device of FIG. 56.
Figure 59:
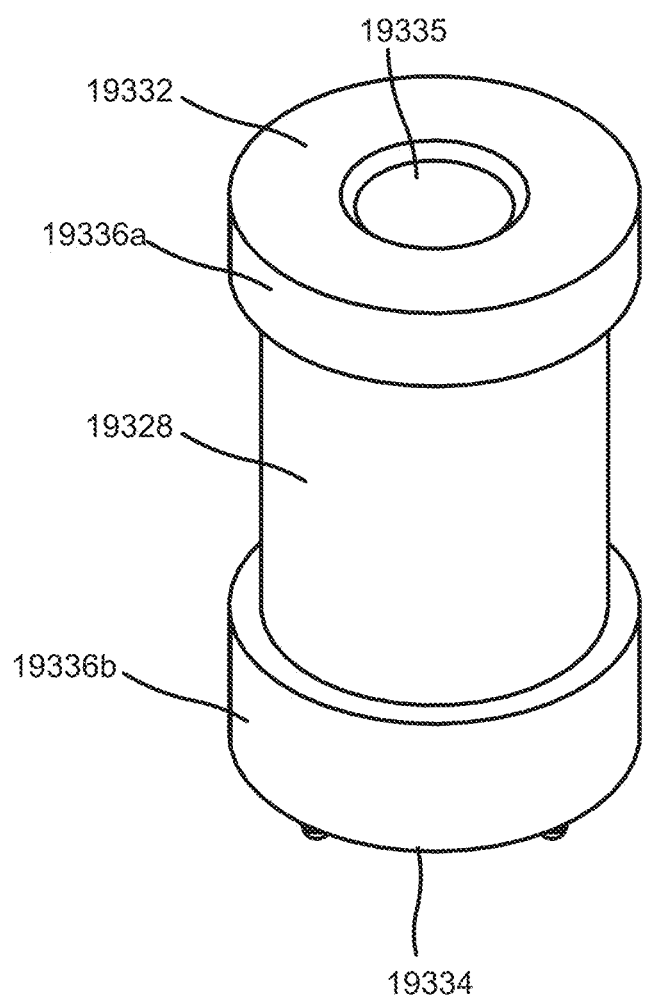
FIG. 59 shows a top perspective view of a plug included in the delivery device of FIG. 56.
Figure 60:
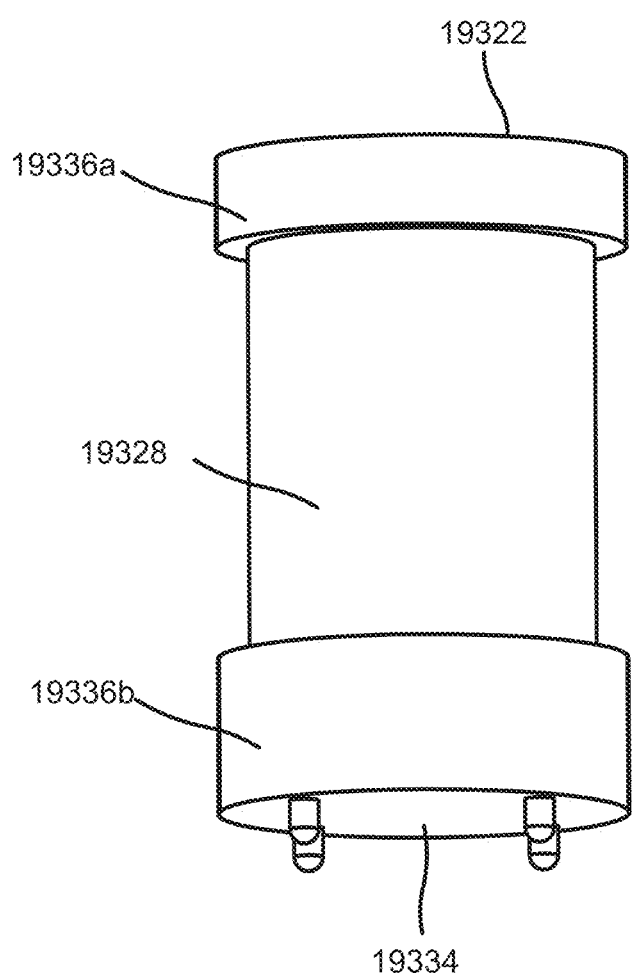
FIG. 60 shows a bottom perspective view of the plug of FIG. 59.
Figure 61:
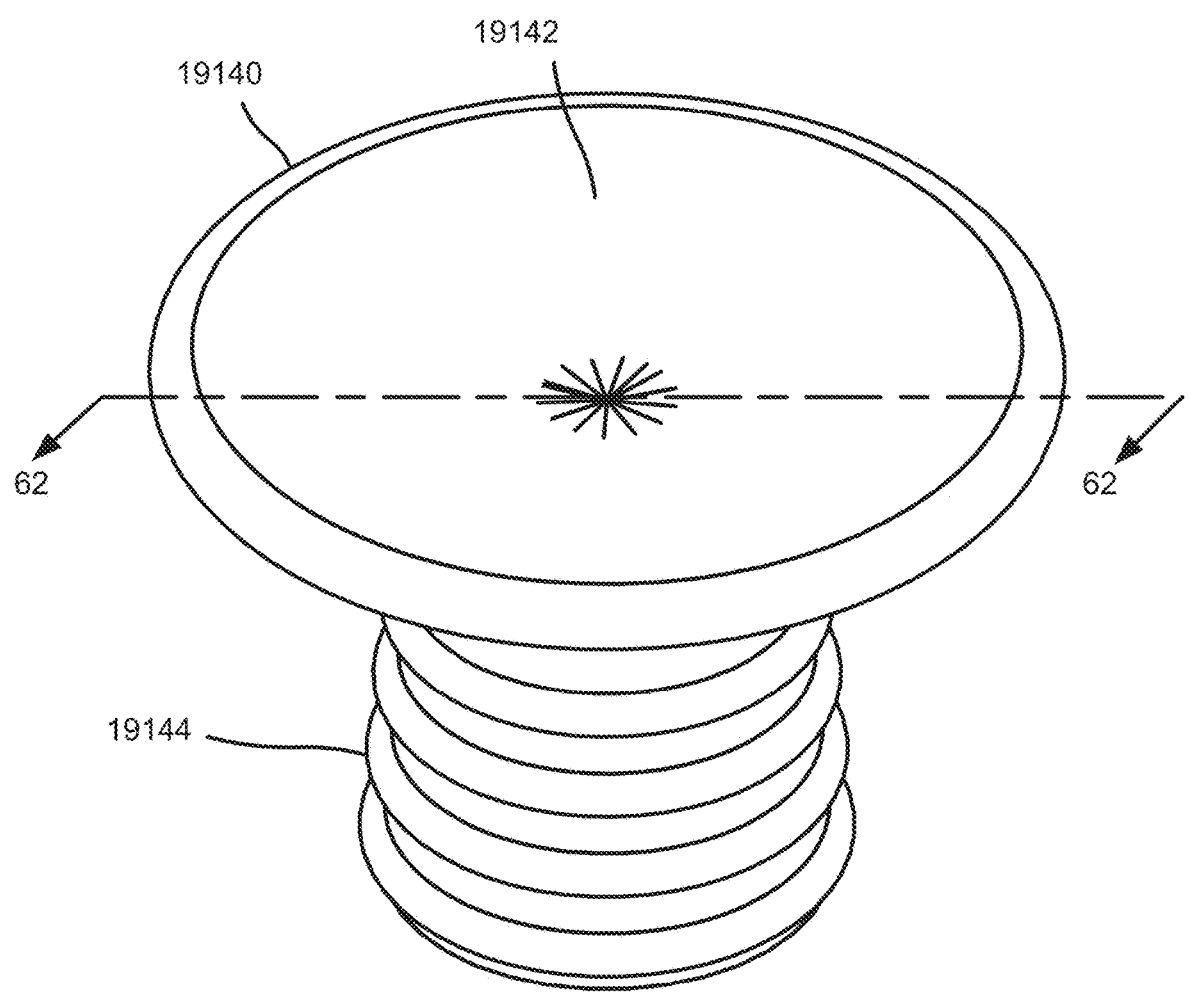
FIG. 61 shows a top perspective view of an actuator included in the delivery device of FIG. 56.
Figure 62:
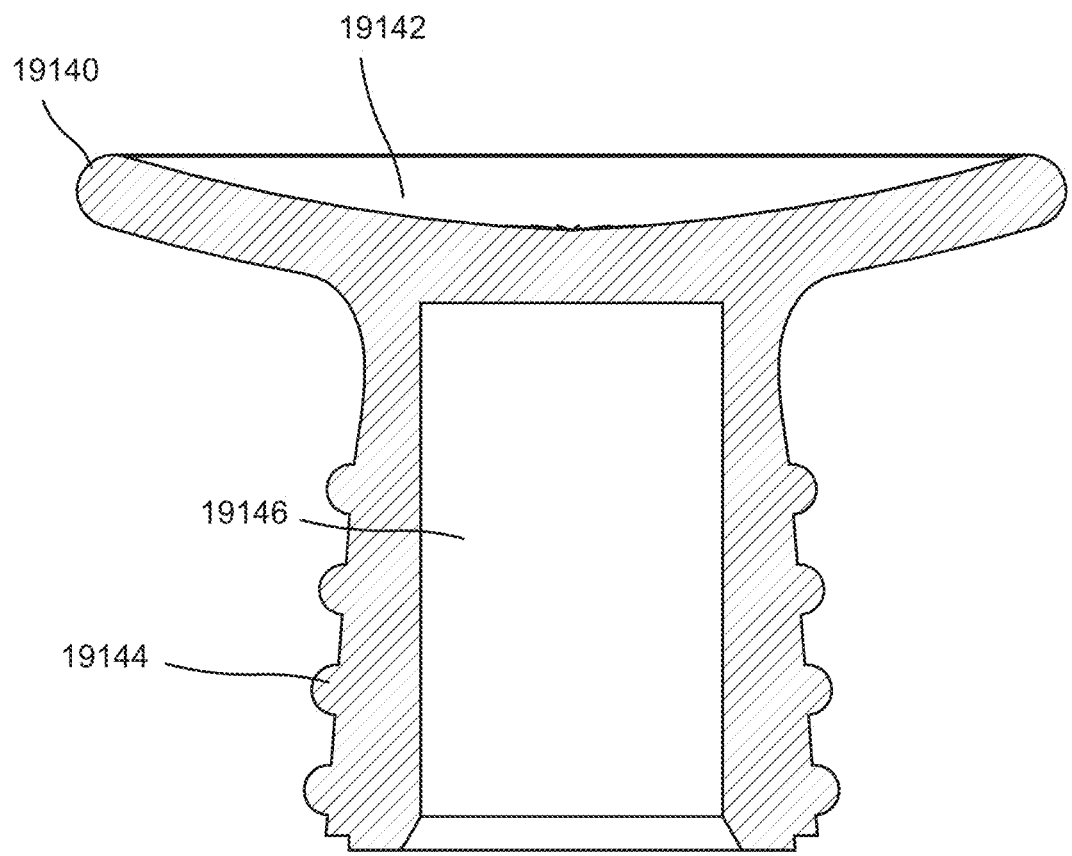
FIG. 62 shows a side cross-section view of the actuator of FIG. 61, taken along the line 62-62 shown in FIG. 61.

As shown in FIGS. 57 and 58, the actuator 19320 includes an engagement portion 19322 and a plunger portion 19324. The engagement portion 19322 includes a set of ribs 19323 slidably disposed in the set of slots 19118 of the housing 19110, as described before. A portion of the engagement portion 19322 is disposed in a cavity 19146 defined by the actuating member 19140 (see, e.g., FIG. 62). The plunger portion 19324 includes a protrusion 19327 disposed on a distal end of the actuator 19320. The protrusion 19327 can be configured to be disposed in a recess 19335 defined by a plug 19328 with close tolerance (e.g., friction fit), as described herein. The plug 19328 (FIGS. 59-60) is disposed in the internal volume 19316 defined by the medicament containment chamber 19310. The plug 19328 includes a proximal end 19332 coupled to the plunger portion 19324 of the actuator 19320 and a distal end 19334 in fluid communication with a medicament or any other liquid disposed in the internal volume 19316 defined by the medicament containment chamber 19310. The plug 19328 can be made of a rigid but soft material, for example, rubber, and includes the recess 19335 configured to receive the protrusion 19327 of the actuator 19320 with close tolerance (e.g., friction fit). The plug 19328 includes a first sidewall 19336*a* and a second sidewall 19336*b* (collectively referred to as the "sidewalls 19336) in contact with a sidewall of the internal volume 19316 of the medicament containment chamber 19310. The sidewalls 19336 form a substantially fluid-tight seal with the sidewalls of the inner volume 19316 defined by the medicament containment chamber 19310. In this manner, the plug 19328 can prevent leakage of the liquid medicament from the internal volume 19316, for example, leakage of the medicament into a portion of the internal volume 19316 within which the plunger portion 19324 of the actuator 19320 is disposed.

The actuation member 19140 (FIGS. 61-62) includes a depression 19142, shaped to conform to a thumb of a user, for example, to allow easy displacement of the actuating member 19140 by the user. The actuating member 19140 also includes ridges 19144 configured to allow easy gripping of the actuating member 19140, for example, when loading a medicament into the medicament containment chamber 19310. The actuation member 19140 also includes a cavity 19146, configured to slidably receive a portion of the engagement portion 19322 of the actuator 19320 with close tolerance (e.g., friction fit). In some embodiments, the actuating member 19140 can be configured to be engaged by the user to manually move the plunger portion 19324 of the actuator 19320 within the internal volume 19316 of the medicament containment chamber 19310. In some embodiments, the actuating member 19140 can be included in an injection assembly, for example, the injection assembly 100, 2100, or any other injection assembly described herein, that can be included in the system 19000. The actuating member 19140 can be configured to activate the injection assembly, for example, to release and/or move the actuator 19320 such that the plunger portion 19324 moves within the internal volume 19316 and expels at least a portion of the medicament through the needle 19240 (e.g., into the SCS of the eye).

Figure 63:
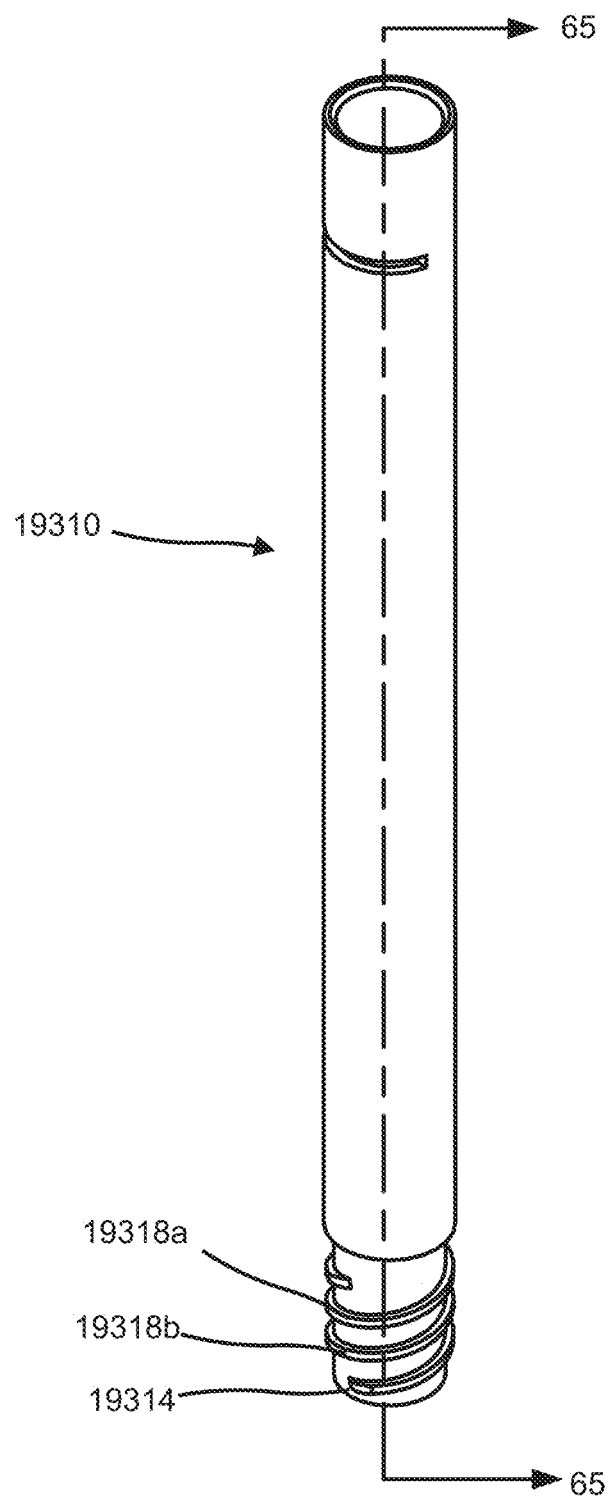
FIG. 63 shows a top perspective view of a medicament containment chamber included in the delivery device of FIG. 56.
Figure 64:
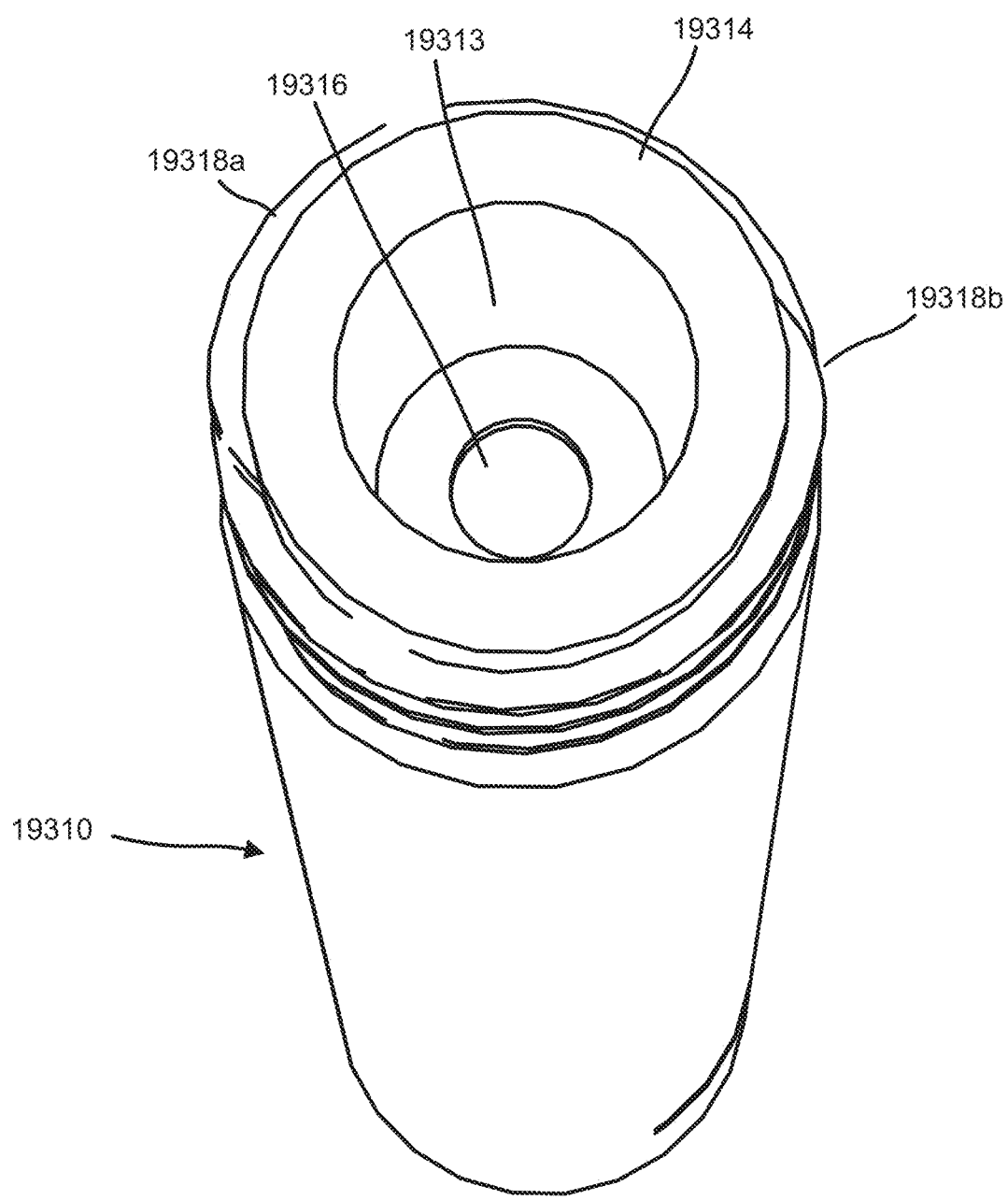
FIG. 64 shows a bottom perspective view of the medicament containment chamber of FIG. 63.
Figure 65:
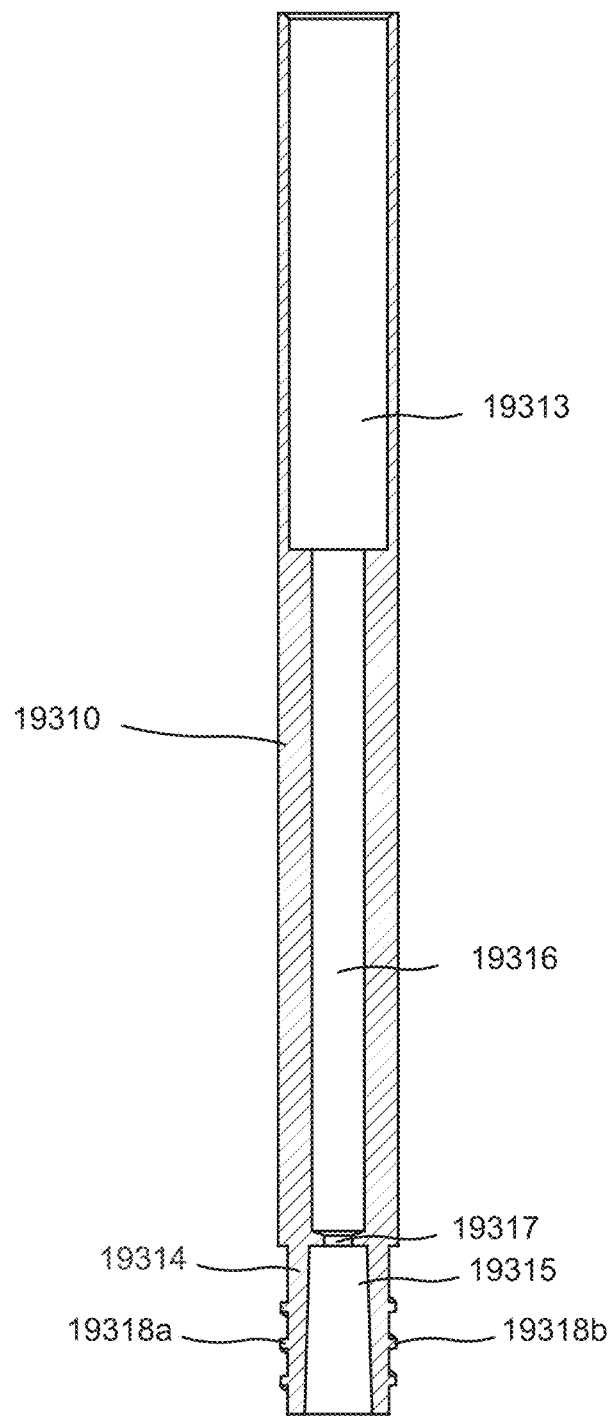
FIG. 65 shows a side cross-section view of the medicament containment chamber of FIG. 63 taken along the line 65-65 shown in FIG. 63.

As shown in FIGS. 63-65, the medicament containment chamber 19310 defines an internal volume 19316, configured to house a medicament. The medicament containment chamber 19310 includes a delivery portion 19324. A first set of threads 19318*a* and a second set of threads 19318*b* (FIG. 63) are formed on an outer wall of the delivery portion 19314. Said another way, the outer wall of the delivery portion 19314 includes double-start threads. The threads 19318 are configured to allow coupling of the medicament containment chamber 19310 to a coupling portion 19272 of the hub 19270. In some embodiments, any other hub, an injection site marker, for example, the injection site marker 20280 described below, and/or an extraction device, for example extraction device 21280, can be coupled to the delivery portion 19324 via the threads 19318. The delivery portion 19314 includes a first cavity 19315 configured to receive an engagement portion 19273 (e.g., a nozzle) of the hub 19270, such that a fluidic channel 19317 included in the delivery portion 19314 is in fluid communication with a first fluidic channel 19277 included in the engagement portion 19273 of the hub 19270. The medicament containment chamber 19310 also includes a second cavity 19313. The engagement portion 19322 of the actuator 19320 is disposed within the second cavity 19313 and is configured to be slidably displaced within the second cavity 19313.

Figure 67:
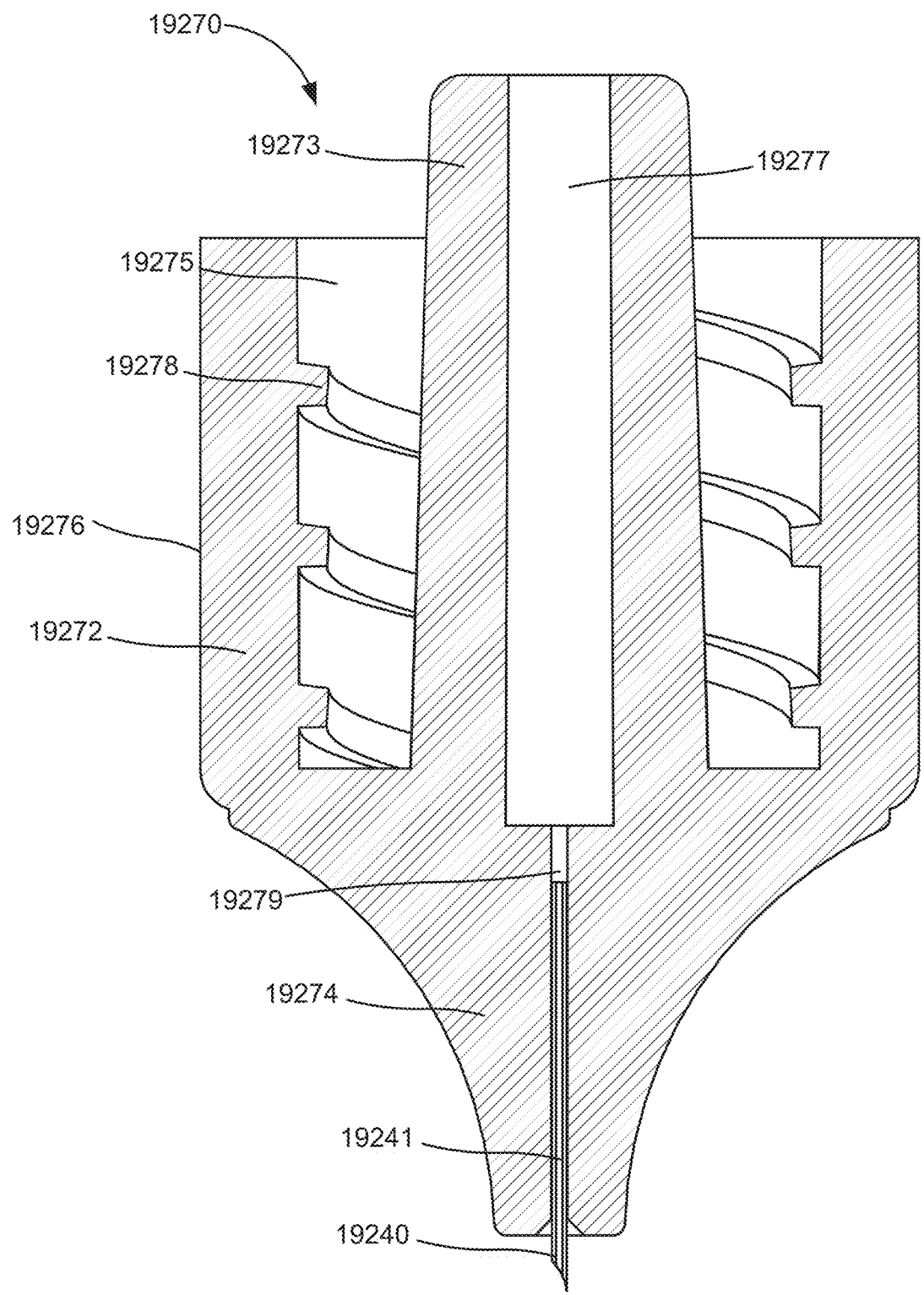
FIG. 67 show a side cross-section view of the hub of FIG. 66 taken along the line 67-67 shown in FIG. 66.

As shown in FIGS. 66-67, the hub 19270 includes an engagement portion 19273, a coupling portion 19272, and a delivery portion 19274. An inner sidewall of the engagement portion 19273 and an outer sidewall of the coupling portion 19272 define a recess 19275 configured to receive the delivery portion 19314 of the medicament containment chamber 19310. The inner sidewall of the coupling portion 19272 includes threads 19278, configured to engage the threads 19318*a* and/or 19318*b* of the medicament containment chamber 19310, thereby coupling the hub 19270 to the medicament containment chamber 19310. An outer sidewall of the coupling portion 19272 includes a set of ridges 19276. The ridges 19276 can facilitate a user to grip the hub 19270, for example, for coupling or uncoupling the hub 19270 from the medicament containment chamber 19230. The engagement portion 19273, defines a fluidic channel 19277 configured to engage the fluidic channel 19317 of the medicament containment chamber 19130 and establish fluidic communication between the medicament containment chamber 19130 and the hub 19270. The delivery portion 19274, defines a second fluidic channel 19279 configured to removably receive the needle 19240, for example, a microneedle (e.g., any suitable microneedle described herein). The needle 19240 is configured to be disposed within a target tissue, for example, ocular tissue and defines a lumen 19241 such that the needle 19240 is configured to establish fluidic communication between the medicament containment chamber 19310 and the portion of the user's body (e.g., the eye). In some embodiments, the needle 19240 can be fixedly disposed in the second fluidic channel 19279. In some embodiments, the needle 19240 can be monolithically formed with the hub 19270 such that the second fluidic channel 19279 and the lumen of the needle 19241 are continuously and/or seamlessly formed.

Figure 68:
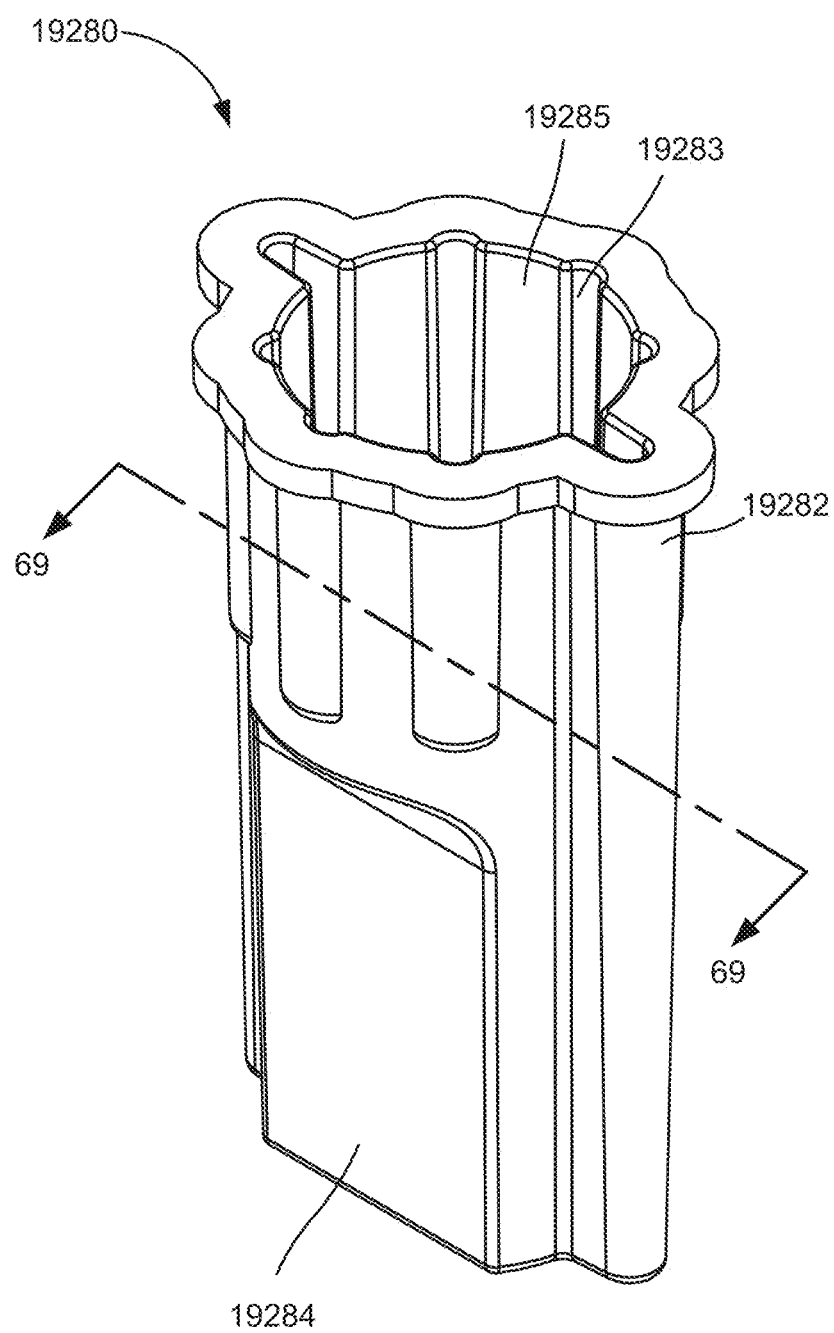
FIG. 68 shows a top perspective view of a cap included in the delivery device of FIG. 56.
Figure 69:
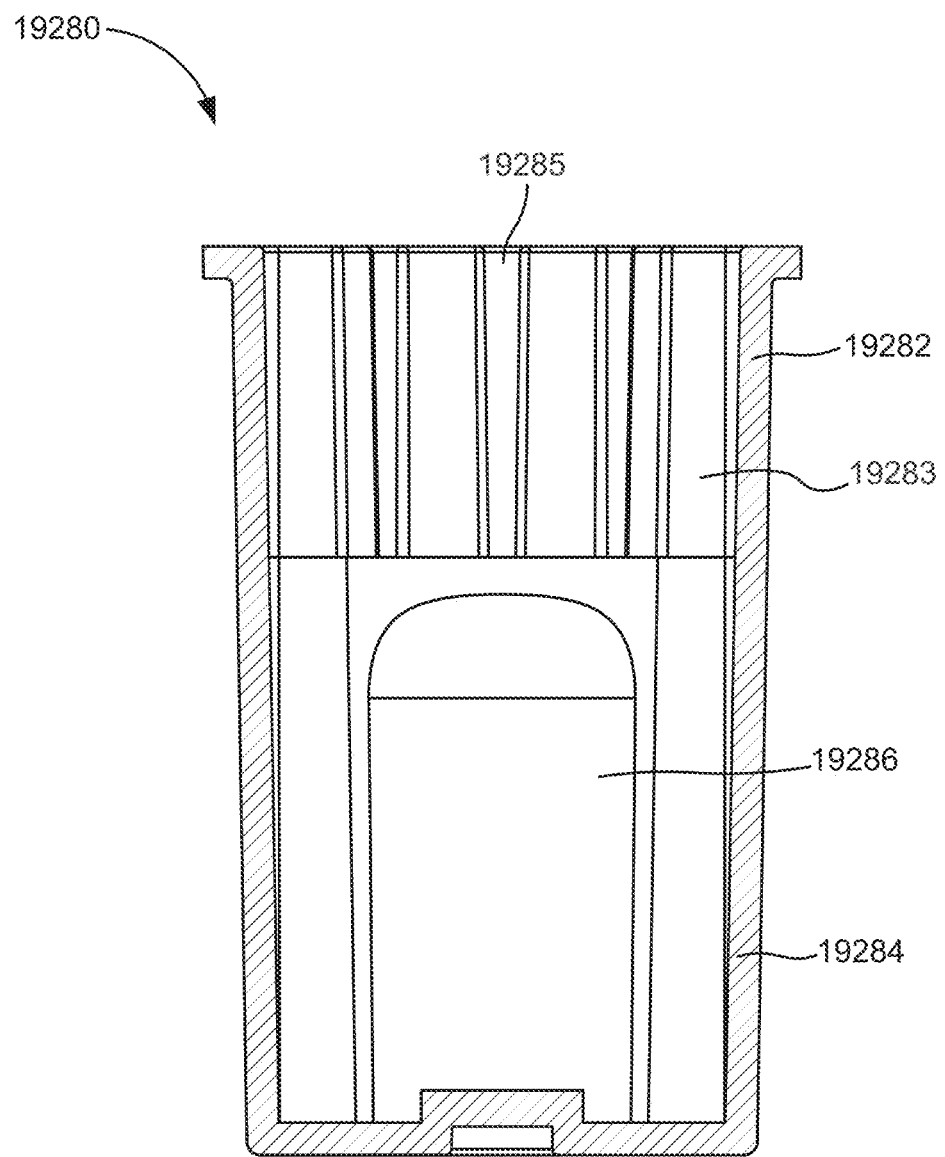
FIG. 69 shows a side cross-section view of the cap of FIG. 68 taken along the line 69-69 shown in FIG. 68.

As shown in FIGS. 68 and 69, the cap 19280 includes a coupling portion 19282 that includes a first cavity 19283 configured to slidably receive the coupling portion 19272 of the hub 19270. A set of grooves 19285 is formed on an inner sidewall of the coupling portion 19282 configured to mate with the set of ridges 19276 of the hub 19270 with close tolerance (e.g., friction fit). The cap 19280 also includes an engagement portion 19284 that defines a second cavity 19284 configured to receive the delivery portion 19274 of the hub 19270. At least a portion of an outer sidewall of the engagement portion 19284 is substantially flat, for example, to allow a user to grip the cap 19280 with ease (e.g., to couple or uncouple the hub 19270 from the medicament containment chamber 1150). The cap 19280 can thus enable safe coupling/uncoupling of hub 19270 to the medicament containment chamber 19310 and/or prevent accidental piercing of a portion of a user's body by the needle 19240 during handling of the system 19000.

Figure 70:
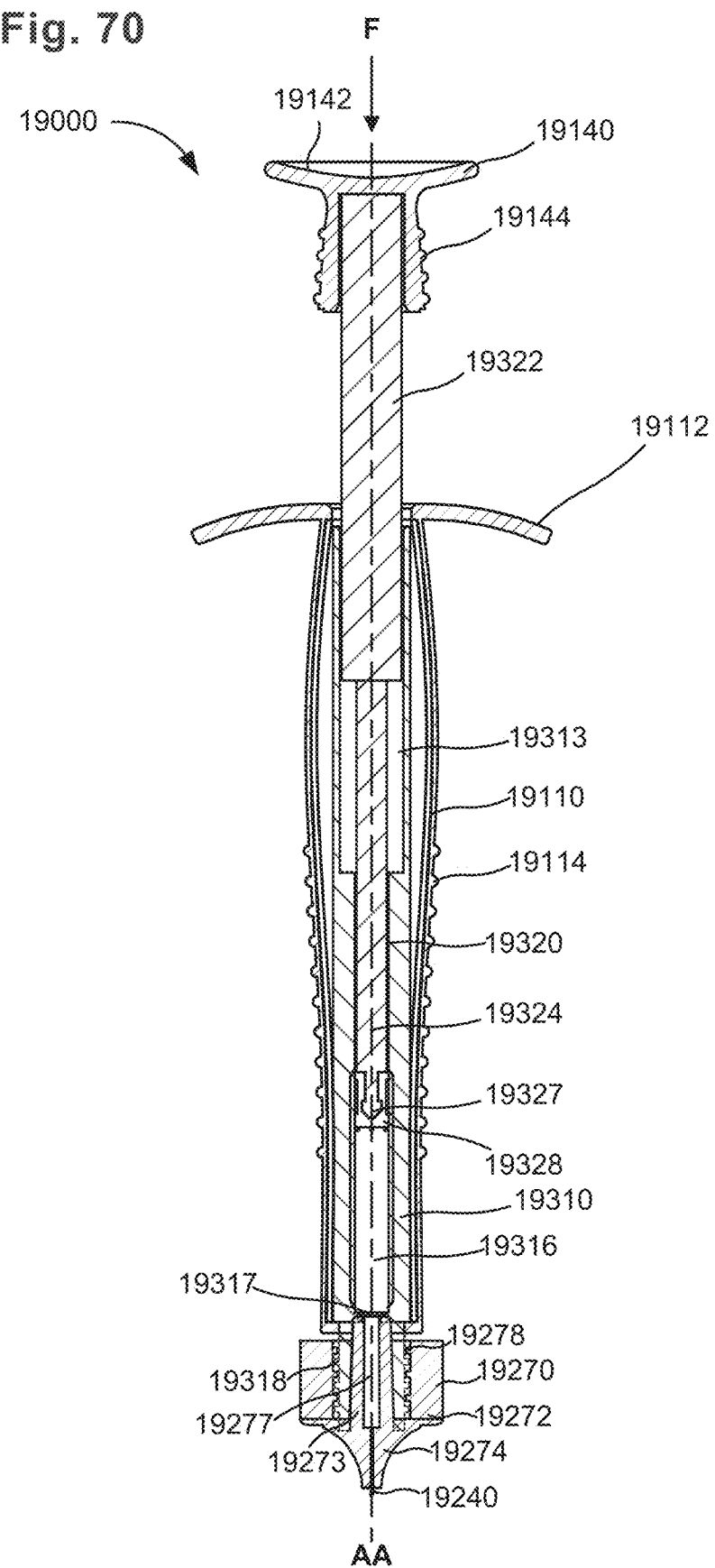
FIGS. 70 and 71 show side cross-section views of the delivery device of FIG. 56 in a first configuration and a second configuration, respectively.
Figure 71:
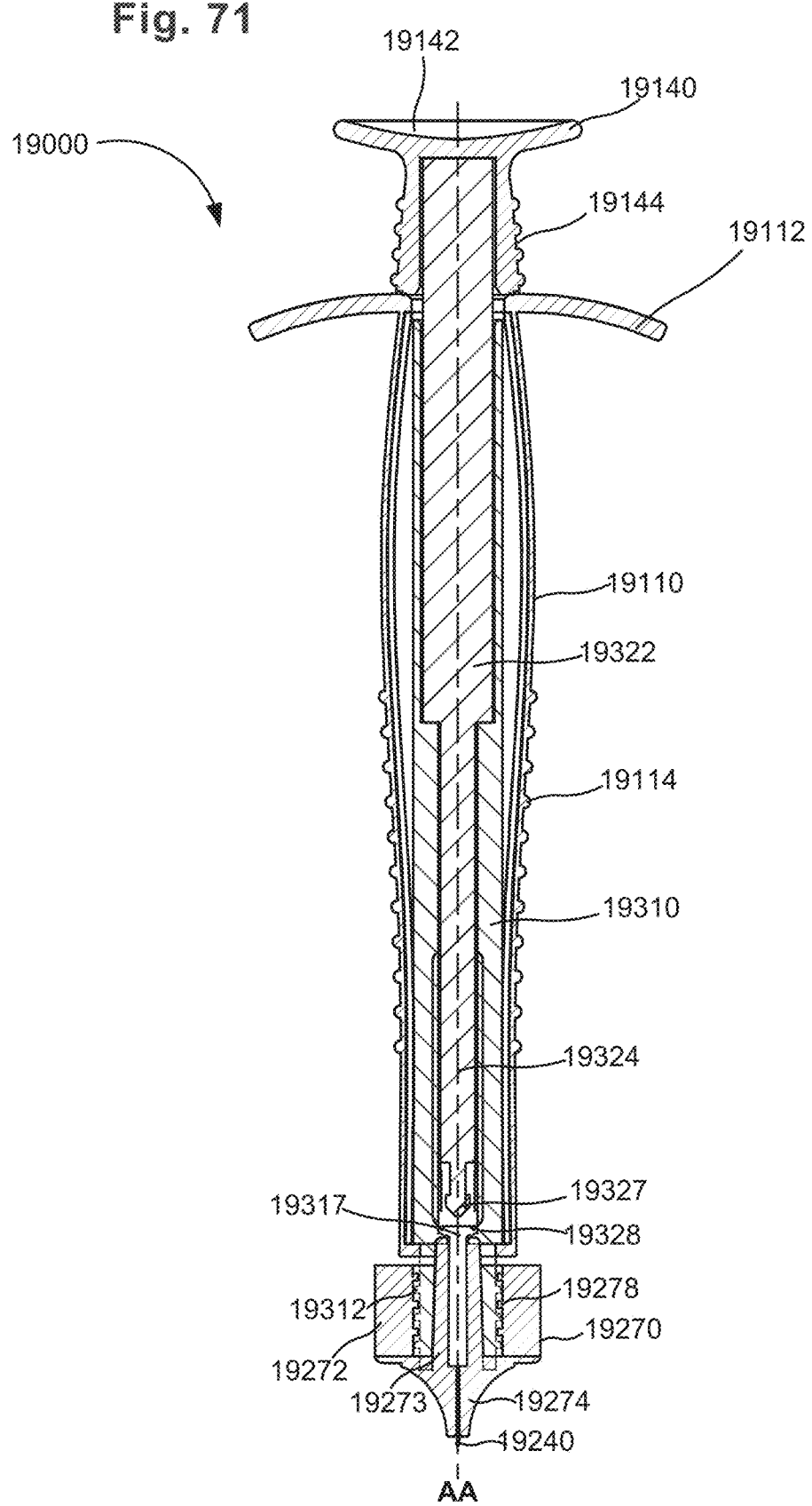

Referring now to FIGS. 70-71, FIG. 70 shows the system 19000 in a first configuration, such that the actuator 19320 and the actuating member 19140 are in a first position and the internal volume 19316 of the medicament containment chamber 19310 is at least partially filled with the medicament. A user can now engage the actuating member 19140 by applying a force in the direction shown by the arrow F on the actuating member 19140, for example, using a thumb of the user. This urges the actuator 19320, which is coupled to the actuating member 19140, to displace along a longitudinal axis AA of the system 19000 and urge the system 19000 into the second configuration as shown in FIG. 71. In the second configuration, the actuator 19320 is displaced from the first position to a second position within the internal volume 19316 of the medicament containment chamber 19310. This displacement causes the plug 19328, which is in fluid communication with the medicament, to slide from the first position to the second position within the internal volume 19316. The movement expels the medicament from the internal volume 19316 into the fluidic channel 19277 of the hub 19270, and further through the lumen 19241 of the needle 19240 into the target tissue (e.g., the eye).

Figure 72:
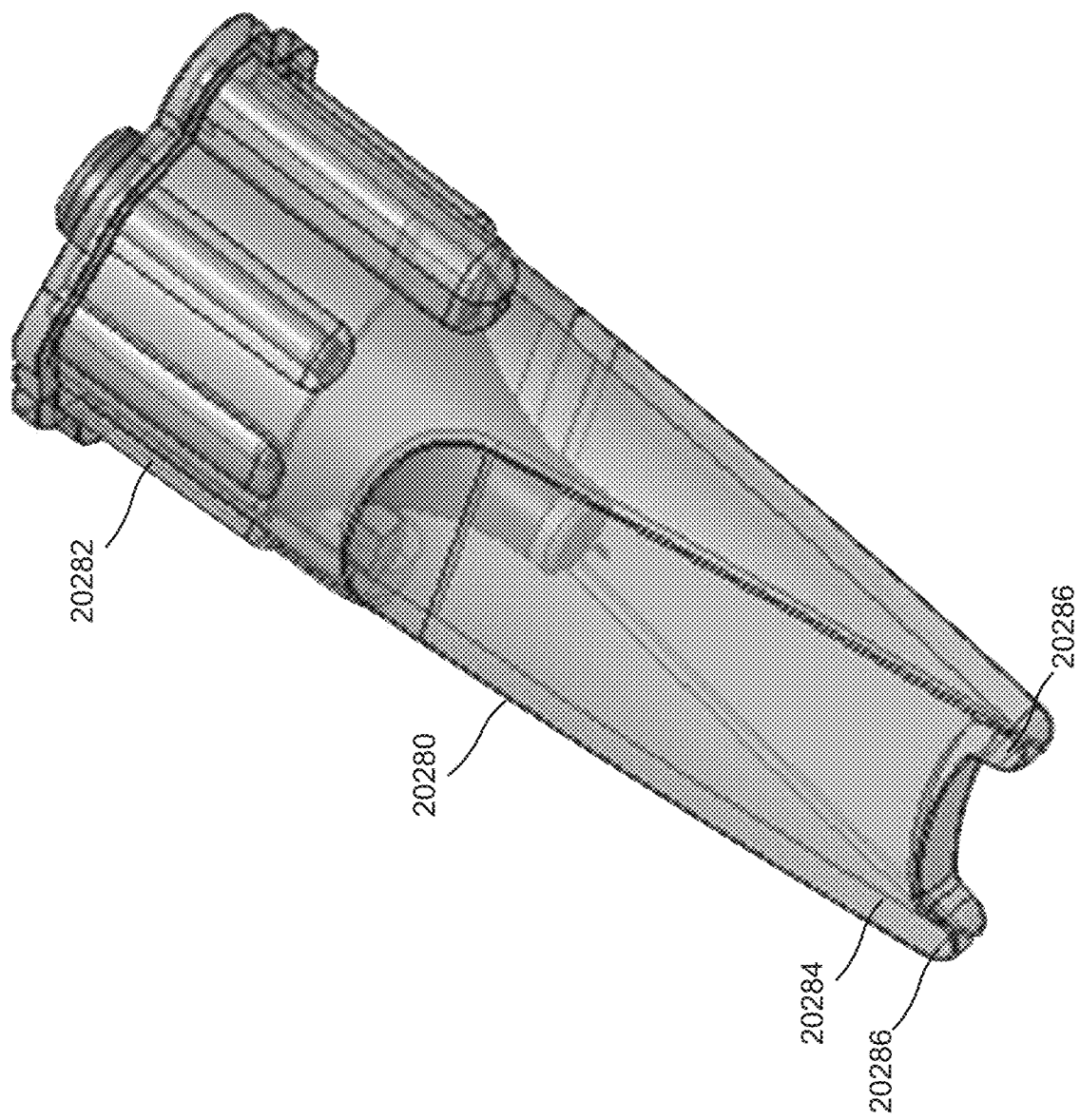
FIG. 72 shows a perspective view of an injection marker that can be included in a delivery system, according to an embodiment.
Figure 73:
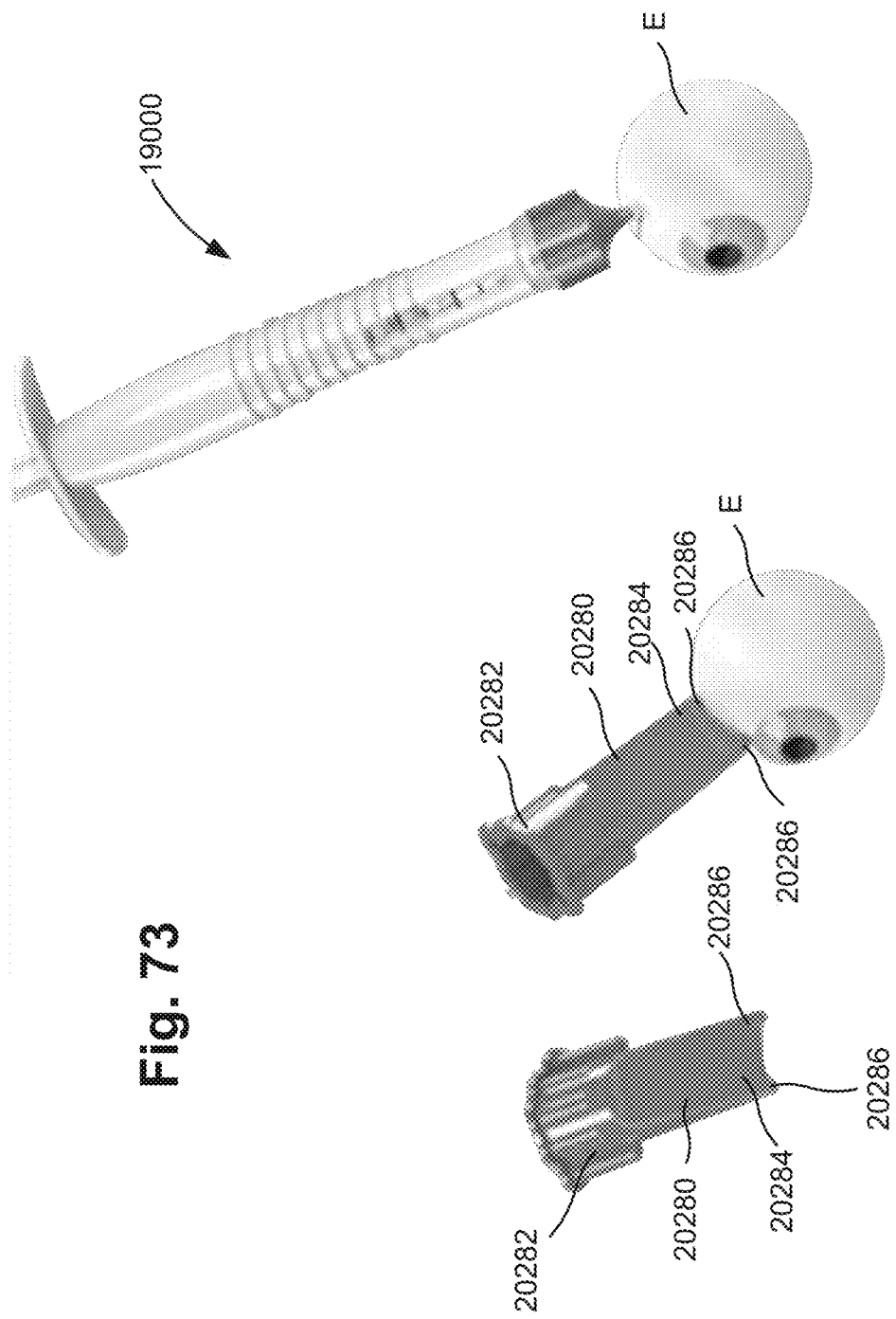
FIG. 73 shows the injection marker of FIG. 72 being used to mark an injection site on an eye.

In some embodiments, a system for ocular injection can include an injection marker for marking an injection site on a target tissue, for example, ocular tissue. FIG. 72-73 show perspective views of an injection site marker 20280 according to an embodiment. As shown, a proximal end 20282 of the injection site marker 20280 can be coupled to a delivery device, for example, coupled to the coupling portion 19272 of the hub 19270 included in the system 19000. The injection site marker 20280 has a distal end 20284, which includes a set of protrusions 20286 disposed on a distal end surface of the distal end 20284. In some embodiments, the proximal end 20282 of the injection site marker 20280 can be used in conjunction with and/or coupled to any of the hubs, engagement members and/or adjustment members described herein. For example, in some embodiments, the injection site marker 20280 can be threadedly coupled to a hub of a delivery device (e.g., hub 19270 of delivery device 19000). In other embodiments, for example, the injection site marker 20280 can be coupled by way of friction (e.g., interference fit, press fit, friction fit, etc.)

In some embodiments, the protrusions 20286 of the distal end 20284 of the injection site marker 20280 can be configured to contact a portion of the eye (e.g., the eye 10 shown in FIG. 1). In some embodiments, for example, the protrusions 20286 of the injection site marker 20280 can be configured leave a marking on a portion of the eye. The marking, for example, can indicate an injection site. For example, the markings can appear as parallel indentations on the conjunctiva of the eye indicating to the user that the injection is to be performed in the region between the parallel markings. Further to this example, in some embodiments, the injection site marker 20280 can be removably coupled to a delivery device (e.g., the delivery device 19000). In such embodiments, the injection site marker 20280 can be removed from the delivery device after marking the injection site on the target tissue. A needle assembly and/or hub that includes a needle, for example, the needle 19240 coupled thereto, can then be coupled to the delivery device which can be used to deliver the medicament to the injection site marked by the injection site marker 20280. In some embodiments, an injection site marker can define a passageway to allow a needle to pass therethrough. In such embodiments, the injection site marker can remain coupled to the delivery device during delivery of the medicament to the target tissue.

In some embodiments, a system for delivering medicaments can include an extraction device for extracting medicaments or any other fluid from a container, for example, a vial. Referring now to FIG. 74-80, a system 21000 includes a housing 21110, an actuator (not shown), an actuating member 21140, a medicament containment chamber 21310, and an extraction member 21280. The system 21000, that includes the extraction member 21280, can be used to extract a liquid medicament from a medicament container 21294. The housing 21110, the actuator, the medicament containment chamber 21310, and actuating member 21140 of the system 21000 can be substantially similar in structure and function to the components of the system 19000 described earlier, and are therefore not described in further detail herein.

Figure 74:
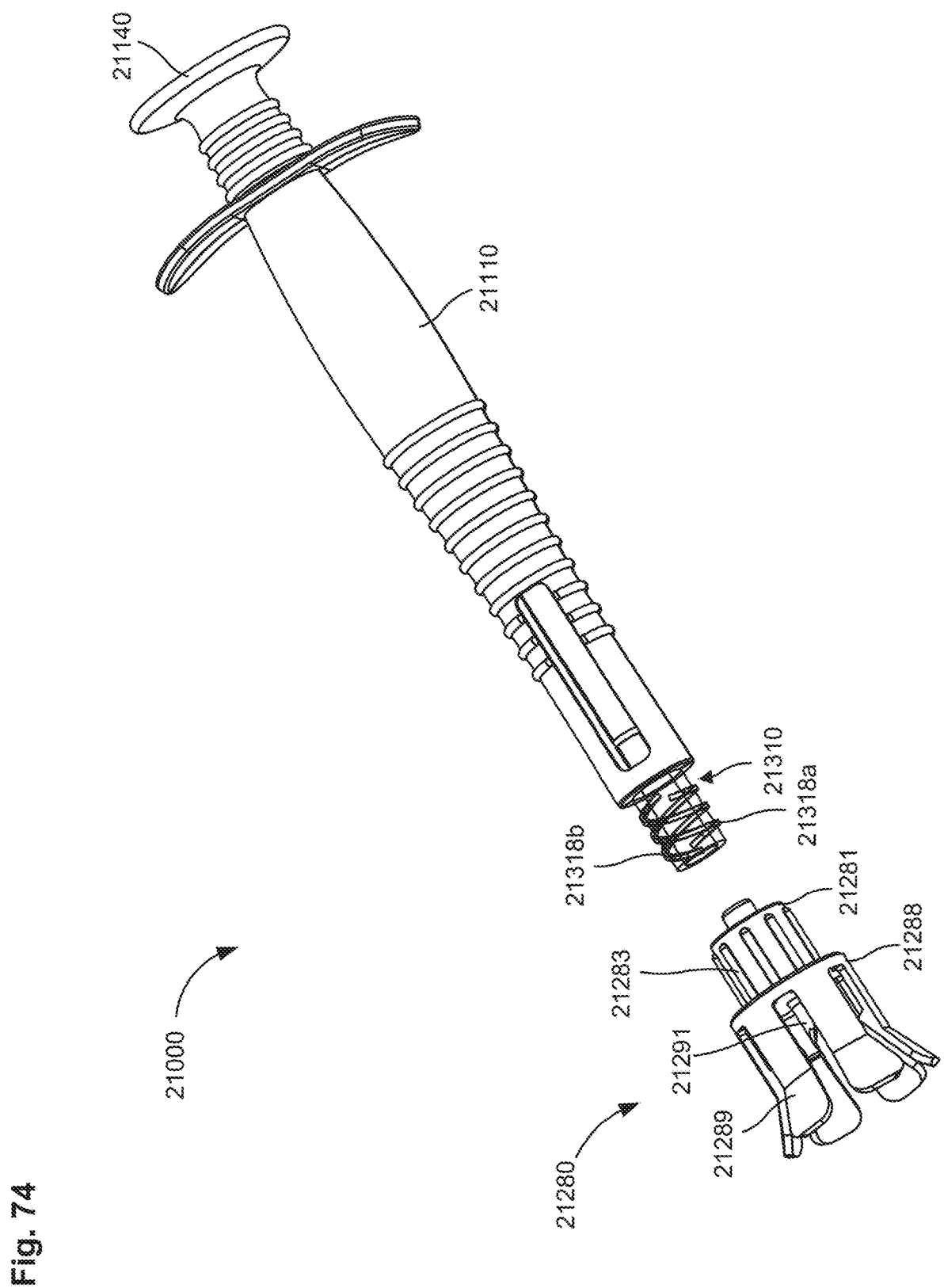
FIG. 74 shows a perspective view of a delivery device and an extraction member configured to be coupled to the delivery device, according to an embodiment.
Figure 75:
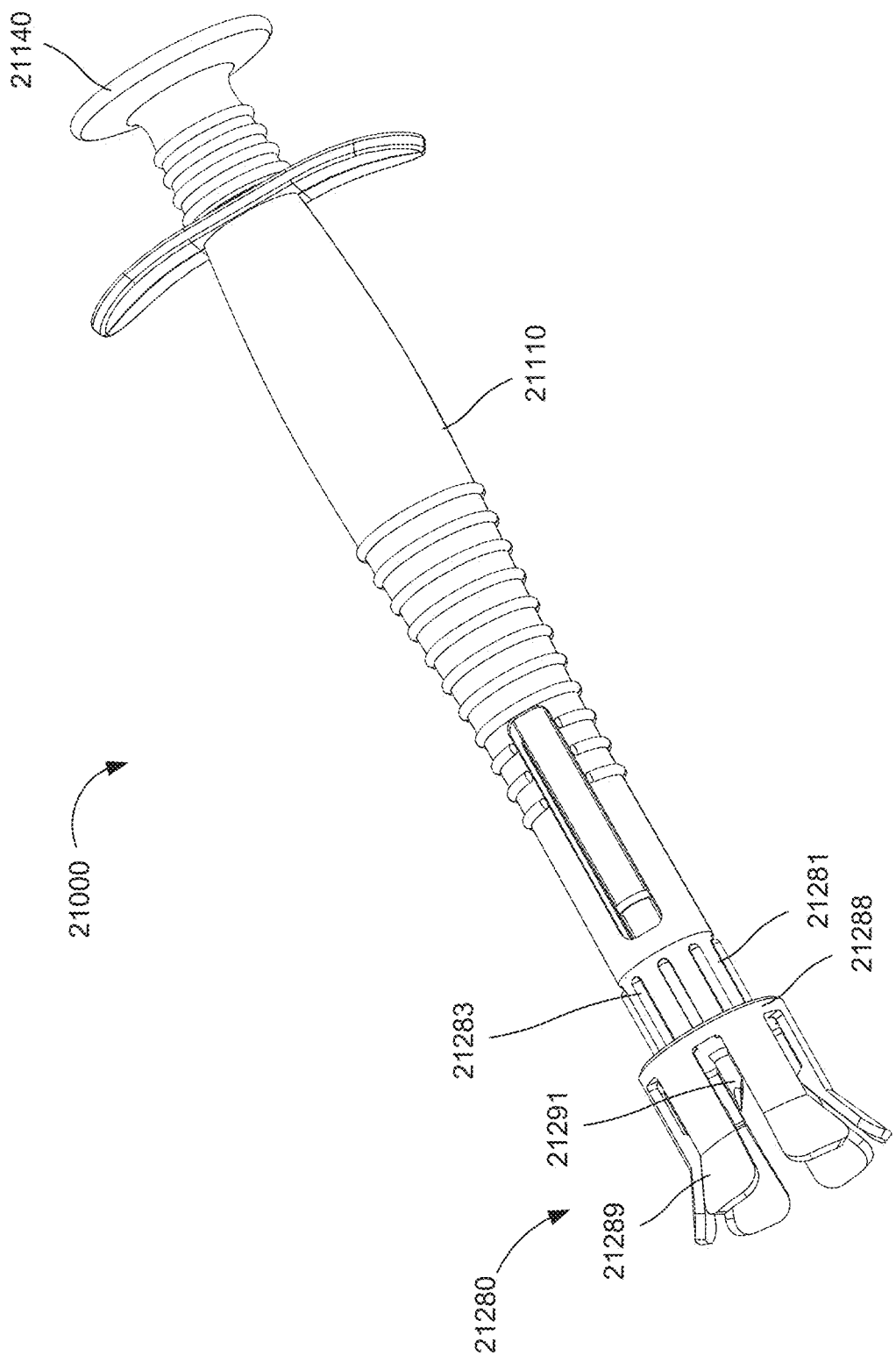
FIG. 75 shows a perspective view of the delivery device of FIG. 74 with the extraction member coupled thereto.
Figure 76:
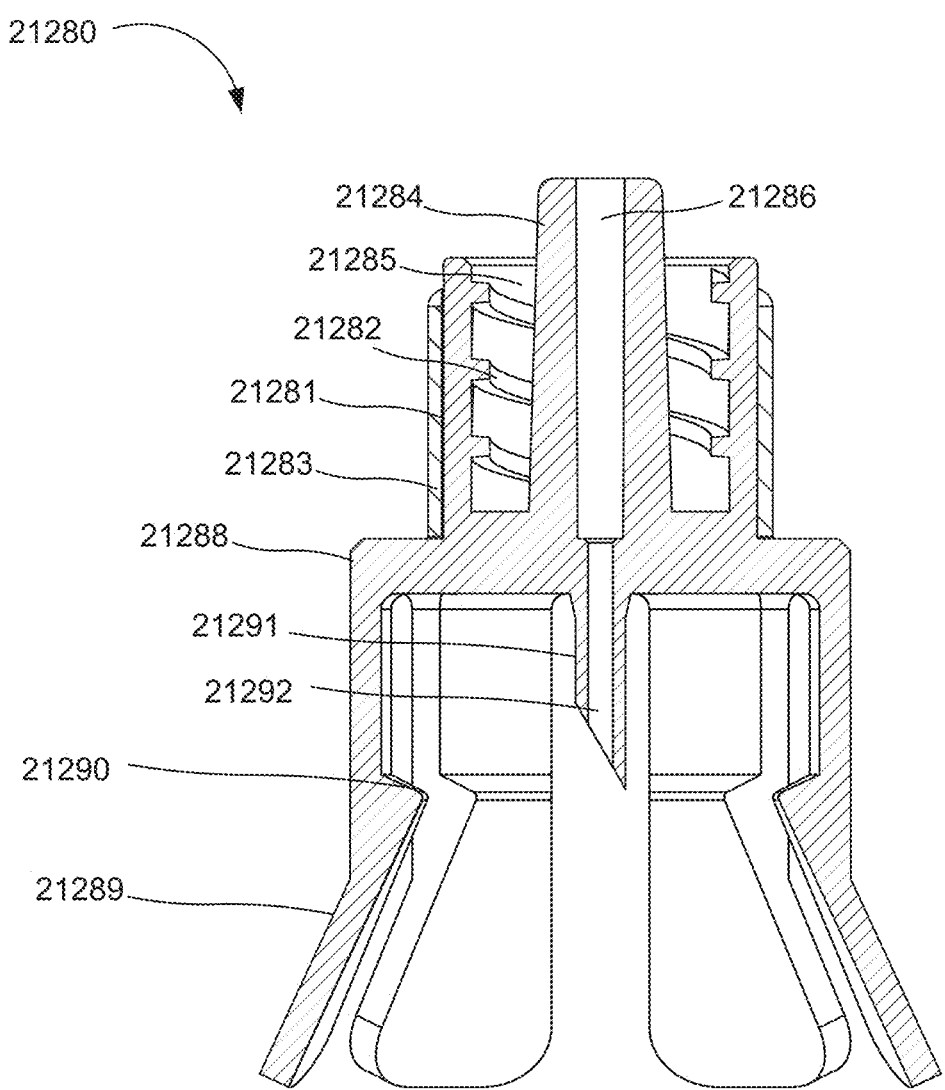
FIG. 76 shows a side cross-section view of the extraction member of FIG. 74.

FIG. 74 shows the extraction member 21280 uncoupled from the medicament containment chamber 21310 while FIG. 75 shows the extraction member 21280 coupled to the medicament containment chamber 21310. As shown in FIG. 76, the extraction member 21280 includes a coupling portion 21281, an engagement portion 21284 and an extraction portion 21288. Threads 21282 are formed on an inner side wall of the coupling portion that are configured to mate with the threads of 21318*a* and 21318*b* of the medicament containment chamber 21310 and to couple the extraction member 21280 to the medicament containment chamber 21310. A set of ridges 21283 are formed on an outer sidewall of the coupling portion 21281. The ridges 21283 can, for example, serve as grips to facilitate a user to couple/uncouple the extraction member 21280 to the medicament containment chamber 21250. The inner sidewall of the coupling portion 21281 and an outer sidewall of the engagement portion 21284 define a cavity 21285, configured to receive a portion of the medicament containment chamber 21310, when the extraction member 21280 is coupled to the medicament containment chamber 21310. The engagement portion 21284 includes a fluidic channel 21286 configured to establish fluid communication between the extraction member 21280 and the medicament containment chamber 21250, for example, to allow communication of fluid from the extraction member 21280 (e.g., liquid medicament extracted from a medicament vial) to the medicament containment chamber 21250.

The extraction portion 21288 is configured to be releasably coupled to a container a container 21294 that contains a medicament, and establish fluid communication between the container 21294 and the medicament containment chamber 21310 via the extraction member 21280. The extraction portion 21288 includes a set of arms 21289. Each of the set of arms 21289 has an angled portion configured to flex open for receiving a cap of the container, for example, the container 21294. Each of the set of arms 21289 also include a ledge 21290 configured to secure the cap of the container, for example container 21294 when the container is coupled to the extraction member 21280, as shown in FIG. 75. The extraction portion 21288 also includes a puncturing member 21291 that defines a fluidic channel 21292. The puncturing member 21291 is configured to puncture a seal of a container, for example, container 21294, and establish fluid communication between the container and the medicament containment chamber 21310, via the extraction member 21280, as described herein.

Figure 77:
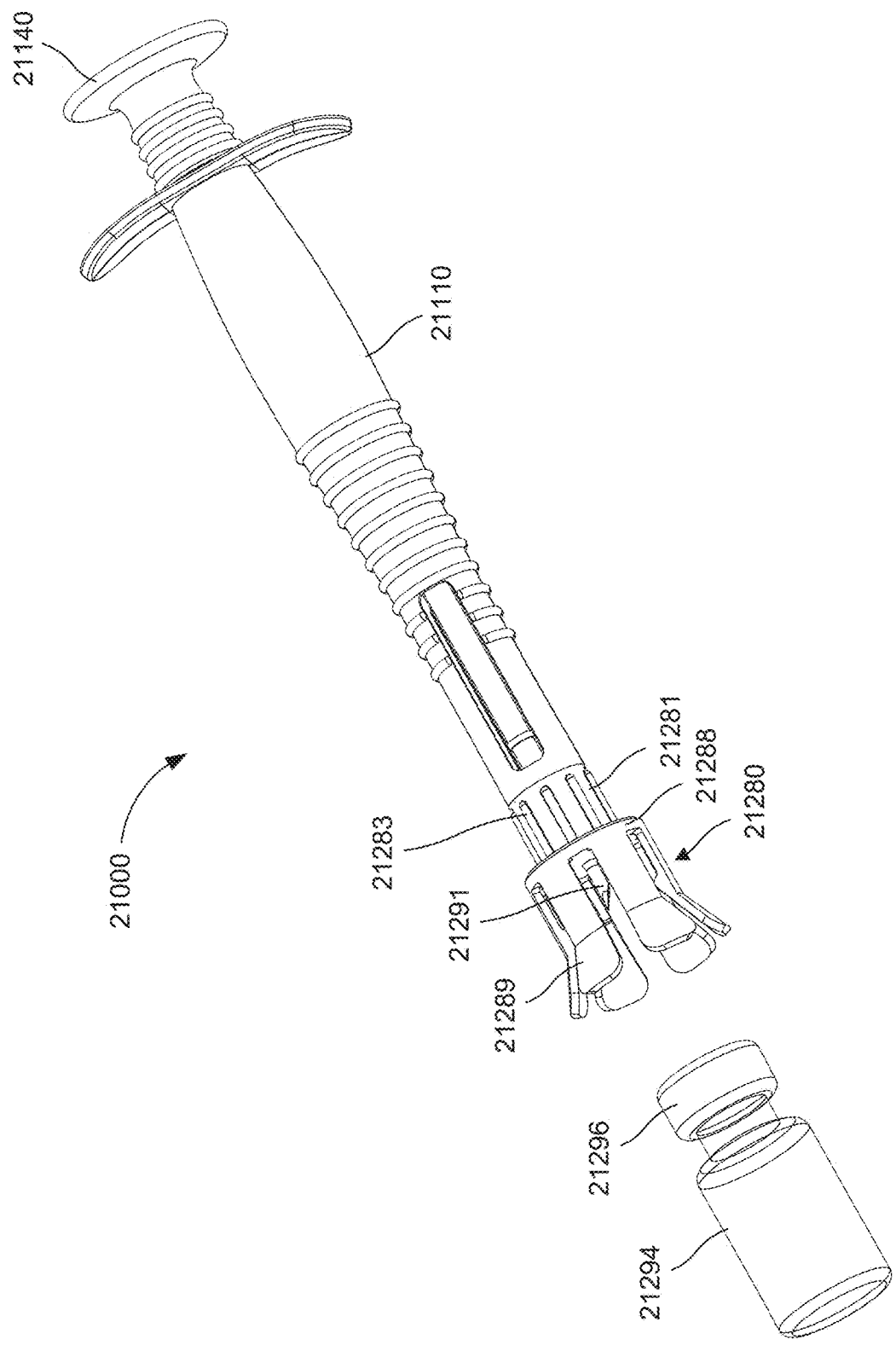
FIG. 77 shows a perspective view of the delivery device of FIG. 75 and a medicament vial, the extraction member configured to be coupled to the vial.
Figure 78:
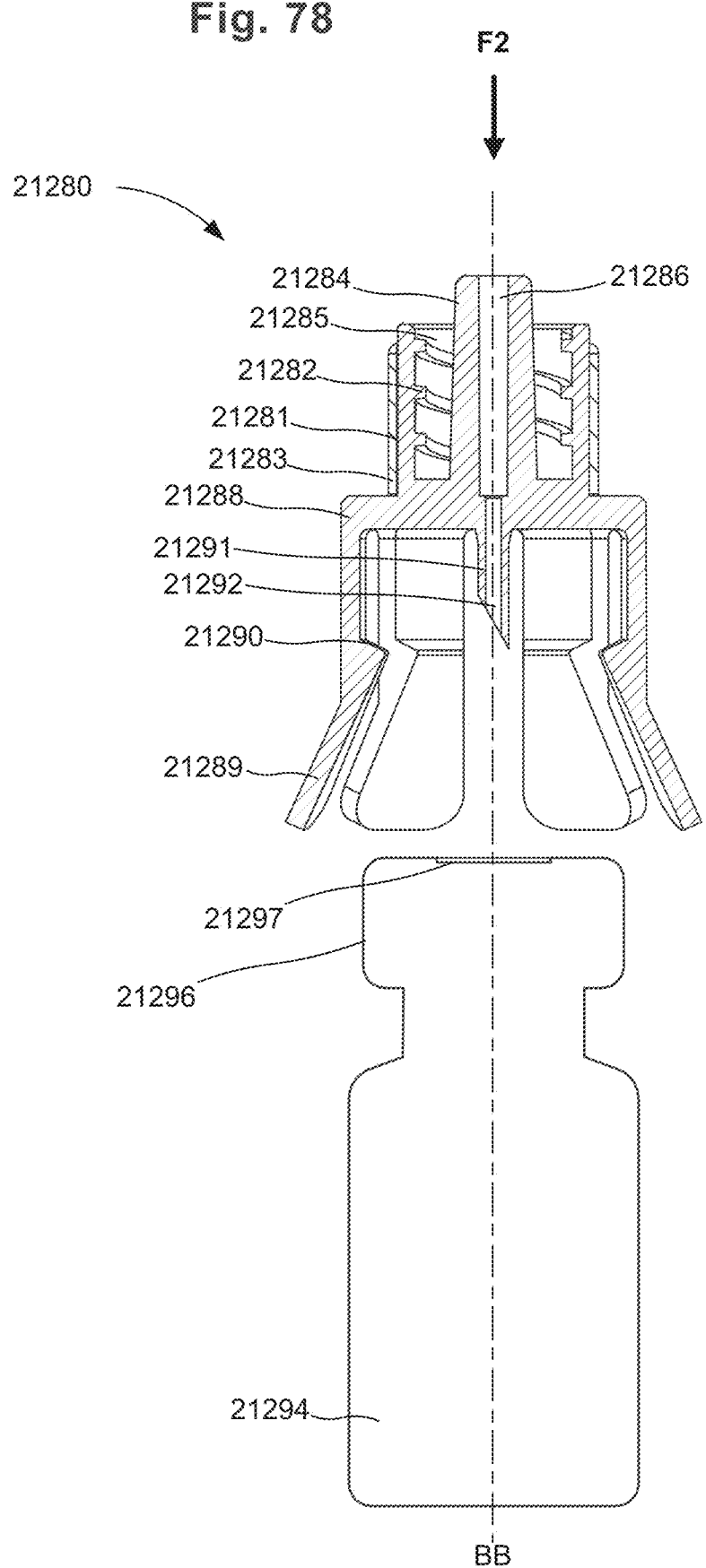
FIG. 78 shows a side cross-section view of the extraction member and vial of FIG. 77 in an uncoupled configuration.
Figure 79:
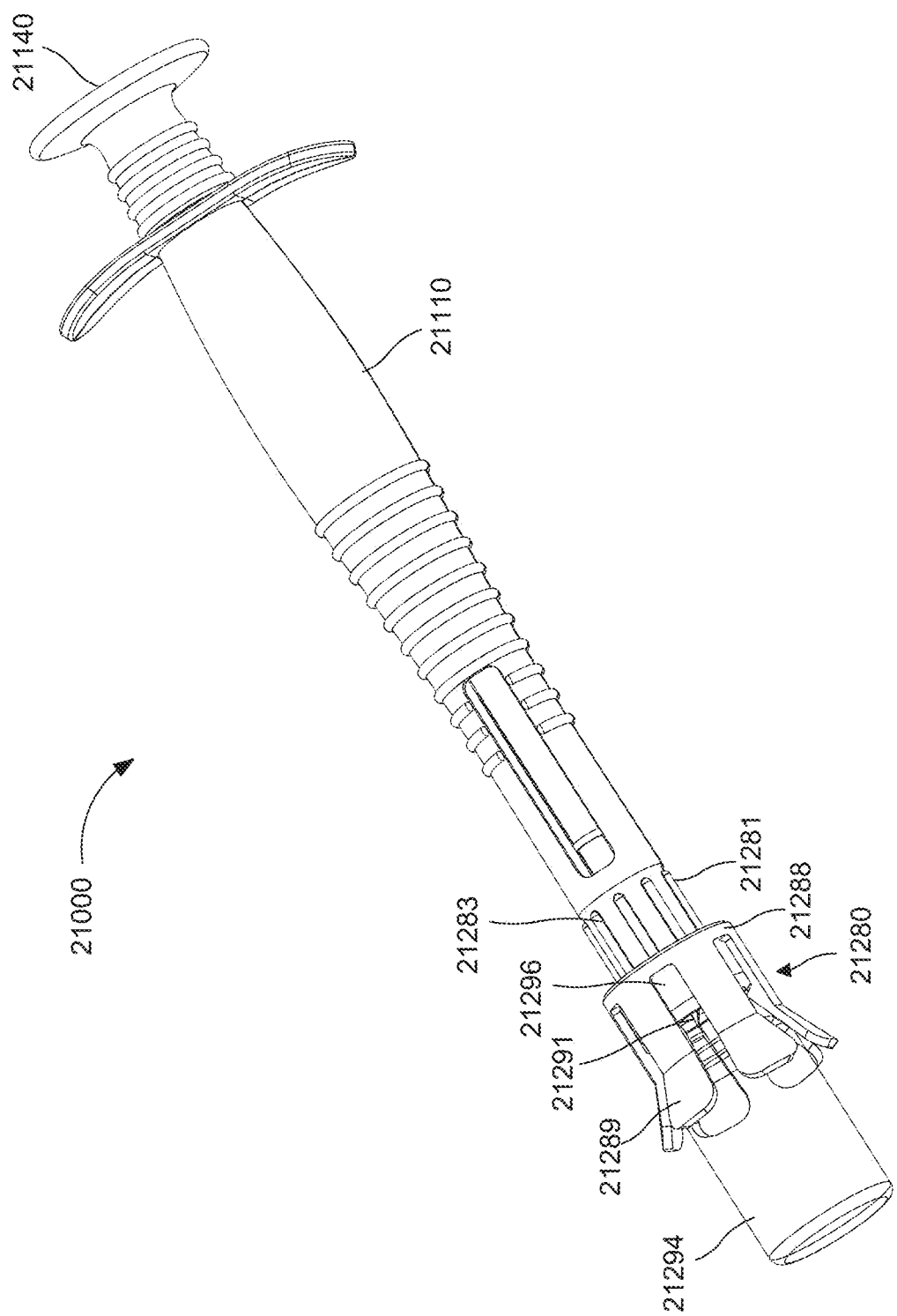
FIG. 79 shows the extraction member of the delivery device of FIG. 77 coupled to the vial.
Figure 80:
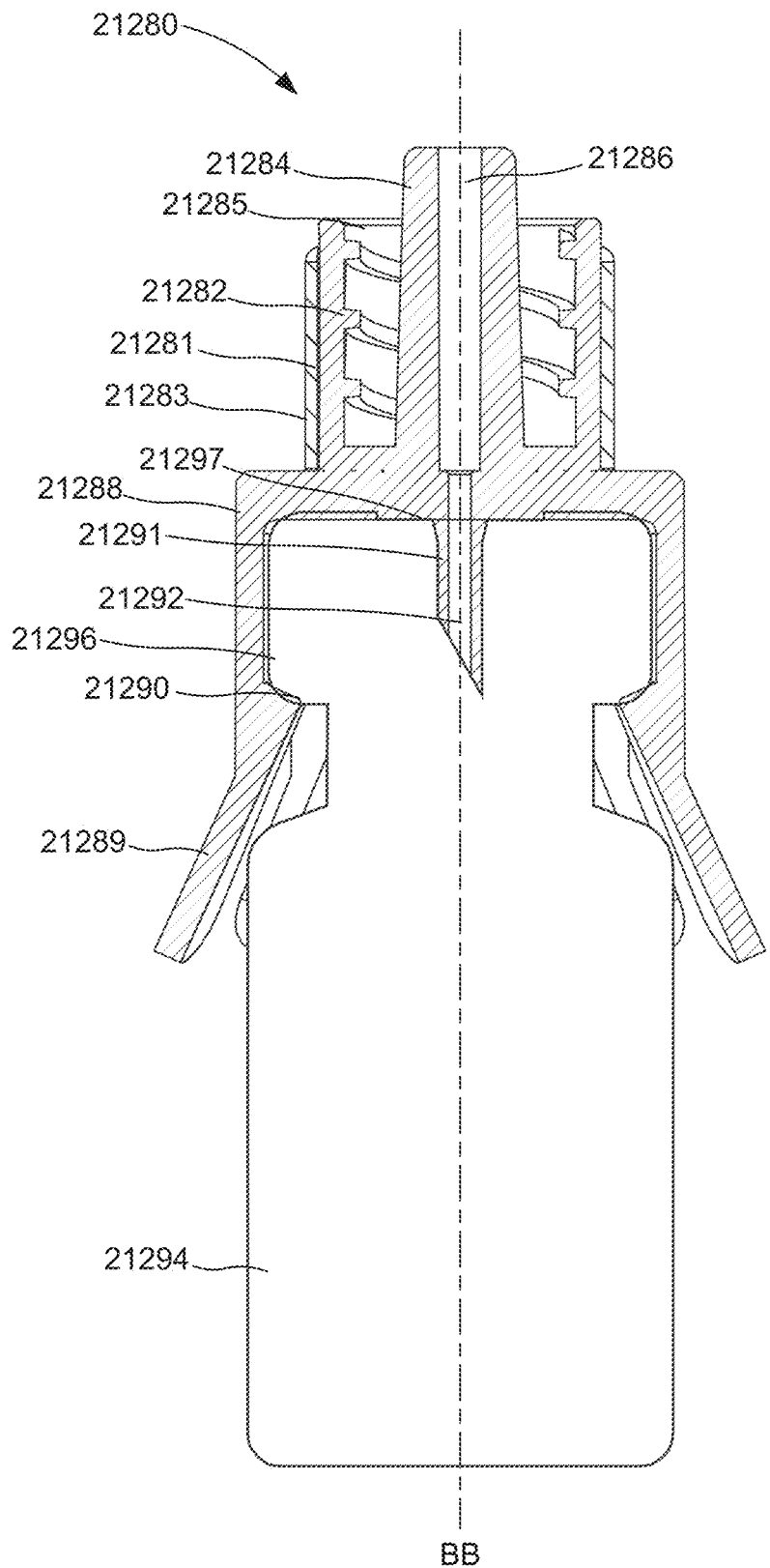
FIG. 80 shows a side cross-section view of the extraction member and vial of FIG. 79 in a coupled configuration.

FIG. 77 shows a perspective view of the system 21000 in a first configuration, such that the container 21294 is uncoupled from the extraction member 21280. The container 21294 includes a cap 21296 that has a seal 21297, for example, a septum (e.g., a rubber septum), and defines an internal volume for housing a liquid medicament. FIG. 78 shows a sectioned view of the perspective view shown in FIG. 77, but only the extraction member 21280 and the container 21294 are shown for clarity. A user can apply a force shown by the arrow $F_2$ (FIG. 78) along a longitudinal axis BB of the system 21000 to urge the extraction member 21280 towards the container 21294. Optionally, a force can also be applied to the container 21294 to urge the container 21294 towards the extraction member 21280. This urges the system 21000 into the second configuration (FIGS. 79-80) such that extraction member 21280 is releasably coupled to the cap 1296 of the container 21294. As shown in the sectioned view of FIG. 80, in the second configuration a surface of the ledge 21290 included in the each of the set of arms 21289 of the extraction member 21280, are contacting a small portion of a bottom surface of the cap 21296 of the container 21294. In this manner, the container 21294 is releasably secured to the extraction member 21280. Furthermore, the puncturing member 21291 punctures the seal 21297 of the cap 21296 included in the container 21294 to establish fluid communication between the container 21294 and the medicament containment chamber 21310 via the extraction member 21280. Medicament can now be extracted from the container 21294 by a user by engaging the actuating member 21240, as described herein with reference to system 19000 (FIGS. 70-71). To uncouple the container 21294 from the extraction member 21280, the user can simple pull the container 21294 away from the extraction member in a direction opposing the direction indicated by arrow F2 (FIG. 78).

Figure 81:
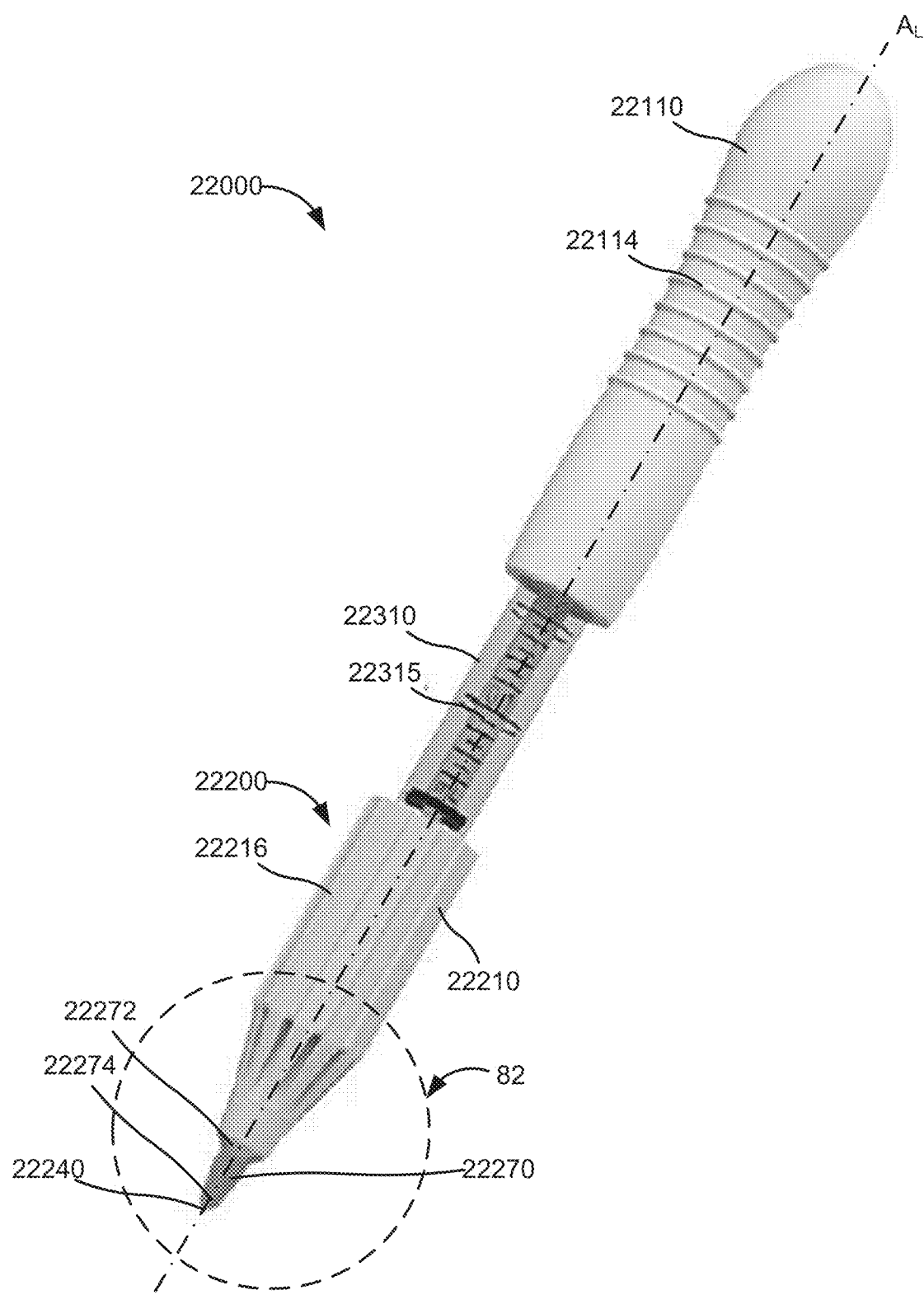
FIG. 81 shows a system for delivering a medicament to an eye, according to an embodiment, in a first configuration.
Figure 82:
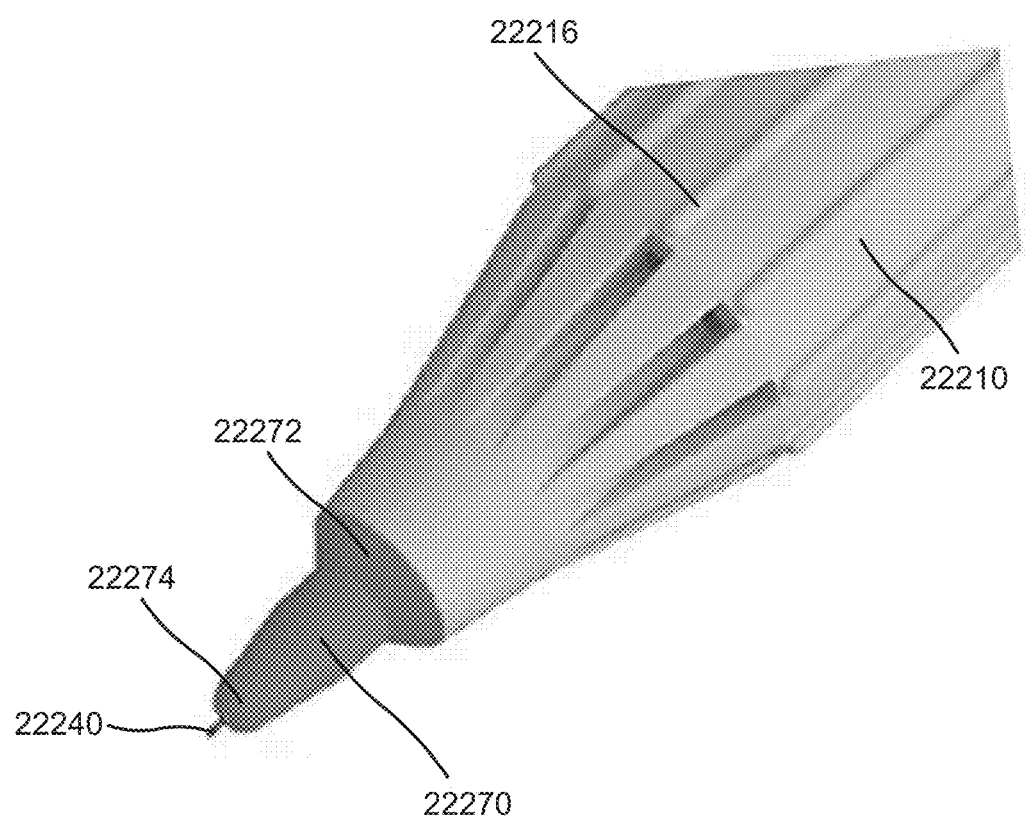
FIG. 82 shows an enlarged view of a portion of the system of FIG. 81 shown by the arrow 82 in FIG. 81.
Figure 83:
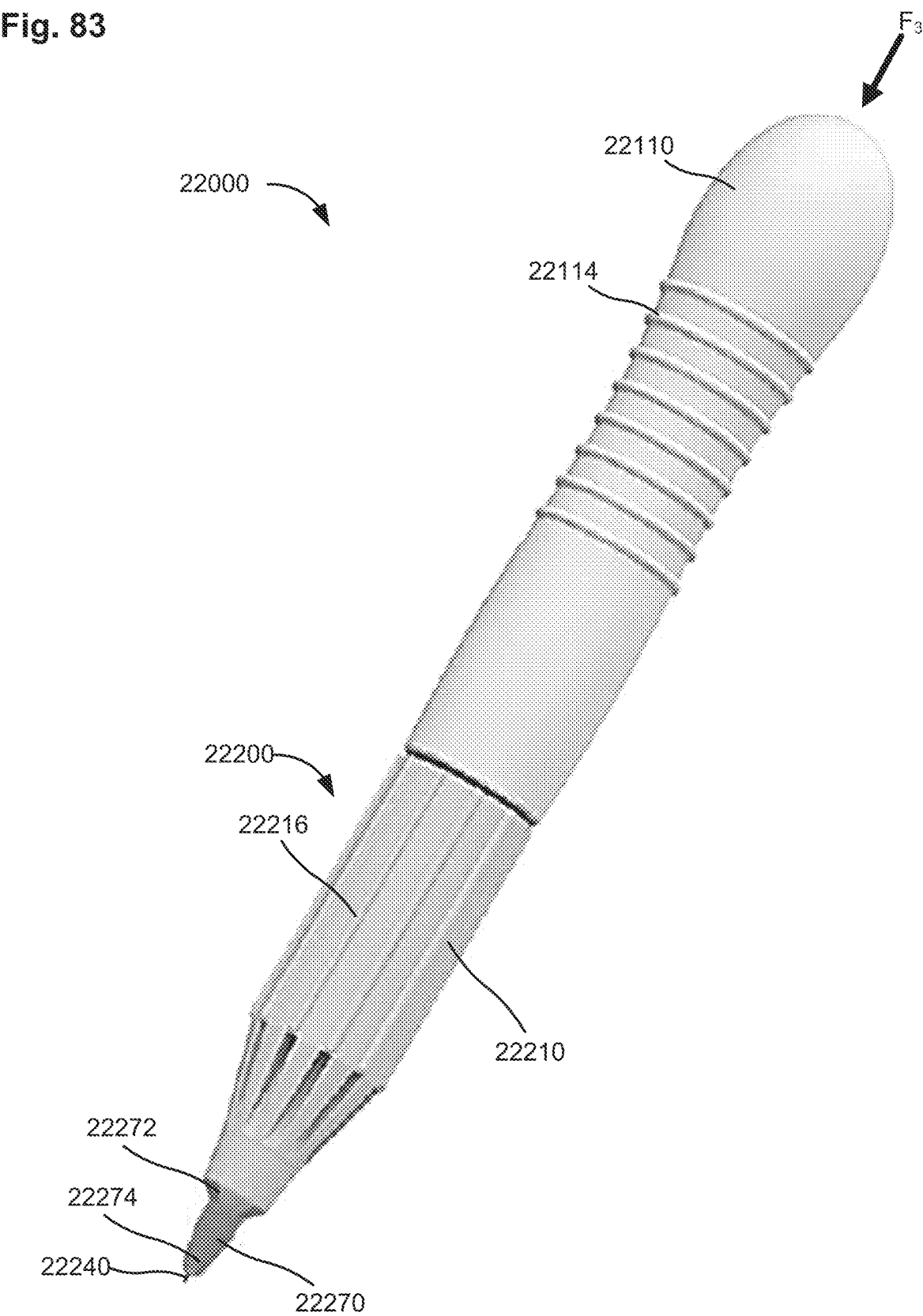
FIG. 83 shows a perspective view of the system of FIG. 81 in a second configuration.

In some embodiments, a system for injection of a medicament into an ocular tissue, for example, the SCS can include a mechanism for insertion of the puncturing member as well as delivering the medicament. Referring now to FIGS. 81-83, a system 22000 includes a housing 22110, a needle assembly 22200 that includes a puncturing member 22240 and a hub 22270, and a medicament containment chamber 22310. At least a portion of an actuator (not shown) can be disposed in the medicament containment chamber 22310. The actuator is configured to communicate a medicament disposed in an internal volume of the medicament containment chamber 22310 into an ocular tissue, for example, the SCS of an eye.

The housing 22110 has an ergonomic shape and includes ridges 22114 to allow a user to easily grip the housing 22110. The housing 22110 can define an internal volume within which at least a portion of the medicament containment chamber 22310 and the actuator can be disposed. In some embodiments, an injector assembly, for example, the injector assembly 2100 or any other injector assembly described herein can be disposed in the housing 22110. The housing 22110 is configured to move laterally along a longitudinal axis $A_L$ of the system 22000, between a first configuration shown in FIG. 81 and a second configuration shown in FIG. 83. In this manner, the housing 22110 can move the actuator and draw in or expel out a medicament from the medicament containment chamber 22310. In some embodiments, the housing 22110 can also be configured to insert the puncturing member 22240 into the ocular tissue.

The medicament containment chamber 22310 defines an internal volume within which a medicament can be disposed. A set of markings 22315 can be defined on an outer surface of the medicament containment chamber 22310. The medicament containment chamber 22310 can be substantially transparent such that the user can visually observe a volume of the medicament disposed in the internal volume and use the markings 22315 to determine the quantity of the remaining medicament. In some embodiments, the medicament containment chamber 22310 can be substantially similar to the medicament containment chamber 1310, 2310, 3310, or any other medicament containment chamber described herein.

The needle assembly 22200 includes a housing 22210 that can define an internal volume configured to house the components of the needle assembly 22200. A plurality of ridges 22216 are disposed on an outer surface of the housing 22210. The ridges 22216 are configured to allow a user to easily grip the housing 22210 (e.g., for rotating the housing 22210). The needle assembly 22200 can be configured to adjust a length of the puncturing member 22240 protruding from a distal end 22274 of the hub 22270. For example, a user can rotate the needle assembly 22200 about the longitudinal axis $A_L$ to adjust a length of the puncturing member 22240 protruding from a distal end 22272 of the hub 22270. In some embodiments, the needle assembly 22200 can include an adjustment member, a lead screw, bushing, bearing, locking pin, markings, or any other components as described with respect to the needle assembly 3200 described herein.

The puncturing member 22240 is configured to be inserted into the eye and to deliver a medicament into the eye. The puncturing member 22240 can be substantially similar to the puncturing member 3240 or any other puncturing member described herein. At least a portion of the puncturing member 22240 is disposed in the hub 22270. For example, a proximal end portion of the puncturing member 22240 can be disposed in a passageway defined by the hub 22270. The hub 22270 includes a proximal end 22272 and a distal end 22274. The distal end 22274 can be curved, for example, define a convex or hemispherical shape. A distal end surface of the distal end 22274 can define a sealing portion configured to contact an outer surface of the eye, for example, the conjunctiva, and form a substantially fluid-tight seal around an insertion site of the puncturing member 22240, as described with respect to the hub 7270. The proximal end 22272 of the hub 22270 can be removably or fixedly coupled to a distal portion of the housing 22210. For example, the proximal end 22272 can include a friction fit, snap fit, threads, grooves, notches, indents, detents, or any other suitable coupling mechanism to couple the hub 22270 to the housing 22210. In some embodiments, the hub 3270, 7270, 8270, 9270, or any other hub described herein can be coupled to the housing 22210.

In a first configuration shown in FIG. 81, the housing 22210 can be disposed distally relative to the needle assembly 22200 and the medicament containment chamber 22310. The medicament can be disposed in the internal volume of the medicament containment chamber 22310. In the second configuration, shown in FIG. 83, a user can dispose the hub 22270 of the system 22000 on an outer layer of the eye (e.g., the conjunctiva C). The user can then exert a force on the housing 22110 in the direction shown by the arrow $F_3$ to move the housing 22110 proximally relative to the needle assembly 22200. This can cause the puncturing member 22240 to be inserted into the ocular tissue, for example, a sclera of the eye, and the medicament to be expelled from the internal volume of the medicament containment chamber 22310. The user can use the needle assembly 22200 to adjust an insertion depth of the puncturing member 22240 to ensure that the medicament is communicated to the target ocular tissue (e.g., the SCS).

Figure 84B:
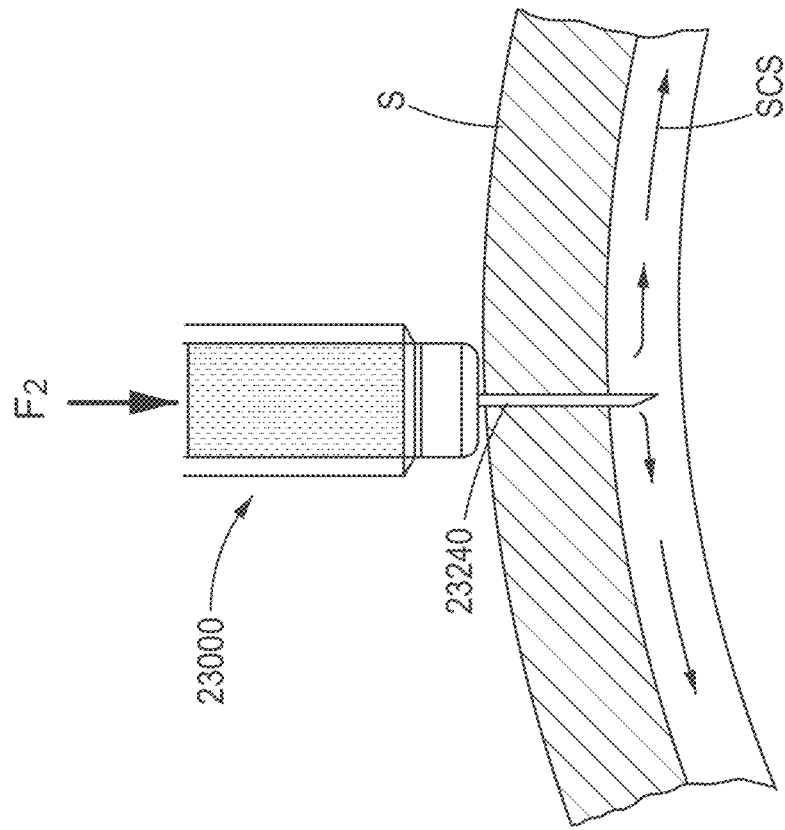
FIGS. 84A-B shows a schematic illustration of a delivery device that includes a mechanism to adjust the length of an insertion depth of a needle included in the delivery device in a first configuration and a second configuration respectively, according to an embodiment.
Figure 84A:
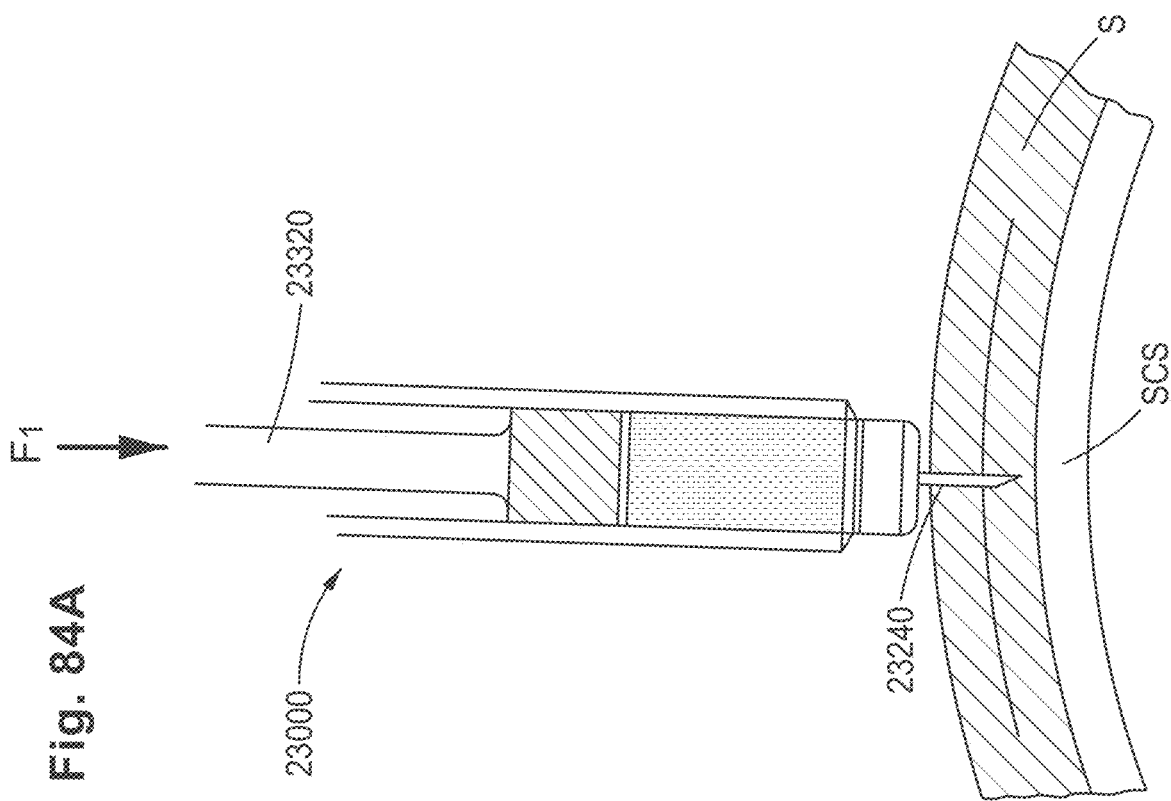

In some embodiments, a needle adjustment mechanism can include adjusting the insertion depth of a needle into a target tissue, for example, ocular tissue, by varying the force on an actuation rod included in a medical injector. For example, FIGS. 84A and 84B show a portion of a medical injector 23000, that includes an actuation rod 23320 and a needle disposed in a target tissue in a first configuration and a second configuration, respectively, according to an embodiment. A distal end portion of the actuation rod 23320 is disposed in a medicament container included in the medical injector. The medical injector can be substantially similar to the medicament container 130, 1310, 2310, 3310, or any other medicament container described herein. The needle 23240 can be any suitable puncture member, for example, a microneedle (e.g., a 27 gauge needle, a 30 gauge needle, or even smaller). The medical injector 23000 also includes a needle adjustment mechanism that can be used to adjust the distance a distal tip of the needle 23240 travels into the target tissue, for example, ocular tissue based on the magnitude of force applied on an proximal portion, for example, an engagement portion of the actuation rod 23320. By way of example, in some embodiments, the needle adjustment assembly can include any suitable mechanism configured to increase the distance that the distal tip of the needle 23240 travels into the target tissue based on the force applied on the actuation rod 23320. The force applied on the actuation rod 23320 can continue to increase the distance travelled by the distal tip of the needle 23240 without delivering the medicament from the distal tip of the needle 23240, until the distal tip of the needle 23240 is disposed within a target region (e.g., the SCS) of the target tissue. The force can then, for example, overcome the backpressure of the target region of the target tissue such that the distal tip of the needle 23240 does not travel any further into the target tissue and the medicament is delivered to the target region. The needle adjustment mechanism can include any suitable components such as, for example, a biasing member (e.g., a spring or a hydraulic biasing member), one or more valves, and, or a force sensing mechanism. In some embodiments, the force applied on the actuation rod 23320 can be adjusted manually, for example, via haptic feedback to a user engaging the actuation rod 23320. In some embodiments, an automated force adjustment mechanism, for example, included in the needle adjustment mechanism or an injection assembly (e.g., the injection assembly 100, 2100, or any other injection assembly described herein) can be used to adjust the force and thereby, control the insertion depth of the distal tip of the needle 23240.

For example, the distal tip of the needle 23240 can be inserted into an ocular tissue and configured to deliver a medicament to the SCS of the ocular tissue. In the first configuration shown in FIG. 84A, a first force $F_1$ is applied on the actuation rod 23320. The first force $F_1$ (e.g., less than about 2N) can be sufficient to overcome the backpressure of the conjunctiva (not shown) and get inserted into the sclera S, but insufficient to urge the distal tip of the needle 23240 to travel across the thickness of the sclera S and be disposed in the SCS. The user can then apply a second force $F_2$ greater than the first force $F_1$ and sufficient to overcome a backpressure and/or density of the sclera S such that the distal tip of the needle 23240 travels through the sclera S and is disposed within or near the SCS. In some embodiments, the second $F_2$ can be between about 2 N and about 6 N, for example, about 3 N, about 4 N, about 5 N, or any other range or value therebetween. The user can maintain the force $F_2$ such that once the distal tip of the needle 23240 reaches the SCS, the force $F_2$ can overcome the backpressure of the SCS and thereby, deliver the medicament to the SCS. In some embodiments, the transition from the first force $F_1$ to the second force $F_2$ can be gradual. For example, the force applied on the actuator can be increased slowly from the force $F_1$ until the force has a sufficient magnitude (e.g., substantially equal to the second force $F_2$) to urge the distal tip of the needle 23240 to travel through the sclera S and be disposed in the SCS.

Figure 85A:
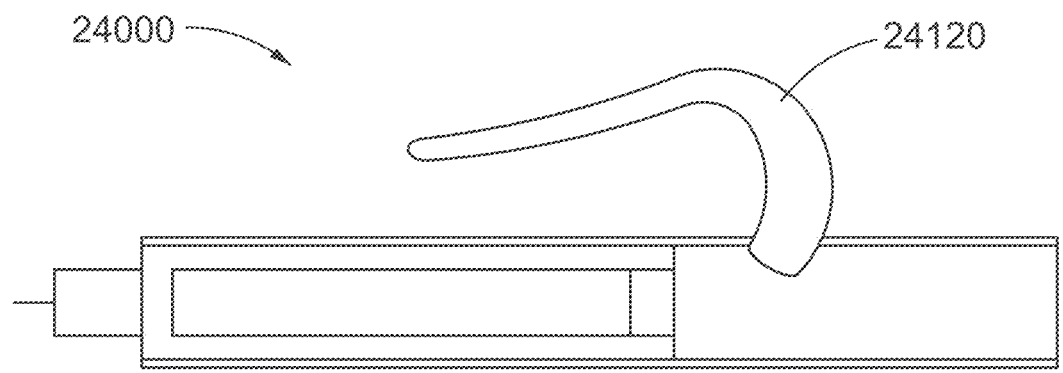
FIGS. 85A-B shows a schematic illustration of a delivery device that includes an injection assist assembly in a first configuration and a second configuration respectively, according to an embodiment.
Figure 85B:
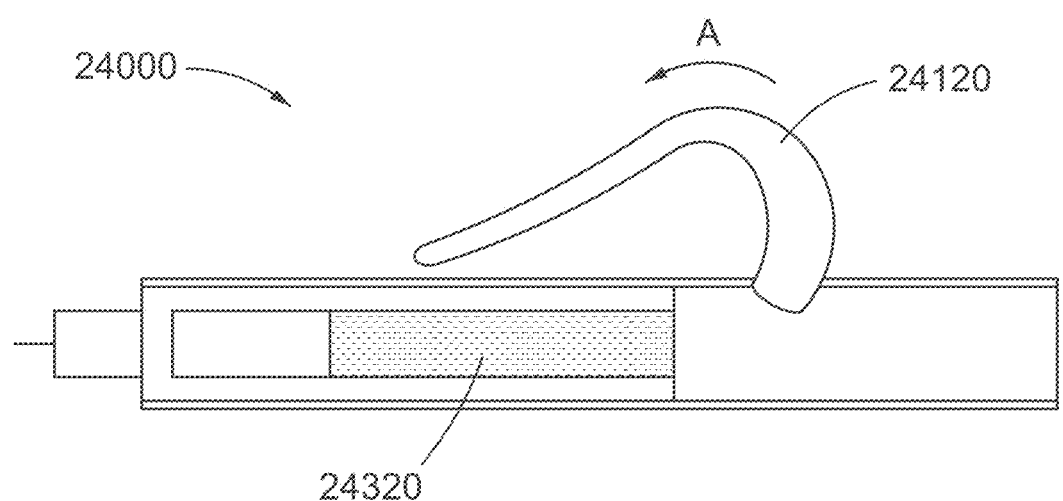

In some embodiments, a medical injector can include an injection assembly that includes an actuation member configured to actuate an actuation rod included in the medical injector. For example, FIGS. 85A and 85B show a medical injector 24000 that includes medicament container, a needle, and an injection assembly, in a first and a second configuration respectively, according to an embodiment. The injection assembly includes an actuation member 24120 and an actuation rod 24320. The injection assembly can include other components such as, for example, an energy storage member (e.g., a spring, a compressed gas cylinder, or a propellant container), a release member (e.g., a lock, latch, a pawl), a guide rod, or any other components described with respect to the injection assembly 100, 2100, or any other injection assembly described herein. In some embodiments, the actuation member 24120 can be configured to engage and/or secure a proximal end portion of the actuation rod 24320. In some embodiments, the actuation member 24120 can be configured to engage a release member that is configured to engage or otherwise secure a proximal end portion of the actuation rod 24120. The actuation member 24120 can be engaged by a user such that the actuation member 24120 releases the actuation rod 24320 or urges the release member to release the actuation rod 24320. This can enable a distal end portion of the actuation rod 24320 to move within the medicament container, as shown in FIG. 85B.

For example, as shown in FIG. 84A-B, the actuation member 24120 includes a lever like member that can be disposed on a sidewall of a housing coupled to the medicament container. In the first configuration shown in FIG. 84A, the actuation member can be a in a first position in which a distal end of the actuation member 24120 is distally disposed from the medicament container. In the first configuration, a proximal end portion of the actuation member 24120 can be engaged by the actuation member 24120 or the release member and prevent a distal end portion of the actuation rod 24320 from moving within the medicament container. Furthermore, an energy storage member or a biasing member can be coupled to the proximal end portion of the actuation rod 24320. In the second configuration shown in FIG. 84B, a user can engage the actuation member 24120, for example, move a distal end of the actuation member 24120 proximally relative to the medicament containment chamber in a direction shown by the arrow A. This can urge the actuation member to release the proximal end portion of the actuation rod 24320. In some embodiments, the engaging of the actuation member 24120 can engage a release member engaging or otherwise securing the proximal end portion of the actuation rod 2320 such that the release member releases the proximal end portion of the actuation rod 24320. The energy storage member or biasing member coupled to the proximal end portion of the actuation rod 24320 can then urge the distal end portion of the actuation rod 24320 to move within the medicament container and thereby, deliver medicament to a target tissue via the needle.

Figure 86:
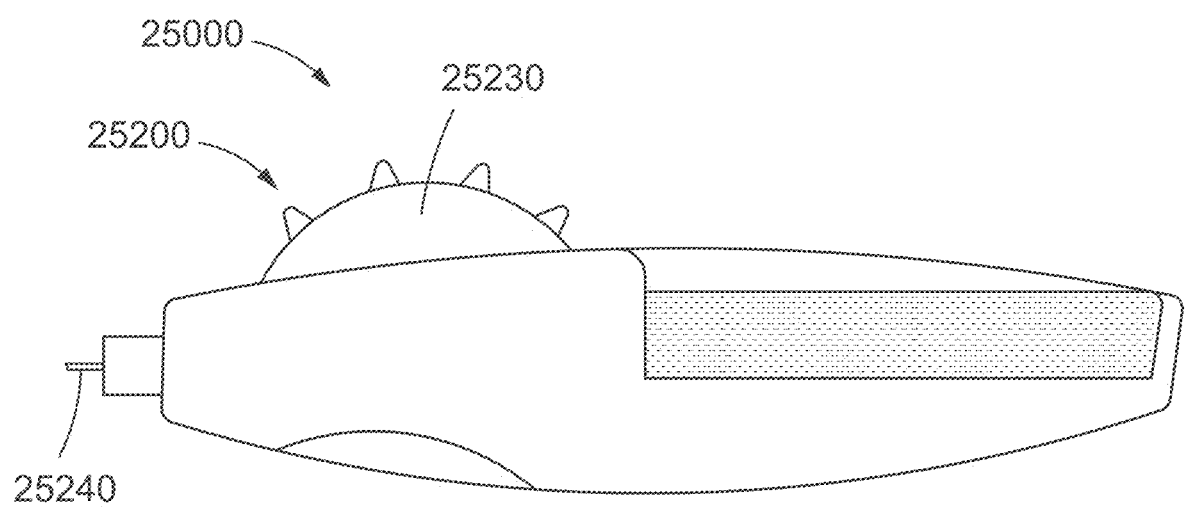
FIG. 86 shows a schematic illustration of a delivery device that includes an adjustment member, according to an embodiment.

In some embodiments, a medical injector can include a needle adjustment mechanism that includes a wheel. For example, FIG. 86 shows a medical injector 25000 that can include a medicament container, a needle assembly 25200, and a needle 25240. The needle adjustment mechanism 25200 includes a wheel 25230. The wheel 25230 is pivotally mounted in a housing of the medical injector 25000. The wheel 25230 can include a plurality of protrusions defined thereon, which can be engaged by a user to move or otherwise rotate the wheel 25230. The wheel 25230 can be configured to be rotated in discrete angular displacements, such that each discrete angular displacement corresponds to a discrete adjustment of the length of a portion of the needle 25240 emerging from a distal end of a housing, or a hub coupled to the housing. In some embodiments, each discrete angular displacement can correspond to a length adjustment of about 100 microns of the needle 25240. In this manner, the wheel 25230 can allow for digital adjustment of the length of the needle 25240. For example, a user can insert a distal tip of the needle a first distance (e.g. corresponding to the depth of the sclera) of a target tissue (e.g., ocular tissue). The user can then engage the wheel 25230 by rotating the wheel 25230 about its pivot mount in discrete increments as described herein. This can adjust the length of the needle 25240 such that a distal tip of the needle 25240 travels a second distance into the target tissue (e.g., corresponding to the depth of the SCS) such that the distal tip of the needle 25240 is disposed within or near a target region (e.g., the SCS) of the target tissue. The medical injector 25000 can deliver at least a portion of the medicament disposed within the medicament container into the target tissue (e.g., the SCS). For example, an injection assembly (e.g., the injection assembly 100, 2100, or any other injection assembly described herein) included in the medical injector 25000 can be configured to initiate delivery of the medicament into the target region (e.g., the SCS), thereby informing the user that the distal tip of the needle 25240 is disposed in the target region. In some embodiments, the wheel 25230 can also be configured to move a distal end of an actuation rod disposed within the medicament container, for example, to deliver the medicament to the target tissue via the needle 25240.

Figure 87:
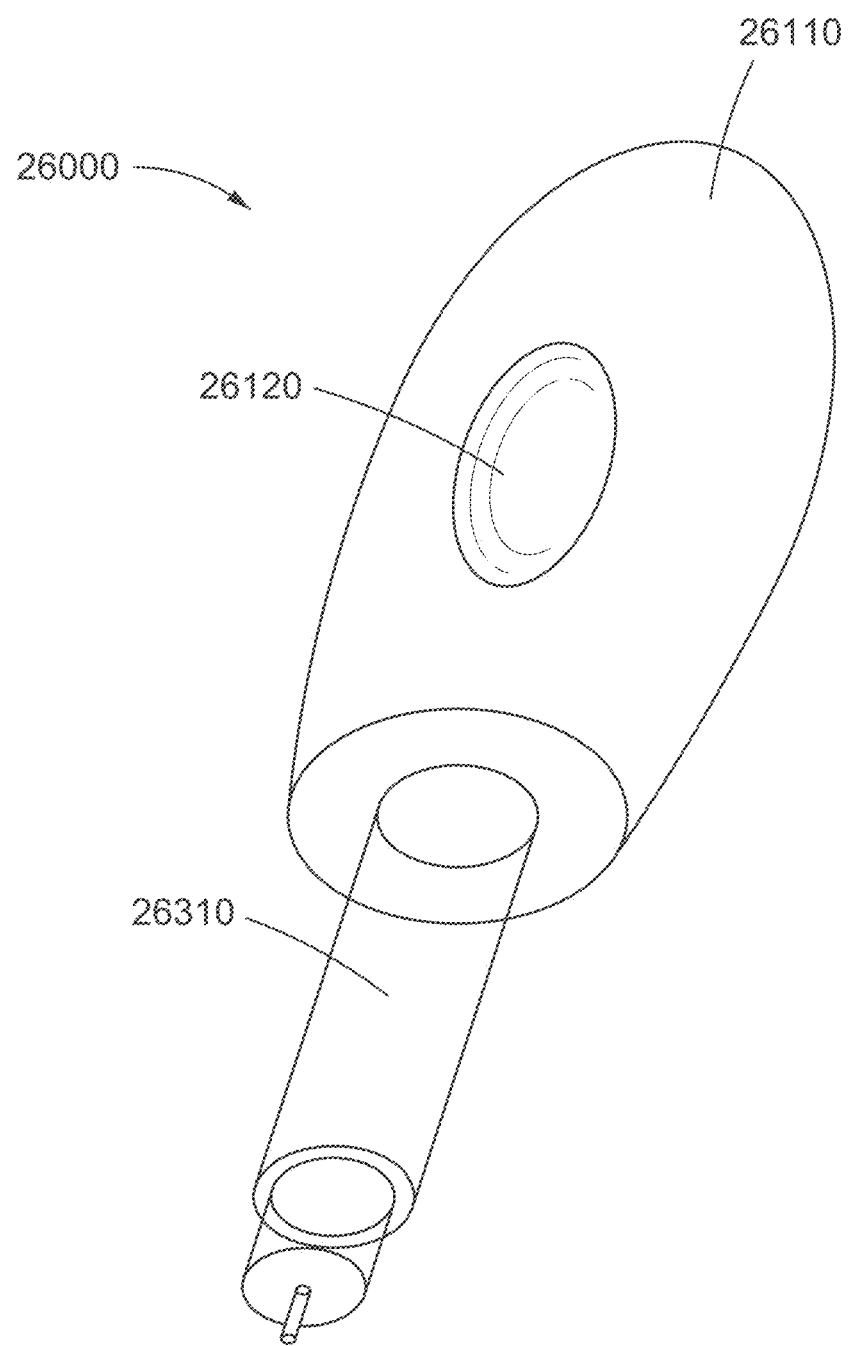
FIG. 87 shows a schematic illustration of a delivery device that includes an injection assembly, according to an embodiment.

In some embodiments, a medical injector can include a pressure assist assembly configured to exert a pressure on a proximal end portion of an actuation rod and assist, facilitate and/or affect the delivery of a medicament from a medicament container. For example, FIG. 87 shows a portion of a medical injector 26000 that includes a housing 26110, a pressure assist assembly that includes an actuation member 26120, and a medicament container 26310 coupled to the housing 26110. A needle is also coupled to the medicament container 26310 and in fluidic communication with a medicament disposed within the medicament container 26310. As shown, in some embodiments, the actuation member 26120 can be a button disposed within a sidewall of the housing 26110. The pressure assist assembly can also include other components such as, for example, one or more energy storage members (e.g., a spring, a compressed gas container, or a propellant container). The energy storage member can be coupled to a proximal end portion of an actuation rod included in the medical injector 26000. A distal end portion of the actuation rod can be disposed within the medicament container 26310 and configured to move within the medicament container 26310. In some embodiments, the pressure assist assembly can also include a release member configured to engage or otherwise secure the proximal end portion of the actuation rod in a first configuration in which the medicament container is filled with a volume of the medicament. In such embodiments, the actuation member 26120 can be configured to engage the release member and urge the release member to release the proximal end portion of the actuation rod. For example, in a second configuration, the actuation member 26120 can be engaged (e.g., depressed) by a user thereby urging the release member to release the proximal end portion of the actuation rod. The energy storage member can now exert a force on the proximal end portion of the actuation rod configured to move a distal end portion of the actuation rod within the medicament container 26310. This applies a pressure on the medicament disposed within the medicament container 26310 and dispels the medicament through a distal end of the needle.

Figure 88:
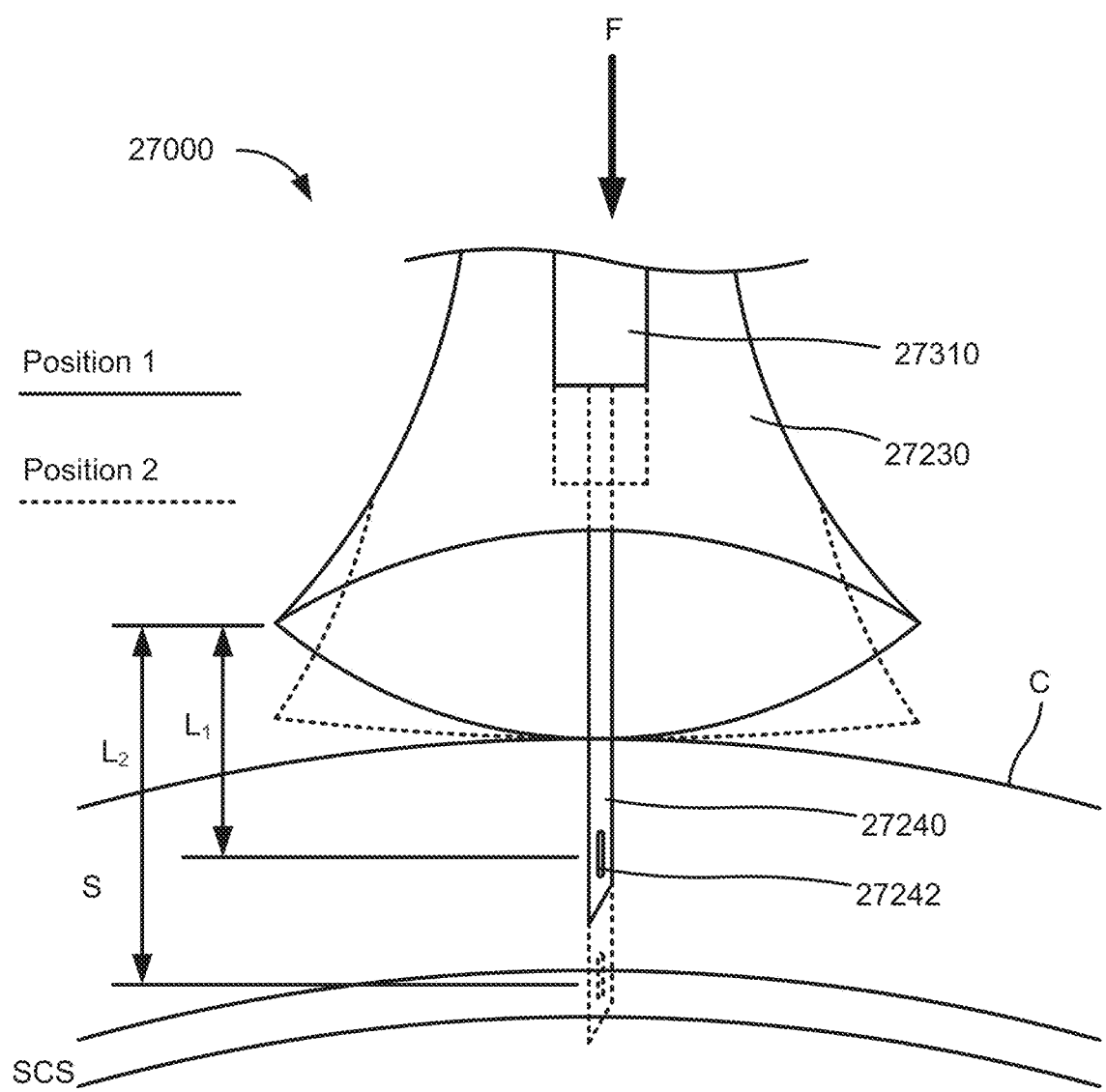
FIG. 88 shows a schematic illustration of a portion of a delivery device that includes an adjustment member, according to an embodiment.

In some embodiments, a medical injector can include a needle adjustment mechanism that includes a leaf spring. For example, FIG. 88 shows a portion of a medical injector 27000 that includes a medicament container 27310, a leaf spring 27230, and a needle 27240 in a first position (solid lines) and a second configuration (dotted lines). The leaf spring 27230 can be coupled to the medicament container 27310 or a hub coupled to the medicament container 27310, and configured to move from a first position to a second position in response to a force applied in a direction shown by the arrow F. The movement of the leaf spring 27230 is configured to allow a distal tip of the needle 27240 to be disposed within a target region. More force can be required to move the leaf spring 27230 more and move the distal tip of the needle deeper into the target tissue (e.g., an ocular tissue). For example, as shown in FIG. 88, in the first configuration a distal end surface of the leaf spring 27230 can be in contact with the outer surface of the conjunctiva C of an eye. Furthermore, a limbus 27242 defined on a distal end of the needle 27240 can be disposed a first distance $L_1$ into the eye as measured form a distal end of the leaf spring 27230 such that the limbus 27242 is disposed in the sclera S of the eye. A force F can be applied to move or otherwise compress the leaf spring 27230 and move the limbus 27242 deeper into the eye. For example, a magnitude of the force F can be increased until the leaf spring 27230 moves into the second configuration. This also urges the distal end of the needle 27240 to move deeper into the eye, until in the second configuration, the limbus 27242 is disposed a second distance $L_2$ into the eye as measured from the distal end of the leaf spring 27230. The second distance $L_2$ can correspond to a depth of the suprachoroidal space within the eye, such that the limbus 27242 is disposed within or near the suprachoroidal space SCS (e.g., the target region) in the second configuration. In this manner, the leaf spring 27230 can be used to adjust a length of the needle 27240 thereby, facilitating delivery of a medicament to the target region of a target tissue. In some embodiments, the movement of the leaf spring 27230 from the first position to the second position can be configured to move the needle a predetermined distance corresponding to the depth of a target region of a target tissue (e.g., the SCS).

Figure 89A:
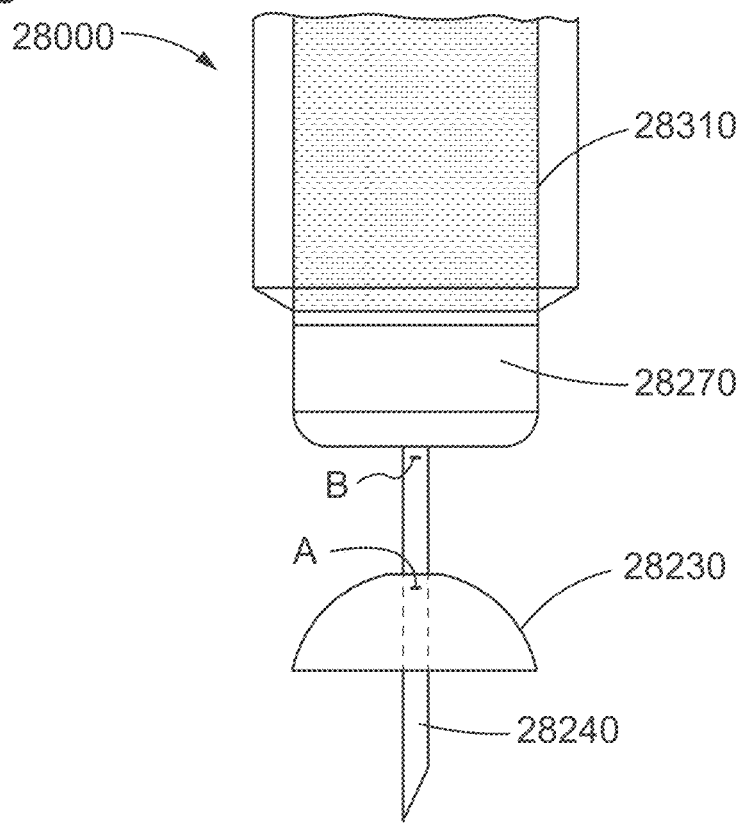
FIGS. 89A-B show schematic illustrations of a portion of a delivery device that includes an adjustment member in a first configuration and a second configuration respectively, according to an embodiment.
Figure 89B:
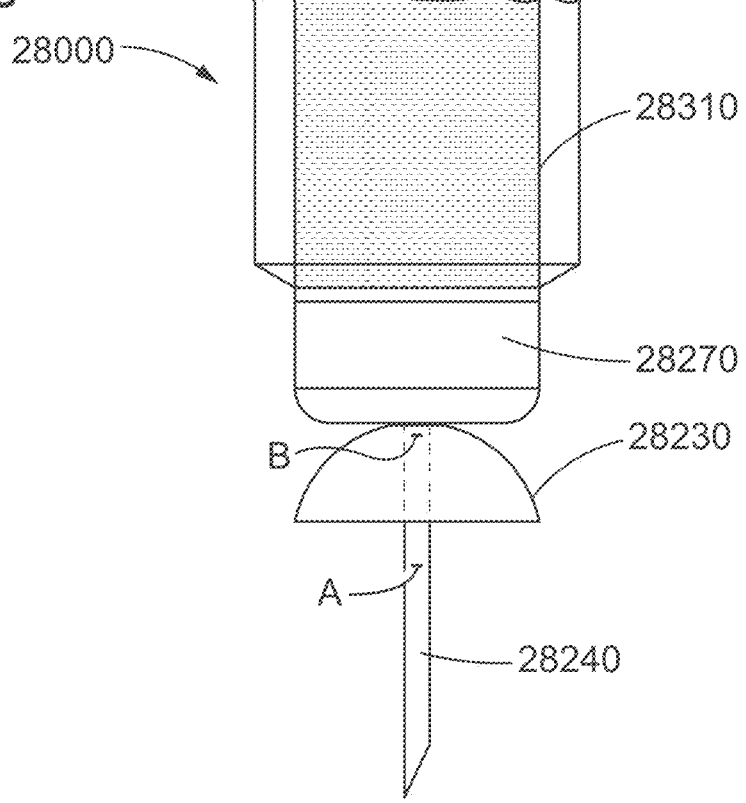

In some embodiments, a needle adjustment mechanism can include an adjustment member movable between a first position and a second position to adjust a distance a distal tip of a needle travels within a target tissue. For example, FIGS. 89A and 89B show a portion of a medical injector 28000 that includes a medicament container 28310, a hub 28270, an adjustment member 28230 and a needle 28240 in a first configuration and a second configuration, respectively. The medicament container 28310 can be substantially similar to the medicament container 130, 1310, 2310, 3310, or any other medicament container described herein. The proximal end portion of the hub 28270 can be coupled to the medicament container 28310 and a distal end portion of the hub 28270 can be coupled to a proximal end of the needle 28240 such that a medicament contained within the medicament container 28310 is in fluid communication with the needle 28240. The hub 28270 can be substantially similar to the hub 7270, 8270, 9270, or any other hub described herein. The adjustment member 28230 can be slidably disposed about the needle 28240 and be configured to be movable between a first position A and a second position B. As shown, the adjustment member 28230 defines a curved surface, which can be configured to conform the curved surface of a target tissue, for example, an eye. The movement of the adjustment member 28230 can be used to adjust a distance that a distal tip of the needle 28240 can be inserted into the target tissue, for example, ocular tissue.

For example, in the first configuration shown in FIG. 89A, the adjustment member 28230 can be disposed at the first position A and a distal tip of the needle 28240 can be inserted a first distance into a target tissue (e.g., within the sclera of an eye). Furthermore, the curved surface of the adjustment member 28230 can be in contact with and conformal to an outer surface of the target tissue (e.g., the conjunctiva of the eye). A force can be applied on the medical injector 28000, for example, on a proximal end portion of the medicament container 28310, or a proximal end portion of an actuation rod included in the medical injector 28000. This can urge the adjustment member 28230 to slide and move about the needle 28240 proximally relative to the medicament container 28310. The force can be maintained until the adjustment member 28230 moves to position B. This increases the distance the distal tip of the needle 28240 travels within the target tissue (e.g., ocular tissue), for example, until the distal tip of the needle 28240 is disposed within or near a target region (e.g., the SCS) of the target tissue. In this manner, the medicament disposed within the medicament container 28310 can be delivered to the target region (e.g., the SCS) of the target tissue.

In some embodiments, a needle adjustment assembly can include an adjustment member configured to adjust the length of a needle in discrete increments. For example, FIGS. 90A-C show a medical injector 29000 that includes a medicament container 29310, a needle adjustment assembly 29200, and a needle 29240 fluidically coupled to the medicament container 29310, in a first, second, and third configuration, according to an embodiment. The medicament container 29310 can be substantially similar to the medicament container 130, 1310, 2310, 3310, or any other medicament container described herein. The needle 29240 can include any suitable puncture member, for example, a microneedle, or any other needle described herein. The needle adjustment mechanism 29200 includes an adjustment member 29230 configured to be engaged by a user to adjust a length of the needle 29240, for example, to a control a distance a distal tip of the needle 29240 travels into a target tissue. By way of example, the adjustment member 29230 can be configured to move in discrete increments, for example, increments of 100 microns such that the length of the needle 29240 can be digitally adjusted. For example, as shown in the first configuration of FIG. 90A, the needle can have a first length $L_1$ (e.g., about 750 microns) measured from a distal tip of the needle to a distal end of the medicament container 29310, or a hub (e.g., any of the hubs described herein) coupled to the distal end of the medicament container 29310. The length $L_1$ can be sufficient to insert the distal tip of the needle 29240 in a target tissue such that the distal tip is disposed short of a target region (e.g., the SCS) of the target tissue (e.g., ocular tissue). The adjustment member 29230 can be engaged, for example, depressed into the medicament chamber by a first increment by applying a force F on the adjustment member 29230. This can increase the length of the needle 29240 to a second length $L_2$ (e.g., about 850 microns), as shown in FIG. 90B measured from the distal tip of the needle 29240 to the distal end of the medicament container 29310, or a hub (e.g., any of the hubs described herein) coupled to the distal end of the medicament container 29310. The second length $L_2$ can be sufficient to insert the distal tip of the needle 29240 deeper into the target tissue but still insufficient to dispose the distal tip of the needle 29240 into the target tissue. The adjustment member 29230 can be engaged a second time applying the force F again on the adjustment member 29230. This can further increase the length of the needle 29240 to a third length $L_3$ (e.g., about 950 microns) measured from the distal tip of the needle 29240 to the distal end of the medicament container 29310, as shown in FIG. 90C. The third length $L_3$ can be sufficient to insert the distal tip of the needle 29240 deeper into the target tissue such that the distal tip of the needle 29240 is disposed within the target region (e.g., the SCS) of the target tissue. Thus, delivery of the medicament contained within the medicament container 29310 can be initiated to the target region (e.g., the SCS) of the target tissue, for example, via an injection assembly included in the medical injector 29000.

Figure 91:
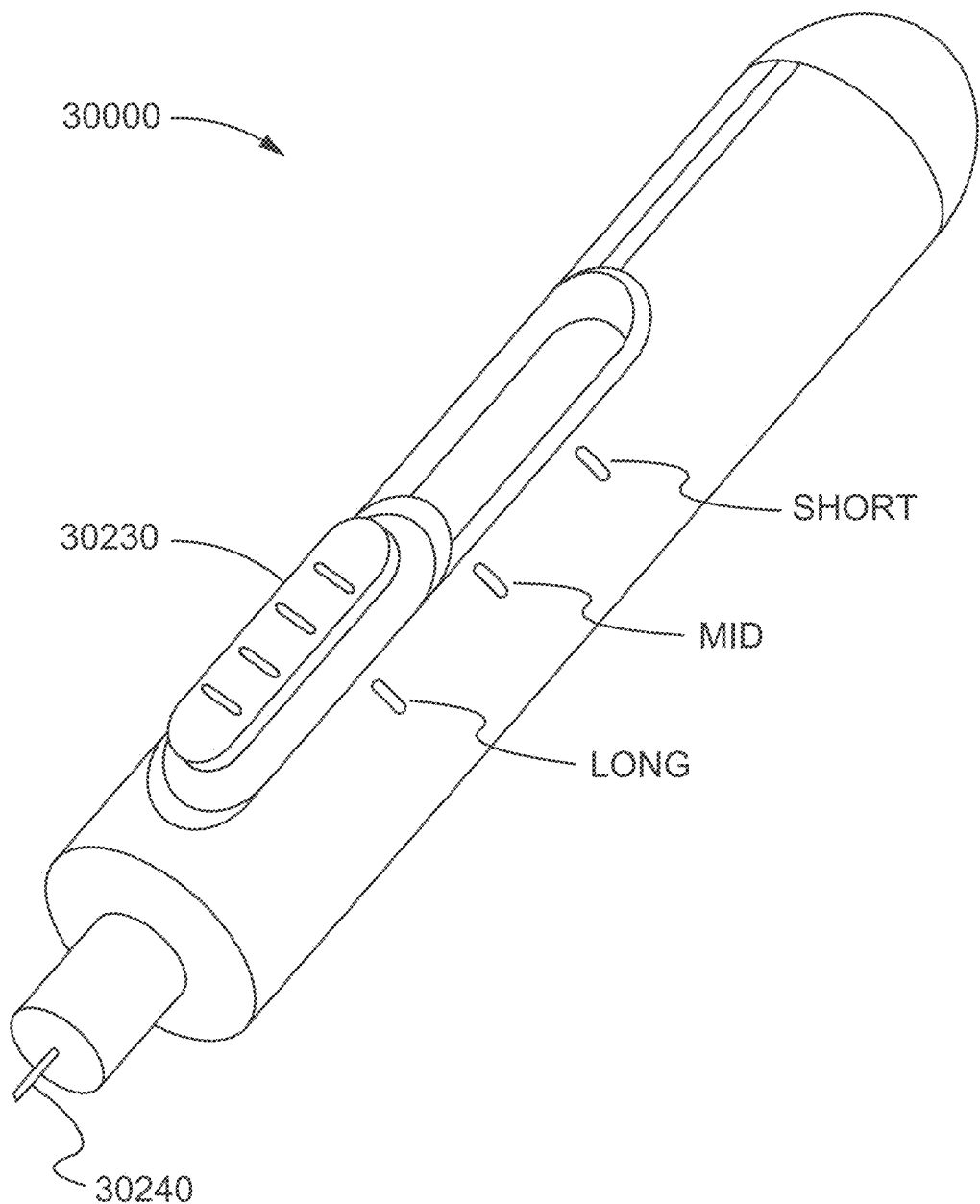
FIG. 91 shows a schematic illustration of a delivery device that includes a needle assembly and an adjustment member, according to an embodiment.

In some embodiments, a medical injector can include a needle adjustment mechanism configured to allow adjustment of a length of a needle included in the medical injector in a small set of qualitative increments. For example, FIG. 91 shows a medical injector 30000 that includes a needle adjustment mechanism including an adjustment member 30230, and a needle 30240 fluidically coupled to a medicament container. The adjustment member 30230 is slidably disposed within a sidewall of a housing of the medical injector 30000. The adjustment member 30230 can be configured to be moved between three discrete positions corresponding to a short length, an intermediate (mid) length, and a long length of the needle emerging from a distal end of the medical injector 30000. The needle adjustment mechanism can include other components such as, for example, notches, grooves, indents, detents, a lock ball, a biasing member, or any other component configured to allow the adjustment member 30230 to be moved in the discrete increments as described herein.

In some embodiments, a medical injector can include a hub configured to allow adjustment of a length of a needle inserted into a target tissue. For example, FIGS. 92A and 92B show a portion of a medical injector 31000 that includes a housing 31110, a hub 31270, and a needle 31240, according to an embodiment. The needle 31240 is fixedly coupled to a distal end of the housing 31110, for example, fluidically coupled with a medicament container disposed within the housing 31110. The hub 31270 is coupled to a distal end portion of the housing 31110 such that the distal end portion can move within a passageway defined by the hub 31270. Furthermore, the distal end portion of the hub 31270 can define a curved surface configured to conform to a curved surface of a target tissue, for example, an eye. The housing 31110 includes a first ridge 31114*a* and a second ridge 31114*b* configured to be matingly disposed within a groove 31272 defined on an inner surface of the hub 31270. While shown as including two ridges, the housing 31110 can include any number of ridges disposed thereon for example, 3, 4, 5, or even more. Furthermore, the hub 31270 can be formed from a flexible material, for example, rubber, plastics, polymers, or any other flexible material described herein. This can enable the ridges 31114 from sliding out of the groove 31272 into the channel defined by the hub 31270 by application of a force on the housing 31110. In this manner, either the first groove 31114*a* or the second groove 31114*b* can be mated with the groove 31272 to adjust the length of the needle 31240.

For example, as shown in FIG. 92B, in a first configuration the hub 31270 can be disposed on a conjunctiva of an eye, such that the curved surface of the distal end portion of the hub 31270 conformally contacts the curved conjunctiva. In the first configuration, the first ridge 31114*a* can be disposed in the groove 31272 such that a distal tip of the needle 31240 is not inserted into the eye. A force can be exerted on the housing 31110 to displace the housing 31110 within the channel defined by the hub 31270 while maintaining the curved surface of the hub 31270 in contact with the conjunctiva. This can urge the medical injector 31000 into a second configuration in which the second ridge 31114*b* is disposed within the groove 31272. The moving of the housing 31110 can also urge the needle 31240 to move within the channel defined by the hub 31270 until a distal tip of the needle 31240 pierces the eye. The distal tip of the needle 31240 can continue travelling into the eye tissue until the second ridge 31114*b* is disposed in the groove 31272. In some embodiments, the distal tip of the needle 31240 can be disposed within a target region, for example, the SCS in the second configuration. In some embodiments, the distal tip of the needle 31240 can be disposed near but not within the target region, for example, the SCS of the eye. In such embodiments, the user can increase the force on the housing 31110 to insert the distal tip of the needle 31240 further into the eye, for example, by a flexing of the sidewalls of the hub, such that the distal tip of the needle 31240 can be disposed within the target region (e.g., the SCS) of the target tissue.

Figure 93A:
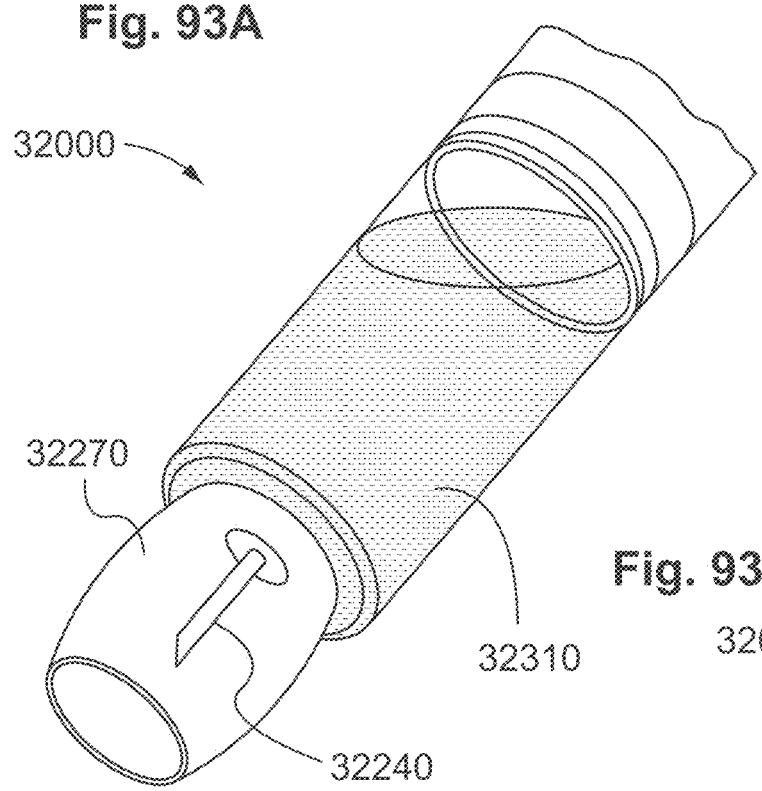
FIG. 93A shows a perspective view of a delivery device that includes a hub, according to an embodiment.

In some embodiments, a medical injector can include a hub configured to contact an outer surface of the target tissue and flex or bend to allow a needle included in the medical injector to be inserted into the target tissue. For example, FIG. 93A shows a perspective view of a portion of a medical injector 32000. The medical injector includes a hub 32270, a medicament container 32310 and needle 32240 that can be fluidically coupled to a medicament container included in the medical injector 32000. The hub 33270 is coupled to a distal end portion of the medicament container 32310. The hub 32270 has a hemispherical or a semi-hemispherical shape and defines a region therewithin. The hub 32270 is configured to be disposed on the distal end portion of the housing 32110 such that the needle 32240 is disposed within the region defined by the hub 32270. A distal end surface of the hub 32240 is configured to contact an outer surface of a target tissue, for example, the conjunctiva of an eye. Furthermore, the hub 32270 can be formed from a flexible material, for example, rubber, plastic, polymers, silicone, or any flexible material described herein or a combination thereof. The hub 32270 is configured to flex or bend, for example, by application of a force on the medicament container 32110. The bending or otherwise flexing can reduce the distance between a distal tip of the needle 32240 and the target tissue, such that the distal tip of the needle 32240 can be disposed within the target tissue.

Figure 93B:
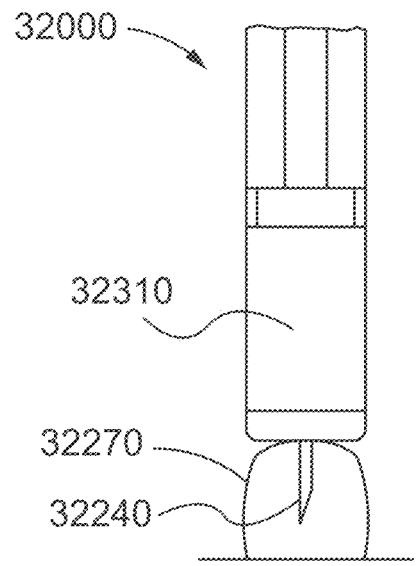
FIG. 93B-C show side cross-section views of the delivery device of FIG. 93A in a first configuration and a second configuration.
Figure 93C:
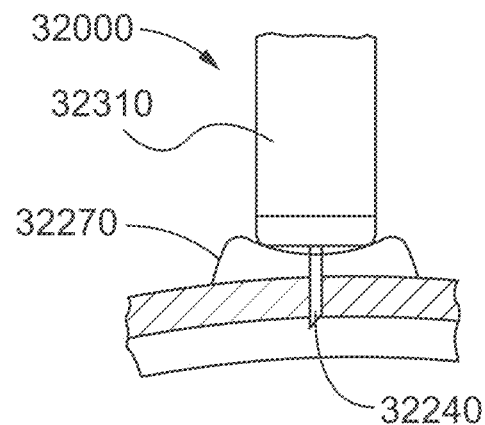

For example, FIGS. 93B and 93C show the medical injector 32000 in a first configuration and a second configuration, respectively. In the first configuration, the distal end surface of the hub 32270 is disposed on a target tissue, for example, the conjunctiva of the eye such that a distal tip of the needle 32240 is distal from the outer surface of the target tissue. Said another way, in the first configuration no force is exerted on the hub 32270 such that the hub 32270 is not bent, and the needle 32240 is not inserted into the target tissue. In the second configuration, a force can be applied on the medicament container 32310, or any other portion of the medical injector 32000 such that the hub flexes or otherwise bends reducing the distance between the distal tip of the needle 32240 and the outer surface of the target tissue. The force can be maintained until the distal tip of the needle pierces target tissue and is disposed within a target tissue (e.g., the SCS) of the target tissue (e.g., an eye).

Figure 94A:
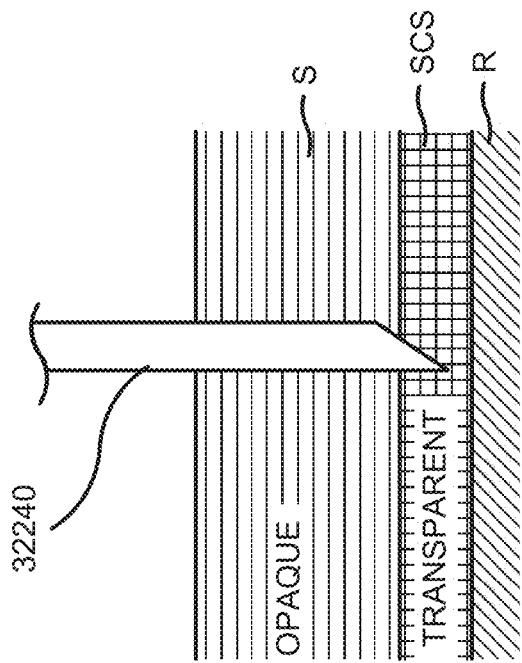
FIGS. 94A-B show schematic illustrations of a needle configured to communicate light inserted a first distance within ocular tissues and a second distance within the ocular tissue respectively, according to an embodiment.
Figure 94B:
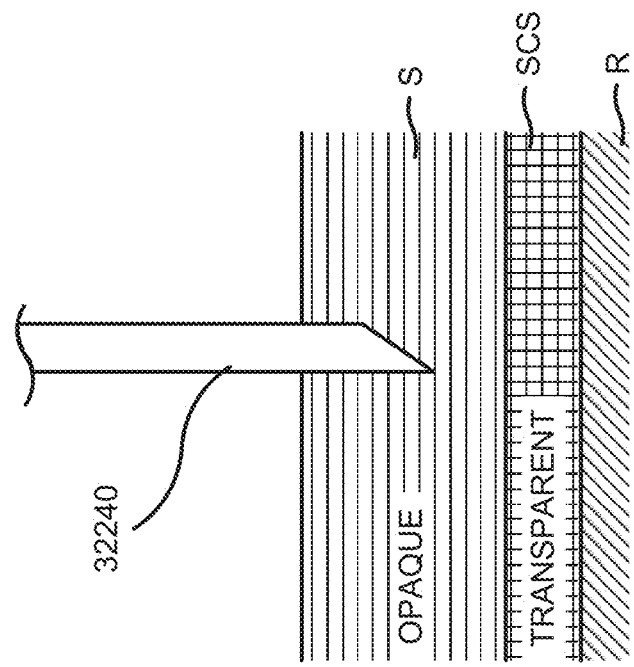

In some embodiments, a medical injector can include a puncture member included in a medical injector can be configured to sense light to determine the depth of insertion of the puncture member. For example, FIGS. 94A and 94B show a portion of a puncture member 32240 that can be included in a medical injector, for example, the medical injector 100, 1000, 2000, or any other medical injector described herein, in a first configuration and a second configuration, respectively, according to an embodiment. The puncture member 32240 can be configured to communicate light from the target tissue to a light sensor, for example, a photodiode included in the medical injector. The puncture member 32240 can be formed from any suitable optically transparent material, for example, an optical fiber. A distal end of the optical fiber can be beveled or otherwise formed into a sharp tip to pierce a target tissue. Furthermore, the distal tip can be optically transparent such that the puncture member can communicate light from the target tissue to the light sensor. The presence, absence, or otherwise amount of light communicated by the puncture member 32240 to the sensor can be used to determine the insertion depth and thereby, the region of the target tissue in which the distal end of the puncture member 32240 is disposed.

For example, in the first configuration shown in FIG. 94A, the distal end of the puncture member 32240 can be disposed in the sclera S of an eye. The sclera S is opaque so no light is communicated from the puncture member 32240 to the light sensor. In the second configuration, the distal tip of the puncture member 32240 is inserted deeper into the ocular tissue until at least a portion of the distal tip is disposed within the suprachoroidal space SCS which can be the target region for delivering a medicament. Since the suprachoroidal space SCS is transparent, light entering the eye and impinging on the retina R also penetrates into the suprachoroidal space SCS. The light can be communicated from the distal tip of the puncture member 32240 to the light sensor included in the medical injector thus confirming that the distal tip of the puncture member 32240 is indeed disposed in the target region of the eye. In some embodiments, the medical injector that includes the puncture member 32240 can alert a user that the distal tip of the puncture member 32240 is disposed within the suprachoroidal space SCS using an audible alert (e.g., a beep, an alarm, etc.), a haptic alert (e.g., vibrations, or minor electric current), or a visible alert (e.g., a light such as, for example, an LED light, or a visual message). Thus, a user can initiate delivery of the medicament through the puncture member 32240 only when the distal tip of the puncture member 32240 is within the suprachoroidal space SCS.

In some embodiments, a kit that includes a medical injector for delivering a medicament to a target region of a target tissue can include all or parts of the concepts described herein. For example, in some embodiments, a kit can include a medical injector (e.g., the medical injector 10, 1000, 2000, 3000, 21000, or any other medical injector described herein), a transfer assembly that can include, for example, an extraction member (e.g., the extraction member 21280), an injection assist housing (e.g., the injection assembly 2100 or any other injection assembly described herein), a needle adjustment mechanism (e.g., the needle assembly 3200, or any other needle assembly described herein), a container or vial of a substance, for example a medicament or any other substance described herein, replacement needles and/or hubs, one or more speculums, swabs, wipes, anti-biotic ointments, eye drops, or any other device or apparatus configured to facilitate delivery of the medicament to the target tissue, for example, the eye.

Figure 95:
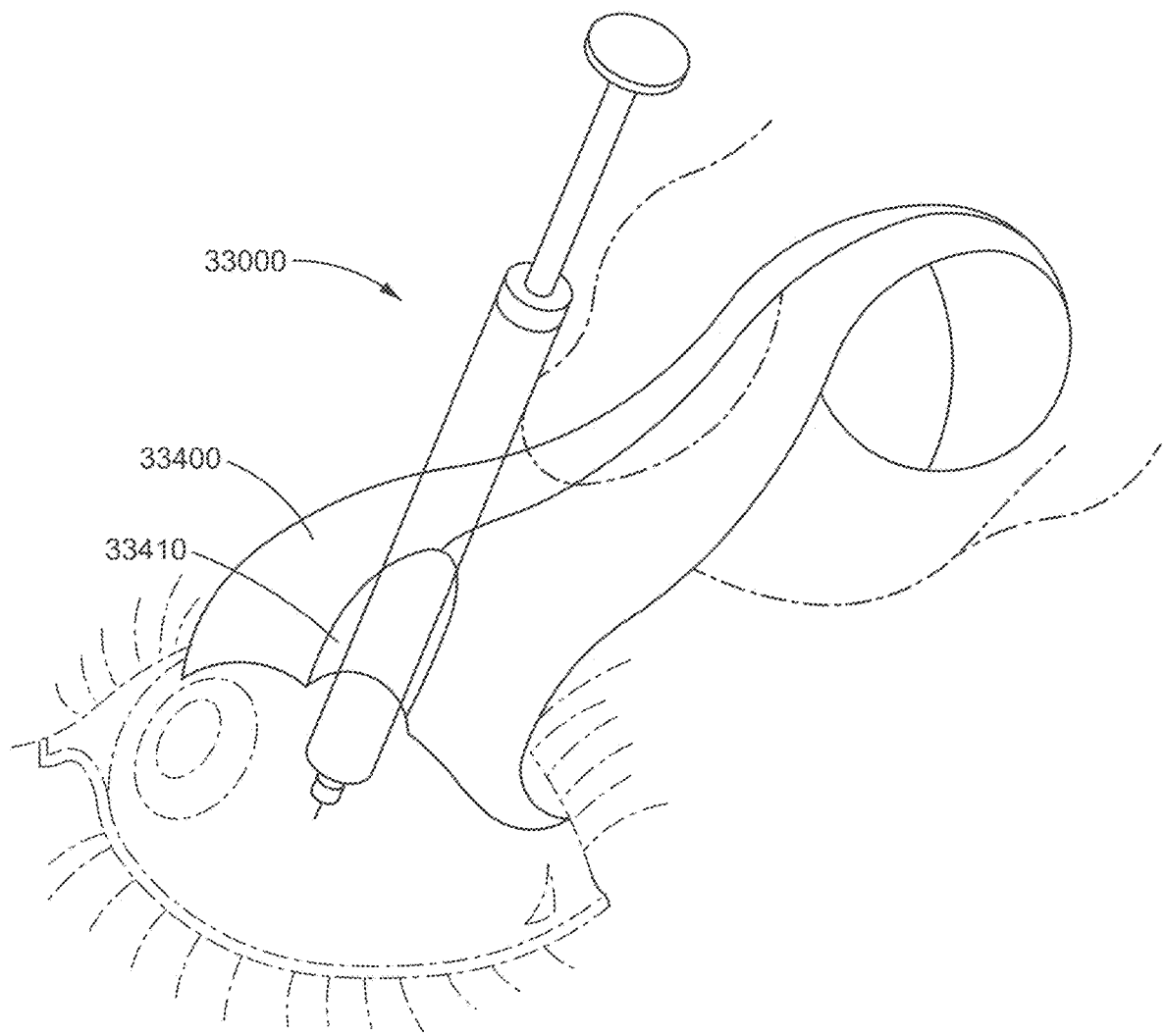
FIG. 95 shows a speculum configured to position a delivery device for ocular injection into an eye, according to an embodiment.

For example, FIG. 95 shows a speculum 33400 that can be included in a kit that includes a medical injector 33000, according to an embodiment. The medical injector 33000 can be substantially similar to the medical injector 100, 1000, 2000, 3000, or any other medical injector described herein. The speculum 33400 can be configured to be placed on an outer surface of the conjunctiva of the eye and open the eye lids of a patient. In this manner, the speculum 33400 can facilitate access to the surface of the eye such that the medical injector can be used to deliver a medicament to a target tissue of the eye, for example, the SCS. The speculum 33400 can include an ergonomic handle, which can be comfortably gripped by a user during use. The speculum 33400 also includes a cavity 33410 configured to receive at least a portion of the medical injector 33000. In use, a user can disposed the speculum 33400 on the conjunctiva of the eye such that the eyelids are forced open. Furthermore, the cavity 33410 can be located on a target portion of the eye. The user can dispose a distal end portion of the medical injector 33000 into the cavity 33410 and deliver the medicament to a target region (e.g., the SCS) of the eye. In some embodiments, the cavity 33410 can be oriented such that a center line of a delivery passageway of the medical injector 33000 and a surface line tangent of to the target surface of the eye (e.g., the conjunctiva, the sclera, and/or the suprachoroidal space SCS) defines an angle of entry of between about 75 degrees and about 105 degrees, for example, about 90 degrees. Moreover, the cavity 33410 can be configured to prevent lateral movement of the medical injector such that the centerline of the needle remains substantially normal to the target surface during delivery of the medicament.

Figure 96:
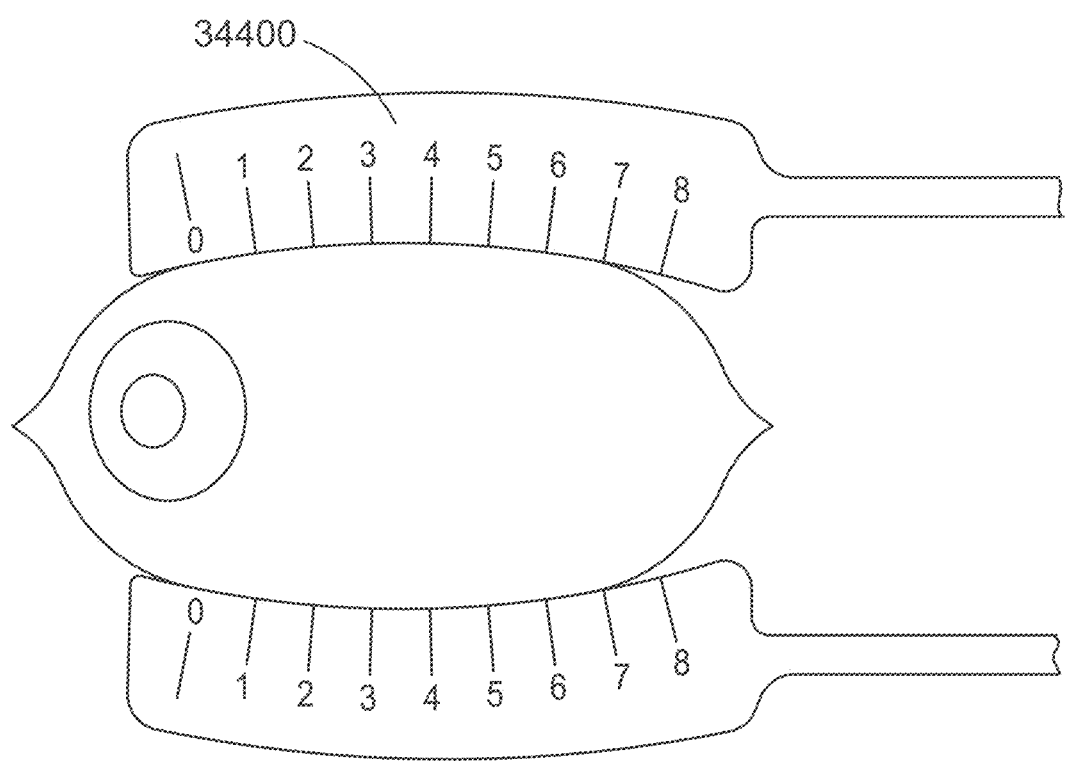
FIG. 96 shows a speculum that includes markings for sizing an eye, according to an embodiment.

In some embodiments, a speculum can include markings to enable measurement of a size, radius, diameter or otherwise cross-section of an eye. For example, FIG. 96 shows a speculum 34400 that can be included in a kit that includes a medical injector (e.g., the medical injector 100, 1000, 2000, 3000, or any other medical injector described herein. The speculum 34400 includes two arms. A distal end portion of the each of the arms is configured to disposed on the first and the second eyelid. The distal end portions can be moved apart to open the eyelids and allow access to the surface of the eye. The distal portions also include a plurality of markings or indicia. The markings can be used to measure a size of the eye, for example, a size, radius, diameter, or otherwise, cross section of the eye. Information on the size of the eye can be used to determine, for example, the thickness of individual layers, for example, the sclera and the SCS. In this manner, a user can predict how far a needle has to be penetrated into the eye such that a distal tip of the needle is disposed in a target region (e.g., the SCS) of the eye.

Figure 97:
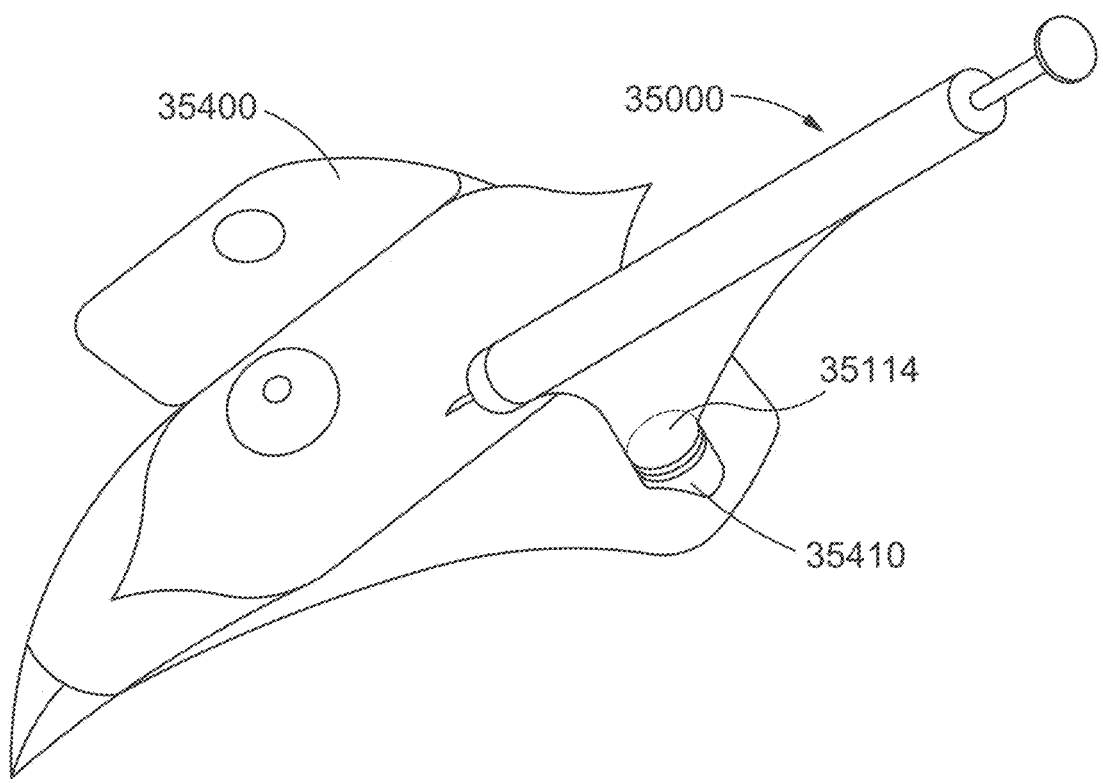
FIG. 97 shows a speculum that includes a mount configured to receive a mounting portion included in a delivery device and position the delivery device for ocular injection into an eye, according to an embodiment.

In some embodiments, a speculum can include mounting features to mount a medical injector. Referring now to FIG. 97, a speculum 35400 includes a set of arms configured to open the eyelids of a patient and provide access to the eye. The speculum 35400 includes a mount 35410 configured to receive mounting member 35114 included in a medical injector 35000. The medical injector 35000 can be substantially similar to the medical injector 100, 1000, 2000, 3000, or any other medicament container described herein. The mounting member 35410 can include any suitable mounting features, for example, a magnet, threads, snap-fit mechanism, friction-fit mechanism, or any other suitable mounting mechanism configured to mount the medical injector 35000 via the mounting member 35114. In some embodiments, the mount 35114 can include a magnet. In such embodiments, the mounting member 35114 can be formed from a magnetic material, for example, a ferrous material, such that mounting member 35114 can be coupled to the mount 35410 via magnetic coupling. In use, the speculum 35400 can be disposed on an eye of a patient. Each arm of the speculum 35400 can be used to open an eyelid of the patient to allow access to the eye. The medical injector 35000 can be mounted on the mount 35410 via the mounting feature 35114, for example, via magnetic coupling. Mounting the medical injector 35000 can prevent inadvertent movements of the medical injector 34000 during medicament injection thereby minimizing the risk of injury to the eye. Furthermore, the speculum 35400 can reduce the risk of an error by the user by positioning the medical injector 35000 for the user so that the user can focus on delivering the medicament to a target region of the eye instead of correctly positioning the medical injector 35000 on the eye.

Figure 98A:
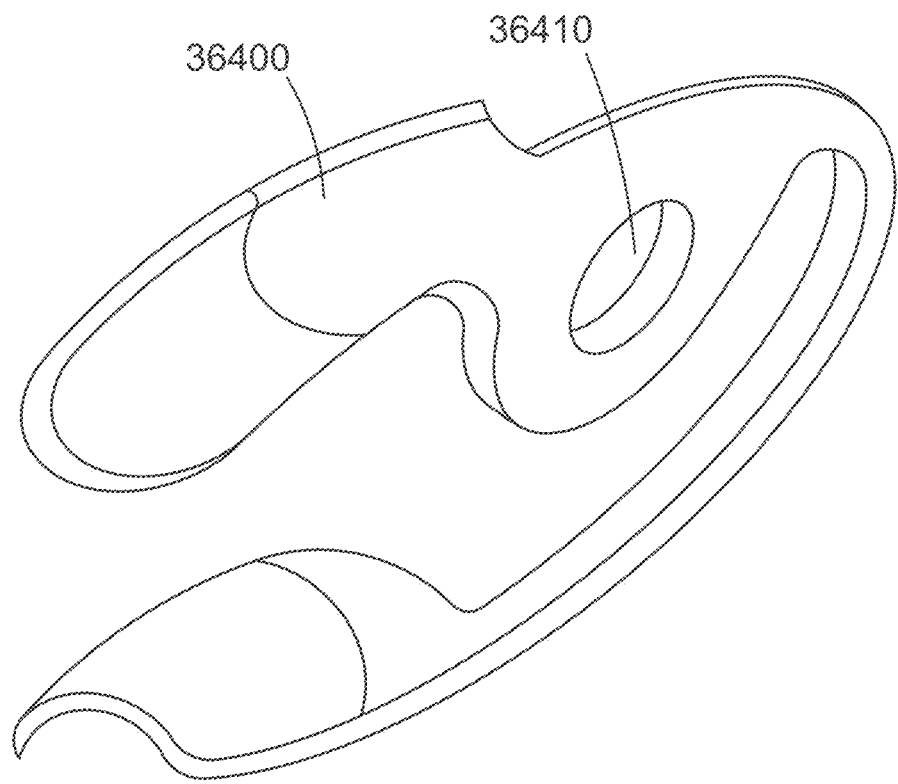
FIG. 98A shows a perspective view of a one-piece speculum.
Figure 98B:
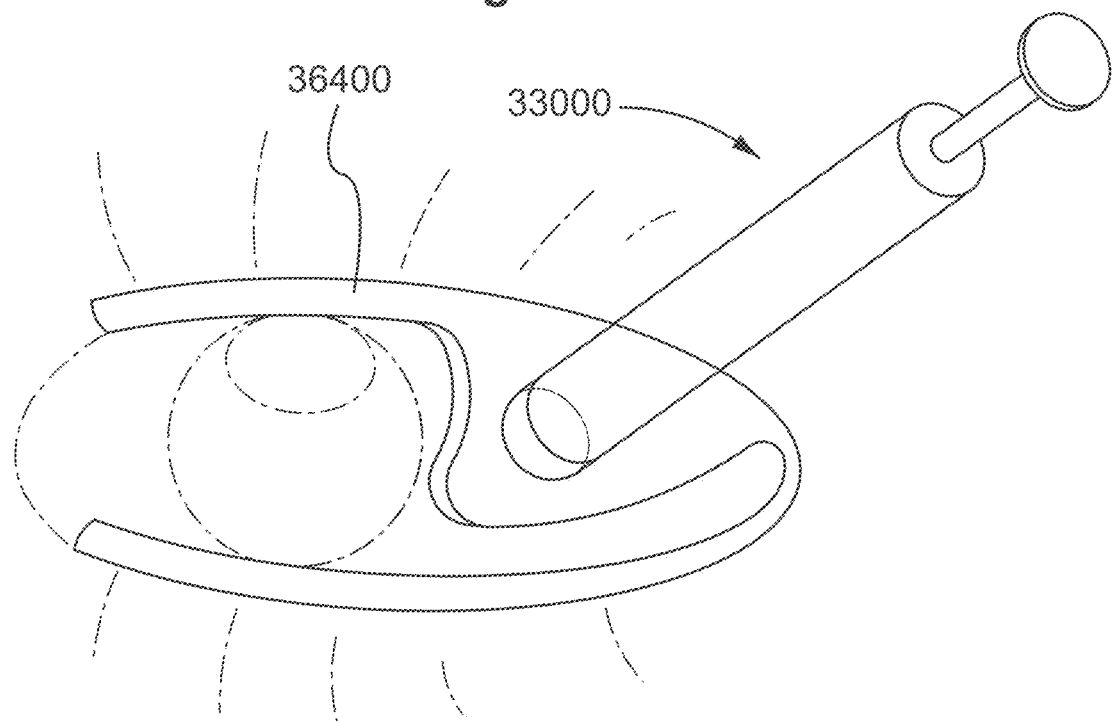
FIG. 98B shows the speculum of FIG. 98A disposed on a eye and delivery device coupled thereto, according to an embodiment.

In some embodiments, a speculum can include a single piece speculum. For example, FIG. 98A shows a single piece speculum 36400 configured to be disposed on a surface of an eye and open the eyelids of the patient. The speculum 36400 defines a cavity 36410 configured to receive at least a portion of a medical injector, for example, the medical injector 33000 or any other medical injector described herein. For example, as shown in FIG. 98B, the speculum 36400 can be disposed on the eye such that the cavity 36410 is disposed over a target location of the eye. At least a portion of the medical injector 33000 is then disposed in the cavity 36410 thereby positioning the medical injector 33000 over the target location of the eye for delivering the medicament to a target region within the target location.

Figure 99:
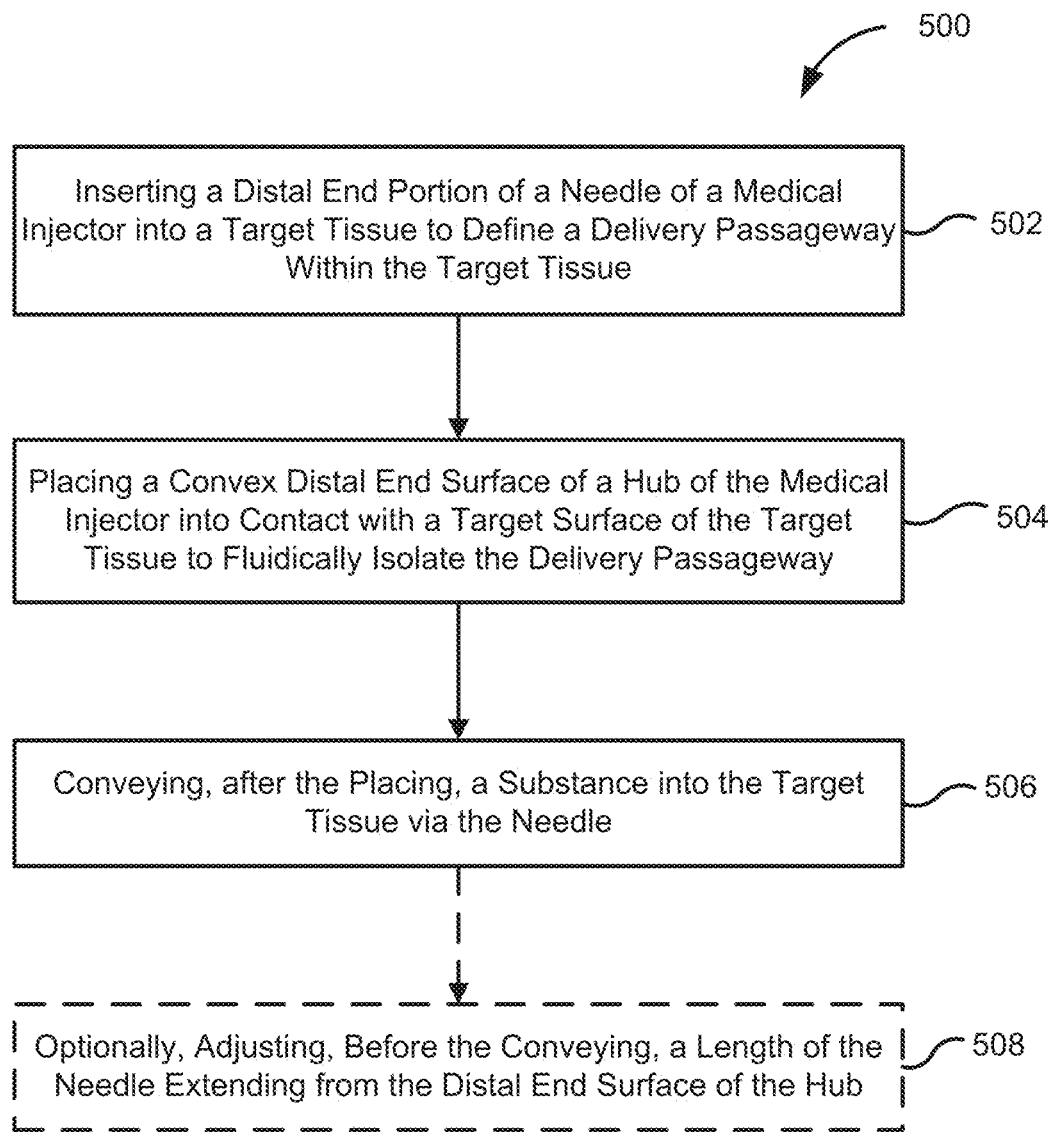
FIG. 99 shows a flow diagram of a method of injecting a substance into an eye using a medical injector that includes a hub such that a convex distal end of the hub forms a seal with a target surface to fluidically isolate a delivery passageway, according to an embodiment.

FIG. 99 shows a schematic flow diagram of a method 500 for delivering a medicament to a target tissue using a medical injector that includes a hub having a convex distal end surface (e.g., the hub 7270, 8270, or the hub 9720), coupled thereto. The medical injector can include any of the medical injectors described herein. The method includes inserting a distal end portion of a needle of a medical injector into a target tissue to define a delivery passageway within the target tissue 502. The needle can include any suitable puncture member, for example, a microneedle (e.g., a 27 gauge needle, a 30 gauge needle, or even smaller), or any other puncture member described herein. In some embodiments, the target tissue can be ocular tissue including the conjunctiva, the sclera, and the suprachoroidal space. In some embodiments, the inserting is performed such that centerline of the delivery passageway and a surface line tangent to the target surface defines an angle of entry of between about 75 degrees and about 105 degrees, for example, about 90 degrees. In some embodiments, the inserting can be performed such that the centerline of the needle is substantially normal to the target surface. This can, for example, minimize tissue damage and provide the shortest path for a distal tip of the needle to reach a target region of the target tissue (e.g., the SCS). Next, the convex distal end surface of the hub is placed in contact with a target surface of the target tissue to fluidically isolate the delivery passageway 504. In some embodiments, the placing can include deforming the target surface. For example, the distal end surface of the hub can include a sealing portion configured to contact and define a substantially fluid-tight seal with the target surface, for example, the conjunctiva of the eye (e.g., as defined with respect to the sealing portion 7277 included in the hub 7270). In such embodiments, the sealing portion can be substantially symmetrical around a centerline of the needle. In some embodiments, the sealing portion can be convex. In some embodiments, only a portion of the sealing portion can be configured to contact the target surface of the target tissue to form the substantially fluid-tight seal. For example, a circular band of the sealing portion can contact the target surface and form the substantially fluid tight seal surrounding the centerline of the needle.

The method 500 further includes conveying, after the placing, a substance into the target tissue via the needle 506. In some embodiments, the substance can include a medicament such as, for example, a VEGF, a VEGF inhibitor, or a combination thereof. The substance can be disposed within an internal volume of a medicament container included in the medical injector. An actuation rod can be included in the medical injector, which can be configured to be engaged by a user to fluidically communicate the substance from the medicament container to the target tissue via the needle. The medicament container and the actuation rod can be substantially similar to the medicament container and/or the actuation rod included in the system 100, 1000, 2000, 3000, or any other system or apparatus described herein. In some embodiments, the target tissue can be an eye, and the target surface can be a conjunctiva of the eye. In such embodiments, the delivery passageway can extend through a sclera of the eye such that the conveying includes conveying the substance into at least one of a suprachoroidal space or a lower portion of the sclera.

In some embodiments, the method 500 can further include adjusting, before the conveying, a length of the needle extending from the distal end surface of the hub. For example, the medical injector can include a needle assembly, for example, the needle assembly 3200 or any other needle assembly described herein. The needle assembly can be used to adjust the length of the needle extending from the distal end surface of the hub until a distal tip of the needle is disposed within a target region, for example, the SCS of the eye. The substance, for example, as medicament as described herein, can then be conveyed to the target region of the eye.

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and alloys thereof. The polymer may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

The microneedles described herein can be fabricated by a variety of methods. For example, in some embodiments, the hollow microneedle is fabricated using a laser or similar optical energy source. In one example, a microcannula may be cut using a laser to represent the desired microneedle length. The laser may also be use to shape single or multiple tip openings. Single or multiple cuts may be performed on a single microncannula to shape the desired microneedle structure. In one example, the microcannula may be made of metal such as stainless steel and cut using a laser with a wavelength in the infrared region of the light spectrum (0.7-300 μm). Further refinement may be performed using metal electropolishing techniques familiar to those in the field. In another embodiment, the microneedle length and optional bevel is formed by a physical grinding process, which for example may include grinding a metal cannula against a moving abrasive surface. The fabrication process may further include precision grinding, micro-bead jet blasting and ultrasonic cleaning to form the shape of the desired precise tip of the microneedle.

A wide range of ocular diseases and disorders may be treated by the methods and devices described herein. Non-limiting examples of ocular diseases include uveitis, glaucoma, diabetic macular edema or retinopathy, macular degeneration, retinoblastoma, and genetic diseases. The methods described herein are particularly useful for the local delivery of drugs that need to be administered to the posterior region of the eye, for example the retinochoroidal tissue, macula, and optic nerve in the posterior segment of the eye. In one embodiment, the delivery methods and devices described herein may be used in gene-based therapy applications. For example, the methods may administer a fluid drug formulation into the suprachoroidal space to deliver select DNA, RNA, or oligonucleotides to targeted ocular tissues.

The microneedles can be used to target delivery to specific tissues or regions within the eye or in neighboring tissue. In various embodiments, the methods may be designed for drug delivery specifically to the sclera, the choroid, the Bruch's membrane, the retinal pigment epithelium, the subretinal space, the retina, the macula, the optic disk, the optic nerve, the ciliary body, the trabecular meshwork, the aqueous humor, the vitreous humor, and other ocular tissue or neighboring tissue in need of treatment.

A wide range of drugs may be formulated for delivery to ocular tissues using the present systems and devices described herein. Moreover, any of the delivery devices and/or methods described herein can involve, include and/or contain any of the drugs described herein. For example, in some embodiments, the medicament containment chamber 1310, 2310, 3310, or any other medicament containment chamber can contain any of the drugs and/or formulations described herein. As used herein, the term "drug" refers to any prophylactic, therapeutic, or diagnostic agent (e.g., a contrast agent). The drug may be selected from suitable proteins, peptides and fragments thereof, which can be naturally occurring, synthesized or recombinantly produced. Representative examples of types of drugs for delivery to ocular tissues include antibodies, anti-viral agents, chemotherapeutic agents (e.g., topoisomerase inhibitors), analgesics, anesthetics, aptamers, antihistamines, anti-inflammatory agents, and anti-neoplastic agents. In one embodiment, the drug is triamcinolone or triamcinolone acetonide.

The term "antibody" is intended to refer broadly to any immunologic binding agent such as IgG, IgM, IgA, IgD and IgE. An antibody can be monoclonal or polyclonal, and in one embodiment, is a humanized antibody. The term "antibody" is also used to refer to any antibody-like molecule that has an antigen binding region, and includes antibody fragments such as Fab', Fab, F(ab')$_2$, single domain antibodies (DABs), Fv, scFv (single chain Fv), and engineering multivalent antibody fragments such as dibodies, tribodies and multibodies. The techniques for preparing and using various antibody-based constructs and fragments are well known in the art (see, e.g., Antibodies: A Laboratory Manual, Cold Spring Harbor Laboratory, 1988; incorporated herein by reference).

Non-limiting examples of specific drugs and classes of drugs include β-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), topoisomerase inhibitors (e.g., topotecan, irinotecan, camptothecin, lamellarin D, etoposide, teniposide, doxorubicin, mitoxantrone, amsacrine), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors and treatments of age-related macular degeneration such as pegagtanib sodium, ranibizumab, aflibercept and bevacizumab.

In one embodiment, the drug is an integrin antagonist, a selectin antagonist, an adhesion molecule antagonist (e.g., intercellular adhesion molecule (ICAM)-1, ICAM-2, ICAM-3, platelet endothelial adhesion molecule (PCAM), vascular cell adhesion molecule (VCAM)), a leukocyte adhesion-inducing cytokine or growth factor antagonist (e.g., tumor necrosis factor-α (TNF-α), interleukin-1β (IL-1β), monocyte chemotactic protein-1 (MCP-1), or a vascular endothelial growth factor (VEGF)). In some embodiments, a vascular endothelial growth factor (VEGF) inhibitor is administered with one of the microneedles described herein. In some embodiments, two drugs are delivered by the methods described herein. The compounds may be administered in one formulation, or administered serially, in two separate formulations. For example, both a VEGF inhibitor and VEGF are provided. In some embodiments, the VEGF inhibitor is an antibody, for example a humanized monoclonal antibody. In further embodiments, the VEGF antibody is bevacizumab. In another embodiment, the VEGF inhibitor is ranibizumab, aflibercept or pegaptanib. In still other embodiments, the devices and methods described herein can be used to deliver one or more of the following VEGF antagonists: AL8326, 2C3 antibody, AT001 antibody, HyBEV, bevacizumab (Avastin), ANG3070, APX003 antibody, APX004 antibody, ponatinib (AP24534), BDM-E, VGX100 antibody (VGX100 CIRCADIAN), VGX200 (c-fos induced growth factor monoclonal antibody), VGX300, COSMIX, DLX903/1008 antibody, ENMD2076, Sutent (sunitinib malate), INDUS815C, R84 antibody, KD019, NM3, allogenic mesenchymal precursor cells combined with an anti-VEGF agent or antibody, MGCD265, MG516, VEGF-Receptor kinase inhibitors, MP0260, NT503, anti-DLL4/VEGF bispecific antibody, PAN90806, Palomid 529, BD0801 antibody, XV615, lucitanib (AL3810, E3810), AMG706 (motesanib diphosphate), AAV2-sFLT01, soluble Flt1 receptor, Cediranib (Recentin), AV-951 (Tivozanib, KRN-951), Stivarga (regorafenib), Volasertib (BI6727), CEP11981, KH903, Lenvatinib (E7080), terameprocol (EM1421), ranibizumab (Lucentis), Votrient (pazopanib hydrochloride), PF00337210, PRS050, SP01 (curcumin), Carboxyamidotriazole orotate, hydroxychloroquine, linifanib (ABT869, RG3635), Iluvien (fluocinolone acetonide), ALG1001, AGN150998, DARPin MP0112, AMG386, ponatinib (AP24534), AVA101, Vargatef (nintedanib), BMS690514, KH902, golvatinib (E7050), Afinitor (everolimus), Dovitinib lactate (TKI258, CHIR258), ORA101, ORA102, Axitinib (Inlyta, AG013736), Plitidepsin (Aplidin), Lenvatinib mesylate, PTC299, aflibercept (Zaltrap, Eylea), pegaptanib sodium (Macugen, LI900015), Visudyne (verteporfin), bucillamine (Rimatil, Lamin, Brimani, Lamit, Boomiq), R3 antibody, AT001/r84 antibody, troponin (BLS0597), EG3306, vatalanib (PTK787), Bmab100, GSK2136773, Anti-VEGFR Alterase, Avila, CEP7055, CLT009, ESBA903, HuMax-VEGF antibody, GW654652, HMPL010, GEM220, HYB676, JNJ17029259, TAK593, XtendVEGF antibody, Nova21012, Nova21013, CP564959, Smart Anti-VEGF antibody, AG028262, AG13958, CVX241, SU14813, PRS055, PG501, PG545, PTI101, TG100948, ICS283, XL647, enzastaurin hydrochloride (LY317615), BC194, quinolines, COT601M06.1, COT604M06.2, MabionVEGF, SIR-Spheres coupled to anti-VEGF or VEGF-R antibody, Apatinib (YN968D1), and AL3818. In addition, delivery of a VEGF inhibitor or VEGF antagonist using the microneedle devices and methods disclosed herein may be combined with one or more agents listed herein or with other agents known in the art.

In one embodiment, delivery of a VEGF antagonist to the suprachoroidal space of the eye using the devices and methods disclosed herein is used to treat, prevent and/or ameliorate a disease or disorder selected from leukemia, relapsed/refractory leukemia, acute lymphoblastic leukemia, Acute myelogenous leukemia, relapsed or refractory acute myeloid leukemia, atopic dermatitis, recurrent or metastatic carcinoma of the urothelium, advanced urothelial carcinoma, blood disorders, myelofibrosis, brain tumor, glioblastoma, glioma, meningioma, cancer, carcinomatous meningitis (neoplastic meningitis), choroidal neovascularization (CNV), subfoveal choroidal neovascularization, chronic lymphocytic leukemia, chronic myelogenous leukemia, refractory chronic myelogenous leukemia, colon cancer, colorectal cancer, degenerative nerve diseases, Neurodegenerative diseases, diabetic macular edema, visual Impairment due to diabetic macular edema, diabetic retinopathy, dry eye syndrome (inflammation and corneal tissue damage of dry Eye), endometrial cancer, eye diseases, ocular diseases, ocular neovascularization, eye cancer, Neurofibromatosis Type II, head and neck cancer, hematological malignancies, Kaposi's Sarcoma, Hepatocellular Carcinoma, Lung cancer, macular degeneration, age related macular degeneration, exudative age-related macular degeneration, neovascular (wet) age-related macular degeneration (AMD)), subfoveal Neovascular Age-Related macular degeneration, macular edema, macular edema associated with Branch Retinal Vein Occlusion, macular edema following retinal vein occlusion, macular edema with Retinal Vein Occlusion (RVO), multiple myeloma, relapsed or refractory multiple myeloma, multiple sclerosis, myopia, pathological myopia, neuroendocrine tumor, carcinoid tumor, neuroendocrine tumor, non-Hodgkin's Lymphoma, Diffuse Large B-Cell Lymphoma, Non-Small-Cell Lung cancer, Non-Squamous Non-Small-Cell Lung cancer, Non-small-cell-lung Adenocarcinoma, Squamous Non-Small-Cell Lung cancer, corneal graft rejection, osteoarthritis, recurrent symptomatic malignant ascites, peripheral T-cell lymphoma, androgen Independent Psoriasis, pulmonary Fibrosis, Idiopathic Pulmonary Fibrosis, respiratory diseases, retinal detachment, retinal disorders, retinitis pigmentosa, retinal vein occlusion, branch retinal vein occlusion, central retinal vein occlusion, rheumatoid arthritis, sarcoma, alveolar soft part sarcoma, soft tissue sarcoma, scleroderma/systemic sclerosis, solid tumors, refractory germ cell tumors, thyroid cancer, differentiated or medullar thyroid cancer, and West Syndrome (Infantile Spasm).

In certain embodiments, the drug delivered to the suprachoroidal space using the devices and methods disclosed herein is rapamycin (Sirolimus, Rapamune). In one embodiment, the devices (e.g., microneedle devices) and methods disclosed herein are used in conjunction with rapamycin to treat, prevent and/or ameliorate a wide range of diseases or disorders including, but not limited to: abdominal neoplasms, acquired immunodeficiency syndrome, acute coronary syndrome, acute lymphoblastic leukemia, acute myelocytic leukemia, acute non-lymphoblastic leukemia, adenocarcinoma, adenoma, adenomyoepithelioma, adnexal diseases, anaplastic astrocytoma, anaplastic large cell lymphoma, anaplastic plasmacytoma, anemia, angina pectoris, angioimmunoblastic lymphadenopathy with dysproteinemia, angiomyolipoma, arterial occlusive diseases, arteriosclerosis, astrocytoma, atherosclerosis, autoimmune diseases, B-cell lymphomas, blood coagulation disorders, blood protein disorders, bone cancer, bone marrow diseases, brain diseases, brain neoplasms, breast beoplasms, bronchial neoplasms, carcinoid syndrome, carcinoid Tumor, carcinoma, squamous cell carcinoma, central nervous system diseases, central nervous system neoplasms, choroid diseases, choroid plexus neoplasms, choroidal neovascularization, choroiditis, chronic lymphocytic leukemia, chronic myeloid leukemia, chronic myelomonocytic leukemia, chronic myeloproliferative disorders, chronic neutrophilic leukemia, clear cell renal cell carcinoma, colonic diseases, colonic neoplasms, colorectal neoplasms, coronary artery disease, coronary disease, coronary Occlusion, coronary restenosis, coronary stenosis, coronary thrombosis, cutaneous T-cell lymphoma, diabetes mellitus, digestive system neoplasms, dry eye syndromes, ear diseases, edema, endocrine gland neoplasms, endocrine system diseases, endometrial neoplasms, Endometrial stromal tumors, Ewing's sarcoma, exanthema, eye neoplasms, fibrosis, follicular lymphoma, gastrointestinal diseases, gastrointestinal neoplasms, genital neoplasms, glioblastoma, glioma, gliosarcoma, graft vs host disease, hematologic diseases, hematologic neoplasms, hemorrhagic disorders, hemostatic disorders, Hodgkin disease, Hodgkin lymphoma, homologous wasting disease, immunoblastic lymphadenopathy, immunologic deficiency syndromes, immunoproliferative disorders, infarction, inflammation, intestinal diseases, intestinal neoplasms, ischemia, kidney cancer, kidney diseases, kidney neoplasms, leukemia, B-Cell, leukemia, lymphoid, liver cancer, liver diseases, lung diseases, lymphatic diseases, lymphoblastic lymphoma, lymphoma, macular degeneration, macular edema, melanoma, mouth neoplasms, multiple myeloma, myelodysplastic syndromes, myelofibrosis, myeloproliferative disorders, neuroectodermal tumors, neuroendocrine tumors, neuroepithelioma, neurofibroma, renal cancer, respiratory tract diseases, retinal degeneration, retinal diseases, retinal neoplasms, retinoblastoma, rhabdomyosarcoma, thoracic neoplasms, uveitis, vascular diseases, Waldenstrom Macroglobulinemia, and wet macular degeneration. In addition, delivery of rapamycin using the microneedle devices and methods disclosed herein may be combined with one or more agents listed herein or with other agents known in the art.

In one embodiment, the drug delivered to ocular tissue, for example the sclera or suprachoroidal space, using the microneedle devices and methods disclosed herein reduces, inhibits, prevents and/or ameliorates inflammation. Examples of drugs that reduce, inhibit, prevent and/or ameliorate inflammation include (but are not limited to): 19AV Agonists, 19GJ agonists, 2MD Analogs, 4SC101, 4SC102, 57-57, 5-HT2 Receptor Antagonist, 64G12, A804598, A967079, AAD2004, AB1010, AB224050, abatacept, Abegrin, Abevac, AbGn134, AbGn168, Abki, ABN912, ABR215062, ABR224050, Abrammune, Abreva, ABS15, ABS4, ABS6, ABT122, ABT325, ABT494, ABT874, ABT963, ABXIL8, ABXRB2, AC430, Accenetra, Acdeam, ACE772, Acebid, Acebloc, aceclofenac, acetaminophen, chlorzoxazone, serrapeptase, tizanidine hydrochloride, betadex, Aceclogesic Plus, Aceclon, Acecloren, Aceclorism, acecrona, Aceffein, acemetacin, Acenac, Acenterine, Acetal-SP, ibuprofen, Acetyl-G, acetylsalicylate dl-lysine, acetylsalicylic acid, Acicot, Acifine, Acik, Aclocen, Acloflam-P, Aclomore, Aclon, A-CQ, ACS15, actarit, Actemra, Acthelea liofilizado, Actifast, Actimab-B, Actiquim, Actirin, Actis PLUS, activated leukocyte cell adhesion molecule antibody, Acular X, AD452, adalimumab, ADAMTSS Inhibitor, ADC1001, Adco-Diclofenac, Adco-Indomethacin, Adco-Meloxicam, Adco-Naproxen, Adco-Piroxicam, Adcort, Adco-Sulindac, adenosine triphosphate disodium, AdenosineA2a Receptor Agonist, Adimod, Adinos, Adioct, Adiodol, Adipoplus, adipose derived stem and/or regenerative cells, Adizen, Adpep, Advacan, Advagraf, Advel, Adwiflam, AEB071, Aental, Afenac, Affen Plus, Afiancen, Afinitor, Aflamin, Aflazacort, Aflogen, Afloxan, AFM15, AFM16, AFM17, AFM23, Afpred-Dexa, AFX200, AG011, Agafen, aganirsen, AGI1096, Agidex, AGS010, Agudol, A-Hydrocort, AIK1, AIN457, Airtal, AIT110, AJM300, ajulemic acid, AK106, AL-24-2A1, AL4-1A1, Ala Cort, Alanz, Albumin immune-globulin, alclometasone dipropionate, ALD518, aldesleukin, Aldoderma, alefacept, alemtuzumab, Alequel, Alergolon, Alergosone, Aletraxon, Alfenac, Algason, Algin vek coat, Algioflex, Algirex, Algivin Plus, alicaforsen sodium, Alin, Alinia, Aliviodol, Aliviosin, alkaline phosphatase, ALKS6931, allantoin, Allbupen, Allmol, Allochrysine, allogeneic endothelial cells, allogeneic mesenchymal precursor cells, allogeneic mesenchymal stem cells, alminoprofen, alpha 1 antitrypsin, Alpha 7 nicotinic agonists, alpha amylase, alpha chymotrypsin, alpha fetoprotein, alpha linolenic acid, Alpha-1-antitrypsin, Alpha2Beta1 Integrin Inhibitors, Alphacort, Alphafen, alpha-hexidine, alpha-trypsin, Alphintern, Alpinamed mobility omega 3, Alpoxen, AL-Rev1, Alterase, ALX0061, ALX0761, ALXN1007, ALXN1102, AM3840, AM3876, AMAB, AMAP102, Amason, Ambene, AmbezimG, amcinonide, AME133v, Amecin, Ameloteks, A-Methapred, Amevive, AMG108, AMG139, AMG162, AMG181, AMG191, AMG220, AMG623, AMG674, AMG714, AMG719, AMG729, AMG827, Amidol, amifampridine phosphate, Amifenac, Amimethacin, amiprilose hydrochloride, Amiprofen, Ammophos, Amoflam, AMP110, Ampikyy, Ampion, ampiroxicam, amtolmetin guacil, AMX256, AN6415, ANA004, ANA506, Anabu, Anacen, Anaflam, Anaflex ACI, Anaida, anakinra, Analgen Artritis, Anapan, Anaprox, Anavan, Anax, Anco, andrographis, Aneol, Anergix, Anervax.RA, Anflene, ANG797, Anilixin, Anmerushin, Annexin 1 peptides, annexin A5, Anodyne, Ansaid, Anspirin, Antarene, Anti BST2 antibody, Anti C5a MAb, Anti ILT7 antibody, Anti VLA1 antibody, Anti-alphal 1 antibody, Anti-CD4 802-2, Anti-CD86 Monoclonal Antibody, Anti-chemokine, Anti-DC-SIGN, Anti-HMGB-1 MAb, Anti-IL-18 Mab, Anti-IL-1R MAb, Anti-IL-1R MAb, Anti-IL23 BRISTOL, Anti-inflammatory Peptides, Anti-interleukin 1Beta antibody, Anti-LIGHT antibody, Anti-LIGHT antibody, Anti-MIF Antibody, Anti-MIF Antibody, Anti-miR181a, antioxidant inflammation modulators, Antiphlamine, AntiRAGE MAb, antithrombin III, Anti-TIRC-7 MAb, Anusol-HC, Anyfen, AP105, AP1089, AP1189, AP401, AP501, apazone, APD334, Apentac, APG103, Apidone, apilimod mesylate, Apitac, Apitoxin, Apizel, APN Inhibitor, apo-Azathioprine, Apo-Dexamethasone, ApoE mimetics, ApoFasL, apo-Indomethacin, apo-mefenamic, apo-methotrexate, apo-nabumetone, Apo-Napro-NA, apo-Naproxen, aponidin, apo-Phenylbutazone, apo-Piroxicam, apo-Sulin, Apo-Tenoxicam, apo-Tiaprofenic, Apranax, apremilast, apricoxib, Aprofen, Aprose, Aproxen, APX001 antibody, APX007 antibody, APY0201, AqvoDex, AQX108, AQX1125, AQX131135, AQX140, AQX150, AQX200, AQX356, AQXMN100, AQXMN106, ARA290, Arava, Arcalyst, Arcoxia, Arechin, Arflur, ARG098, ARG301, arginine aescin, arginine deiminase (pegylated), ARGX109 antibody, ARGX110, Arheuma, Aristocort, Aristospan, Ark-AP, ARN4026, Arofen, Aroff EZ, Arolef, Arotal, Arpibru, Arpimune, Arpu Shuangxin, ARQ101, Arrestin SP, Arrox, ARRY162, ARRY3717976, ARRY614, ARRY872, ART621, Artamin, Arthfree, Artho Tech, Arthrexin, Arthrispray, Arthrotec, Arthrovas, Artifit, Artigo, Artin, Artinor, Artisid, Artoflex, Artren Hipergel, Artridol, Artrilase, Artrocaptin, Artrodiet, Artrofen, Artropan, Artrosil, Artrosilene, Artrotin, Artrox, Artyflam, Arzerra, AS604850, AS605858, Asacol, ASA-Grindeks, Asazipam, Aseclo, ASF1096, ASF1096, ASK8007, ASKP1240, ASLAN003, Asmo ID, Asonep, ASP015K, ASP2408, ASP2409, Aspagin, Aspeol, Aspicam, Aspirimex, aspirin, AST120, astaxanthin, AstroCort, Aszes, AT002 antibody, AT007, AT008 antibody, AT008 antibody, AT010, AT1001, atacicept, Ataspin, Atepadene, Atgam, ATG-Fresenius, Athrofen, ATI003, atiprimod, ATL1222, ATN103, ATN192, ATR107, Atri, Atrmin, Atrosab antibody, ATX3105, AU801, auranofin, Aurobin, Auropan, Aurothio, aurotioprol, autologous adipose derived regenerative cells, Autonec, Avandia, AVE9897, AVE9940, Avelox, Avent, AVI3378, Avloquin, AVP13546, AVP13748, AVP28225, AVX002, Axcel Diclofenac, Axcel Papain, Axen, AZ17, AZ175, Azacortid, AZA-DR, Azafrine, Azamun, Azanin, Azap, Azapin, Azapren, Azaprin, Azaram, Azasan, azathioprine, AZD0275, AZD0902, AZD2315, AZD5672, AZD6703, AZD7140, AZD8309, AZD8566, AZD9056, Azet, Azintrel, azithromycin, Az-od, Azofit, Azolid, Azoran, Azulene, Azulfidine, Azulfin, B1 antagonists, Baclonet, BAF312, BAFF Inhibitor, Bages, Baily S.P., Baleston, Balsolone, baminercept alfa, bardoxolone methyl, baricitinib, Barotase, Basecam, basiliximab, Baxmune, Baxo, BAY869766, BB2827, BCX34, BCX4208, Becfine, Beclate-C, Beclate-N, Beclolab Q, beclomethasone dipropionate, Beclorhin, Becmet-CG, Begita, Begti, belatacept, belimumab, Belosalic, Bemetson, Ben, Benevat, Benexam, Benflogin, Benisan, Benlysta, Benlysta, benorilate, Benoson, benoxaprofen, Bentol, benzydamine hydrochloride, Benzymin, Beofenac, Berafen, Berinert, Berlofen, Bertanel, Bestamine, Bestofen, Beta Nicip, Betacort, Betacorten G, Betafoam, beta-glucan, Betalar, Beta-M, Betamed, Betamesol, betamethasone, betamethasone dipropionate, betamethasone sodium, betamethasone sodium phosphate, betamethasone valerate, Betane, Betanex, Betapanthen, Betapar, Betapred, Betason, Betasonate, Betasone, Betatrinta, Betaval, Betazon, Betazone, Betesil, Betnecort, Betnesol, Betnovate, Bextra, BFPC13, BFPC18, BFPC21, BFPT6864, BG12, BG9924, BI695500, BI695501, BIA12, Big-Joint-D, BIIB023 antibody, Bi-ksikam, Bingo, BioBee, Bio-Cartilage, Bio-C-Sinkki, Biodexone, Biofenac, Bioreucam, Biosone, Biosporin, BIRB796, Bitnoval, Bitvio, Bivigam, BKT140, BKTP46, BL2030, BL3030, BL4020, BL6040, BL7060, BLI1300, blisibimod, Blokium B12, Blokium Gesic, Blokium, BMS066, BMS345541, BMS470539, BMS561392, BMS566419, BMS582949, BMS587101, BMS817399, BMS936557, BMS945429, BMS-A, BN006, BN007, BNP166, Bonacort, Bonas, bone marrow stromal cell antigen 2 antibody, Bonflex, Bonifen, Boomiq, Borbit, Bosong, BRO2001, BR3-FC, Bradykinin B1 Receptor Antagonist, Bredinin, Brexecam, Brexin, Brexodin, briakinumab, Brimani, briobacept, Bristaflam, Britten, Broben, brodalumab, Broen-C, bromelains, Bromelin, Bronax, Bropain, Brosiral, Bruace, Brufadol, Brufen, Brugel, Brukil, Brusil, BT061, BTI9, BTK kinase inhibitors, BTT1023 antibody, BTT1507, bucillamine, Bucillate, Buco Reigis, bucolome, Budenofalk, budesonide, Budex, Bufect, Bufencon, Bukwang Ketoprofen, Bunide, Bunofen, Busilvex, busulfan, Busulfex, Busulipo, Butartrol, Butarut B12, Butasona, Butazolidin, Butesone, Butidiona, BVX10, BXL628, BYM338, B-Zone, C1 esterase inhibitor, C243, c4462, c5997, C5aQb, c7198, c9101, C9709, c9787, CAB101, cadherin 11 antibody, caerulomycin A, CAL263, Calcort, Calmatel, CAM3001, Camelid Antibodies, Camlox, Camola, Campath, Camrox, Camtenam, canakinumab, *Candida albicans* antigen, Candin, cannabidiol, CAP1.1, CAP1.2, CAP2.1, CAP2.2, CAP3.1, CAP3.2, Careram, Carimune, Cariodent, Cartifix, CartiJoint, Cartilago, Cartisafe-DN, Cartishine, Cartivit, Cartril-S, Carudol, CaspaCIDe, CaspaCIDe, Casyn, CAT1004, CAT1902, CAT2200, Cataflam, Cathepsin S inhibitor, Catlep, CB0114, CB2 agonist, CC0478765, CC10004, CC10015, CC1088, CC11050, CC13097, CC15965, CC16057, CC220, CC292, CC401, CC5048, CC509, CC7085, CC930, CCR1 Antagonist, CCR6 Inhibitor, CCR7 Antagonist, CCRL2 antagonist, CCX025, CCX354, CCX634, CD Diclofenac, CD102, CD103 Antibody, CD103 Antibody, CD137 antibody, CD16 antibody, CD18 antibody, CD19 antibody, CD1d Antibody, CD20 antibody, CD200Fc, CD209 antibody, CD24, CD3 antibody, CD30 antibody, CD32A antibody, CD32B antibody, CD4 antibody, CD40 ligand, CD44 antibody, CD64 antibody, CDC839, CDC998, CDIM4, CDIM9, CDK9-Inhibitor, CDP146, CDP323, CDP484, CDP6038, CDP870, CDX1135, CDX301, CE224535, Ceanel, Cebedex, Cebutid, Ceclonac, Ceex, CEL2000, Celact, Celbexx, Celcox, Celebiox, Celebrex, Celebrin, Celecox, celecoxib, Celedol, Celestone, Celevex, Celex, CELG4, Cell adhesion molecule antagonists, CellCept, Cellmune, Celosti, Celoxib, Celprot, Celudex, cenicriviroc mesylate, cenplace1-1, CEP11004, CEP37247, CEP37248, Cephyr, Ceprofen, Certican, certolizumab pegol, Cetofenid, Cetoprofeno, cetylpyridinium chloride, CF101, CF402, CF502, CG57008, CGEN15001, CGEN15021, CGEN15051, CGEN15091, CGEN25017, CGEN25068, CGEN40, CGEN54, CGEN768, CGEN855, CGI1746, CGI560, CGI676, Cgtx-Peptides, CH1504, CH4051, CH4446, chaperonin 10, chemokine C—C motif ligand 2, chemokine C—C motif ligand 2 antibody, chemokine C—C motif ligand 5 antibody, chemokine C—C motif receptor 2 antibody, chemokine C—C motif receptor 4 antibody, chemokine C—X—C motif ligand 10 antibody, chemokine C—X—C motif ligand 12 aptamer, Chemotaxis Inhibitor, Chillmetacin, chitinase 3-like 1, Chlocodemin, Chloquin, chlorhexidine gluconate, chloroquine phosphate, choline magnesium trisalicylate, chondroitin sulfate, Chondroscart, CHR3620, CHR4432, CHR5154, Chrysalin, Chuanxinlian, Chymapra, Chymotase, chymotrypsin, Chytmutrip, CI202, CI302, Cicloderm-C, Ciclopren, Cicporal, Cilamin, Cimzia, cinchophen, cinmetacin, cinnoxicam, Cinoderm, Cinolone-S, Cinryze, Cipcorlin, cipemastat, Cipol-N, Cipridanol, Cipzen, Citax F, Citogan, Citoken T, Civamide, CJ042794, CJ14877, c-Kit monoclonal antibody, cladribine, Clafen, Clanza, Claversal, clazakizumab, Clearoid, Clease, Clevegen, Clevian, Clidol, Clindac, Clinoril, Cliptol, Clobenate, Clobequad, clobetasol butyrate, clobetasol propionate, Clodol, clofarabine, Clofen, Clofenal LP, Clolar, Clonac, Clongamma, clonixin lysine, Clotasoce, Clovacort, Clovana, Cloxin, CLT001, CLT008, C-MAF Inhibitor, CMPX1023, Cnac, CND0201, CNI1493, CNTO136, CNTO148, CNT01959, Cobefen, CoBenCoDerm, Cobix, Cofenac, Cofenac, COG241, COL179, colchicine, Colchicum Dispert, Colchimax, Colcibra, Coledes A, Colesol, Colifoam, Colirest, collagen, type V, Comcort, complement component (3b/4b) receptor 1, Complement Component C1s Inhibitors, complement component C3, complement factor 5a receptor antibody, complement factor 5a receptor antibody, complement factor D antibody, Condrosulf, Condrotec, Condrothin, conestat alfa, connective tissue growth factor antibody, Coolpan, Copaxone, Copiron, Cordefla, Corhydron, Cort S, Cortan, Cortate, Cort-Dome, Cortecetine, Cortef, Corteroid, Corticap, Corticas, Cortic-DS, corticotropin, Cortiderm, Cortidex, Cortiflam, Cortinet M, Cortinil, Cortipyren B, Cortiran, Cortis, Cortisolu, cortisone acetate, Cortival, Cortone acetate, Cortopin, Cortoral, Cortril, Cortypiren, Cosamine, Cosone, cosyntropin, COT Kinase Inhibitor, Cotilam, Cotrisone, Cotson, Covox, Cox B, COX-2/5-LO Inhibitors, Coxeton, Coxflam, Coxicam, Coxitor, Coxtral, Coxypar, CP195543, CP412245, CP424174, CP461, CP629933, CP690550, CP751871, CPSI2364, C-quin, CR039, CR074, CR106, CRA102, CRAC channel inhibitor, CRACM Ion Channel Inhibitor, Cratisone, CRB15, CRC4273, CRC4342, C-reactive protein 2-methoxyethyl phosphorothioate oligonucleotide, CreaVax-RA, CRH modulators, critic-aid, Crocam, Crohnsvax, Cromoglycic acid, cromolyn sodium, Cronocorteroid, Cronodicasone, CRTX803, CRx119, CRx139, CRx150, CS502, CS670, CS706, CSF1R Kinase Inhibitors, CSL324, CSL718, CSL742, CT112, CT1501R, CT200, CT2008, CT2009, CT3, CT335, CT340, CT5357, CT637, CTP05, CTP10, CT-P13, CTP17, Cuprenil, Cuprimine, Cuprindo, Cupripen, Curaquin, Cutfen, CWF0808, CWP271, CX1020, CX1030, CX1040, CX5011, Cx611, Cx621, Cx911, CXC chemokine receptor 4 antibody, CXCL13 antibodies, CXCR3 antagonists, CXCR4 antagonist, Cyathus 1104 B, Cyclo-2, Cyclocort, cyclooxygenase-2 inhibitor, cyclophosphamide, Cyclorine, Cyclosporin A Prodrug, Cyclosporin analogue A, cyclosporine, Cyrevia, Cyrin CLARIS, CYT007TNFQb, CYT013IL1bQb, CYT015IL17Qb, CYTO20TNFQb, CYT107, CYT387, CYT99007, cytokine inhibitors, Cytopan, Cytoreg, CZC24832, D1927, D9421C, daclizumab, danazol, Danilase, Dantes, Danzen, dapsone, Dase-D, Daypro, Daypro Alta, Dayrun, Dazen, DB295, DBTP2, D-Cort, DD1, DD3, DE096, DE098, Debio0406, Debio0512, Debio0615, Debio0618, Debio1036, Decaderm, Decadrale, Decadron, Decadronal, Decalon, Decan, Decason, Decdan, Decilone, Declophen, Decopen, Decorex, Decorten, Dedema, Dedron, Deexa, Defcort, De-flam, Deflamat, Deflan, Deflanil, Deflaren, Deflaz, deflazacort, Defnac, Defnalone, Defnil, Defosalic, Defsure, Defza, Dehydrocortison, Dekort, Delagil, delcasertib, delmitide, Delphicort, Deltacorsolone, Deltacortril, Deltafluorene, Deltasolone, Deltasone, Deltastab, Deltonin, Demarin, Demisone, Denebola, denileukin diftitox, denosumab, Denzo, Depocortin, Depo-medrol, Depomethotrexate, Depopred, Deposet, Depyrin, Derinase, Dermol, Dermolar, Dermonate, Dermosone, Dersone, Desketo, desonide, desoxycorticosterone acetate, Deswon, Dexa, Dexabene, Dexacip, Dexacort, Dexacortisone, Dexacotisil, Dexadic, Dexadrin, Dexadron, Dexafar, Dexahil, Dexalab, Dexalaf, Dexalet, Dexalgen, Dexallion, Dexalocal, Dexalone, Dexa-M, Dexamecortin, Dexamed, Dexamedis, Dexameral, Dexameta, Dexamethasone, dexamethasone acetate, dexamethasone palmitate, dexamethasone phosphate, dexamethasone sodium metasulfobenzoate, dexamethasone sodium phosphate, Dexamine, Dexapanthen, Dexa-S, Dexason, Dexatab, Dexatopic, Dexaval, Dexaven, Dexazolidin, Dexazona, Dexazone, Dexcor, Dexibu, dexibuprofen, Dexico, Dexifen, Deximune, dexketoprofen, dexketoprofen trometamol, Dexmark, Dexomet, Dexon I, Dexonalin, Dexonex, Dexony, Dexoptifen, Dexpin, Dextan-Plus, dextran sulfate, Dezacor, Dfz, diacerein, Diannexin, Diastone, Dicarol, Dicasone, Dicknol, Diclo, Diclobon, Diclobonse, Diclobonzox, Diclofast, Diclofen, diclofenac, diclofenac beta-dimethylaminoethanol, diclofenac deanol, diclofenac diethylamine, diclofenac epolamine, diclofenac potassium, diclofenac resinate, diclofenac sodium, Diclogen AGIO, Diclogen Plus, Diclokim, Diclomed, Diclo-NA, Diclonac, Dicloramin, Dicloran, Dicloreum, Diclorism, Diclotec, Diclovit, Diclowal, Diclozem, Dico P, Dicofen, Dicoliv, Dicorsone, Dicron, Dicser, Difena, Diffutab, diflunisal, dilmapimod, Dilora, dimethyl sulfone, Dinac, D-Indomethacin, Dioxaflex Protect, Dipagesic, Dipenopen, Dipexin, Dipro AS, Diprobeta, Diprobetasone, Diproklenat, Dipromet, Dipronova, Diprosone, Diprovate, Diproxen, Disarmin, Diser, Disopain, Dispain, Dispercam, Distamine, Dizox, DLT303, DLT404, DM199, DM99, DMI9523, dnaJP1, DNX02070, DNX04042, DNX2000, DNX4000, docosanol, Docz-6, Dolamide, Dolaren, Dolchis, Dolex, Dolflam, Dolfre, Dolgit, Dolmax, Dolmina, Dolo Ketazon, Dolobest, Dolobid, Doloc, Dolocam, Dolocartigen, Dolofit, Dolokind, Dolomed, Dolonac, Dolonex, Dolotren, Dolozen, Dolquine, Dom0100, Dom0400, Dom0800, Domet, Dometon, Dominadol, Dongipap, Donica, Dontisanin, doramapimod, Dorixina Relax, Dormelox, Dorzine Plus, Doxatar, Doxtran, DP NEC, DP4577, DP50, DP6221, D-Penamine, DPIV/APN Inhibitors, DR1 Inhibitors, DR4 Inhibitors, DRA161, DRA162, Drenex, DRF4848, DRL15725, Drossadin, DSP, Duexis, Duo-Decadron, Duoflex, Duonase, DV1079, DV1179, DWJ425, DWP422, Dymol, DYN15, Dynapar, Dysmen, E5090, E6070, Easy Dayz, Ebetrexat, EBI007, ECO286, EC0565, EC0746, Ecax, *Echinacea purpurea* extract, EC-Naprosyn, Econac, Ecosprin 300, Ecosprin 300, Ecridoxan, eculizumab, Edecam, efalizumab, Efcortesol, Effigel, Eflagen, Efridol, EGFR Antibody, EGS21, eIF5A1 siRNA, Ekarzin, elafin, Eldoflam, Elidel, Eliflam, Elisone, Elmes, Elmetacin, ELND001, ELND004, elocalcitol, Elocom, elsibucol, Emanzen, Emcort, Emifen, Emifenac, emorfazone, Empynase, emricasan, Emtor, Enable, Enbrel, Enceid, EncorStat, Encortolon, Encorton, Endase, Endogesic, Endoxan, Enkorten, Ensera, Entocort, Enzylan, Epanova, Eparang, Epatec, Epicotil, epidermal growth factor receptor 2 antibody, epidermal growth factor receptor antibody, Epidixone, Epidron, Epiklin, EPPA1, epratuzumab, EquiO, Erac, Erazon, ERB041, ERB196, Erdon, EryDex, *Escherichia coli* enterotoxin B subunit, Escin, E-Selectin Antagonists, Esfenac, ESN603, esonarimod, Esprofen, estetrol, Estopein, Estrogen Receptor beta agonist, etanercept, etaracizumab, ETC001, ethanol propolis extract, ETI511, etiprednol dicloacetate, Etodin, Etodine, Etodol, etodolac, Etody, etofenamate, Etol Fort, Etolac, Etopin, etoricoxib, Etorix, Etosafe, Etova, Etozox, Etura, Eucob, Eufans, eukaryotic translation initiation factor 5A oligonucleotide, Eunac, Eurocox, Eurogesic, everolimus, Evinopon, EVT401, Exaflam, EXEL9953, Exicort, Expen, Extra Feverlet, Extrapan, Extrauma, Exudase, F16, F991, Falcam, Falcol, Falzy, Farbovil, Farcometacin, Farnerate, Farnezone, Farnezone, Farotrin, fas antibody, Fastflam, FasTRACK, Fastum, Fauldmetro, FcgammaRIA antibody, FE301, Febrofen, Febrofid, felbinac, Feldene, Feldex, Feloran, Felxicam, Fenac, Fenacop, Fenadol, Fenaflan, Fenamic, Fenaren, Fenaton, Fenbid, fenbufen, Fengshi Gutong, Fenicort, Fenopine, fenoprofen calcium, Fenopron, Fenris, Fensupp, Fenxicam, fepradinol, Ferovisc, Feverlet, fezakinumab, FG3019, FHT401, FHTCT4, FID114657, figitumumab, Filexi, filgrastim, Fillase, Final, Findoxin, fingolimod hydrochloride, firategrast, Firdapse, Fisiodar, Fivasa, FK778, Flacoxto, Fladalgin, Flagon, Flamar, Flamcid, Flamfort, Flamide, Flaminase, Flamirex Gesic, Flanid, Flanzen, Flaren, Flaren, Flash Act, Flavonoid Anti-inflammatory Molecule, Flebogamma DIF, Flenac, Flex, Flexafen 400, Flexi, Flexidol, Flexium, Flexon, Flexono, Flogene, Flogiatrin B12, Flogomin, Flogoral, Flogosan, Flogoter, Flo-Pred, Flosteron, Flotrip Forte, Flt3 inhibitors, fluasterone, Flucam, Flucinar, fludrocortisone acetate, flufenamate aluminum, flumethasone, Flumidon, flunixin, fluocinolone, fluocinolone acetonide, fluocinonide, fluocortolone, Fluonid, fluorometholone, Flur, flurbiprofen, Fluribec, Flurometholone, Flutal, fluticasone, fluticasone propionate, Flutizone, Fluzone, FM101 antibody, fms-related tyrosine kinase 1 antibody, Folitrax, fontolizumab, formic acid, Fortecortin, Fospeg, fostamatinib disodium, FP1069, FP13XX, FPA008, FPA031, FPT025, FR104, FR167653, Framebin, Frime, Froben, Frolix, FROUNT Inhibitors, Fubifen PAP, Fucole ibuprofen, Fulamotol, Fulpen, Fungifin, Furotalgin, fusidate sodium, FX002, FX141L, FX201, FX300, FX87L, Galectin modulators, gallium maltolate, Gamimune N, Gammagard, Gamma-LV., GammaQuin, Gamma-Venin, Gamunex, Garzen, Gaspirin, Gattex, GBR500, GBR500 antibody, GBT009, G-CSF, GED0301, GED0414, Gefenec, Gelofen, Genepril, Gengraf, Genimune, Geniquin, Genotropin, Genz29155, Gerbin, Gerbin, gevokizumab, GF01564600, Gilenia, Gilenya, givinostat, GL0050, GL2045, glatiramer acetate, Globulin, Glortho Forte, Glovalox, Glovenin-I, GLPG0259, GLPG0555, GLPG0634, GLPG0778, GLPG0974, Gluco, Glucocerin, glucosamine, glucosamine hydrochloride, glucosamine sulfate, Glucotin, Gludex, Glutilage, GLY079, GLY145, Glycanic, Glycefort up, Glygesic, Glysopep, GMCSF Antibody, GMI1010, GMI1011, GMI1043, GMR321, GN4001, Goanna Salve, Goflex, gold sodium thiomalate, golimumab, GP2013, GPCR modulator, GPR15 Antagonist, GPR183 antagonist, GPR32 antagonist, GPR83 antagonist, G-protein Coupled Receptor Antagonists, Graceptor, Graftac, granulocyte colony-stimulating factor antibody, granulocyte-macrophage colony-stimulating factor antibody, Gravx, GRC4039, Grelyse, GS101, GS9973, GSC100, GSK1605786, GSK1827771, GSK2136525, GSK2941266, GSK315234, GSK681323, GT146, GT442, Gucixiaotong, Gufisera, Gupisone, gusperimus hydrochloride, GW274150, GW3333, GW406381, GW856553, GWB78, GXP04, Gynestrel, Haloart, halopredone acetate, Haloxin, HANALL, Hanall Soludacortin, Havisco, Hawon Bucillamin, HB802, HC31496, HCQ 200, HD104, HD203, HD205, HDAC inhibitor, HE2500, HE3177, HE3413, Hecoria, Hectomitacin, Hefasolon, Helen, Helenil, HemaMax, Hematom, hematopoietic stem cells, Hematrol, Hemner, Hemril, heparinoid, Heptax, HER2 Antibody, Herponil, hESC Derived Dendritic Cells, hESC Derived Hematopoietic stem cells, Hespercorbin, Hexacorton, Hexadrol, hexetidine, Hexoderm, Hexoderm Salic, HF0220, HF1020, HFT-401, hG-CSFR ED Fc, Hibema, high mobility group box 1 antibody, Hiloneed, Hinocam, hirudin, Hirudoid, Hison, Histamine H4 Receptor Antagonist, Hitenercept, Hizentra, HL036, HL161, HMPL001, HMPL004, HMPL004, HMPL011, HMPL342, HMPL692, honey bee venom, Hongqiang, Hotemin, HPH116, HTI101, HuCAL Antibody, Human adipose mesenchymal stem cells, anti-MHC class II monoclonal antibody, Human Immunoglobulin, Human Placenta Tissue Hydrolysate, HuMaxCD4, HuMax-TAC, Humetone, Humicade, Humira, Huons Betamethasone sodium phosphate, Huons dexamethasone sodium phosphate, Huons Piroxicam, Huons Talniflumate, Hurofen, Huruma, Huvap, HuZAF, HX02, Hyalogel, hyaluronate sodium, hyaluronic acid, hyaluronidase, Hy aron, Hy cocin, Hy cort, Hy-Cortisone, hydrocortisone, hydrocortisone acetate, hydrocortisone butyrate, hydrocortisone hemisuccinate, hydrocortisone sodium phosphate, hydrocortisone sodium succinate, Hydrocortistab, Hydrocortone, Hydrolin, Hydroquine, Hydro-Rx, Hydrosone HIKMA, hydroxychloroquine, hydroxychloroquine sulfate, Hylase Dessau, HyMEX, Hypen, HyQ, Hysonate, HZN602, I.M.75, IAP Inhibitors, Ibalgin, Ibalgin, Ibex, ibrutinib, IBsolvMIR, Ibu, Ibucon, Ibudolor, Ibufen, Ibuflam, Ibuflex, Ibugesic, Ibu-Hepa, Ibukim, Ibumal, Ibunal, Ibupental, Ibupril, Ibuprof, ibuprofen, Ibuscent, Ibusoft, Ibusuki Penjeong, Ibususpen, Ibutard, Ibutop, Ibutop, Ibutrex, IC487892, ichthammol, ICRAC Blocker, IDEC131, IDECCE9.1, Ides, Idicin, Idizone, IDN6556, Idomethine, IDR1, Idyl SR, Ifen, iguratimod, IK6002, IKK-beta inhibitor, IL17 Antagonist, IL-17 Inhibitor, IL-17RC, IL18, IL1Hy1, IL1R1, IL-23 Adnectin, IL23 Inhibitor, IL23 Receptor Antagonist, IL-31 mAb, IL-6 Inhibitor, IL6Qb, Ilacox, Ilaris, ilodecakin, ILV094, ILV095, Imaxetil, IMD0560, IMD2560, Imesel Plus, Iminoral, Immodin, IMMU103, IMMU106, Immucept, Immufine, Immunex Syrup, immunoglobulin, immunoglobulin G, Immunoprin, ImmunoRel, Immurin, IMO8400, IMP731 antibody, Implanta, Imunocell, Imuran, Imurek, Imusafe, Imusporin, Imutrex, IN0701, Inal, INCB039110, INCB18424, INCB28050, INCB3284, INCB3344, Indexon, Indic, Indo, Indo-A, Indobid, Indo-Bros, Indocaf, Indocarsil, Indocid, Indocin, Indomehotpas, Indomen, Indomet, Indometacin, indomethacin, Indomethasone, Indometin, Indomin, Indopal, Indoron, Indotroxin, INDUS830, INDUS83030, Infladase, Inflamac, Inflammasome inhibitor, Inflavis, Inflaxen, Inflectra, infliximab, Ingalipt, Inicox dp, Inmecin, Inmunoartro, Innamit, InnoD06006, IN07997, Inocin, Inoten, Inovan, Inpra, Inside Pap, Insider-P, Instacyl, Instracool, Intafenac, Intaflam, Inteban, Inteban Spansule, integrin, alpha 1 antibody, integrin, alpha 2 antibody, Intenurse, interferon alfa, interferon beta-1a, interferon gamma, interferon gamma antibody, Interking, interleukin 1 Hy1, interleukin 1 antibody, interleukin 1 receptor antibody, interleukin 1, beta antibody, interleukin 10, interleukin 10 antibody, interleukin 12, interleukin 12 antibody, interleukin 13 antibody, interleukin 15 antibody, interleukin 17 antibody, interleukin 17 receptor C, interleukin 18, interleukin 18 binding protein, interleukin 18 antibody, interleukin 2 receptor, alpha antibody, interleukin 20 antibody, Interleukin 21 mAb, interleukin 23 aptamer, interleukin 31 antibody, interleukin 34, Interleukin 6 Inhibitor, interleukin 6 antibody, interleukin 6 receptor antibody, interleukin 7, interleukin 7 receptor antibody, interleukin 8, interleukin 8 antibody, interleukin-18 antibody, Intidrol, Intradex, Intragam P, Intragesic, Intraglobin F, Intratect, Inzel, Iomab B, IOR-T3, IP751, IPH2201, IPH2301, IPH24, IPH33, IPI145, Ipocort, IPP201007, I-Profen, Iprox, Ipson, Iputon, IRAK4 Inhibitor, Iremod, Irtonpyson, IRX3, IRX5183, ISA247, ISIS104838, ISIS2302, ISISCRPRx, Ismafron, IsoQC inhibitor, Isox, ITF2357, Iveegam EN, Ivepred, IVIG-SN, IW001, Izilox, J607Y, J775Y, JAK Inhibitor, JAK3 inhibitor, JAK3 kinase inhibitor, JI3292, JI4135, Jinan Lida, JNJ10329670, JNJ18003414, JNJ26528398, JNJ27390467, JNJ28838017, JNJ31001958, JNJ38518168, JNJ39758979, JNJ40346527, JNJ7777120, JNT-Plus, Joflam, Joint Glucosamin, Jointec, Jointstem, Joinup, JPE1375, JSM10292, JSM7717, JSM8757, JTE051, JTE052, JTE522, JTE607, Jusgo, K412, K832, Kaflam, KAHR101, KAHR102, KAI9803, Kalymin, Kam Predsol, Kameton, KANAb071, Kappaproct, KAR2581, KAR3000, KAR3166, KAR4000, KAR4139, KAR4141, KB002, KB003, KD7332, KE298, keliximab, Kemanat, Kemrox, Kenacort, Kenalog, Kenaxir, Kenketsu Venoglobulin-IH, Keplat, Ketalgipan, Keto Pine, Keto, Ketobos, Ketofan, Ketofen, Ketolgan, Ketonal, Ketoplus Kata Plasma, ketoprofen, Ketores, Ketorin, ketorolac, ketorolac trometh-amine, Ketoselect, Ketotop, Ketovail, Ketricin, Ketroc, Ketum, Keyi, Keyven, KF24345, K-Fenac, K-Fenak, K-Gesic, Kifadene, Kilcort, Kildrol, KIM127, Kimotab, Kinase Inhibitor 4SC, Kinase N, Kincort, Kindorase, Kineret, Kineto, Kitadol, Kitex, Kitolac, KLK1 Inhibitor, Klofen-L, Klotaren, KLS-40or, KLS-40ra, KM277, Knavon, Kodolo orabase, Kohakusanin, Koide, Koidexa, Kolbet, Konac, Kondro, Kondromin, Konshien, Kontab, Kordexa, Kosa, Kotase, KPE06001, KRP107, KRP203, KRX211, KRX252, KSB302, K-Sep, Kv 1.3 Blocker, Kv1.3 4SC, Kv1.3 inhibitor, KVK702, Kynol, L156602, Labizone, Labohydro, Labopen, Lacoxa, Lamin, Lamit, Lanfetil, laquinimod, larazotide acetate, LAS186323, LAS187247, LAS41002, Laticort, LBEC0101, LCP3301, LCP-Siro, LCP-Tacro, LCsA, LDP392, Leap-S, Ledercort, Lederfen, Lederlon, Lederspan, Lefenine, leflunomide, Leflux, Lefno, Lefra, Leftose, Lefumide, Lefunodin, Lefva, lenalidomide, lenercept, LentiRA, LE015520, Leodase, Leukine, Leukocyte function-associated antigen-1 antagonist, leukocyte immunoglobulin-like receptor, subfamily A, member 4 antibody, Leukothera, leuprolide acetate, levalbuterol, levomenthol, LFA-1 Antagonist, LFA451, LFA703, LFA878, LG106, LG267 Inhibitors, LG688 Inhibitors, LGD5552, Li Life, LidaMantle, Lidex, lidocaine, lidocaine hydrochloride, Lignocaine hydrochloride, LIM0723, LIM5310, Limethason, Limus, Limustin, Lindac, Linfonex, Linola acute, Lipcy, lisofylline, Listran, Liver X Receptor modulator, Lizak, LP1207, LJP920, Lobafen, Lobu, Locafluo, Localyn, Locaseptil-Neo, Locpren, Lodine, Lodotra, Lofedic, Loflam, Lofnac, Lolcam, Lonac, lonazolac calcium, Loprofen, Loracort, Lorcam, Lorfenamin, Lorinden Lotio, Lomcrat, lornoxicam, Lorox, losmapimod, loteprednol etabonate, Loteprednol, Lotirac, Low Molecular Ganoderma Lucidum Polysaccharide, Loxafen, Loxfenine, Loxicam, Loxofen, Loxonal, Loxonin, loxoprofen sodium, Loxoron, LP183A1, LP183A2, LP204A1, LPCN1019, LT1942, LT1964, LTNS101, LTNS103, LTNS106, LTNS108, LTS1115, LTZMP001, Lubor, lumiracoxib, Lumitect, LX2311, LX2931, LX2932, LY2127399, LY2189102, LY2439821, LY294002, LY3009104, LY309887, LY333013, lymphocyte activation gene 3 antibody, Lymphoglobuline, Lyser, lysine aspirin, Lysobact, Lysoflam, Lysozyme hydrochloride, M3000, M834, M923, mAb hG-CSF, MABP1, macrophage migration inhibitory factor antibody, Maitongna, Majamil prolongatum, major histocompatibility complex class II DR antibody, major histocompatibility complex class II antibody, Malidens, Malival, mannan-binding lectin, mannan-binding lectin-associated serine protease-2 antibody, Map-Kap Kinase 2 Inhibitor, maraviroc, Marlex, masitinib, Maso, MASP2 antibody, MAT304, Matrix Metalloprotease Inhibitor, mavrilimumab, Maxiflam, Maxilase, Maximus, Maxisona, Maxius, Maxpro, Maxrel, Maxsulid, Maxy12, Maxy30, MAXY4, Maxy735, Maxy740, Mayfenamic, MB11040, MBPY003b, MCAF5352A, McCam, McRofy, MCS18, MD707, MDAM, MDcort, MDR06155, MDT012, Mebicam, Mebuton, meclofenamate sodium, Meclophen, Mecox, Medacomb, Medafen, Medamol, Medesone, MEDI2070, MEDI5117, MEDI541, MEDI552, MEDI571, Medicox, Medifen, Medisolu, Medixon, Mednisol, Medrol, Medrolon, medroxyprogesterone acetate, Mefalgin, mefenamic acid, Mefenix, Mefentan, Meflen, Mefnetra forte, Meftagesic-DT, Meftal, Megakaryocyte Growth and Development Factor, Megaspas, Megaster, megestrol acetate, Meite, Meksun, Melbrex, Melcam, Melcam, Melflam, Melic, Melica, Melix, Melocam, Melocox, Mel-One, Meloprol, Melosteral, Melox, Meloxan, Meloxcam, Meloxic, Meloxicam, Meloxifen, Meloxin, Meloxiv, Melpred, Melpros, Melurjin, Menamin, Menisone, Menthomketo, Menthoneurin, Mentocin, Mepa, Mepharen, meprednisone, Mepresso, Mepsolone, mercaptopurine, Mervan, Mesadoron, mesalamine, Mesasal, Mesatec, Mesenchymal Precursor Cells, mesenchymal stem cell, Mesipol, Mesren, Mesulan, Mesulid, Metacin, Metadaxan, Metaflex, Metalcaptase, metalloenzyme inhibitors, Metapred, Metax, Metaz, Meted, Metedic, Methacin, Methaderm, Methasone, Methotrax, methotrexate, methotrexate sodium, Methpred, Methyl prednisolone acetate, methyl salicylate, methyl sulphonyl methane, Methylon, Methylpred, methylprednisolone, methylprednisolone acetate, methylprednisolone sodium succinate, methylprednisolone succinate, Methylprednisolone, Methysol, Metindol, Metoart, Metoject, Metolate, Metoral, Metosyn, Metotab, Metracin, Metrex, metronidazole, Metypred, Mevamox, Mevedal, Mevilox, Mevin SR, Mexilal, Mexpharm, Mext, Mextran, MF280, M-FasL, MHC class II beta chain peptide, Micar, Miclofen, Miclofenac, Micofenolato Mofetil, Micosone, Microdase, microRNA 181a-2 oligonucleotide, MIF Inhibitors, MIFQb, MIKA-Ketoprofen, Mikametan, milodistim, Miltax, Minafen, Minalfen, Minalfene, Minesulin, Minocort, Mioflex, Miolox, Miprofen, Miridacin, Mirloks, Misoclo, Misofenac, MISTB03, MISTB04, Mitilor, mizoribine, MK0359, MK0812, MK0873, MK2 Inhibitors, MK50, MK8457, MK8808, MKC204, MLN0002, MLN0415, MLN1202, MLN273, MLN3126, MLN3701, MLN3897, MLNM002, MM093, MM7XX, MN8001, Mobic, Mobicam, Mobicox, Mobifen Plus, Mobilat, Mobitil, Mocox, Modigraf, Modrasone, Modulin, Mofecept, Mofetyl, mofezolac sodium, Mofilet, Molace, molgramostim, Molslide, Momekin, Momen Gele, Moment 100, Momesone, Momesun, Mometamed, mometasone, mometasone furoate, Monimate, monosodium alpha-luminol, Mopik, MOR103, MOR104, MOR105, MOR208 antibody, MORAb022, Moricam, morniflumate, Mosuolit, Motoral, Movaxin, Mover, Movex, Movix, Movoxicam, Mox Forte, Moxen, moxifloxacin hydrochloride, Mozobil, MP, MP0210, MP0270, MP1000, MP1031, MP196, MP435, MPA, mPGES-1 inhibitor, MPSS, MRX7EAT, MSL, MT203, MT204, mTOR Inhibitor, MTRX1011A, Mucolase, Multicort, MultiStem, muramidase, muramidase, muramidase hydrochloride, muromonab-CD3, Muslax, Muspinil, Mutaze, Muvera, MX68, Mycept, Mycocell, Mycocept, Mycofenolatmofetil Actavis, Mycofet, Mycofit, Mycolate, My col dos a, My comun, My conol, mycophenolate mofetil, mycophenolate sodium, mycophenolic acid, Mycotil, myeloid progenitor cells, Myfenax, Myfetil, Myfortic, Mygraft, Myochrysine, Myocrisin, Myprodol, Mysone, nab-Cyclosporine, Nabentac, nabiximols, Nabton, Nabuco, Nabucox, Nabuflam, Nabumet, nabumetone, Nabuton, Nac Plus, Nacta, Nacton, Nadium, Naklofen SR, NAL1207, NAL1216, NAL1219, NAL1268, NAL8202, Nalfon, Nalgesin S, namilumab, Namsafe, nandrolone, Nanocort, Nanogam, Nanosomal Tacrolimus, Napageln, Napilac, Naprelan, Napro, Naprodil, Napronax, Napropal, Naproson, Naprosyn, Naproval, Naprox, naproxen, naproxen sodium, Naproxin, Naprozen, Narbon, Narexsin, Naril, Nasida, natalizumab, Naxdom, Naxen, Naxin, Nazovel, NC2300, ND07, NDC01352, Nebumetone, NecLipGCSF, Necsulide, Necsunim, Nelsid-S, Neo Clobenate, Neo Swiflox FC, Neocoflan, Neo-Drol, Neo-Eblimon, Neo-Hydro, Neoplanta, Neoporine, Neopreol, Neoprox, Neoral, Neotrexate, Neozen, Nepra, Nestacort, Neumega, Neupogen, Neuprex, Neurofenac, Neurogesic, Neurolab, Neuroteradol, Neuroxicam, Neutalin, neutrazumab, Neuzym, New Panazox, Newfenstop, NewGam, Newmafen, Newmatal, Newsicam, NEX1285, sFcRIIB, Nextomab, NF-kappaB Inhibitor, NF-kB inhibitor, NGD20001, NHP554B, NHP554P, NI0101 antibody, NI0401, NI0501 antibody, NI0701, NI071, NI1201 antibody, NI1401, Nicip, Niconas, Nicool, NiCord, Nicox, Niflumate, Nigaz, Nikam, Nilitis, Nimace, Nimaid, Nimark-P, Nimaz, Nimcet Juicy, Nime, Nimed, Nimepast, nimesulide, Nimesulix, Nimesulon, Nimica Plus, Nimkul, Nimlin, Nimnat, Nimodol, Nimpidase, Nimsaid-S, Nimser, Nimsy-SP, Nimupep, Nimusol, Nimutal, Nimuwin, Nimvon-S, Nincort, Niofen, Nipan, Nipent, Nise, Nisolone, Nisopred, Nisoprex, Nisulid, nitazoxanide, Nitcon, nitric oxide, Nizhvisal B, Nizon, NL, NMR1947, NN8209, NN8210, NN8226, NN8555, NN8765, NN8828, NNC014100000100, NNC051869, Noak, Nodevex, Nodia, Nofenac, Noflagma, Noflam, Noflamen, Noflux, Non-antibacterial Tetracyclines, Nonpiron, Nopain, Normferon, Notpel, Notritis, Novacort, Novagent, Novarin, Novigesic, NOXA12, NOXD19, Noxen, Noxon, NPI1302a-3, NPI1342, NPI1387, NPI1390, NPRCS1, NPRCS2, NPRCS3, NPRCS4, NPRCS5, NPRCS6, NPS3, NPS4, nPT-ery, NU3450, nuclear factor NF-kappa-B p65 subunit oligonucleotide, Nucort, Nulojix, Numed-Plus, Nurokind Ortho, Nusone-H, Nutrikemia, Nuvion, NVO7alpha, NX001, Nyclobate, Nyox, Nysa, Obarcort, 00002417, OC2286, ocaratuzumab, OCTSG815, Oedemase, Oedemase-D, ofatumumab, Ofgyl-O, Ofvista, OHR118, OKi, Okifen, Oksamen, Olai, olokizumab, Omeprose E, Omnacortil, Omneed, Omniclor, Omnigel, Omniwel, onercept, ONO4057, ONS1210, ONS1220, Ontac Plus, Ontak, ONX0914, OPC6535, opebacan, OPN101, OPN201, OPN302, OPN305, OPN401, oprelvekin, OPT66, Optifer, Optiflur, OptiMIRA, Orabase Hca, Oradexon, Oraflex, OralFenac, Oralog, Oralpred, Ora-sed, Orasone, orBec, Orbone forte, Orcl, ORE10002, ORE10002, Orencia, Org214007, Org217993, Org219517, Org223119, Org37663, Org39141, Org48762, Org48775, Orgadrone, Ormoxen, Orofen Plus, Oromylase Biogaran, Orthal Forte, Ortho Flex, Orthoclone OKT3, Orthofen, Orthoflam, Orthogesic, Orthoglu, Ortho-II, Orthomac, Ortho-Plus, Ortinims, Ortofen, Orudis, Oruvail, OS2, Oscart, Osmetone, Ospain, Ossilife, Ostelox, Osteluc, Osteocerin, osteopontin, Osteral, otelixizumab, Otipax, Ou Ning, OvaSave, OX40 Ligand Antibody, Oxa, Oxagesic CB, Oxalgin DP, oxaprozin, OXCQ, Oxeno, Oxib MD, Oxibut, Oxicam, Oxiklorin, Oximal, Oxynal, oxyphenbutazone, Oxyphenbutazone, ozoralizumab, P13 peptide, P1639, P21, P2X7 Antagonists, p38 Alpha Inhibitor, p38 Antagonist, p38 MAP kinase inhibitor, p38alpha MAP Kinase Inhibitor, P7 peptide, P7170, P979, PA401, PA517, Pabi-dexamethasone, PAC, PAC10649, paclitaxel, Painoxam, Paldon, Palima, pamapimod, Pamatase, Panafcort, Panafcortelone, Panewin, PanGraf, Panimun Bioral, Panmesone, Panodin SR, Panslay, Panzem, Panzem NCD, PAP1, papain, Papirzin, Pappen K Pap, Paptinim-D, paquinimod, PAR2 Antagonist, Paracetamol, Paradic, Parafen TAJ, Paramidin, Paranac, Parapar, Parci, parecoxib, Parixam, Parry-S, Partaject Busulfan, pateclizumab, Paxceed, PBI0032, PBI1101, PBI1308, PBI1393, PBI1607, PBI1737, PBI2856, PBI4419, PBI4419, P-Cam, PCI31523, PCI32765, PCI34051, PCI45261, PCI45292, PCI45308, PD360324, PD360324, PDA001, PDE4 inhibitor, PDE-IV Inhibitor, PDL241 antibody, PDL252, Pediapred, Pefree, pegacaristim, Peganix, Peg-Interleukin 12, pegsunercept, Pegsunercept, PEGylated arginine deiminase, peldesine, pelubiprofen, Penacle, penicillamine, Penostop, Pentalgin, Pentasa, Pentaud, pentostatin, Peon, Pepdase, Pepser, Peptirase, Pepzen, Pepzol, Percutalgine, Periochip, Peroxisome Proliferator Activated Receptor gamma modulators, Petizene, PF00344600, PF04171327, PF04236921, PF04308515, PF05230905, PF05280586, PF251802, PF3475952, PF3491390, PF3644022, PF4629991, PF4856880, PF5212367, PF5230896, PF547659, PF755616, PF9184, PG27, PG562, PG760564, PG8395, PGE3935199, PGE527667, PHS, PH797804, PHA408, Pharmaniaga Mefenamic acid, Pharmaniaga Meloxicam, Pheldin, Phenocept, phenylbutazone, PHY702, PI3K delta inhibitor, PI3K Gamma/Delta Inhibitor, PI3K Inhibitor, Picalm, pidotimod, piketoprofen, Pilelife, Pilopil, Pilovate, pimecrolimus, Pipethanen, Piractam, Pirexyl, Pirobet, Piroc, Pirocam, Pirofel, Pirogel, Piromed, Pirosol, Pirox, Piroxen, Piroxicam, piroxicam betadex, Piroxifar, Piroxil, Piroxim, Pixim, Pixykine, PKC Theta Inhibitor, PL3100, PL5100 Diclofenac, Placenta Polypeptide, Plaquenil, plerixafor, Plocfen, PLR14, PLR18, Plutin, PLX3397, PLX5622, PLX647, PLX-BMT, pms-Diclofenac, pms-Ibuprofen, pms-Leflunomide, pms-Meloxicam, pms-Piroxicam, pms-Prednisolone, pms-Sulfasalazine, pms-Tiaprofenic, PMX53, PN0615, PN100, PN951, podofilox, POL6326, Polcortolon, Polyderm, Polygam S/D, Polyphlogin, Poncif, Ponstan, Ponstil Forte, Porine-A Neoral, Potaba, potassium aminobenzoate, Potencort, Povidone, povidone iodine, pralnacasan, Prandin, Prebel, Precodil, Precortisyl Forte, Precortyl, Predfoam, Predicort, Predicorten, Predilab, Predilone, Predmetil, Predmix, Predna, Prednesol, Predni, prednicarbate, Prednicort, Prednidib, Prednifarma, Prednilasca, prednisolone, prednisolone acetate, prednisolone sodium phosphate, prednisolone sodium succinate, prednisolone sodium succinate, prednisone, prednisone acetate, Prednitop, Prednol-L, Prednox, Predone, Predonema, Predsol, Predsolone, Predsone, Predval, Preflam, Prelon, Prenaxol, Prenolone, Preservex, Preservin, Presol, Preson, Prexige, Priliximab, Primacort, Primmuno, Primofenac, prinaberel, Privigen, Prixam, Probuxil, Procarne, Prochymal, Procider-EF, Proctocir, Prodase, Prodel B, Prodent, Prodent Verde, Proepa, Profecom, Profenac L, Profenid, Profenol, Proflam, Proflex, Progesic Z, proglumetacin, proglumetacin maleate, Prograf, Prolase, Prolixan, promethazine hydrochloride, Promostem, Promune, PronaB, pronase, Pronat, Prongs, Pronison, Prontoflam, Propaderm-L, Propodezas, Propolisol, Proponol, propyl nicotinate, Prostaloc, Prostapol, Protacin, Protase, Protease Inhibitors, Protectan, Proteinase Activated Receptor 2 Inhibitor, Protofen, Protrin, Proxalyoc, Proxidol, Proxigel, Proxil, Proxym, Prozym, PRT062070, PRT2607, PRTX100, PRTX200, PRX106, PRX167700, Prysolone, PS031291, PS375179, PS386113, PS540446, PS608504, PS826957, PS873266, Psorid, PT, PT17, PTL101, P-Transfer Factor peptides, PTX3, Pulminiq, Pulsonid, Purazen, Pursin, PVS40200, PX101, PX106491, PX114, PXS2000, PXS2076, PYM60001, Pyralvex, Pyranim, pyrazinobutazone, Pyrenol, Pyricam, Pyrodex, Pyroxi-Kid, QAX576, Qianbobiyan, QPI1002, QR440, qT3, Quiacort, Quidofil, R107s, R125224, R1295, R132811, R1487, R1503, R1524, R1628, R333, R348, R548, R7277, R788, rabeximod, Radix Isatidis, Radofen, Raipeck, Rambazole, Randazima, Rapacan, Rapamune, Raptiva, Ravax, Rayos, RDEA119, RDEA436, RDP58, Reactine, Rebif, REC200, Recartix-DN, receptor for advanced glycation end products antibody, Reclast, Reclofen, recombinant HSA-TIMP-2, recombinant human alkaline Phosphatase, recombinant Interferon Gamma, Recominant human alkaline phosphatase, Reconil, Rectagel HC, Recticin, Recto Menaderm, Rectos, Redipred, Redolet, Refastin, Regenica, REGN88, Relafen, Relaxib, Relev, Relex, Relifen, Relifex, Relitch, Rematof, remestemcel-1, Remesulidum, Remicade, Remsima, Remsima, Remsima, ReN1869, Renacept, Renfor, Renodapt, Renodapt-S, Renta, Reosan, Repare-AR, Reparilexin, reparixin, Repertaxin, Repisprin, Resochin, Resol, resolvin E1, Resurgil, Re-tin-colloid, Retoz, Reumacap, Reumacon, Reumadolor, Reumador, Reumanisal, Reumazin, Reumel, Reumotec, Reuquinol, revamilast, Revascor, Reviroc, Revlimid, Revmoksikam, Rewalk, Rexalgan, RG2077, RG3421, RG4934 antibody, RG7416, RG7624, Rheila, Rheoma, Rheprox, Rheudenolone, Rheufen, Rheugesic, Rheumacid, Rheumacort, Rheumatrex, Rheumesser, Rheumid, Rheumon, Rheumox, Rheuoxib, Rhewlin, Rhucin, RhuDex, Rhulef, Ribox, Ribunal, Ridaura, rifaximin, rilonacept, rimacalib, Rimase, Rimate, Rimatil, Rimesid, risedronate sodium, Ritamine, Rito, Rittman, rituximab, RNS60, RO1138452, Ro313948, RO3244794, RO5310074, Rob803, Rocamix, Rocas, Rofeb, rofecoxib, Rofee, Rofewal, Roficip Plus, Rojepen, Rokam, Rolodiquim, Romacox Fort, Romatim, romazarit, Ronaben, ronacaleret, Ronoxcin, ROR Gamma T Antagonist, ROR gamma t inverse agonists, Rosecin, rosiglitazone, Rosmarinic acid, Rotan, Rotec, Rothacin, Roxam, Roxib, Roxicam, Roxopro, Roxygin DT, RP54745, RPI78, RPI78M, RPI78MN, RPIMN, RQ00000007, RQ00000008, RTA402, R-Tyflam, Rubicalm, Rubifen, Ruma pap, Rumalef, Rumidol, Rumifen, Runomex, rusalatide acetate, ruxolitinib, RWJ445380, RX10001, Rycloser MR, Rydol, SIP Receptor Agonists, SP Receptor Modulators, S1P1 Agonist, S1P1 receptor agonist, S2474, S3013, SA237, SA6541, Saaz, S-adenosyl-L-methionine-sulfate-p-toluene sulfonate, Sala, Salazidin, Salazine, Salazopyrin, Salcon, Salicam, salsalate, Sameron, SAN300, Sanaven, Sandimmun, Sandoglobulin, Sanexon, SangCya, SAR153191, SAR302503, SAR479746, Sarapep, sargramostim, Sativex, Savantac, Save, Saxizon, Sazo, SB1578, SB210396, SB217969, SB242235, SB273005, SB281832, SB683698, SB751689, SBI087, SC080036, SC12267, SC409, Scaflam, SCD ketoprofen, SCI0323, SCI0469, SD-15, SD281, SDP051 antibody, Sd-rxRNA, secukinumab, Sedase, Sedilax, Sefdene, Seizyme, SEL113, Seladin, Selecox, selectin P ligand antibody, Glucocorticoid Receptor Agonist, Selectofen, Selektine, SelK1 antibody, Seloxx, Selspot, Selzen, Selzentra, Selzentry, semapimod, semapimod hydrochloride, semparatide, Semparatide, Senafen, Sendipen, Senterlic, SEP119249, Sepdase, Septirose, Seractil, Serafen-P, Serase, Seratid D, Seratiopeptidase, Serato-M, Seratoma Forte, Serazyme, Serezon, Sero, Serodase, Serpicam, Serra, serrapeptase, Serratin, Serratiopeptidase, Serrazyme, Servisone, Seven E P, SGI1252, SGN30, SGN70, SGX203, shark cartilage extract, Sheril, Shield, Shifazen, Shifazen-Fort, Shincort, Shincort, Shiosol, ShK186, Shuanghuangxiaoyan, SI615, SI636, Sigmasporin, Sigmasporin, SIM916, Simpone, Simulect, Sinacort, Sinalgia, Sinapol, Sinatrol, Sinsia, siponimod, Sirolim, sirolimus, Siropan, Sirota, Sirova, sirukumab, Sistal Forte, SKF105685, SKF105809, SKF106615, SKF86002, Skinalar, Skynim, Skytrip, SLAM family member 7 antibody, Slo-indo, SM101, SM201 antibody, SM401, SMAD family member 7 oligonucleotide, SMART Anti-IL-12 Antibody, SMP114, SN0030908, SNO070131, sodium aurothiomalate, sodium chondroitin sulfate, sodium deoxyribonucleotide, sodium gualenate, sodium naproxen, sodium salicylate, Sodixen, Sofeo, Soleton, Solhidrol, Solicam, Soliky, Soliris, Sol-Melcort, Solomet, Solondo, Solone, Solu-Cort, Solu-Cortef, Solu-Decortin H, Solufen, Solu-Ket, Solumark, Solu-Medrol, Solupred, Somalgen, somatropin, Sonap, Sone, sonepcizumab, Sonexa, Sonim, Sonim P, Soonil, Soral, Sorenil, sotrastaurin acetate, SP-10, SP600125, Spanidin, SP-Cortil, SPD550, Spedace, sperm adhesion molecule 1, Spictol, spleen tyrosine kinase oligonucleotide, Sporin, S-prin, SPWF1501, SQ641, SQ922, SR318B, SR9025, SRT2104, SSR150106, SSR180575, SSS07 antibody, ST1959, STA5326, stabilin 1 antibody, Stacort, Stalogesic, stanozolol, Staren, Starmelox, Stedex IND-SWIFT, Stelara, Stemin, Stenirol, Sterapred, Steriderm S, Steno, Sterisone, Steron, stichodactyla helianthus peptide, Stickzenol A, Stiefcortil, Stimulan, STNM01, Store Operated Calcium Channel (SOCC) Modulator, STP432, STP900, Stratasin, Stridimmune, Strigraf, SU Medrol, Subreum, Subuton, Succicort, Succimed, Sulan, Sulcolon, Sulfasalazin Heyl, Sulfasalazin, sulfasalazine, Sulfovit, Sulidac, Sulide, sulindac, Sulindex, Sulinton, Sulphafine, Sumilu, SUN597, Suprafen, Supretic, Supsidine, Surgam, Surgamine, Surugamu, Suspen, Suton, Suvenyl, Suwei, SW Dexasone, Syk Family Kinase Inhibitor, Syn1002, Synacran, Synacthen, Synalar C, Synalar, Synavive, Synercort, Sypresta, T cell cytokine-inducing surface molecule antibody, T cell receptor antibody, T5224, T5226, TA101, TA112, TA383, TA5493, tabalumab, Tacedin, Tacgraf, TACIFc5, Tacrobell, Tacrograf, Tacrol, tacrolimus, Tadekinig alpha, Tadolak, TAFA93, Tafirol Artro, Taizen, TAK603, TAK715, TAK783, Takfa, Taksta, talarozole, Talfin, Talmain, talmapimod, Talmea, Talnif, talniflumate, Talos, Talpain, Talumat, Tamalgen, Tamceton, Tamezon, Tandrilax, tannins, Tannosynt, Tantum, tanzisertib, Tapainbeta, Tapoein, Tarenac, tarenflurbil, Tarimus, Tarproxen, Tauxib, Tazomust, TBR652, TC5619, T-cell, immune regulator 1, ATPase, H+ transporting, lysosomal V0 subunit A3 antibody, TCK1, T-cort, T-Dexa, Tecelac, Tecon, teduglutide, Teecort, Tegeline, Tementil, temoporfin, Tencam, Tendrone, Tenefuse, Tenfly, tenidap sodium, Tenocam, Tenoflex, Tenoksan, Tenotil, tenoxicam, Tenoxim, Tepadina, Teracort, Teradol, tetomilast, TG0054, TG1060, TG20, TG20, tgAAC94, Th1/Th2 Cytokine Synthase Inhibitor, Th-17 cell inhibitors, Thalido, thalidomide, Thalomid, Themisera, Thenil, Therafectin, Therapyace, thiarabine, Thiazolopyrimidines, thioctic acid, thiotepa, THR090717, THR0921, Threenofen, Thrombate III, Thymic peptide, Thymodepressin, Thymogam, Thymoglobulin, Thymoglobuline, Thymoject thymic peptides, thymomodulin, thymopentin, thymopolypetides, tiaprofenic acid, tibezonium iodide, Ticoflex, tilmacoxib, Tilur, T-immune, Timocon, Tiorase, Tissop, TKB662, TL011, TLR4 antagonists, TLR8 inhibitor, TM120, TM400, TMX302, TNF Alpha inhibitor, TNF alpha-TNF receptor antagonist, TNF antibody, TNF receptor superfamily antagonists, TNF TWEAK Bi-Specific, TNF-Kinoid, TNFQb, TNFR1 antagonist, TNR001, TNX100, TNX224, TNX336, TNX558, tocilizumab, tofacitinib, Tokuhon happ, TOL101, TOL102, Tolectin, ToleriMab, Tolerostem, Tolindol, toll-like receptor 4 antibody, toll-like receptor antibody, tolmetin sodium, Tongkeeper, Tonmex, Topflame, Topicort, Topleucon, Topnac, Toppin Ichthammol, toralizumab, Toraren, Torcoxia, Toroxx, Tory, Toselac, Totaryl, Touch-med, Touchron, Tovok, Toxic apis, Toyolyzom, TP4179, TPCA1, TPI526, TR14035, Tradil Fort, Traficet-EN, Tramace, tramadol hydrochloride, tranilast, Transimune, Transporina, Tratul, Trexall, Triacort, Triakort, Trialon, Triam, triamcinolone, triamcinolone acetate, triamcinolone acetonide, triamcinolone acetonide acetate, triamcinolone hexacetonide, Triamcort, Triamsicort, Trianex, Tricin, Tricort, Tricortone, TricOs T, Triderm, Trilac, Trilisate, Trinocort, Trinolone, Triolex, triptolide, Trisfen, Trivaris, TRK170, TRK530, Trocade, trolamine salicylate, Trolovol, Trosera, Trosera D, Troycort, TRX1 antibody, TRX4, Trymoto, Trymoto-A, TT301, TT302, TT32, TT32, TT33, TTI314, tumor necrosis factor, tumor necrosis factor 2-methoxyethyl phosphorothioate oligonucleotide, tumor necrosis factor antibody, tumor necrosis factor kinoid, tumor necrosis factor oligonucleotide, tumor necrosis factor receptor superfamily, member 1B antibody, tumor necrosis factor receptor superfamily1B oligonucleotide, tumor necrosis factor superfamily, member 12 antibody, tumor necrosis factor superfamily, member 4 antibody, tumor protein p53 oligonucleotide, tumour necrosis factor alpha antibody, TuNEX, TXA127, TX-RAD, TYK2 inhibitors, Tysabri, ubidecarenone, Ucerase, ulodesine, Ultiflam, Ultrafastin, Ultrafen, Ultralan, U-Nice-B, Uniplus, Unitrexate, Unizen, Uphaxicam, UR13870, UR5269, UR67767, Uremol-HC, Urigon, U-Ritis, ustekinumab, V85546, Valcib, Valcox, valdecoxib, Valdez, Valdixx, Valdy, Valentac, Valoxib, Valtune, Valus AT, Valz, Valzer, Vamid, Vantal, Vantelin, VAP-1 SSAO Inhibitor, vapaliximab, varespladib methyl, Varicosin, Varidase, vascular adhesion protein-1 antibody, VB110, VB120, VB201, VBY285, Vectra-P, vedolizumab, Vefren, VEGFR-1 Antibody, Veldona, veltuzumab, Vendexine, Venimmun N, Venoforte, Venoglobulin-IH, Venozel, Veral, Verax, vercirnon, vero-Dexamethasone, Vero-Kladribin, Vetazone, VGX1027, VGX750, Vibex MTX, vidofludimus, Vifenac, Vimovo, Vimultisa, Vincort, Vingraf, Vioform-HC, Vioxl, Vioxx, Virobron, visilizumab, Vivaglobin, Vivalde Plus, Vivian-A, VLST002, VLST003, VLST004, VLST005, VLST007, Voalla, voclosporin, Vokam, Vokmor, Volmax, Volna-K, Voltadol, Voltagesic, Voltanase, Voltanec, Voltaren, Voltarile, Voltic, Voren, vorsetuzumab, Votan-SR, VR909, VRA002, VRP1008, VRS826, VRS826, VT111, VT214, VT224, VT310, VT346, VT362, VTX763, Vurdon, VX30 antibody, VX467, VX5, VX509, VX702, VX740, VX745, VX745, VX850, W54011, Walacort, Walix, WC3027, Wilgraf, Winflam, Winmol, Winpred, Winsolve, Wintogeno, WIP901, Woncox, WSB711 antibody, WSB712 antibody, WSB735, WSB961, X071NAB, X083NAB, Xantomicin Forte, Xedenol, Xefo, Xefocam, Xenar, Xepol, X-Flam, Xibra, Xicam, Xicotil, Xifaxan, XL499, XmAb5483, XmAb5485, XmAb5574, XmAb5871, XOMA052, Xpress, XPro1595, XtendTNF, XToll, Xtra, Xylex-H, Xynofen SR, Yang Shu-IVIG, YHB14112, YM974, Youfeline, Youfenac, Yuma, Yumerol, Yuroben, YY piroxicam, Z104657A, Zacy, Zaltokin, zaltoprofen, Zap70 Inhibitor, Zeepain, Zeloxim Fort, Zema-Pak, Zempack, Zempred, Zenapax, Zenas, Zenol, Zenos, Zenoxone, Zerax, Zerocam, Zerospasm, ZFNs, zinc oxide, Zipsor, ziralimumab, Zitis, Zix-S, Zocort, Zodixam, Zoftadex, zoledronic acid, Zolfin, Zolterol, Zopyrin, Zoralone, ZORprin, Zortress, ZP1848, zucapsaicin, Zunovate, Zwitterionic polysaccharides, ZY1400, Zybodies, Zycel, Zyrofen, Zyrogen Inhibitors, Zyser, Zytrim, and Zywin-Forte. In addition, the anti-inflammatory drugs, as listed above, may be combined with one or more agents listed above or herein or with other agents known in the art.

In one embodiment, a drug that reduces, inhibits, prevents and/or ameliorates inflammation, for example, one of the drugs provided above, is delivered to the suprachoroidal space of the eye using the microneedle devices and methods disclosed herein, and is used to treat, prevent and/or ameliorate a disease or disorder selected from arthritis, degenerative arthritis, psoriatic arthritis, arthritic disorders, arthritic pain, arthrosis, autoimmune arthritis, autoimmune diseases, autoimmune disorders, axial spondyloarthritis, chronic prosthetic joint infection, collagen induced arthritis, osteoarthritis, rheumatoid arthritis, senile arthritis, seronegative oligoarthritis of the knee, allergic and autoimmune inflammatory diseases, inflammatory diseases, inflammatory disorders, collagen diseases, discoid Lupus Erythematosus, immune deficiencies, immune diseases, immune disorders, immunodeficiency diseases, immunodeficiency disorders, immunoglobulin (IgG2) deficiency, immunoglobulin deficiency, Inflammation, Lambert-Eaton myasthenia syndrome, polymyositis, dermatomyositis, polyneuritis, post-operative ocular inflammation, polychondritis, sporadic inclusion body myositis, Systemic Lupus Erythematosus, T cell deficiency, TNF-receptor associated periodic syndrome, tropical spastic paraparesis, Wegener Granulomatosis, X-linked severe combined immunodeficiency disease, Behcet's disease, Crohn's disease, Crohn's Fistula, cutaneous Lupus Erythematosus, acute inflammation, acute inflammatory edema, adrenocortical insufficiency, cerebral inflammation, chronic lung inflammation, corticoid-responsive inflammatory skin disorders, cutaneous inflammation, dermal inflammation, dry skin inflammatory disease, ear edema, ear inflammation, glossitis, inflammatory bowel disease, inflammatory degenerative disease, inflammatory disorders of the eye and/or ear, inflammatory lesions in fungal infections, inflammatory lesions, inflammatory pain, inflammatory skin diseases or disorders, mouth and gum inflammation, mouth and throat inflammation, musculoskeletal disorders, otitis, pelvic inflammatory disease, perianal inflammation, post operative inflammation, pulmonary inflammation, rectal inflammation, refractory idiopathic inflammatory myopathies, seborrhoeic dermatitis, swelling, aphthous ulcerations, chronic polyarthritis, juvenile rheumatoid arthritis, rheumatic diseases, Sjogren's syndrome, opthalmic for Sjogren's syndrome, transplant rejection, acute allograft rejection, chronic graft rejection, graft versus host disease, humoral rejection in heart transplantation, humoral rejection in kidney transplantation, organ rejection in renal transplantation, solid organ transplant rejection, bronchiolitis obliterans after lung transplantation, rejection of bone marrow transplant, chronic lung transplant rejection, Corneal graft rejection, delayed graft function in kidney transplantation, heart transplant rejection, Homotransplantation rejection, immune rejection of hESC-derived therapeutic grafts, kidney transplant rejection, liver transplant rejection, lung transplant rejection, organ rejection, pancreatic islet transplantation rejection in type I diabetes, renal transplant rejection and xenograft rejection.

In one embodiment, the drug delivered to the suprachoroidal space using the microneedle devices and methods disclosed herein treats, prevents, and/or ameliorates macular degeneration (e.g., age related macular degeneration, dry age related macular degeneration, exudative age-related macular degeneration, geographic atrophy associated with age related macular degeneration, neovascular (wet) age-related macular degeneration, neovascular maculopathy and age related macular degeneration, occult with no classic choroidal neovascularization (CNV) in age-related macular degeneration, Stargardt's disease, Subfoveal wet Age-Related macular degeneration, and Vitreomacular Adhesion (VMA) associated with Neovascular Age Related macular degeneration). Examples of drugs that treat, prevent and/or ameliorate macular degeneration that can be used in conjunction with the devices and methods described herein include, but are not limited to: A0003, A36 peptide, AAV2-sFLT01, ACE041, ACU02, ACU3223, ACU4429, AdPEDF, aflibercept, AG13958, aganirsen, AGN150998, AGN745, AL39324, AL78898A, AL8309B, ALN-VEG01, alprostadil, AM1101, amyloid beta antibody, anecortave acetate, Anti-VEGFR-2 Alterase, Aptocine, APX003, ARC1905, ARC1905 with Lucentis, ATG3, ATP-binding cassette, subfamily A, member 4 gene, ATXS10, Avastin with Visudyne, AVT101, AVT2, bertilimumab, bevacizumab with verteporfin, bevasiranib sodium, bevasiranib sodium; with ranibizumab, brimonidine tartrate, BVA301, canakinumab, Cand5, Cand5 with Lucentis, CERE140, ciliary neurotrophic factor, CLT009, CNT02476, collagen monoclonal antibody, complement component 5 aptamer (pegylated), complement component 5 aptamer (pegylated) with ranibizumab, complement component C3, complement factor B antibody, complement factor D antibody, copper oxide with lutein, vitamin C, vitamin E, and zinc oxide, dalantercept, DE109, dexamethasone with ranibizumab and verteporfin, disitertide, DNA damage inducible transcript 4 oligonucleotide, E10030, E10030 with Lucentis, EC400, eculizumab, EGP, EHT204, embryonic stem cells, human stem cells, endoglin monoclonal antibody, EphB4 RTK Inhibitor, EphB4 Soluble Receptor, ESBA1008, ETX6991, Evizon, Eyebar, EyePromise Five, Eyevi, Eylea, F200, FCFD4514S, fenretinide, fluocinolone acetonide, fluocinolone acetonide with ranibizumab, fms-related tyrosine kinase 1 oligonucleotide, fms-related tyrosine kinase 1 oligonucleotide with kinase insert domain receptor 169, fosbretabulin tromethamine, Gamunex, GEM220, GS101, GSK933776, HC31496, Human n-CoDeR, HYB676, IBI-20089 with Lucentis, iCo-008, Icon1, I-Gold, Ilaris, Iluvien, Iluvien with Lucentis, immunoglobulins, integrin alpha5beta1 immunoglobulin fragments, Integrin inhibitor, IRIS Lutein, I-Sense Ocushield, Isonep, isopropyl unoprostone, JPE1375, JSM6427, KH902, LentiVue, LFG316, LP590, LPO1010AM, Lucentis, Lucentis with Visudyne, Lutein ekstra, Lutein with myrtillus extract, Lutein with zeaxanthin, M200, M200 with Lucentis, Macugen, MC1101, MCT355, mecamylamine, Microplasmin, motexafin lutetium, MP0112, NADPH oxidase inhibitors, Neoretna, neurotrophin 4 gene, Nova21012, Nova21013, NT501, NT503, Nutri-Stulln, ocriplasmin, OcuXan, Oftan Macula, Optrin, ORA102 with Avastin, P144, P17, Palomid 529, PAN90806, Panzem, Panzem, PARP Inhibitors, pazopanib hydrochloride, pegaptanib sodium, PF4523655, PG11047, piribedil, platelet-derived growth factor beta polypeptide aptamer (pegylated), platelet-derived growth factor beta polypeptide aptamer (pegylated) with ranibizumab, PLG101, PMX20005, PMX53, POT4, PRS055, PTK787, ranibizumab, ranibizumab with triamcinolone acetonide, ranibizumabwith verteporfin, ranibizumab with volociximab, RD27, Rescula, Retaane, retinal pigment epithelial cells, RetinoStat, RG7417, RN6G, RT101, RTU007, SB267268, serpin peptidase inhibitor, Glade F, member 1 gene, shark cartilage extract, Shef1, SIR1046, SIR1076, Sirna027, sirolimus, SMTD004, Snelvit, SOD Mimetics, Soliris, sonepcizumab, squalamine lactate, ST602, StarGen, T2TrpRS, TA106, talaporfin sodium, Tauroursodeoxycholic acid, TG100801, TKI, TLCx99, TRC093, TRC105, triamcinolone acetonide with verteporfin, Trivastal Retard, TT30, Ursa, ursodiol, Vangiolux, VAR10200, vascular endothelial growth factor antibody, vascular endothelial growth factor B, vascular endothelial growth factor kinoid, vascular endothelial growth factor oligonucleotide, VAST Compounds, vatalanib, VEGF Inhibitor, verteporfin, Visudyne, Visudyne with Lucentis and dexamethasone, Visudyne with triamcinolone acetonide, Vivis, volociximab, Votrient, XV615, zeaxanthin, ZFP TF, zinc-monocysteine and Zybrestat. In one embodiment, one or more of the macular degeneration treating drugs described above is combined with one or more agents listed above or herein or with other agents known in the art.

In one embodiment, the methods and devices provided herein are used to delivery triamcinolone or triamcinolone acetonide to the suprachoroidal space of an eye of a patient in need thereof. In a further embodiment, the triamcinolone or triamcinolone acetonide is delivered for the treatment of sympathetic ophthalmia, temporal arteritis, uveitis and/or ocular inflammatory conditions. In one embodiment, triamcinolone or triamcinolone acetonide is delivered to the suprachoroidal space of the eye in a patient in need of treatment of sympathetic opthalmia with the methods and devices described herein. In another embodiment, triamcinolone or triamcinolone acetonide is delivered to the suprachoroidal space of the eye in a patient in need of treatment of temporal arteritis with the methods and devices described herein. In yet another embodiment, triamcinolone or triamcinolone acetonide is delivered to the suprachoroidalspace of the eye in a patient in need of treatment of uveitis, with the methods and devices described herein. In another embodiment, triamcinolone or triamcinolone acetonide is delivered to the suprachoroidal space of the eye in a patient in need of treatment of one or more ocular inflammatory conditions, with the methods and devices described herein.

The triamcinolone composition provided herein, in one embodiment, is a suspension comprising microparticles or nanoparticles of triamcinolone or triamcinolone acetonide. The microparticles, in one embodiment, have a $D_{50}$ of about 3 µm or less. In a further embodiment, the $D_{50}$ is about 2 µm. In another embodiment, the $D_{50}$ is about 2 µm or less. In even another embodiment, the $D_{50}$ is about 1000 nm or less. The microparticles, in one embodiment, have a $D_{99}$ of about 10 µm or less. In another embodiment, the $D_{99}$ is about 10

µm. In another embodiment, the $D_{99}$ is less than about 10 µm or less than about 9 µm or less.

In one embodiment, the triamcinolone composition comprises triamcinolone microparticles. In a further embodiment, the composition comprises polysorbate 80. In another embodiment, the triamcinolone composition comprises one or more of $CaCl_2$, $MgCl_2$, sodium acetate and sodium citrate. In one embodiment, the composition comprises polysorbate 80 at a w/v % of 0.02% or about 0.02%, 0.015% or about 0.015%.

In certain embodiments the drug delivered to ocular tissues using the microneedle devices and methods disclosed herein treats, prevents, and/or ameliorates fibrosis (e.g. myelofibrosis, fibrosis in diabetic nephropathy, cystic fibrosis, scarring, and skin fibrosis).

In one embodiment, a drug that treats, prevents and/or ameliorates fibrosis is used in conjunction with the devices and methods described herein, and is delivered to the suprachoroidal space of the eye. In a further embodiment, the drug is Actimmune with Pirfenidone, ACUHTR028, AlphaVBeta5, aminobenzoate potassium, amyloid P, ANG1122, ANG1170, ANG3062, ANG3281, ANG3298, ANG4011, Anti-CTGF RNAi, Aplidin, *Astragalus membranaceus* extract with salvia and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, Galectin-3 inhibitors, GKT137831, GMCT01, GMCT02, GRMD01, GRMD02, GRN510, Heberon Alfa R, interferon alfa-2b, interferon gamma-1b with pirfenidone, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 Fusion Proteins, RXI109, secretin, STX100, TGF-beta Inhibitor, transforming growth factor, beta receptor 2 oligonucleotide, VA999260 or XV615. In one embodiment, one or more of the fibrosis treating drugs described above is combined with one or more agents listed above or herein or with other agents known in the art.

In one embodiment, a drug that treats, prevents and/or ameliorates diabetic macular edema is used in conjunction with the devices and methods described herein, and is delivered to the suprachoroidal space of the eye. In a further embodiment, the drug is AKB9778, bevasiranib sodium, Candy, choline fenofibrate, Cortiject, c-raf 2-methoxyethyl phosphorothioate oligonucleotide, DE109, dexamethasone, DNA damage inducible transcript 4 oligonucleotide, FOV2304, iCo007, KH902, MP0112, NCX434, Optina, Ozurdex, PF4523655, SAR1118, sirolimus, SK0503 or Tri-Lipix. In one embodiment, one or more of the diabetic macular edema treating drugs described above is combined with one or more agents listed above or herein or with other agents known in the art.

In one embodiment, a drug that treats, prevents and/or ameliorates macular edema is used in conjunction with the devices and methods described herein, and is delivered to the suprachoroidal space of the eye. In a further embodiment, the drug is denufosol tetrasodium, dexamethasone, ecallantide, pegaptanib sodium, ranibizumab or triamcinolone. In addition, the drugs delivered to ocular tissues using the microneedle devices and methods disclosed herein which treat, prevent, and/or ameliorate macular edema, as listed above, may be combined with one or more agents listed above or herein or with other agents known in the art.

In one embodiment, a drug that treats, prevents and/or ameliorates ocular hypertension is used in conjunction with the devices and methods described herein and is delivered to the suprachoroidal space of the eye. In a further embodiment, the drug is 2-MeS-beta gamma-CC12-ATP, Aceta Diazol, acetazolamide, Aristomol, Arteoptic, AZD4017, Betalmic, betaxolol hydrochloride, Betimol, Betoptic S, Brimodin, Brimonal, brimonidine, brimonidine tartrate, Brinidin, Calte, carteolol hydrochloride, Cosopt, CS088, DE092, DE104, DE111, dorzolamide, dorzolamide hydrochloride, Dorzolamide hydrochloride with Timolol maleate, Droptimol, Fortinol, Glaumol, Hypadil, Ismotic, isopropyl unoprostone, isosorbide, Latalux, latanoprost, Latanoprost with Timolol maleate, levobunolol hydrochloride, Lotensin, Mannigen, mannitol, metipranolol, mifepristone, Mikelan, Minims Metipranolol, Mirol, nipradilol, Nor Tenz, Ocupress, olmesartan, Ophtalol, pilocarpine nitrate, Piobaj, Rescula, RU486, Rysmon TG, SAD448, Saflutan, Shemol, Taflotan, tafluprost, tafluprost with timolol, Thiaboot, Timocomod, timolol, Timolol Actavis, timolol hemihydrate, timolol maleate, Travast, travoprost, Unilat, Xalacom, Xalatan or Zomilol. In addition, the drugs delivered to ocular tissues using the microneedle devices and methods disclosed herein which treat, prevent, and/or ameliorate ocular hypertension, as listed above, may be combined with one or more agents listed above or herein or with other agents known in the art.

In certain embodiments one or more drugs may be delivered to ocular tissues and/or into the suprachoroidal space via the systems and devices described herein. Delivery of one or more drugs into the suprachoroida lspace using the microneedle device described herein may be accomplished by using one or more microneedles. In addition, combinations of one of more drugs may be delivered to the suprachoroidal space using the microneedle device described herein in combination with delivery of one or more drugs via intravitreal (IVT) administration (e.g., intravitreal injection, intravitreal implant or eye drops). Methods of IVT administration are well known in the art. Examples of drugs that can be administered via IVT include, but are not limited to: A0003, A0006, Acedolone, AdPEDF, aflibercept, AG13958, aganirsen, AGN208397, AKB9778, AL78898A, amyloid P, Angiogenesis Inhibitor Gene Therapy, ARC1905, Aurocort, bevasiranib sodium, brimonidine, Brimonidine, brimonidine tartrate, bromfenac sodium, Candy, CERE140, Ciganclor, CLT001, CLT003, CLT004, CLT005, complement component 5 aptamer (pegylated), complement factor D antibody, Cortiject, c-raf 2-methoxyethyl phosphorothioate oligonucleotide, cyclosporine, triamcinolone, DE109, denufosol tetrasodium, dexamethasone, dexamethasone phosphate, disitertide, DNA damage inducible transcript 4 oligonucleotide, E10030, ecallantide, EG3306, Eos013, ESBA1008, ESBA105, Eylea, FCFD4514S, fluocinolone acetonide, fms-related tyrosine kinase 1 oligonucleotide, fomivirsen sodium, fosbretabulin tromethamine, FOV2301, FOV2501, ganciclovir, ganciclovir sodium, GS101, GS156, hyaluronidase, IBI20089, iCo007, Iluvien, INS37217, Isonep, JSM6427, Kalbitor, KH902, lerdelimumab, LFG316, Lucentis, M200, Macugen, Makyueido, Microplasmin, MK0140, MP0112, NCX434, neurotrophin 4 gene, OC10X, ocriplasmin, ORA102, Ozurdex, P144, P17, Palomid 529, pazopanib hydrochloride, pegaptanib sodium, Plasma Kallikrein Inhibitors, platelet-derived growth factor beta polypeptide aptamer (pegylated), POT4, PRM167, PRS055, QPI1007, ranibizumab, resveratrol, Retilone, retinal pigment epithelium-specific protein 65 kDa gene, Retisert, rod derived cone viability factor, RPE65 Gene Therapy, RPGR Gene Therapy, RTP801, Sd-rxRNA, serpin peptidase inhibitor Glade F member 1 gene, Sirna027, sirolimus, sonepcizumab, SRT501, STP601, TG100948, Trabio, triamcinolone, triamcinolone acetonide, Trivaris, tumor necrosis factor antibody, VEGF/rGel-Op, verteporfin, Visudyne, Vitrase, Vitrasert, Vitravene, Vitreals, volociximab, Votrient, XG102, Xibrom, XV615, and Zybrestat. Accordingly, the methods of the present invention include administrating via IVT one or more of the drugs listed above in combination with one or more drugs disclosed herein administered into the suprachoroidal space using the microneedle device described herein.

In one embodiment, the drug is formulated for storage and delivery via the microneedle device described herein. The "drug formulation" is a formulation of a drug, which typically includes one or more pharmaceutically acceptable excipient materials known in the art. The term "excipient" refers to any non-active ingredient of the formulation intended to facilitate handling, stability, dispersibility, wettability, release kinetics, and/or injection of the drug. In one embodiment, the excipient may include or consist of water or saline.

In one embodiment, the fluid drug formulation includes microparticles or nanoparticles, each of which can include at least one drug. Desirably, the microparticles or nanoparticles provide for the controlled release of drug into the ocular tissue. As used herein, the term "microparticle" encompasses microspheres, microcapsules, microparticles, and beads, having a number average diameter of 1 to 100 μm, most preferably 1 to 25 μm. The term "nanoparticles" are particles having a number average diameter of 1 to 1000 nm. Microparticles may or may not be spherical in shape. "Microcapsules" are defined as microparticles having an outer shell surrounding a core of another material. The core can be liquid, gel, solid, gas, or a combination thereof. In one case, the microcapsule may be a "microbubble" having an outer shell surrounding a core of gas, wherein the drug is disposed on the surface of the outer shell, in the outer shell itself, or in the core. Microbubbles may respond to acoustic vibrations as known in the art for diagnosis and/or can be used to burst the microbubble to release its payload at/into a select ocular tissue site. "Microspheres" can be solid spheres, can be porous and include a sponge-like or honeycomb structure formed by pores or voids in a matrix material or shell, or can include multiple discrete voids in a matrix material or shell. The microparticle or nanoparticles may further include a matrix material. The shell or matrix material may be a polymer, amino acid, saccharride, or other material known in the art of microencapsulation.

The drug-containing microparticles or nanoparticles may be suspended in an aqueous or non-aqueous liquid vehicle. The liquid vehicle may be a pharmaceutically acceptable aqueous solution, and optionally may further include a surfactant. The microparticles or nanoparticles of drug themselves may include an excipient material, such as a polymer, a polysaccharide, a surfactant, etc., which are known in the art to control the kinetics of drug release from particles.

In one embodiment, the fluid drug formulation further includes an agent effective to degrade collagen or GAG fibers in the sclera, which may enhance penetration/release of the drug into the ocular tissues. This agent may be, for example, an enzyme, such a hyaluronidase, a collagenase, or a combination thereof. In a variation of this method, the enzyme is administered to the ocular tissue in a separate step from—preceding or following—infusion of the drug. The enzyme and drug are administered at the same site.

In another embodiment, the drug formulation is one that undergoes a phase change upon administration. For instance, a liquid drug formulation may be injected through hollow microneedles into the suprachoroidal space, where it then gels and the drug diffuses out from the gel for controlled release.

While the embodiments and methods herein describe delivering a medicament to a target tissue, the embodiments described herein can be configured to facilitate a biopsy procedure and/or removal of a substance from a target location.

While the embodiments have been described above in use on ocular tissue, in some instances, the embodiments and methods described herein can be used on any other suitable bodily tissue. For example, in some instances, the use of an adjustable length needle can be beneficial in conjunction with standard phlebotomy techniques during drug infusion and/or blood draw from a vein. Thus, while the embodiments and methods are specifically described above in use on ocular tissue, it should be understood that the embodiments and methods have been presented by way of example only, and not limitation.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although the systems and methods are shown and described herein as providing for delivery of medicaments in the suprachoroidal space, in other embodiments, the systems and the methods described herein can be applicable for delivery of any suitable therapeutic substance to any portion of the eye, such as, the cornea, the retinal area or the vitreous. In other embodiments, any of the systems, methods and devices described herein can be used to deliver any suitable therapeutic substance to any desired target tissue (including non-ocular tissue).

Where schematics and/or embodiments described above indicate certain components arranged in certain orientations or positions, the arrangement of components may be modified. Similarly, where methods and/or events described above indicate certain events and/or procedures occurring in certain order, the ordering of certain events and/or procedures may be modified. While the embodiments have been particularly shown and described, it will be understood that various changes in form and details may be made.

For example, although the injector assembly 2100 is shown and described as including a biasing member 2146 configured to exert a force to move the actuator 2320 to assist in the delivery of a medicament, in other embodiments, the injector assembly 2100 (and any other injector assemblies shown and described herein) can include any suitable mechanism for producing a force to move the actuator 2320. For example, in some embodiments, an injector assembly can include a stored energy member, such as a propellant canister, a compressed gas container, a magnetic energy storage member, an electronic energy storage member (e.g., a battery or a capacitor) or the like.

Although various embodiments have been described as having particular features and/or combinations of components, other embodiments are possible having a combination of any features and/or components from any of embodiments as discussed above. For example, while the extraction member 21280 is described as being included in the system 21000 and configured to be coupled to the medicament container 21310, in some embodiments, the device 2000, 3000, or any other device described herein can be used with and/or include the extraction member 21280, or any other extraction member described herein. Furthermore, while the needle assembly 3200 is shown as being included in the system 3000, in some embodiments, the system 2000, 21000, or any other medical injector described herein can also include the needle assembly 3200 or any other needle assembly described herein. Moreover, while the injection assembly 2100 is described as included with the system 2000, in some embodiments, the injection assembly 2100 can also be included in the system 3000, 21000 or any other system described herein. Similarly, any of the systems described herein (e.g., the system 2000, 3000, or 21000) can include or configured to be coupled to a hub that includes a convex distal end surface such as, for example, the hub 7270, 8270, or 9270.

The invention claimed is:

1. A method, comprising:
    inserting a distal end portion of a puncture member of a medical injector into a target tissue to define a delivery passageway within the target tissue and such that a distal end surface of a housing of the medical injector is in contact with a target surface of the target tissue;
    with the distal end portion of the puncture member disposed within a first region of the target tissue and the distal end surface of the housing in contact with the target surface, exerting a force on an actuation rod of the medical injector, the force configured to produce distal movement of the puncture member relative to the housing such that the distal end portion of the puncture member enters a second region of the target tissue, distal movement of the puncture member relative to the housing in response to the force being limited when the distal end portion of the puncture member is disposed within the second region of the target tissue; and
    conveying, in response to the exerting and the distal end portion of the puncture member being disposed within the second region of the target tissue, a substance from the medical injector into the second region of the target tissue via the puncture member, the force being insufficient to overcome a backpressure of the first region to convey the medicament into the first region of the target tissue via the puncture member when the distal end portion of the puncture member is disposed within the first region.

2. The method of claim 1, wherein the puncture member is moved relative to the housing via hydraulics.

3. The method of claim 1, wherein the force is sufficient to overcome a backpressure of the second region such that movement of the distal end portion of the puncture member relative to the hub is reduced and the substance is conveyed into the second region of the target tissue when the distal end portion of the puncture member moves from the first region to the second region.

4. The method of claim 1, wherein the force is less than about 6 N and is provided by an energy storage member of the medical injector.

5. The method of claim 1, wherein:
    the inserting is performed such that a centerline of the delivery passageway and a surface line tangential to the target surface defines an angle of entry of between about 75 degrees and about 105 degrees.

6. The method of claim 1, wherein the target tissue is an eye and the target surface is any one of a conjunctiva of the eye or a sclera of the eye, the substance being at least one of a VEGF, a VEGF inhibitor, a PDGFR inhibitor, or a combination thereof.

7. The method of claim 1, wherein:
    the target tissue is an eye, the target surface is any one of a conjunctiva of the eye or a sclera of the eye,
    the second region includes at least one of a suprachoroidal space, a lower portion of the sclera, a choroid of the eye, a subretinal space of the eye, or a retina of the eye.

8. The method of claim 7, wherein the first region is an upper portion of a sclera of the eye.

9. The method of claim 1, wherein the inserting includes deforming the target surface with the distal end surface of the housing.

10. The method of claim 1, wherein the distal end surface of the housing includes a sealing portion configured to define a fluid-tight seal with the target surface, the sealing portion being symmetrical about a centerline of the puncture member.

11. The method of claim 1, wherein the inserting is performed before the exerting is performed.

12. The method of claim 1, wherein the exerting the force on the actuation rod causes the actuation rod and the puncture member to move linearly within the housing of the medical injector when the distal end portion of the puncture member is disposed within the first region of the target tissue.

13. The method of claim 12, wherein the exerting the force on the actuation rod causes the actuation rod to move linearly within the medical injector when the distal end portion of the puncture member is disposed within the second region of the target tissue such that the substance from the medicament container is conveyed into the target tissue via the puncture member.

14. The method of 1, further comprising:
    during the exerting the force on the actuation rod, maintaining a sealing force on the medical injector such that distal end surface of the housing forms a substantially fluid-tight seal with the target surface.

15. A method, comprising:
    inserting a distal end portion of a puncture member of a medical injector into a target tissue to define a delivery passageway within the target tissue;
    applying a first force to a housing of the medical injector such that a distal end surface of the housing contacts a target surface of the target tissue to fluidically isolate the delivery passageway; and
    while maintaining the first force, applying a second force to an actuation rod of the medical injector to move the puncture member distally relative to the housing such that a distal end portion of the puncture member moves from a first region within the target tissue to a second region with the target tissue, a substance from within the medical injector being conveyed to the target tissue in response to the distal end portion of the puncture member being disposed in the second region and not the first region,
    the second force being insufficient to overcome a backpressure of the first region to convey the medicament into the first region of the target tissue via the puncture member when the distal end portion of the puncture member is disposed within the first region.

16. The method of claim 15, wherein the puncture member is moved within the medical injector via hydraulics.

17. The method of claim 15, wherein the first force is less than about 6 N.

18. The method of claim 15, wherein:
the inserting is performed such that a centerline of the delivery passageway and a surface line tangent to the target surface defines an angle of entry of between about 75 degrees and about 105 degrees.

19. The method of claim 15, wherein the target tissue is an eye and the target surface is any one of a conjunctiva of the eye or a sclera of the eye, the substance being at least one of a VEGF, a VEGF inhibitor, a PDGFR inhibitor, or a combination thereof.

20. The method of claim 15, wherein:
the target tissue is an eye, the target surface is any one of a conjunctiva of the eye or a sclera of the eye,
the second region includes at least one of a suprachoroidal space, a lower portion of the sclera, a choroid of the eye, a subretinal space of the eye, or a retina of the eye.

21. The method of claim 20, wherein the first region is an upper portion of a sclera of the eye.

22. A method, comprising:
inserting a distal end portion of a puncture member of a medical injector into a first region of a target tissue to define a delivery passageway within the target tissue, the puncture member placing a substance within a housing of the medical injector in fluid communication with the first region, an adjustment member being movably disposed within the medical injector and forming a substantially fluid-tight seal with a side wall of medical injector;
after the inserting and with the distal end portion of the puncture member disposed in the first region of the target tissue, exerting a force on the adjustment member such that the force in conjunction with the substantially fluid-tight seal produces movement of the distal end portion of the puncture member relative to the housing and from the first region to a second region of the target tissue; and
conveying, in response to the exerting, a substance from the medicament container into the target tissue via the puncture member when the distal end portion of the puncture member is disposed within the second region of the target tissue.

23. The method of claim 22, wherein the force is insufficient to overcome a backpressure of the first region to convey the medicament into the target tissue via the puncture member when the distal end portion of the puncture member is disposed within the first region, the force being sufficient to overcome a frictional force formed by the substantially fluid-tight seal such that the force produces distal movement of the adjustment member within the medical injector.

24. The method of claim 23, wherein the force is sufficient to overcome a backpressure of the second region to convey the medicament into the target tissue via the puncture member when the distal end portion of the puncture member is disposed within the second region.

25. The method of claim 22, wherein the adjustment member is moved within the medical injector via hydraulics.

26. The method of claim 22, wherein:
the target tissue is an eye, the target surface is any one of a conjunctiva of the eye or a sclera of the eye,
the second region includes at least one of a suprachoroidal space, a lower portion of the sclera, a choroid of the eye, a subretinal space of the eye, or a retina of the eye.

27. The method of claim 26, wherein the first region is an upper portion of a sclera of the eye.

28. The method of 22, further comprising:
during the exerting the force on the adjustment member, maintaining a force on the medical injector such that a distal end surface of the housing forms a substantially fluid-tight seal with the target surface.

* * * * *

UNITED STATES PATENT AND TRADEMARK OFFICE
CERTIFICATE OF CORRECTION

PATENT NO. : 10,517,756 B2  
APPLICATION NO. : 16/381213  
DATED : December 31, 2019  
INVENTOR(S) : Andino et al.

Page 1 of 2

It is certified that error appears in the above-identified patent and that said Letters Patent is hereby corrected as shown below:

In the Specification

At Column 90, Line 43, please delete "ADAMTSS" and insert therein --ADAMTS5--.

At Column 91, Line 17, please delete "Anti-alpha1 1" and insert therein --Anti-alpha11--.

At Column 91, Line 43, please delete "ARRY3717976" and insert therein --ARRY371797--.

At Column 92, Line 31, please delete "BRO2001" and insert therein --BR02001--.

At Column 93, Line 3, please delete "cenplace1-1" and insert therein --cenplacel-1--.

At Column 93, Line 32, please delete "CND0201" and insert therein --CNDO201--.

At Column 93, Line 33, please delete "CNT01959" and insert therein --CNTO1959--.

At Column 94, Line 5, please delete "CYTO20TNFQb" and insert therein --CYT020TNFQb--.

At Column 94, Line 67, please delete "ECO286" and insert therein --EC0286--.

At Column 95, Line 56, please delete "Gamma-LV." and insert therein --Gamma-I.V.--.

At Column 96, Line 23, please delete "Hibema" and insert therein --Hiberna--.

At Column 96, Lines 36-37, please delete "Hy aron, Hy cocin, Hy cort" and insert therein --Hyaron, Hycocin, Hycort--.

At Column 97, Line 1, please delete "IN07997" and insert therein --INO7997--.

At Column 97, Lines 19-20, please delete "lomab B" and insert therein --Iomab B--.

Signed and Sealed this  
Twenty-third Day of June, 2020

Andrei Iancu  
*Director of the United States Patent and Trademark Office*

CERTIFICATE OF CORRECTION (continued)
U.S. Pat. No. 10,517,756 B2

At Column 97, Line 58, please delete "LE015520" and insert therein --LEO15520--.

At Column 98, Line 1, please delete "LP1207" and insert therein --LJP1207--.

At Column 98, Line 4, please delete "Lomcrat" and insert therein --Lorncrat--.

At Column 99, Lines 18-19, please delete "My col dos a, My comun, My conol" and insert therein --Mycoldosa, Mycomun, Myconol--.

At Column 99, Line 63, please delete "NVO7alpha" and insert therein --NV07alpha--.

At Column 99, Line 64, please delete "00002417" and insert therein --OC002417--.

At Column 100, Line 45, please delete "PHS" and insert therein --PH5--.

At Column 101, Lines 37-38, please delete "remestemcel-1" and insert therein --remestemcel-l--.

At Column 101, Line 52, please delete "Rittman" and insert therein --Rituxan--.

At Column 101, Line 53, please delete "R01138452" and insert therein --RO1138452--.

At Column 101, Line 53, please delete "R03244794, R05310074" and insert therein --RO3244794, RO5310074--.

At Column 101, Line 64, please delete "SIP" and insert therein --S1P--.

At Column 101, Line 64, please delete "SP" and insert therein --S1P--.

At Column 102, Lines 7-8, please delete "SCI0323, SCI0469" and insert therein --SCIO323, SCIO469--.

At Column 102, Line 29, please delete "SN0030908," and insert therein --SNO030908--.

At Column 102, Line 44, please delete "Steno" and insert therein --Sterio--.

At Column 105, Line 42, please delete "CNT02476," and insert therein --CNTO2476--.

At Column 106, Line 18, please delete "Glade" and insert therein --clade--.

At Column 107, Line 48, please delete "Candy" and insert therein --Cand5--.

At Column 108, Line 5, please delete "gamma-CC12" and insert therein --gamma-CCl2--.

At Column 108, Line 45, please delete "Candy" and insert therein --Cand5--.

At Column 109, Line 2, please delete "Glade" and insert therein --clade--.